United States Patent
Badescu et al.

(10) Patent No.: US 8,202,873 B2
(45) Date of Patent: Jun. 19, 2012

(54) 2-[4-(PYRAZOL-4-YLALKYL)PIPERAZIN-1-YL]-3-PHENYL PYRAZINES AS 5-HT7 RECEPTOR ANTAGONISTS

(75) Inventors: Valentina O. Badescu, Fishers, IN (US); Anne Marie Camp, Basingstoke (GB); Barry Peter Clark, Basingstoke (GB); Michael Philip Cohen, Indianapolis, IN (US); Sandra Ann Filla, Franklin, IN (US); Peter Thaddeus Gallagher, Basingstoke (GB); Sarah Lynne Hellman, Indianapolis, IN (US); Michael Philip Mazanetz, Abingdon (GB); Marta Maria Pineiro-Nunez, Brownsburg, IN (US); John Mehnert Schaus, Zionsville, IN (US); Patrick Gianpietro Spinazze, Avon, IN (US); Maria Ann Whatton, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 67 days.

(21) Appl. No.: 12/597,255

(22) PCT Filed: May 7, 2008

(86) PCT No.: PCT/US2008/062834
§ 371 (c)(1), (2), (4) Date: Oct. 23, 2009

(87) PCT Pub. No.: WO2008/141020
PCT Pub. Date: Nov. 20, 2008

(65) Prior Publication Data
US 2010/0120785 A1    May 13, 2010

Related U.S. Application Data

(60) Provisional application No. 60/917,431, filed on May 11, 2007, provisional application No. 60/974,209, filed on Sep. 21, 2007.

(51) Int. Cl.
*A61K 31/4965* (2006.01)
(52) U.S. Cl. ............... 514/255.05; 544/359; 544/405; 548/375.1
(58) Field of Classification Search ............ 514/255.05; 544/359, 405; 548/375.1
See application file for complete search history.

(56) References Cited

FOREIGN PATENT DOCUMENTS
EP          0714896 A        6/1996
WO     WO 2004067703 A    8/2004

OTHER PUBLICATIONS

Leopoldo, M: *Curr. Med. Chem 11*, 629-661; Serotonin(7) Receoptors (5-HT(7)Rs) and their ligands; (2004).

*Primary Examiner* — James O Wilson
*Assistant Examiner* — Douglas M Willis
(74) *Attorney, Agent, or Firm* — R. Craig Tucker

(57) ABSTRACT

The present invention provides selective 5-HT7 receptor antagonist compounds of Formula I and their use in the treatment of migraine, persistent pain, and anxiety:

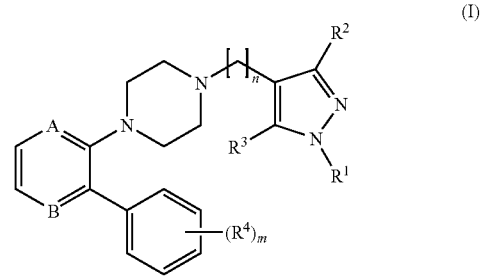

where A and B are each independently —C(H)= or —N=, provided that at least one of A and B is —N=, n is 1-3, m is 0-3, and R1-4 are as defined herein.

9 Claims, No Drawings

2-[4-(PYRAZOL-4-YLALKYL)PIPERAZIN-1-YL]-3-PHENYL PYRAZINES AS 5-HT7 RECEPTOR ANTAGONISTS

This U.S. national stage application of International Application PCT/US2008/062834, filed May 7, 2008, claims priority to U.S. provisional application Ser. No. 60/917,431, filed May 11, 2007, and U.S. provisional application Ser. No. 60/974,209, filed Sep. 21, 2007.

The neurotransmitter serotonin (5-hydroxytryptamine, 5-HT) has a rich pharmacology arising from a heterogeneous population of at least 14 distinct receptors. Each receptor has a distinct, though often overlapping distribution throughout the body and a unique serotonin binding site leading to different affinities for serotonin and different physiological responses to interaction with serotonin. The 5-HT$_7$ receptor has been shown to have important functional roles in thermoregulation, circadian rhythm, learning and memory, hippocampal signaling, and sleep. The 5-HT$_7$ receptor has also been linked to various neurological disorders including migraine and anxiety, as well as to persistent pain, more specifically inflammatory pain and neuropathic pain.

High affinity 5-HT$_7$ receptor antagonists would provide useful therapeutics for the treatment of the above mentioned 5-HT$_7$ receptor-associated disorders including migraine, and persistent pain, particularly, inflammatory and neuropathic pain. High affinity 5-HT$_7$ receptor antagonists that are also selective for the 5-HT$_7$ receptor, would provide such therapeutic benefit without the undesirable adverse events associated with modulation of the other serotonergic receptor subclasses, such as 5-HT$_{1A}$, 5-HT$_{1B}$ and 5-HT$_{1D}$. Achieving selectivity for the 5-HT$_7$ receptor has proven difficult in designing 5-HT$_7$ antagonists. 5-HT$_{1A}$ receptor agonists have been associated with serotonin syndrome. 5-HT$_{1B}$ and 5-HT$_{1D}$ receptor agonists have been associated with adverse events such as chest pain.

Leopoldo, M. (2004) Serotonin (7) receptors (5-HT(7)Rs) and their ligands. Curr. Med. Chem. 11, 629-661), describes various prior approaches to obtaining 5-HT$_7$ receptor ligands.

The present invention provides novel potent 5-HT$_7$ receptor antagonists. Certain compounds of the present invention are selective for the 5-HT$_7$ receptor compared with other serotonin receptors.

The present invention provides selective 5-HT$_7$ receptor antagonist compounds of Formula I:

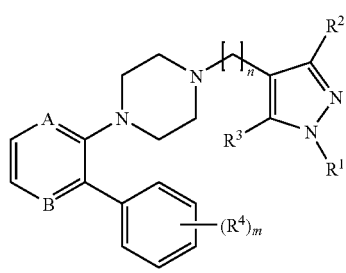

I where:
A and B are each independently —C(H)═ or —N═, provided that at least one of A and B is —N═;
n is 1, 2, or 3;
m is 0, 1, 2, or 3;
$R^1$ is selected from the group consisting of
  i) hydrogen, ii) ($C_1$-$C_6$)alkyl-optionally substituted with hydroxy, cyano, or 1 to 5 fluoro substituents, or alternatively, optionally substituted with hydroxy and 1 to 3 fluoro substituents, iii) ($C_3$-$C_7$)cycloalkyl-($C_0$-$C_2$)alkyl-optionally substituted with hydroxy, iv) ($C_1$-$C_2$)alkyl-O—($C_1$-$C_2$)alkyl-, v) $Ph^1$-($C_0$-$C_2$)alkyl-, vi) $Ar^1$—($C_0$-$C_2$)alkyl-, vii) ($C_1$-$C_2$)alkyl-S(O)$_2$—($C_0$-$C_3$)alkyl-, viii) $Ph^1$-S(O)$_2$—, ix) $Ar^1$—S(O)$_2$—, x) ($C_1$-$C_2$)alkyl-NH—($C_1$-$C_2$)alkyl-, xi) (($C_1$-$C_2$)alkyl)$_2$-N—($C_1$-$C_2$)alkyl-, xii) ($C_1$-$C_2$)alkyl-NH—C(O)—($C_0$-$C_2$)alkyl-, xiii) (($C_1$-$C_2$)alkyl)$_2$-N—C(O)—($C_0$-$C_2$)alkyl-, xiv) pyrrolidin-1-yl-C(O)—($C_0$-$C_2$)alkyl-, xv) ($C_1$-$C_2$)alkyl-C(O)—NH—($C_1$-$C_2$)alkyl-, xvi) ($C_1$-$C_2$)alkyl)-C(O)—N($C_1$-$C_2$ alkyl)-($C_1$-$C_2$)alkyl-, xvii) ($C_1$-$C_2$)alkyl-S(O)$_2$—NH—($C_1$-$C_2$)alkyl-, and xviii) 2-oxo-oxazolidin-5-yl-;
$R^2$ is selected from the group consisting of i) hydrogen, ii) halo, iii) hydroxy, iv) ($C_1$-$C_4$)alkyl-optionally substituted with hydroxy, cyano, or 1 to 5 fluoro substituents, and v) ($C_1$-$C_2$)alkyl-O—($C_0$-$C_2$)alkyl-;
$R^3$ is selected from the group consisting of hydrogen, halo, and ($C_1$-$C_4$)alkyl-;
Each $R^4$ is independently selected from the group consisting of i) halogen, ii) ($C_1$-$C_2$)alkyl optionally further substituted with 1 to 5 fluoro substituents, iii) ($C_1$-$C_2$)alkoxy optionally further substituted with 1 to 5 fluoro substituents, iv) cyclopropyl-($C_0$-$C_1$)alkyl-O—, v) cyano, vi) ($C_1$-$C_2$)alkyl-S(O)$_2$—, and vii) ($C_1$-$C_4$)alkyl-C(O)—,
  or alternatively, m is 1 or 2, one $R^4$ substituent is selected from the group consisting of viii) ($C_1$-$C_4$)alkyl further substituted with a substituent selected from the group consisting of (hydroxy, ($C_1$-$C_4$)alkoxy, cyano, and amino), ix) ($C_1$-$C_2$)alkyl-O—C(O)—, x) ($C_1$-$C_2$)alkyl-S(O)$_2$—($C_1$-$C_2$)alkyl-, xi) ($C_1$-$C_4$)alkyl-C(O)—N($R^6$)—, xii) ($C_1$-$C_4$)alkyl-C(O)—N($R^6$)-methyl-, xiii) cyclopropyl-C(O)—NH-methyl-, xiv) ($C_1$-$C_2$)alkyl-S(O)$_2$—N($R^6$)—($C_1$-$C_2$)alkyl-, xv) ($C_1$-$C_2$)alkyl-O—($C_0$-$C_2$)alkyl-C(O)—N($R^6$)— optionally further substituted with a fluoro group, xvi) ($C_1$-$C_2$)alkyl-O—($C_0$-$C_2$)alkyl-C(O)—N($R^6$)-methyl-optionally further substituted with a fluoro group, xvii) ($R^6$)($R^7$)N—C(O)—($C_1$-$C_2$)alkyl-, xviii) ($C_1$-$C_2$)alkyl-C(O)—NH-methyl-C(O)—, xix) ($R^6$)($R^7$)N—C(O)—N(H)-methyl-, xx) ($R^6$)($R^7$)N—C(S)—N(H)-methyl-, xxi) ($R^6$)($R^7$)N—C(O)—O-methyl-, xxii) ($R^6$)($R^7$)N—C(O) methoxy-, and xxiii) ($R^6$)($R^7$)N—C(O) methoxymethyl-, and if present, the second $R^4$ substituent is fluoro or chloro;
$R^6$ is hydrogen or methyl;
$R^7$ is hydrogen or ($C_1$-$C_3$)alkyl;
$Ph^1$ is phenyl optionally substituted with a substituent selected from the group consisting of halo, ($C_1$-$C_2$)alkyl optionally further substituted with 1 to 3 fluoro substituents, and ($C_1$-$C_2$)alkoxy optionally further substituted with 1 to 3 fluoro substituents;
$Ar^1$ is a heteroaryl moiety selected from pyridyl, pyrimidyl, imidazolyl, pyrrolyl, thienyl, pyrazolyl, oxazolyl, isoxazolyl, thiazolyl, and isothiazolyl, any of which may be optionally further substituted with 1 or 2 substituents independently selected from methyl and ethyl;
or a pharmaceutically acceptable salt thereof.

The present invention also provides pharmaceutical compositions comprising a compound of Formula I, or a pharmaceutically acceptable salt thereof, in association with a pharmaceutically acceptable carrier, diluent, or excipient.

In another aspect of the present invention, there is provided one or more compounds of Formula I, or pharmaceutically acceptable salt(s) thereof for use in therapy. This aspect includes the use of one or more compounds of Formula I, or pharmaceutically acceptable salt(s) thereof for use as a pharmaceutical. Likewise, this aspect of the invention provides one or more compounds of Formula I, or pharmaceutically acceptable salt(s) thereof for the treatment of migraine in mammals, particularly humans, the prophylactic treatment of migraine in mammals, the treatment of persistent pain, particularly inflammatory or neuropathic pain, in mammals, particularly humans.

One embodiment of this aspect of the invention provides a method for treating migraine in mammals comprising administering to a mammal in need of such treatment an effective amount of a compound of Formula I, or a pharmaceutically acceptable salt thereof.

Another embodiment of this aspect of the invention provides a method for the prophylactic treatment of migraine in mammals comprising administering to a mammal in need of such treatment, that is to say a mammal that is susceptible to migraine, an effective amount of a compound of Formula I, or a pharmaceutically acceptable salt thereof.

Yet another embodiment of this aspect of the invention provides a method for treating persistent pain in mammals comprising administering to a mammal in need of such treatment an effective amount of a compound of Formula I, or a pharmaceutically acceptable salt thereof. Particular embodiments of this are the treatment of inflammatory pain and/or neuropathic pain.

Yet another embodiment of this aspect of the invention provides a method for treating anxiety in mammals comprising administering to a mammal in need of such treatment an effective amount of a compound of Formula I, or a pharmaceutically acceptable salt thereof.

In preferred embodiments of the above methods of treatment utilizing the compounds of Formula I, or pharmaceutically acceptable salts thereof, the mammal is a human.

In another aspect of the present invention, there is provided the use of a compound of Formula I, or pharmaceutically acceptable salt thereof, in the manufacture of a medicament for the treatment and/or the prophylactic treatment of migraine.

In another aspect of the present invention, there is provided the use of a compound of Formula I, or pharmaceutically acceptable salt thereof, in the manufacture of a medicament for the treatment of persistent pain, particularly inflammatory and/or neuropathic pain.

In another aspect of the present invention, there is provided the use of a compound of Formula I, or pharmaceutically acceptable salt thereof, in the manufacture of a medicament for the treatment of anxiety.

Additionally, the present invention provides a pharmaceutical formulation adapted for the treatment of migraine and/or for the prophylactic treatment of migraine, comprising a compound of Formula I, or a pharmaceutically acceptable salt thereof, in association with a pharmaceutically acceptable carrier, diluent or excipient.

Likewise, the present invention provides a pharmaceutical formulation adapted for the treatment of persistent pain, particularly inflammatory and/or neuropathic pain, comprising a compound of Formula I, or a pharmaceutically acceptable salt thereof, in association with a pharmaceutically acceptable carrier, diluent or excipient.

Additionally, the present invention provides a pharmaceutical formulation adapted for the treatment of anxiety comprising a compound of Formula I, or a pharmaceutically acceptable salt thereof, in association with a pharmaceutically acceptable carrier, diluent or excipient.

The general chemical terms used throughout have their usual meanings. For example, the term "alkyl" refers to a branched or unbranched saturated hydrocarbon group. By way of illustration, but without limitation, the term "$(C_1-C_4)$ alkyl" refers to methyl, ethyl, n-propyl, isopropyl, n-butyl, isobutyl, and sec-butyl. The term "$(C_1-C_6)$ alkyl" refers to all branched and unbranched saturated alkyl groups having from one to six carbon atoms. As used herein, the term "$(C_0-C_2)$ alkyl" refers to a single bond, or a methylene or ethylene linker moiety.

The term "$(C_3-C_7)$cycloalkyl" refers to cyclopropyl, cyclobutyl, cyclopentyl, cyclohexyl and cycloheptyl. $(C_3-C_7)$ cycloalkyl($C_0-C_2$)alkyl, refers to a cycloalkyl moiety having from 3 to 7 ring carbon atoms, which is linked through a single bond (i.e. $C_0$-alkyl) or an alkylene linker having 1 or 2 carbon atoms. Each alkyl, cycloalkyl, and cycloalkylalkyl group may be optionally substituted as provided for herein.

The term "alkoxy" refers to an alkyl group that is bonded through an oxygen atom.

The term "halo" refers to fluoro, chloro, bromo, or iodo. Preferred halo groups are fluoro, chloro, and bromo. More preferred halo groups are fluoro and chloro.

The term "amino protecting group" as used in this specification refers to a substituent commonly employed to block or protect an amino functionality while reacting other functional groups on the compound. The species of amino protecting group employed is not critical so long as the derivatized amino group is stable to the conditions of subsequent reactions on other positions of the molecule and can be removed at the appropriate point without disrupting the remainder of the molecule. The selection and use (addition and subsequent removal) of amino protecting groups is well known within the ordinary skill of the art. Further examples of groups referred to by the above terms are described by T. W. Greene and P. G. M. Wuts, "Protective Groups in Organic Synthesis", $3^{rd}$ edition, John Wiley and Sons, New York, N.Y., 1999, chapter 7, hereafter referred to as "Greene".

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and/or salt must be compatible with the active ingredient of the composition (e.g. a compound of Formula I). It is understood by those of ordinary skill in this art that the terms "pharmaceutical formulation" and "pharmaceutical composition" are generally interchangeable, and they are so used for the purposes of this application.

The term "effective amount" means an amount of a compound of Formula I which is capable of antagonizing $5\text{-HT}_7$ receptors and/or eliciting a given pharmacological effect.

The term "suitable solvent" refers to any solvent, or mixture of solvents that sufficiently solubilizes the reactants to afford a medium within which to effect the desired reaction and that does not interfere with the desired reaction.

It is understood that compounds of the present invention may exist as stereoisomers. As such, all enantiomers, diastereomers, and mixtures thereof, are included within the scope of the present invention. Where specific stereochemistries are identified in this application, the Cahn-Prelog-Ingold designations of (R)- and (S)- and the cis and trans designation of relative stereochemistry are used to refer to specific isomers and relative stereochemistry. Known optical rotations are designated by (+) and (−) for dextrorotatary and levorotatary, respectively. Where a chiral compound is resolved into its isomers, but absolute configurations or optical rotations are not determined, the isomers are arbitrarily designated as isomer 1, isomer 2, etc. While all enantiomers, diastereomers, and mixtures thereof, are contemplated within the present invention, preferred embodiments are single enantiomers and single diastereomers.

It is generally understood by those skilled in this art, that compounds intended for use in pharmaceutical compositions are routinely, though not necessarily, converted to a salt form in efforts to optimize such characteristics as the handling properties, stability, pharmacokinetic, and/or bioavailability, etc. Methods for converting a compound to a given salt form are well known in the art (see, e.g., P. Stahl, et al., Handbook of Pharmaceutical Salts Properties, Selection and Use, (VCHA/Wiley-VCH, 2002); Berge, S. M, Bighley, L. D., and Monkhouse, D. C., *J. Pharm. Sci.*, 66:1, (1977)). In that the compounds of the present invention are amines and therefore basic in nature, they readily react with a wide variety of pharmaceutically acceptable organic and inorganic acids to form pharmaceutically acceptable acid addition salts therewith. Such salts are also embodiments of this invention.

It is well known that such compounds can form salts in various molar ratios with the acid to provide, for example, the hemi-acid, mono-acid, di-acid salt, etc. Where in the salt formation procedure, the acid is added in a specific stoichiometric ratio, unless otherwise analyzed to confirm, the salt is presumed, but not known, to form in that molar ratio.

Abbreviations used herein are defined as follows:
"BINAP" means (±)-2,2'-bis(diphenylphosphino)-1,1'-binaphthalene.
"Brine" means a saturated aqueous sodium chloride solution.
"DCE" means 1,2-dichloroethane.
"DCM" means dichloromethane.
"EDC" means 1-[3-(dimethylamino)propyl]-3-ethylcarbodiimide hydrochloride.
"HOBt" means 1-hydroxybenzotriazole hydrate.
"ISPA" means immunoadsorption scintillation proximity assay.
"MsCl" means mesylchloride ($CH_3$—$S(O)_2$—Cl).
"MS (ES)" means mass spectroscopy using electrospray ionization.
"MTBE" means t-butyl methyl ether.
"PPE" means plasma protein extravasation
"SCX chromatography" means chromatography on a SCX column or cartridge.
"SCX column" or "SCX cartridge", as used herein, refers to a Varian Bond Elute® silica based strong cation exchange resin column or disposable cartridge or equivalent (as for example a SCX-2 cartridge).
"SPA" means scintillation proximity assay, which may or may not be an immunoadsorption type assay.
"TBAS" means tetrabutylammonium bisulfate.

While all of the compounds of the present invention are useful as $5\text{-}HT_7$ antagonists, certain classes are preferred, as for example, compounds having the formula I(e)

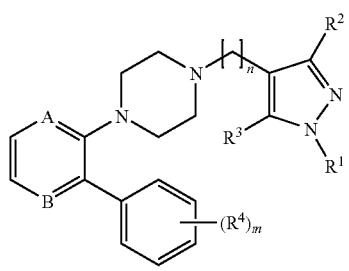

where:
A and B are each independently —C(H)= or —N=, provided that at least one of A and B is —N=;
$R^1$ is selected from the group consisting of
i) hydrogen, ii) ($C_1$-$C_6$)alkyl-optionally substituted with hydroxy, cyano, or 1 to 5 fluoro substituents, or alternatively, optionally substituted with hydroxy and 1 to 3 fluoro substituents, iii) ($C_3$-$C_7$)cycloalkyl-($C_0$-$C_2$)alkyl- optionally substituted with hydroxy, iv) ($C_1$-$C_2$)alkyl-O—($C_1$-$C_2$)alkyl-, v) $Ph^1$-($C_0$-$C_2$)alkyl-, vi) $Ar^1$—($C_0$-$C_2$)alkyl-, vii) ($C_1$-$C_2$)alkyl-$S(O)_2$—($C_0$-$C_3$)alkyl-, viii) $Ph^1$-$S(O)_2$—, ix) $Ar^1$—$S(O)_2$—, x) ($C_1$-$C_2$)alkyl-NH—($C_1$-$C_2$)alkyl-, xi) (($C_1$-$C_2$)alkyl)$_2$-N—($C_1$-$C_2$)alkyl-, xii) ($C_1$-$C_2$)alkyl-NH—C(O)—($C_0$-$C_2$)alkyl-, xiii) (($C_1$-$C_2$)alkyl)$_2$-N—C(O)—($C_0$-$C_2$)alkyl-, xiv) pyrrolidin-1-yl-C(O)—($C_0$-$C_2$)alkyl-, xv) ($C_1$-$C_2$)alkyl-C(O)—NH—($C_1$-$C_2$)alkyl-, xvi) ($C_1$-$C_2$)alkyl)-C(O)—N($C_1$-$C_2$ alkyl)-($C_1$-$C_2$)alkyl-, xvii) ($C_1$-$C_2$)alkyl-$S(O)_2$—NH—($C_1$-$C_2$)alkyl-, and xviii) 2-oxo-oxazolidin-5-yl-;

$R^2$ is selected from the group consisting of i) hydrogen, ii) halo, iii) hydroxy, iv) ($C_1$-$C_4$)alkyl-optionally substituted with hydroxy, cyano, or 1 to 5 fluoro substituents, and v) ($C_1$-$C_2$)alkyl-O—($C_0$-$C_2$)alkyl-;

$R^3$ is selected from the group consisting of hydrogen, halo, and ($C_1$-$C_4$)alkyl-;

Each $R^4$ is independently selected from the group consisting of halogen, ($C_1$-$C_2$)alkyl optionally further substituted with 1 to 5 fluoro substituents, ($C_1$-$C_2$)alkoxy optionally further substituted with 1 to 5 fluoro substituents, cyclopropyl-($C_0$-$C_1$)alkyl-O—, cyano, ($C_1$-$C_2$)alkyl-$S(O)_2$—, and ($C_1$-$C_4$)alkyl-C(O)—;

$Ph^1$ is phenyl optionally substituted with a substituent selected from the group consisting of halo, ($C_1$-$C_2$)alkyl optionally further substituted with 1 to 3 fluoro substituents, and ($C_1$-$C_2$)alkoxy optionally further substituted with 1 to 3 fluoro substituents;

$Ar^1$ is a heteroaryl moiety selected from pyridyl, pyrimidyl, imidazolyl, pyrrolyl, thienyl, pyrazolyl, oxazolyl, isoxazolyl, thiazolyl, and isothiazolyl, any of which may be optionally further substituted with 1 or 2 substituents independently selected from methyl and ethyl;

n is 1, 2, or 3;
m is 0, 1, 2, or 3;
or a pharmaceutically acceptable salt thereof.

Other preferred classes of compounds of Formula I and I(e) are compounds having any of the following enumerated selections of substituents:

1) $R^1$ is hydrogen, ($C_1$-$C_3$)alkyl optionally substituted with hydroxy, cyano, or 1 to 3 fluoro substituents, ($C_1$-$C_2$)alkoxy-($C_1$-$C_2$)alkyl, $Ph^1$-($C_0$-$C_2$)alkyl, $Ar^1$—($C_0$-$C_2$)alkyl, ($C_1$-$C_2$)alkyl-$S(O)_2$—($C_0$-$C_3$)alkyl, $Ph^1$—$S(O)_2$—, $Ar^1$—$S(O)_2$—, ($C_1$-$C_2$)alkyl-NH—($C_1$-$C_2$)alkyl, (($C_1$-$C_2$)alkyl)$_2$-N—($C_1$-$C_2$)alkyl, ($C_1$-$C_2$)alkyl-NH—C(O)—($C_0$-$C_2$)alkyl, (($C_1$-$C_2$)alkyl)$_2$-N—C(O)—($C_0$-$C_2$)alkyl, ($C_1$-$C_2$)alkyl-C(O)—NH—($C_1$-$C_2$)alkyl, ($C_1$-$C_2$)alkyl)-C(O)—N($C_1$-$C_2$ alkyl)-($C_1$-$C_2$)alkyl, ($C_1$-$C_2$)alkyl-$S(O)_2$—NH—($C_1$-$C_2$)alkyl, or ($C_1$-$C_2$)alkyl-$S(O)_2$—N($CH_3$)—($C_1$-$C_2$)alkyl;

2) $R^1$ is hydrogen, ($C_1$-$C_3$)alkyl optionally substituted with hydroxy, cyano, or 1 to 3 fluoro substituents, ($C_1$-$C_2$)alkoxy-($C_1$-$C_2$)alkyl, $Ph^1$-($C_0$-$C_2$)alkyl, or $Ar^1$—($C_0$-$C_2$)alkyl;

3) $R^1$ is hydrogen, ($C_1$-$C_2$)alkyl optionally substituted with 1 to 3 fluoro substituents, ($C_2$-$C_3$)alkyl optionally substituted with hydroxy or hydroxyl and 1 to 3 fluoro substituents, ($C_1$-$C_2$)alkoxy-($C_1$-$C_2$)alkyl, $Ph^1$-($C_0$-$C_2$)alkyl, or $Ar^1$—($C_0$-$C_2$)alkyl;

4) $R^1$ is ($C_1$-$C_2$)alkyl optionally substituted with 1 to 3 fluoro substituents, ($C_2$-$C_3$)alkyl optionally substituted with hydroxy or hydroxyl and 1 to 3 fluoro substituents, or ($C_1$-$C_2$)alkoxy-($C_1$-$C_2$)alkyl;

5) $R^1$ is ($C_1$-$C_2$)alkyl optionally substituted with 1 to 3 fluoro substituents, or ($C_1$-$C_2$)alkoxy-($C_1$-$C_2$)alkyl;

6) $R^1$ is $Ph^1$-($C_0$-$C_2$)alkyl or $Ar^1$—($C_0$-$C_2$)alkyl;

7) $R^1$ is phenyl or benzyl optionally substituted with fluoro;

8) $R^1$ is pyridinyl, imidazolyl, or pyrrazolyl;

9) $R^1$ is $(C_1-C_5)$alkyl-C(O)—, $Ph^1$-$(C_0-C_2)$alkyl-C(O)—, or $Ar^1$—$(C_0-C_2)$alkyl-C(O)—;
10) $R^1$ is $(C_1-C_2)$alkyl-S(O)$_2$—$(C_0-C_3)$alkyl, $Ph^1$-S(O)$_2$—, or $Ar^1$—S(O)$_2$—;
11) $R^1$ is $(C_1-C_2)$alkyl-NH—$(C_1-C_2)$alkyl, $((C_1-C_2)$alkyl)$_2$-N—$(C_1-C_2)$alkyl, $(C_1-C_2)$alkyl-NH—C(O)—$(C_1-C_2)$alkyl, $((C_1-C_2)$alkyl)$_2$-N—C(O)—$(C_1-C_2)$alkyl, $(C_1-C_2)$alkyl-C(O)—NH—$(C_1-C_2)$alkyl, or $(C_1-C_2)$alkyl)-C(O)—N($C_1-C_2$ alkyl)-$(C_1-C_2)$alkyl;
12) $R^1$ is $(C_1-C_2)$alkyl-S(O)$_2$—NH—$(C_1-C_2)$alkyl or $(C_1-C_2)$alkyl-S(O)$_2$—N(CH$_3$)—$(C_1-C_2)$alkyl;
13) $R^2$ is hydrogen, halo, methyl, ethyl, —CF$_3$, —CH$_2$CF$_3$, hydroxy, hydroxymethyl, methoxymethyl;
14) $R^2$ is hydrogen, chloro, methyl, ethyl, or —CF$_3$;
15) $R^2$ is hydrogen or methyl;
16) $R^3$ is hydrogen, halo, methyl, or ethyl;
17) $R^3$ is hydrogen or methyl;
18) $R^4$ is halo, $(C_1-C_2)$alkyl optionally further substituted with 1 to 3 fluoro substituents, $(C_1-C_2)$alkoxy optionally further substituted with 1 to 3 fluoro substituents, cyano, or CH$_3$—C(O)—;
19) $R^4$ is fluoro, chloro, —CF$_3$, $(C_1-C_2)$alkoxy optionally further substituted with 1 to 3 fluoro substituents, cyano, or CH$_3$—C(O)—;
20) $R^4$ is fluoro, chloro, —CF$_3$, methoxy, —O—CF$_3$, or CH$_3$—C(O)—;
21) $R^4$ is fluoro, chloro, —CF$_3$, methoxy, or —O—CF$_3$;
22) $R^4$ is fluoro or chloro;
23) $R^4$ is fluoro;
24) $R^4$ is 4-fluoro.
25) $R^4$ is chloro;
26) $R^4$ is 4-chloro;

Generally, for compounds where m is 2 or 3, particularly preferred compounds are those where each $R^4$ is fluoro, chloro, methyl, or —CF$_3$. Of these preferred compounds, more preferred are those compounds where each $R^4$ is fluoro or chloro.

One favored group of compounds of the present invention is that represented by Formula (Ia):

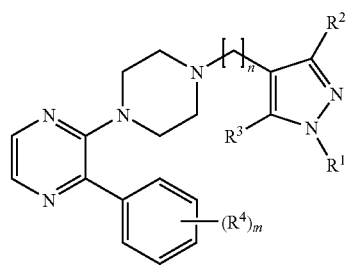

Ia where:
$R^1$ is selected from the group consisting of
i) hydrogen, ii) $(C_1-C_6)$alkyl-optionally substituted with hydroxy, cyano, or 1 to 5 fluoro substituents, or alternatively, optionally substituted with hydroxy and 1 to 3 fluoro substituents, iii) $(C_3-C_7)$cycloalkyl-$(C_0-C_2)$alkyl-optionally substituted with hydroxy, iv) $(C_1-C_2)$alkyl-O—$(C_1-C_2)$alkyl-, v) $Ph^1$-$(C_0-C_2)$alkyl-, vi) $Ar^1$—$(C_0-C_2)$alkyl-, vii) $(C_1-C_2)$alkyl-S(O)$_2$—$(C_0-C_3)$alkyl-, viii) $Ph^1$-S(O)$_2$—, ix) $Ar^1$—S(O)$_2$—, x) $(C_1-C_2)$alkyl-NH—$(C_1-C_2)$alkyl-, xi) $((C_1-C_2)$alkyl)$_2$-N—$(C_1-C_2)$alkyl-, xii) $(C_1-C_2)$alkyl-NH—C(O)—$(C_0-C_2)$alkyl-, xiii) $((C_1-C_2)$alkyl)$_2$-N—C(O)—$(C_0-C_2)$alkyl-, xiv) pyrrolidin-1-yl-C(O)—$(C_0-C_2)$alkyl-, xv) $(C_1-C_2)$alkyl-C(O)—NH—$(C_1-C_2)$alkyl-, xvi) $(C_1-C_2)$alkyl)-C(O)—N($C_1-C_2$ alkyl)-$(C_1-C_2)$alkyl-, xvii) $(C_1-C_2)$alkyl-S(O)$_2$—NH—$(C_1-C_2)$alkyl-, and xviii) 2-oxo-oxazolidin-5-yl-;
$R^2$ is selected from the group consisting of i) hydrogen, ii) halo, iii) hydroxy, iv) $(C_1-C_4)$alkyl-optionally substituted with hydroxy, cyano, or 1 to 5 fluoro substituents, and v) $(C_1-C_2)$alkyl-O—$(C_0-C_2)$alkyl-;
$R^3$ is selected from the group consisting of hydrogen, halo, and $(C_1-C_4)$alkyl-;
Each $R^4$ is independently selected from the group consisting of halogen, $(C_1-C_2)$alkyl optionally further substituted with 1 to 5 fluoro substituents, $(C_1-C_2)$alkoxy optionally further substituted with 1 to 5 fluoro substituents, cyclopropyl-$(C_0-C_1)$alkyl-O—, cyano, $(C_1-C_2)$alkyl-S(O)$_2$—, and $(C_1-C_4)$alkyl-C(O)—;
$Ph^1$ is phenyl optionally substituted with a substituent selected from the group consisting of halo, $(C_1-C_2)$alkyl optionally further substituted with 1 to 3 fluoro substituents, and $(C_1-C_2)$alkoxy optionally further substituted with 1 to 3 fluoro substituents;
$Ar^1$ is a heteroaryl moiety selected from pyridyl, pyrimidyl, imidazolyl, pyrrolyl, thienyl, pyrazolyl, oxazolyl, isoxazolyl, thiazolyl, and isothiazolyl, any of which may be optionally further substituted with 1 or 2 substituents independently selected from methyl and ethyl;
n is 1, 2, or 3;
m is 0, 1, 2, or 3;
or a pharmaceutically acceptable salt thereof.

Another favored group of compounds of the present invention is that represented by Formula (Ib):

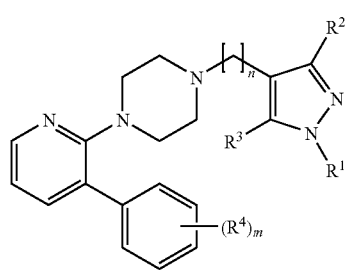

Ib where:
$R^1$ is selected from the group consisting of
i) hydrogen, ii) $(C_1-C_6)$alkyl-optionally substituted with hydroxy, cyano, or 1 to 5 fluoro substituents, or alternatively, optionally substituted with hydroxy and 1 to 3 fluoro substituents, iii) $(C_3-C_7)$cycloalkyl-$(C_0-C_2)$alkyl-optionally substituted with hydroxy, iv) $(C_1-C_2)$alkyl-O—$(C_1-C_2)$alkyl-, v) $Ph^1$-$(C_0-C_2)$alkyl-, vi) $Ar^1$—$(C_0-C_2)$alkyl-, vii) $(C_1-C_2)$alkyl-S(O)$_2$—$(C_0-C_3)$alkyl-, viii) $Ph^1$-S(O)$_2$—, ix) $Ar^1$—S(O)$_2$—, x) $(C_1-C_2)$alkyl-NH—$(C_1-C_2)$alkyl-, xi) $((C_1-C_2)$alkyl)$_2$-N—$(C_1-C_2)$alkyl-, xii) $(C_1-C_2)$alkyl-NH—C(O)—$(C_0-C_2)$alkyl-, xiii) $((C_1-C_2)$alkyl)$_2$-N—C(O)—$(C_0-C_2)$alkyl-, xiv) pyrrolidin-1-yl-C(O)—$(C_0-C_2)$alkyl-, xv) $(C_1-C_2)$alkyl-C(O)—NH—$(C_1-C_2)$alkyl-, xvi) $(C_1-C_2)$alkyl)-C(O)—N($C_1-C_2$ alkyl)-$(C_1-C_2)$alkyl-, xvii) $(C_1-C_2)$alkyl-S(O)$_2$—NH—$(C_1-C_2)$alkyl-, and xviii) 2-oxo-oxazolidin-5-yl-;
$R^2$ is selected from the group consisting of i) hydrogen, ii) halo, iii) hydroxy, iv) $(C_1-C_4)$alkyl-optionally substituted with hydroxy, cyano, or 1 to 5 fluoro substituents, and v) $(C_1-C_2)$alkyl-O—$(C_0-C_2)$alkyl-;

$R^3$ is selected from the group consisting of hydrogen, halo, and $(C_1-C_4)$alkyl-;

Each $R^4$ is independently selected from the group consisting of halogen, $(C_1-C_2)$alkyl optionally further substituted with 1 to 5 fluoro substituents, $(C_1-C_2)$alkoxy optionally further substituted with 1 to 5 fluoro substituents, cyclopropyl-$(C_0-C_1)$alkyl-O—, cyano, $(C_1-C_2)$alkyl-S(O)$_2$—, and $(C_1-C_4)$alkyl-C(O)—;

$Ph^1$ is phenyl optionally substituted with a substituent selected from the group consisting of halo, $(C_1-C_2)$alkyl optionally further substituted with 1 to 3 fluoro substituents, and $(C_1-C_2)$alkoxy optionally further substituted with 1 to 3 fluoro substituents;

$Ar^1$ is a heteroaryl moiety selected from pyridyl, pyrimidyl, imidazolyl, pyrrolyl, thienyl, pyrazolyl, oxazolyl, isoxazolyl, thiazolyl, and isothiazolyl, any of which may be optionally further substituted with 1 or 2 substituents independently selected from methyl and ethyl;

n is 1, 2, or 3;

m is 0, 1, 2, or 3;

or a pharmaceutically acceptable salt thereof.

Yet another favored group of compounds of the present invention is that represented by Formula (Ic):

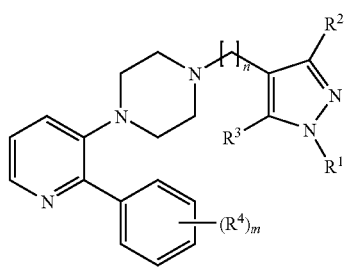

where:
$R^1$ is selected from the group consisting of
i) hydrogen, ii) $(C_1-C_6)$alkyl-optionally substituted with hydroxy, cyano, or 1 to 5 fluoro substituents, or alternatively, optionally substituted with hydroxy and 1 to 3 fluoro substituents, iii) $(C_3-C_7)$cycloalkyl-$(C_0-C_2)$alkyl- optionally substituted with hydroxy, iv) $(C_1-C_2)$alkyl-O—$(C_1-C_2)$alkyl-, v) $Ph^1$-$(C_0-C_2)$alkyl-, vi) $Ar^1$—$(C_0-C_2)$alkyl-, vii) $(C_1-C_2)$alkyl-S(O)$_2$—$(C_0-C_3)$alkyl-, viii) $Ph^1$-S(O)$_2$—, ix) $Ar^1$—S(O)$_2$—, x) $(C_1-C_2)$alkyl-NH—$(C_1-C_2)$alkyl-, xi) $((C_1-C_2)$alkyl$)_2$-N—$(C_1-C_2)$alkyl-, xii) $(C_1-C_2)$alkyl-NH—C(O)—$(C_0-C_2)$alkyl-, xiii) $((C_1-C_2)$alkyl$)_2$-N—C(O)—$(C_0-C_2)$alkyl-, xiv) pyrrolidin-1-yl-C(O)—$(C_0-C_2)$alkyl-, xv) $(C_1-C_2)$alkyl-C(O)—NH—$(C_1-C_2)$alkyl-, xvi) $(C_1-C_2)$alkyl)-C(O)—N$(C_1-C_2$ alkyl)-$(C_1-C_2)$alkyl-, xvii) $(C_1-C_2)$alkyl-S(O)$_2$—NH—$(C_1-C_2)$alkyl-, and xviii) 2-oxo-oxazolidin-5-yl-;

$R^2$ is selected from the group consisting of i) hydrogen, ii) halo, iii) hydroxy, iv) $(C_1-C_4)$alkyl-optionally substituted with hydroxy, cyano, or 1 to 5 fluoro substituents, and v) $(C_1-C_2)$alkyl-O—$(C_0-C_2)$alkyl-;

$R^3$ is selected from the group consisting of hydrogen, halo, and $(C_1-C_4)$alkyl-;

Each $R^4$ is independently selected from the group consisting of halogen, $(C_1-C_2)$alkyl optionally further substituted with 1 to 5 fluoro substituents, $(C_1-C_2)$alkoxy optionally further substituted with 1 to 5 fluoro substituents, cyclopropyl-$(C_0-C_1)$alkyl-O—, cyano, $(C_1-C_2)$alkyl-S(O)$_2$—, and $(C_1-C_4)$alkyl-C(O)—;

$Ph^1$ is phenyl optionally substituted with a substituent selected from the group consisting of halo, $(C_1-C_2)$alkyl optionally further substituted with 1 to 3 fluoro substituents, and $(C_1-C_2)$alkoxy optionally further substituted with 1 to 3 fluoro substituents;

$Ar^1$ is a heteroaryl moiety selected from pyridyl, pyrimidyl, imidazolyl, pyrrolyl, thienyl, pyrazolyl, oxazolyl, isoxazolyl, thiazolyl, and isothiazolyl, any of which may be optionally further substituted with 1 or 2 substituents independently selected from methyl and ethyl;

n is 1, 2, or 3;

m is 0, 1, 2, or 3;

or a pharmaceutically acceptable salt thereof.

Within each group of favored compounds according to formulae (Ia), (Ib), and (Ic) preferred selections of substituents $R^{1-4}$ are those according to preferred selections 1 through 26 delineated above for general Formula I.

Generally, compounds according to formula (Ia) are preferred over compounds of formulae (Ib) and (Ic).

Also generally preferred of the above preferred groups of compounds are those compounds wherein n is 1.

The preferred definitions listed in paragraphs 1) through 26) are the preferred selections for each substituent $R^1$, $R^2$, $R^3$, and $R^4$ individually and independently from each other. As such, for any given selection of a preferred substituent $R^{1-4}$ above, further preferred compounds are those having the first selected preferred substituent and also having a preferred selection for one or more of the other substituents $R^{1-4}$ above. Likewise, such combinations of preferred selections substituents $R^{1-4}$ apply to preferred compounds of formula (Ia), (Ib), and/or (Ic). As examples of such preferred combinations, but not to be construed as limiting, the following combinations of preferred selections are preferred combinations:

27) any one selection according to paragraphs 1) through 26) wherein n is 1;

28) any one preferred selection according to paragraphs 1) through 12) (i.e. preferred selections for $R^1$) in combination with any one preferred selection according to paragraphs 13) through 15) (i.e. preferred selections for $R^2$) and/or in combination with any one preferred selection according to paragraphs 16) or 17) (i.e. preferred selections for $R^3$);

29) any one preferred combination according to paragraph 28) wherein n is 1.

30) any one preferred combination according to either paragraph 27, 28, or 29 in combination with any one of paragraphs 18) through 26) (i.e. the preferred selections for $R^4$).

Of these preferred combinations, particularly preferred combinations include, but are not limited to:

31) compounds wherein $R^1$ is $(C_1-C_2)$alkyl, $R^2$ and $R^3$ are each independently hydrogen, methyl or ethyl; n is 1, m is 1, and $R^4$ is fluoro, chloro, —CF$_3$, methoxy, —O—CF$_3$, or CH$_3$—C(O)—;

32) compounds wherein $R^1$ is $(C_1-C_2)$alkyl, $R^2$ and $R^3$ are each independently hydrogen, methyl or ethyl; n is 1, m is 2, and each $R^4$ is independently fluoro, chloro, or —CF$_3$;

33) compounds wherein $R^1$ is $Ph^1$-$(C_0-C_2)$alkyl, or $Ar^1$—$(C_0-C_2)$alkyl, $R^2$ and $R^3$ are each independently hydrogen, methyl or ethyl; n is 1, m is 1, and $R^4$ is fluoro, chloro, —CF$_3$, methoxy, —O—CF$_3$, or CH$_3$—C(O)—;

34) compounds wherein $R^1$ is $Ph^1$-$(C_0-C_2)$alkyl, or $Ar^1$—$(C_0-C_2)$alkyl, $R^2$ and $R^3$ are each independently hydrogen, methyl or ethyl; n is 1, m is 2, and each $R^4$ is independently fluoro, chloro, or —CF$_3$.

Yet another favored group of compounds of the present invention is that represented by Formula (Id):

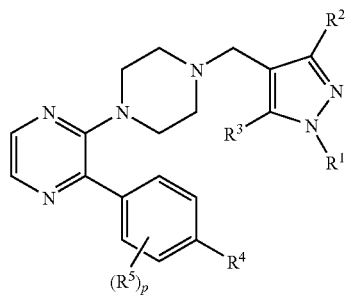

where:
R$^1$ is selected from i) hydrogen, ii) (C$_1$-C$_3$)alkyl-optionally mono-substituted with hydroxy, iii) phenyl, iv) benzyl, and v) pyridyl;
R$^2$ is selected from hydrogen and (C$_1$-C$_3$)alkyl-;
R$^3$ is selected from hydrogen and (C$_1$-C$_3$)alkyl-;
R$^4$ is selected from the group consisting of i) (C$_1$-C$_4$)alkyl further substituted with a substituent selected from the group consisting of (hydroxy, (C$_1$-C$_4$)alkoxy, cyano, and amino), ii) (C$_1$-C$_2$)alkyl-O—C(O)—, iii) (C$_1$-C$_2$)alkyl-S(O)$_2$—(C$_1$-C$_2$)alkyl-, iv) (C$_1$-C$_4$)alkyl-C(O)—N(R$^6$)—, v) (C$_1$-C$_4$)alkyl-C(O)—N(R$^6$)-methyl-, vi)cyclopropyl-C(O)—NH-methyl-, vii) (C$_1$-C$_2$)alkyl-S(O)$_2$—N(R$^6$)—(C$_1$-C$_2$)alkyl-, viii) (C$_1$-C$_2$)alkyl-O—(C$_0$-C$_2$)alkyl-C(O)—N(R$^6$)— optionally further substituted with a fluoro group, ix) (C$_1$-C$_2$)alkyl-O—(C$_0$-C$_2$)alkyl-C(O)—N(R$^6$)-methyl-optionally further substituted with a fluoro group, x) (R$^6$)(R$^7$)N—C(O)—(C$_1$-C$_2$)alkyl-, xi) (C$_1$-C$_2$)alkyl-C(O)—NH-methyl-C(O)—, xii) (R$^6$)(R$^7$)N—C(O)—N(H)-methyl-, xiii) (R$^6$)(R$^7$)N—C(S)—N(H)-methyl-, xiv) (R$^6$)(R$^7$)N—C(O)—O-methyl-, xv) (R$^6$)(R$^7$)N—C(O)methoxy-, and xvi) (R$^6$)(R$^7$)N—C(O)methoxymethyl-;
R$^5$ is fluoro or chloro;
R$^6$ is hydrogen or methyl;
R$^7$ is hydrogen or (C$_1$-C$_3$)alkyl;
p is 0 or 1;
and pharmaceutically acceptable salts thereof.

Of the compounds of Formula (Id), the following enumerated selections of substituents are preferred:

35) R$^1$ is methyl or ethyl;
36) R$^1$ is phenyl or benzyl;
37) R$^2$ is hydrogen or methyl;
38) R$^3$ is hydrogen or methyl;
27) one of R$^2$ or R$^3$ is hydrogen and the other is methyl;
28) R$^2$ is hydrogen and R$^3$ is methyl;
29) R$^4$ is selected from the group consisting of i) hydroxymethyl, ii) hydroxyethyl, iii) methoxymethyl, iv) cyanomethyl, v) methyl-C(O)—N(H)-methyl-, vi) methyl-S(O)$_2$—N(H)-methyl-, vii) methoxy-C(O)—(C$_0$-C$_1$)alkyl-, viii) methoxy-C(O)—NH-methyl-, ix) methoxymethyl-C(O)—NH-methyl-, and x) (R$^6$)(R$^7$)N—C(O)-methyl-;
30) R$^4$ is selected from the group consisting of i) hydroxymethyl, ii) hydroxyethyl, iii) methoxymethyl, iv) cyanomethyl, v) methyl-C(O)—N(H)-methyl-, vi) methyl-S(O)$_2$—N(H)-methyl-, vii) methoxy-C(O)-methyl-, viii) methoxymethyl-C(O)—NH-methyl-, and ix) methyl-N(R$^6$)—C(O)-methyl-;
31) R$^4$ is selected from the group consisting of i) hydroxymethyl, ii) hydroxyethyl, iii) methoxymethyl, iv) cyanomethyl, v) methyl-C(O)—N(H)-methyl-, and vi) methyl-S(O)$_2$—N(H)-methyl-;
32) p is 0;
33) R$^1$ is methyl, ethyl, or phenyl; R$^2$ is hydrogen or methyl; R$^3$ is hydrogen or methyl; p is 0; and R$^4$ is selected from the group consisting of i) hydroxymethyl, ii) hydroxyethyl, iii) methoxymethyl, iv) cyanomethyl, v) methyl-C(O)—N(H)-methyl-, and vi) methyl-S(O)$_2$—N(H)-methyl-;
34) R$^1$ is methyl or ethyl, one of R$^2$ or R$^3$ is hydrogen and the other is methyl, and R$^4$ is selected from the group consisting of i) hydroxymethyl, ii) hydroxyethyl, iii) methoxymethyl, iv) cyanomethyl, v) methyl-C(O)—N(H)-methyl-, and vi) methyl-S(O)$_2$—N(H)-methyl-;
35) R$^1$ is methyl or ethyl, one of R$^2$ or R$^3$ is hydrogen and the other is methyl, and R$^4$ is selected from the group consisting of i) hydroxymethyl, ii) hydroxyethyl, iii) methoxymethyl, and iv) methyl-C(O)—N(H)-methyl-;
36) R$^1$ is phenyl or benzyl, one of R$^2$ or R$^3$ is hydrogen and the other is methyl, and R$^4$ is selected from the group consisting of i) hydroxymethyl, ii) hydroxyethyl, iii) methoxymethyl, iv) cyanomethyl, v) methyl-C(O)—N(H)-methyl-, vi) methyl-S(O)$_2$—N(H)-methyl-, vii) methoxy-C(O)—(C$_0$-C$_1$)alkyl-, viii) methoxy-C(O)—NH-methyl-, ix) methoxymethyl-C(O)—NH-methyl-, and x) (R$^6$)(R$^7$)N—C(O)-methyl-;
37) R$^1$ is phenyl or benzyl, one of R$^2$ or R$^3$ is hydrogen and the other is methyl, and R$^4$ is selected from the group consisting of i) hydroxymethyl, ii) hydroxyethyl, iii) methoxymethyl, iv) cyanomethyl, v) methyl-C(O)—N(H)-methyl-, and vi) methyl-S(O)$_2$—N(H)-methyl-; and
38) R$^5$ is fluoro.

It will be appreciated that the preferred definitions of the various substituents recited herein may be taken alone or in combination with other preferred definitions of other various substituents. As for example, but not to be construed as limiting, the following combinations of preferred selections are preferred combinations:

17) any one selection according to paragraphs 1) through 9) wherein p is 0;
18) preferred selection 1) or 2) (i.e. preferred selections for R$^1$) in combination with any one preferred selection according to paragraphs 3) through 6) (i.e. preferred selections for R$^2$ and/or R$^3$);
19) a preferred combination according to 18) in combination with any one preferred combination according to paragraphs 7) through 9) (i.e. combining one of the preferred substitution patterns for the pyrazolyl moiety with one of the preferred selections for R$^4$).

Specific preferred compounds of the present invention are those described in the Examples herein, including the free bases and the pharmaceutically acceptable salts thereof. Two particularly preferred compounds of the present invention are 2-[4-(3'-Phenyl-2,3,5,6-tetrahydro-[1,2']bipyrazinyl-4-ylmethyl)-pyrazol-1-yl]-ethanol and pharmaceutically acceptable salts thereof (the compound of Example 198) and N-{4-[4-(1,5-Dimethyl-1H-pyrazol-4-ylmethyl)-3,4,5,6-tetrahydro-2H-[1,2']bipyrazinyl-3'-yl]-benzyl}-acetamide and pharmaceutically acceptable salts thereof (the compound of Example 32m).

General Schemes

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I is dependent upon the particular compound being synthesized, the starting compound, and the relative lability of the substituted moieties, as is well appreciated by the skilled chemist. All substituents, unless otherwise indicated, are as previously defined, and all reagents are well known and appreciated in the art.

Scheme I below, shows one suitable four step synthesis for pyrazine compounds of the present invention. In this scheme, 2,3-dichloropyrazine (1) is nucleophilically substituted with mono-N-protected piperazine to provide piperazinopyrazine (2). A Suzuki reaction using an appropriately substituted or unsubstituted phenyl boronic acid (3) in the presence of a suitable palladium catalysis provides the corresponding phenylpiperazinopyrazine (4). Deprotection provides the secondary amine (5) which is then reductively aminated with the appropriately substituted or unsubstituted pyrazoloaldehyde (6) to provide the desired compound (7).

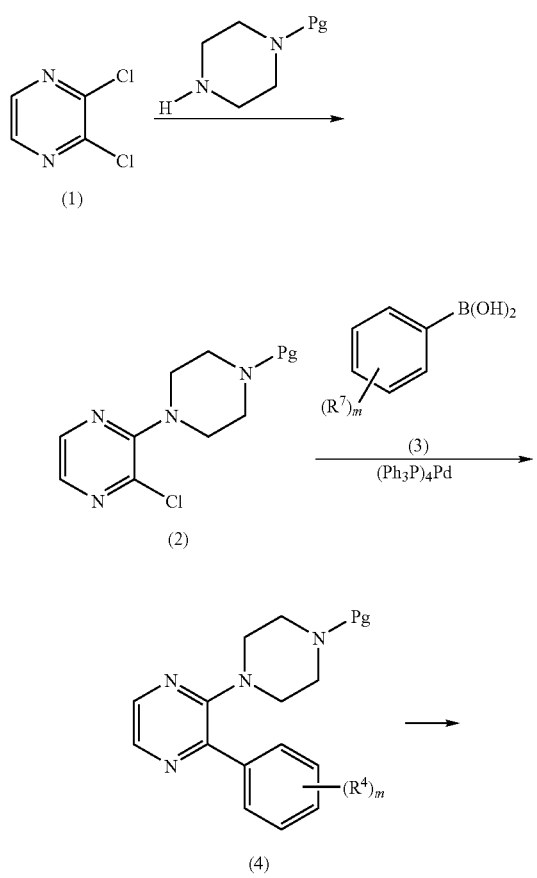

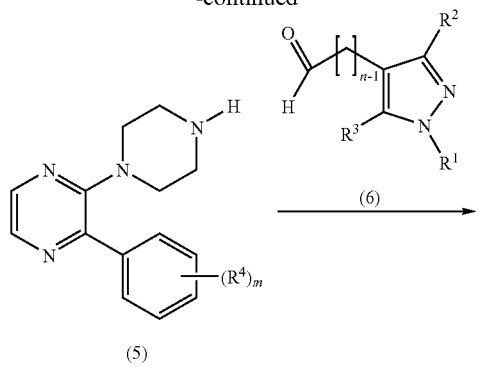

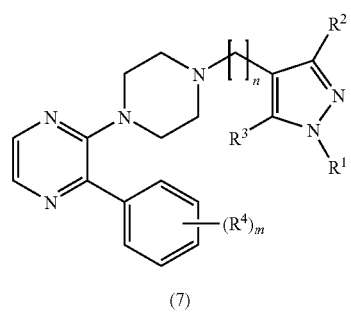

Although phenyl boronic acid (3) is used in the above illustration it will be appreciated that other reagents could be used to provide the phenylpiperazinopyrazines (4) (e.g. phenyl stannanes, phenyl zincates, or phenyl Grignards with an appropriate catalyst). Similarly a variety of N-protecting groups may be used, together with appropriate deprotection methods, as is readily appreciated in the art. Exemplary protecting groups include, but are not limited to Boc, acetyl, benzyl, benzyloxycarbonyl or ethoxycarbonyl. The skilled chemist will also appreciate that the above reactions are amenable to a variety of solvents and reaction conditions and that optimal conditions will depend on the particular compound being synthesized.

The order of the coupling steps in Scheme I may be inverted if desired. Thus the pyrazoloaldehyde (6) may be coupled first with the N-protected piperazine, followed by deprotection and coupling with 2,3-dichloropyrazine (1), followed finally with the Suzuki reaction to add the phenyl moiety.

As an alternative to the reductive amination step, intermediate (5) may be subjected to acylation with carboxylic acids (8) in the presence of EDC and HOBt as shown in Scheme II. This provides amide (9), which upon reduction with borane dimethylsulfide or the like, provides compound (7).

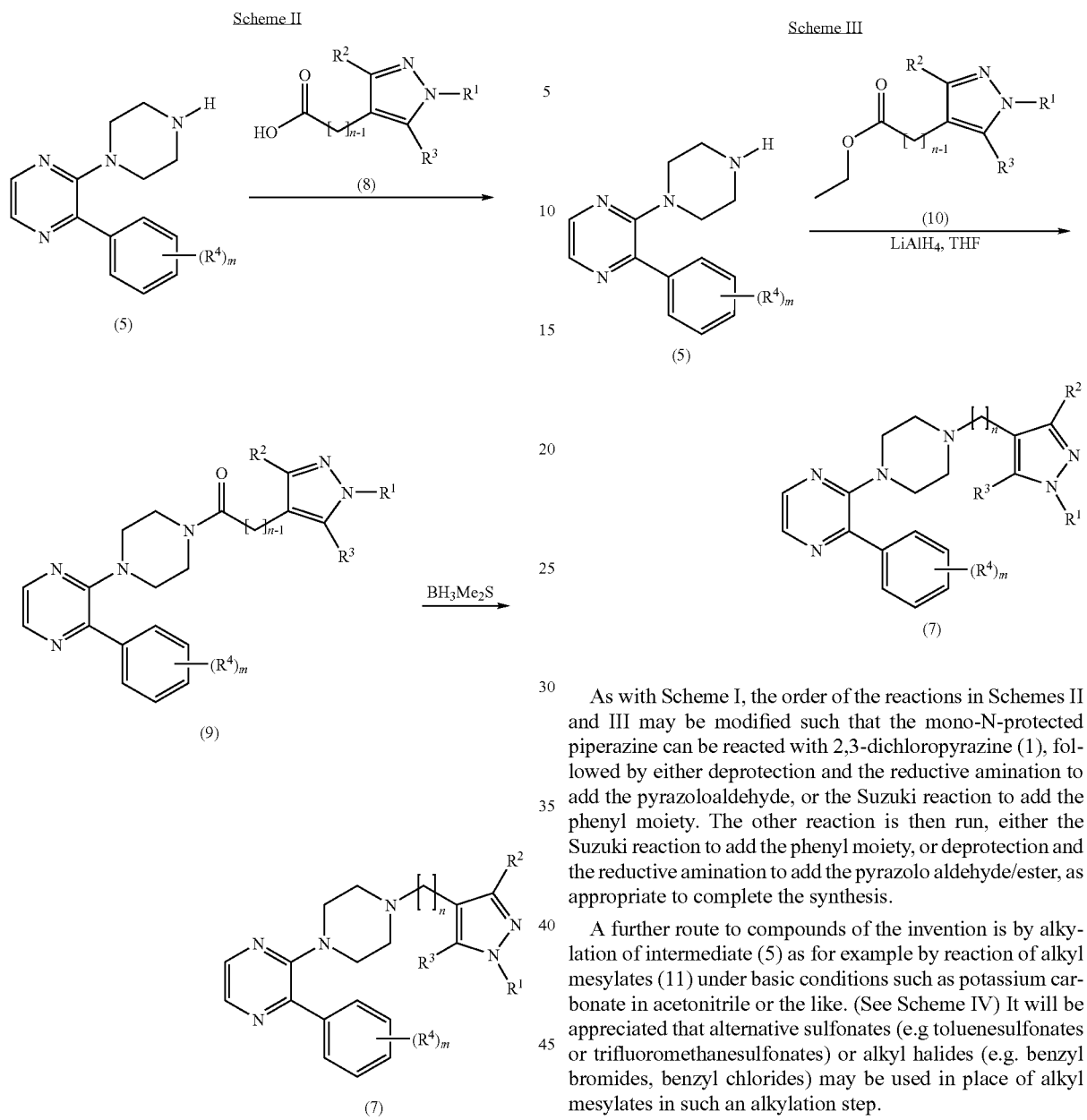

Although the above scheme illustrates the use of EDC and HOBt to activate the carboxylic acid to facilitate coupling with the amine, it will be appreciated that other acylating reagents may be used, as for example, but not limited to, dicyclohexylcarbodiimide or 2-(1H-benzotriazol-1-yl)-1,1,3,3-tetramethyluronium tetrafluoroborate in the presence of diisopropylethylamine. Similarly other reducing agents may be used in the reduction step, as for example, but not limited to, lithium aluminium hydride or diisobutyl aluminium hydride. Likewise, alternative solvents and a variety of reaction conditions may be employed as is apparent to the skilled chemist, as for example sodium triacetoxyborohydride in methylene chloride and the like for the reductive amination step.

Scheme III illustrates a variation on Scheme II wherein the methyl or ethyl ester (10) of the carboxylic acid (8) of Scheme II is used in the presence of a reducing agent such as lithium aluminum hydride to provide compound (7). See Scheme III.

As with Scheme I, the order of the reactions in Schemes II and III may be modified such that the mono-N-protected piperazine can be reacted with 2,3-dichloropyrazine (1), followed by either deprotection and the reductive amination to add the pyrazoloaldehyde, or the Suzuki reaction to add the phenyl moiety. The other reaction is then run, either the Suzuki reaction to add the phenyl moiety, or deprotection and the reductive amination to add the pyrazolo aldehyde/ester, as appropriate to complete the synthesis.

A further route to compounds of the invention is by alkylation of intermediate (5) as for example by reaction of alkyl mesylates (11) under basic conditions such as potassium carbonate in acetonitrile or the like. (See Scheme IV) It will be appreciated that alternative sulfonates (e.g toluenesulfonates or trifluoromethanesulfonates) or alkyl halides (e.g. benzyl bromides, benzyl chlorides) may be used in place of alkyl mesylates in such an alkylation step.

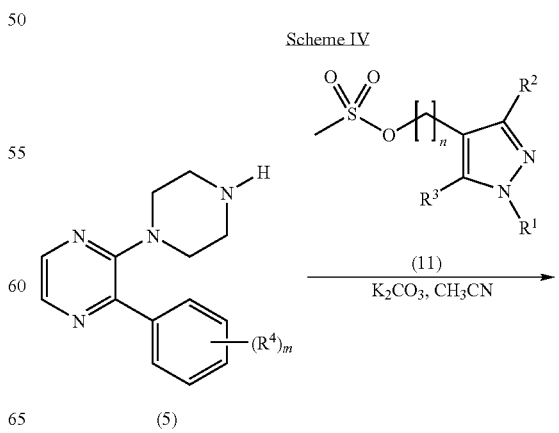

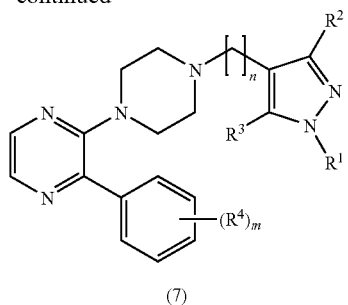

3,5-Dimethylated pyrazole compounds of the present invention may be obtained as illustrated in Scheme V. Thus pentane-2,4-dione is reacted with benzylhydrazine to give N-protected 3,5-dimethylpyrazole (12), which is then formylated with phosphorus oxychloride in DMF to give the corresponding benzyl pyrazole carboxaldehyde (13). Alternatively any symmetrical dione can be used in place of pentane-2,4-dione (e.g. heptane 3,5 dione, or nonane-4,6-dione) to give the corresponding 3,5 dialkyl pyrazoles (e.g. 2,3-diethyl or 3,5 di-propyl pyrazole). These are then reductively aminated with intermediate (5) to provide the benzyldimethylpyrazole compound (14). Other substitutions on the pyrazolyl nitrogen are then easily accessible by removal of the benzyl group as for example, by hydrogenation in the presence of ammonium formate and a suitable palladium catalyst to give (15). It will be understood that under some circumstances the reductive amination can be performed with the pyrazole carboxaldehyde without N-protection, thus leading directly to compound/intermediate (15) without the need for a deprotecting step.

It will be readily appreciated by those skilled in the art, that intermediate (15) can be optionally further derivatized to give additional N-substituted pyrazoles (16-19) by a number of well known methods, as for example, alkylation, acylation, sulfonylation, or epoxide addition, as shown in Scheme V and demonstrated in the preparations and examples below.

Compounds of the invention wherein n is 2 or 3 can be synthesized with analogous methods using bromoacetic acid ethyl ester or bromopropionic acid ethyl ester in a suitable solvent in place of DMF.

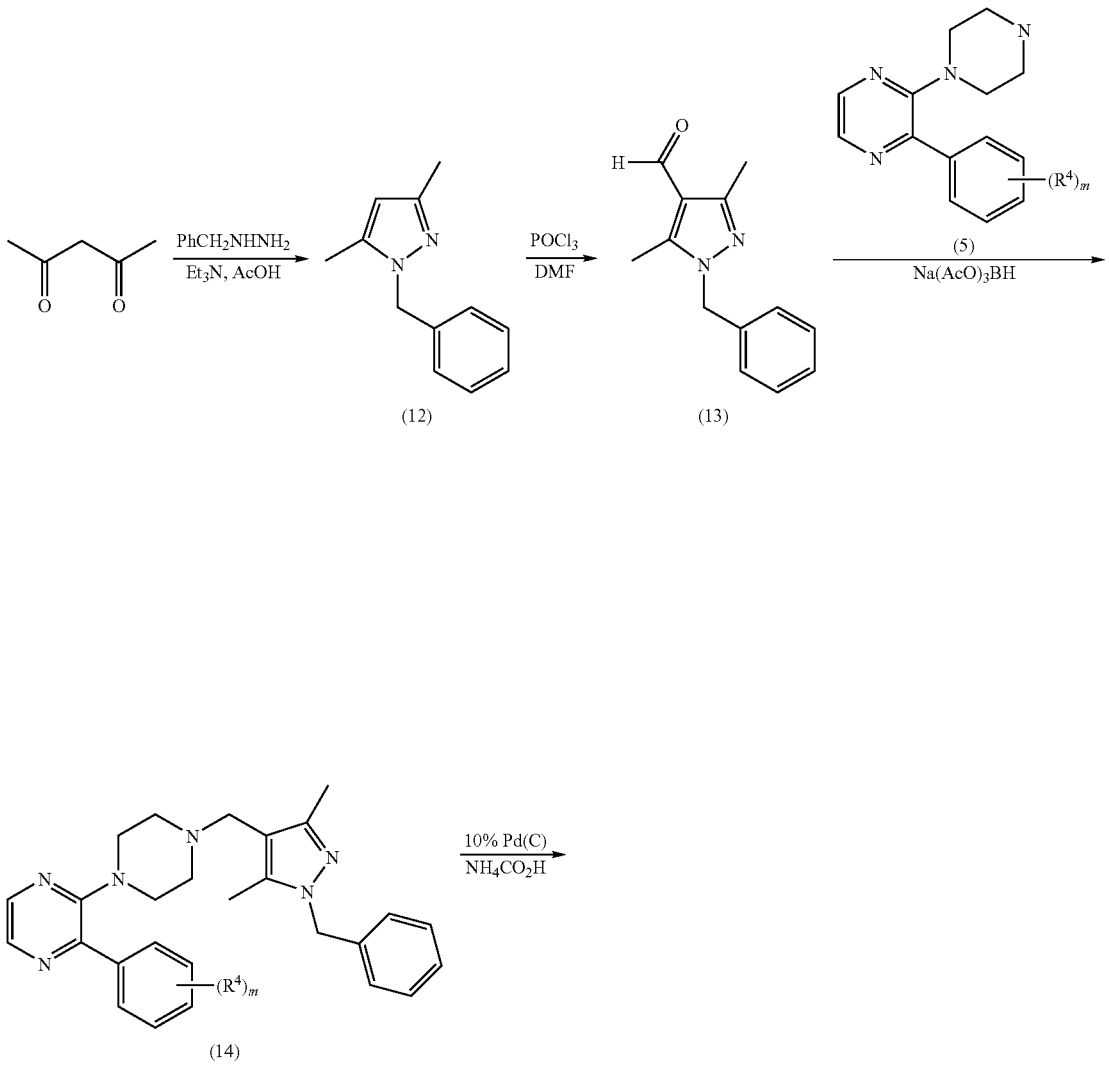

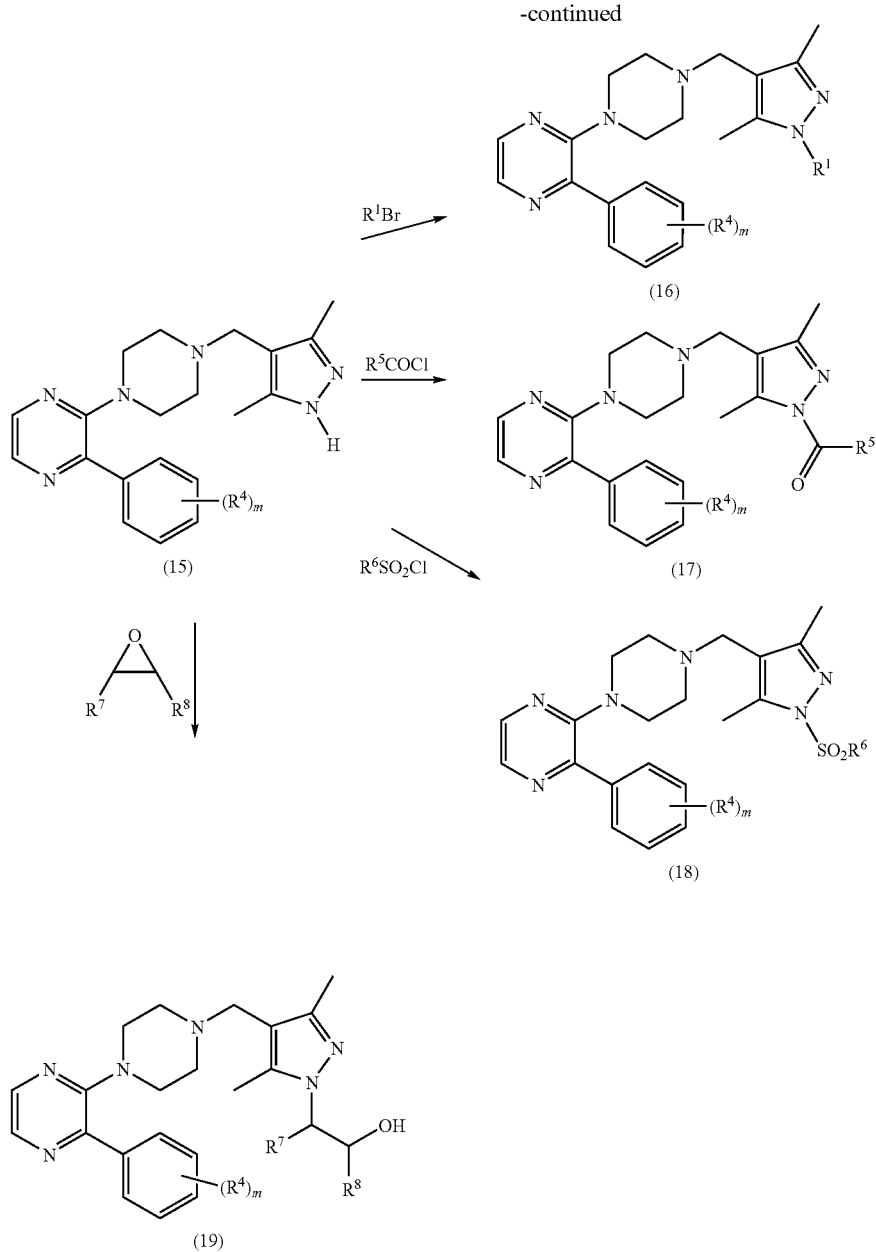

wherein

R[5] is (C$_1$-C$_5$)alkyl-, (C$_3$-C$_7$)cycloalkyl-(C$_1$-C$_2$)alkyl-, Ph[1]-(C$_0$-C$_2$)alkyl-, or Ar[1]—(C$_0$-C$_2$)alkyl-;

R[6] is (C$_1$-C$_2$)alkyl-, Ph[1]-, or Ar[1]—;

R[7] and R[8] are independently hydrogen or (C$_1$-C$_4$)alkyl- optionally substituted with 1 to 3 fluoro substituents, provided that R[7] and R[8] together do not contain more than 4 carbon atoms or more than 3 fluoro substituents.

Compounds wherein R[1] is a sulfonylamidoalkyl moiety may be obtained as illustrated in Scheme VI. The appropriate pyrazolyl intermediate (20) is alkylated with the desired aminoalkyl chloride (R-aminoethyl chloride is illustrated, though alkyl chains of various lengths may be used). The free amine is then sulfonylated with the appropriately substituted sulfonyl chloride. The methylsulfonylamide is illustrated, though other substituents may be obtained in the similar manner.

Scheme VI

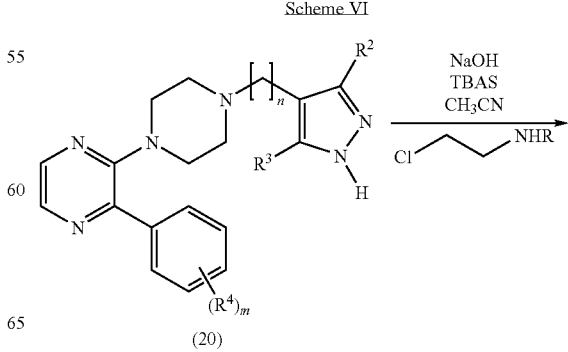

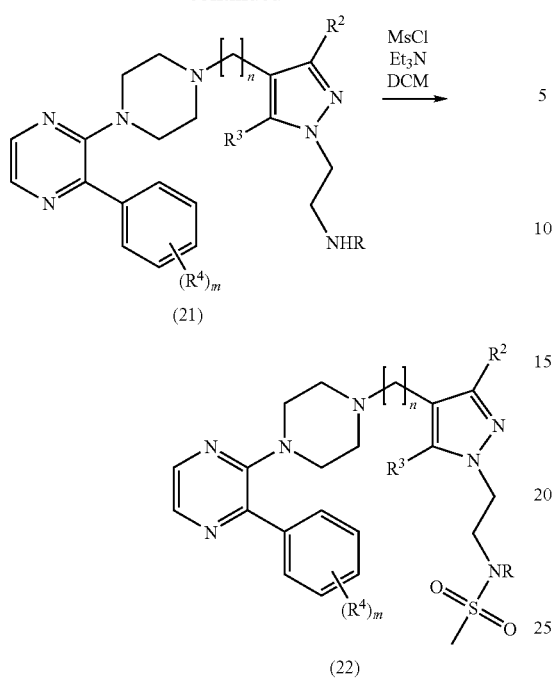

(21)

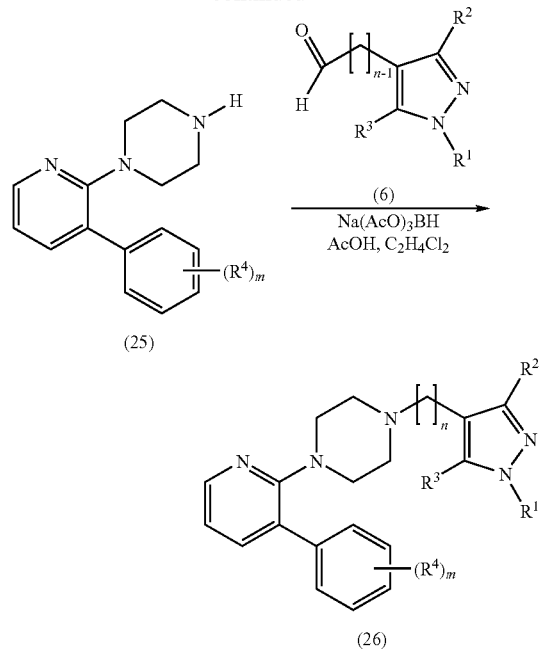

(25)

(22)

R = H, Me

Pyridyl compounds of the present invention may be synthesized by a number of routes using conventional chemistries including those described in Schemes VII-XII. In Scheme VII, pyridyl compounds having the piperazinyl moiety adjacent to the pyridyl nitrogen are provided through a 3 step synthesis. Thus 2-bromopyridine (23) is deprotonated and coupled to phenyl iodides in the presence of zinc chloride and a suitable palladium catalysis to give the 3-phenyl-2-bromopyridine (24). Intermediate (24) is then reacted with piperazine under Buchwald reaction conditions to provide the 3-phenyl-2-piperazinopyridine (25), which in turn is reductively aminated with the appropriate pryazoloaldehyde (6) to provide the desired 3-phenyl-2-(4-pyrazoloalkylpiperazin-1-yl)pyridine compound (26).

Alternatively, 3-bromo-2-chloropyridine may be used as shown in Scheme VIII. Thus, 3-bromo-2-chloropyridine (27) is heated with piperazine to provide 1-(3-bromopyridin-2-yl)piperazine (28), followed by Suzuki coupling of the phenyl moiety to provide the phenylpiperazine intermediate (25).

Scheme VII

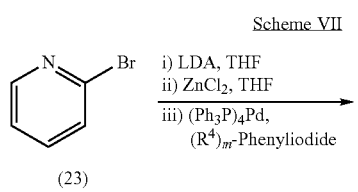

(23)

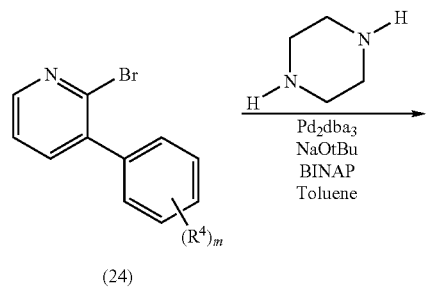

(24)

Scheme VIII

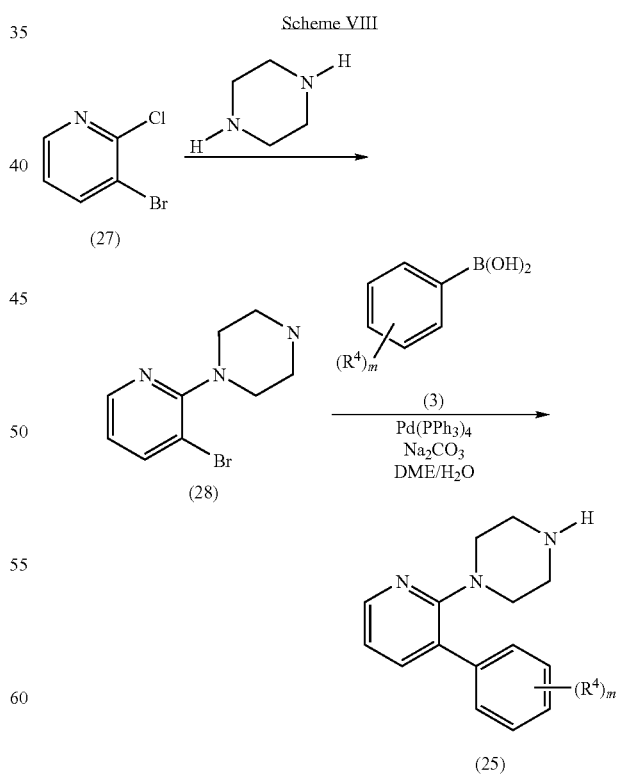

Pyridyl compounds of the present invention having the phenyl moiety adjacent to the pyridyl nitrogen may be obtained by reacting 2,3-dibromopyridine (29) with the appropriate phenyl boronic acid (3) under Suzuki reaction conditions to provide 2-phenyl-3-bromopyridine (30). This in turn can be substituted with piperazine under Buchwald reaction conditions to give the corresponding 2-phenyl-3-piperazinopyridine (31), which can then be reductively aminated with an appropriate pyrazoloaldehyde (6) to provide the final compound (32). (See Scheme IX.)

Scheme IX

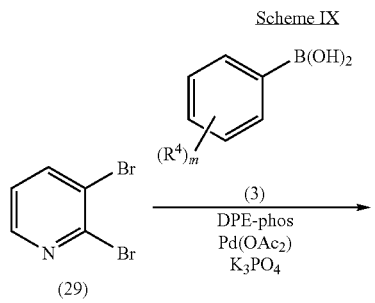

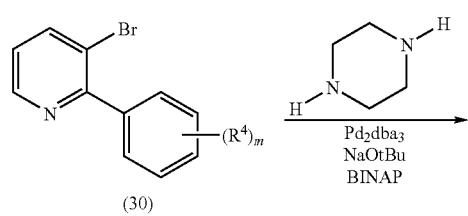

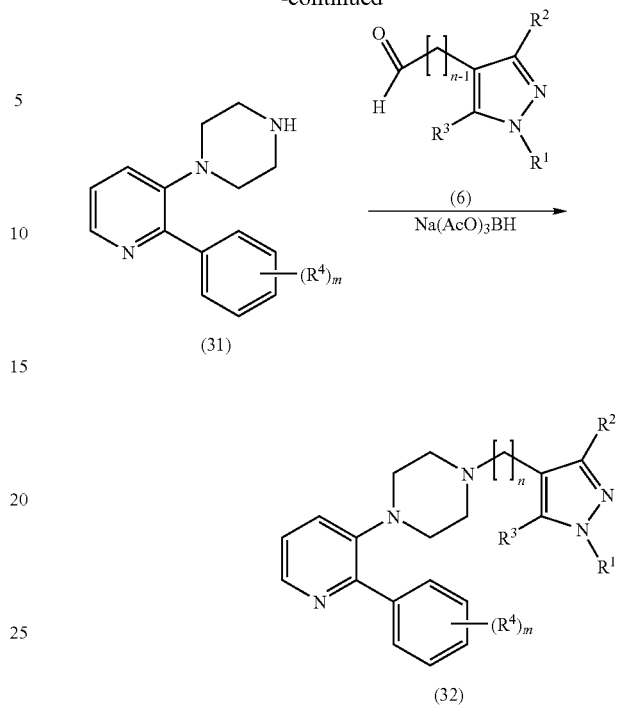

Alternatively, intermediate (31) may be obtained as illustrated in Scheme X below. Thus, 2-chloro-3-iodo-pyridine (33) is coupled with mono-N-protected piperazine (34) in the presence of a suitable palladium catalyst to provide the corresponding N-protected 2-chloro-3-piperazinopyridine (35). This is followed by the Suzuki coupling with the optionally substituted phenyl boronic acid (3) and deprotection as described above to provide the desired intermediate (31).

Scheme X

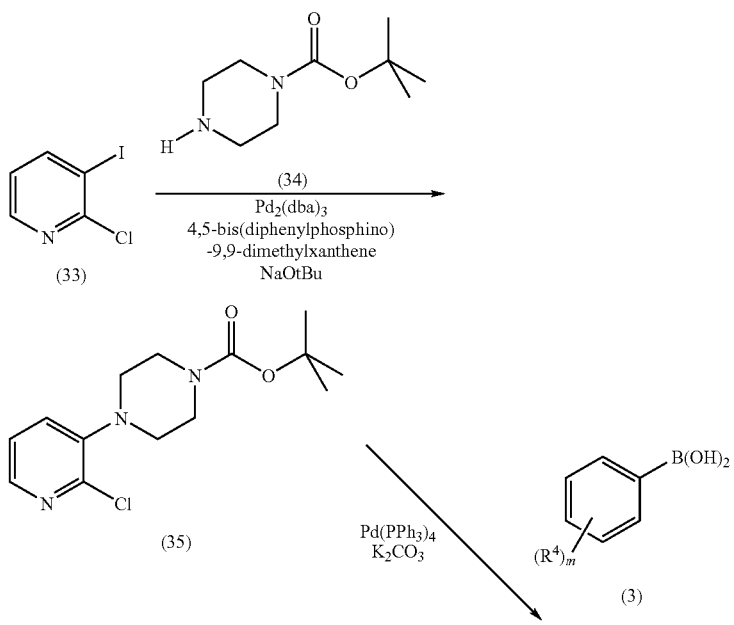

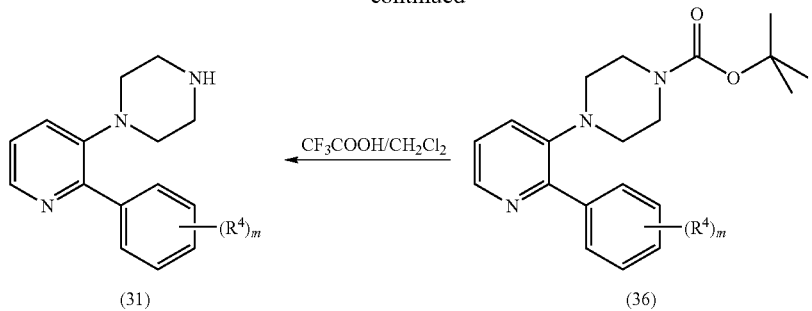

Although a phenyl boronic acid is used in the above illustration, it will be appreciated that other phenylating reagents may also be used (e.g. phenyl stannanes, phenyl zincates, or phenyl Grignards with appropriate catalysis).

As an alternative to the reductive amination step, compounds (25) or (31) may be subjected to acylation with carboxylic acids (8) in the presence of EDC and HOBt as shown in Scheme XI.

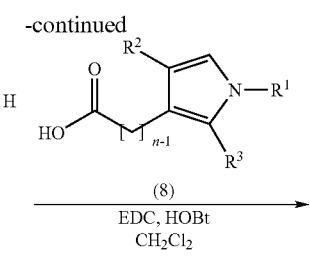

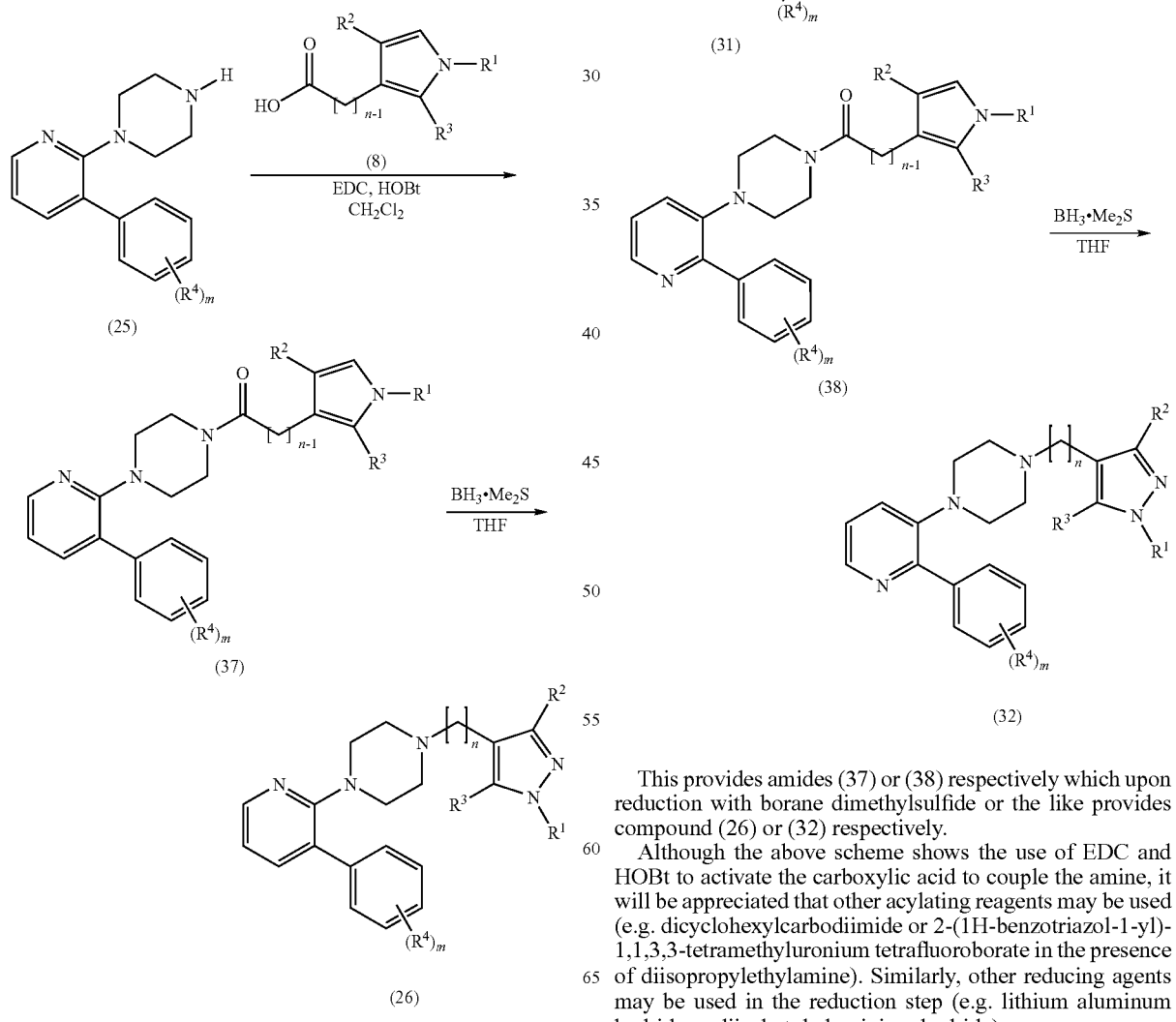

This provides amides (37) or (38) respectively which upon reduction with borane dimethylsulfide or the like provides compound (26) or (32) respectively.

Although the above scheme shows the use of EDC and HOBt to activate the carboxylic acid to couple the amine, it will be appreciated that other acylating reagents may be used (e.g. dicyclohexylcarbodiimide or 2-(1H-benzotriazol-1-yl)-1,1,3,3-tetramethyluronium tetrafluoroborate in the presence of diisopropylethylamine). Similarly, other reducing agents may be used in the reduction step (e.g. lithium aluminum hydride or diisobutyl aluminium hydride).

It will be appreciated that, as with the synthetic schemes for the pyrazinyl compounds of the present invention above, the order of the individual steps for coupling the pyrazole to the piperazine, coupling the piperazine to the pyridine, and coupling the pyridine to the phenyl, is generally unimportant and may be reordered as desired to suit the compound being synthesized. Likewise, the pyrazolyl moiety may be further substituted before or after coupling the pyrazolyl moiety to the piperazinyl moiety. Furthermore, as with the synthesis of the pyrazinyl compounds above, the pyrazolyl moiety may be added by typical alkylation reactions as with mesylates or the like as shown in Scheme XII below.

trile) to provide compounds (26) and (32). It will be appreciated that alternative sulfonates (e.g. toluenesulfonates or trifluoromethanesulfonates) or alkyl halides (e.g. benzyl bromides, benzyl chlorides) may be used in place of the above illustrated alkyl mesylates.

Scheme XIII shows one suitable method for the generation of a boronic ester (509) from a corresponding aryl halide (8). It is to be noted that variations with respect to choice of catalytic palladium source, ligand, base, and solvent are common in the art.

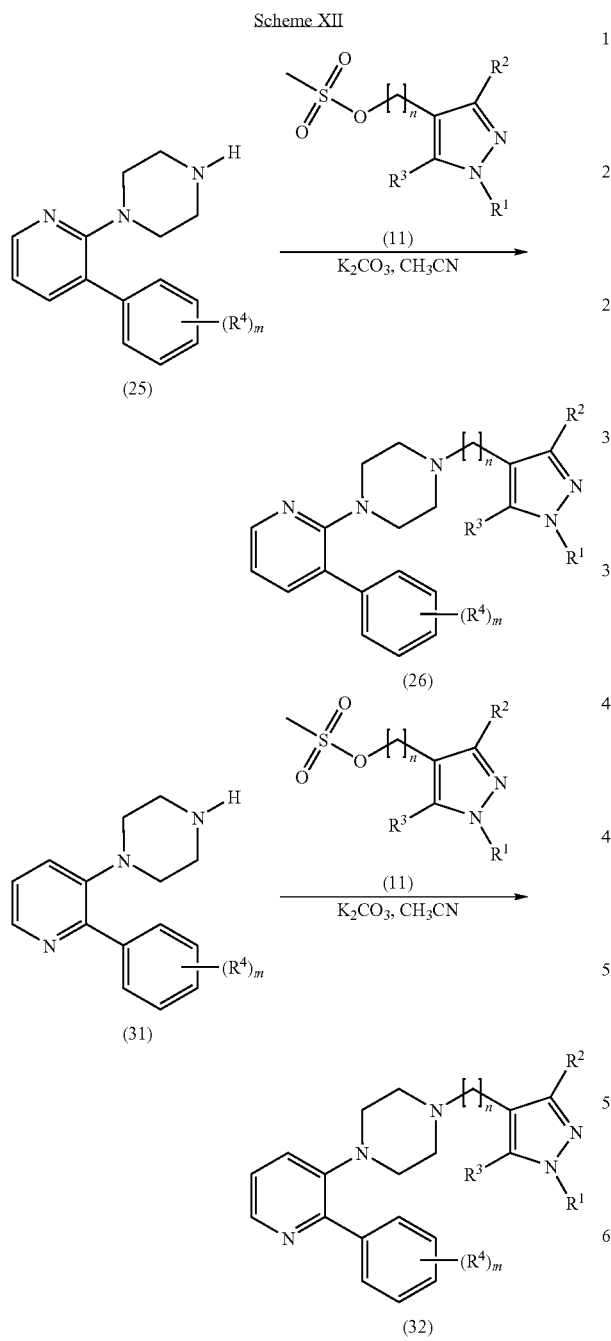

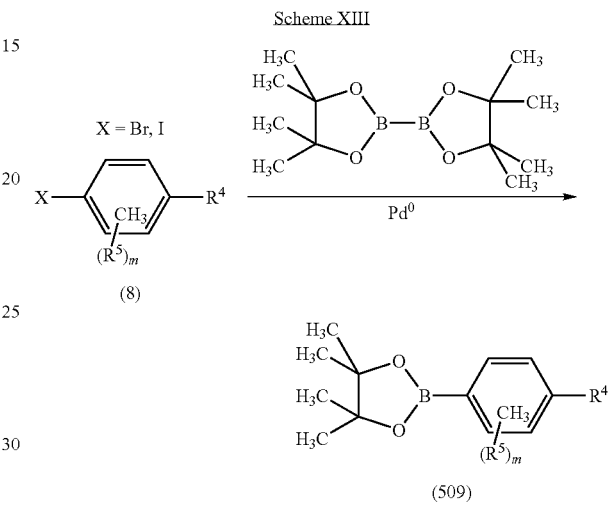

As shown in Scheme XIV, alkylated boronic esters (511) can be synthesized by benzylic deprotination of (510) and reaction with methyl halides such as methyl iodide, to give alkylated products (511)

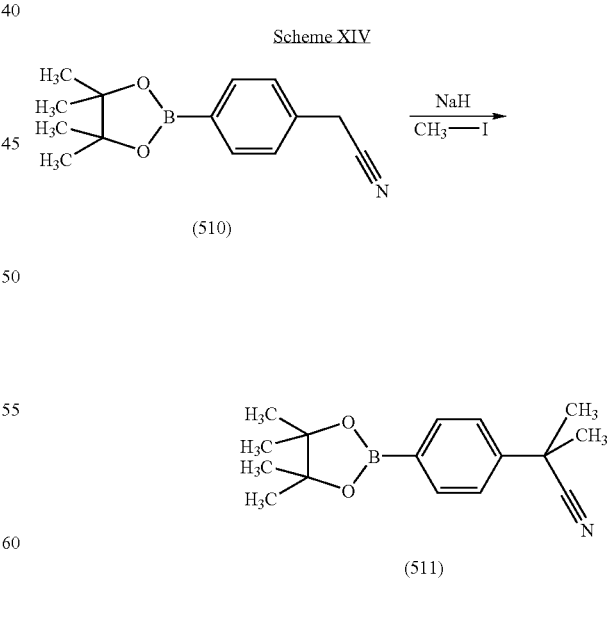

Thus alkyl mesylates (11) may be reacted under basic conditions (as for example potassium carbonate in acetonitrile)

Other boronic esters may be functionalized prior to boronic ester formation as in Scheme XV. Acid chloride (512) is converted to amide (513) which can then be converted to boronic ester (514) using previously described conditions.

Scheme XV

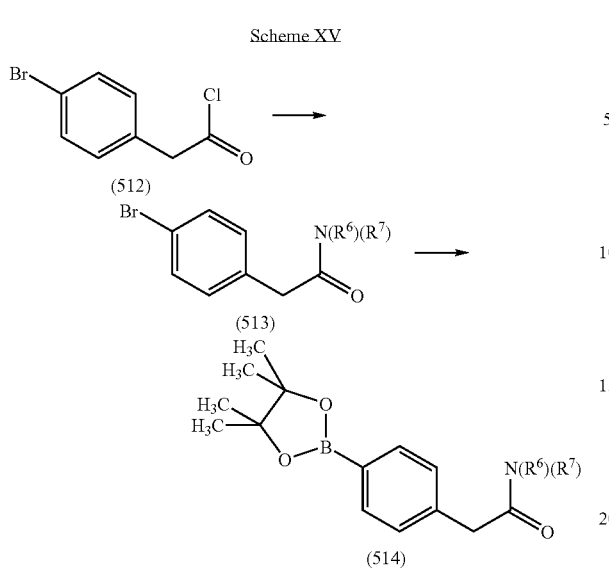

Substituted pyrazoles may be synthesized by the generally known procedure shown in Scheme XVI. When $R^2$ does not equal $R^3$, regioisomeric products (515) must be separated using common chromatographic techniques.

Scheme XVI

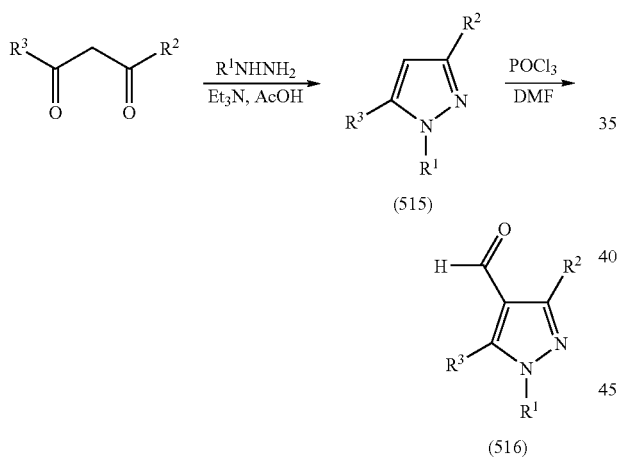

Functionalized pyrazoles (517) can be synthesized as shown in Scheme XVII, particularly where $R^1$ is $(C_1-C_3)$ alkyl-substituted with hydroxy.

Scheme XVII

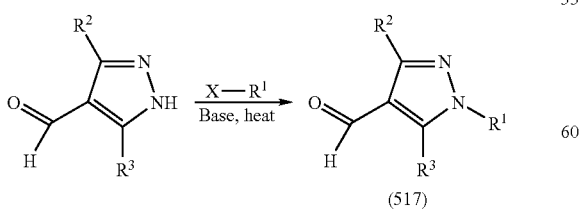

It will be appreciated that functionalized compounds can be further elaborated by utilizing pendant reactive functionality. As an example and as shown in Scheme XVIII, a benzyl alcohol (528) can be reacted with thionyl chloride to form the benzyl chloride (529). The benzyl chloride (529) can then undergo nucleophilic displacement with a variety of nitrogen nucleophiles to arrive at compounds (530). $R^{11}$ is defined by the amine nucleophile used which can include, but is not limited to lactams, triazoles, pyrazoles, imidazoles, ureas, carbamates, sultams, or amides.

Scheme XVIII

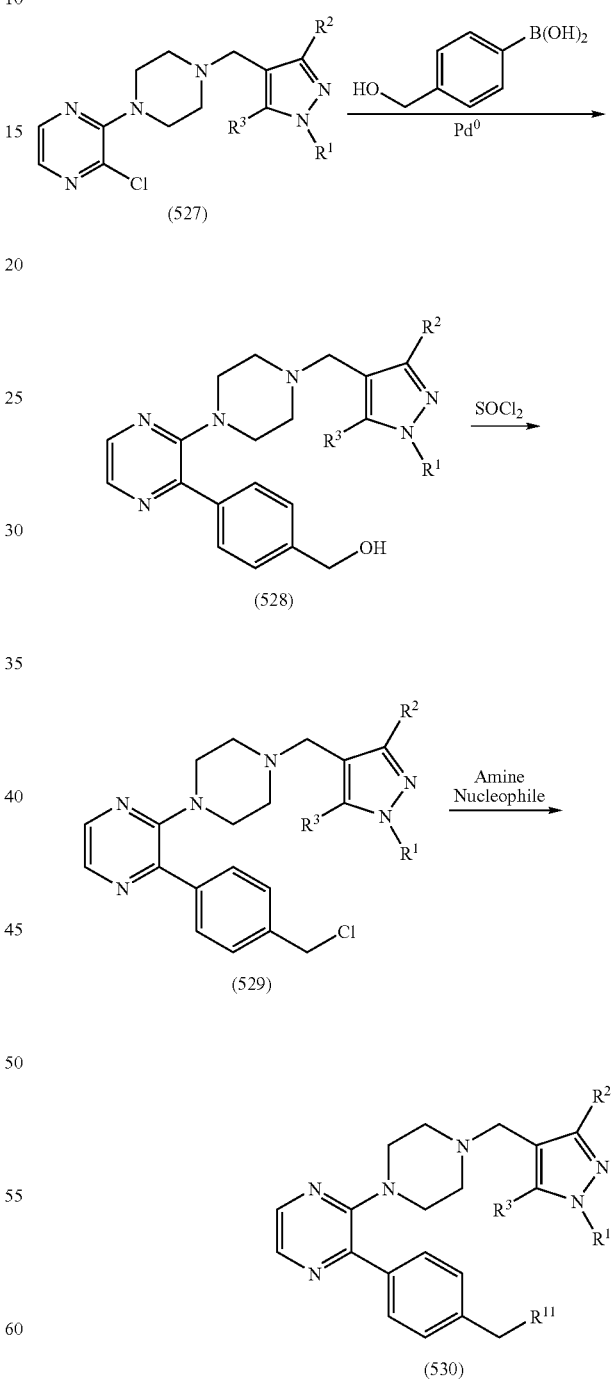

In a similar fashion the electrophilic benzyl chloride (529) can be displaced with a nucleophilic sulphur to give a sulfone (531) as shown in Scheme XIX. $R^8$ can be alkyl or branched alkyl.

Scheme XIX

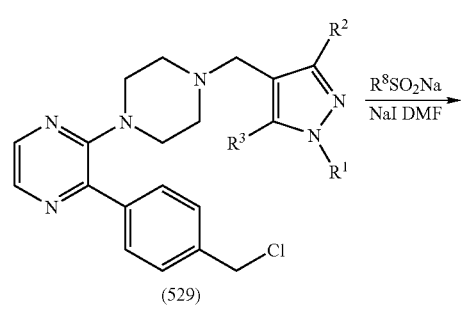

(529)

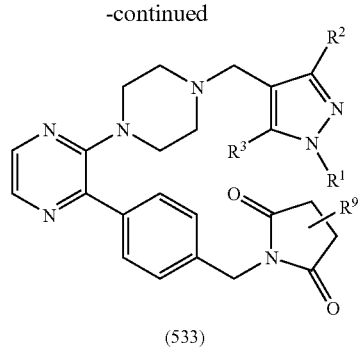

(533)

The pendant benzyl alcohol (528) can also be acylated to give carbamates as in Scheme XXI. Activation of the benzyl alcohol with carbonyl diimidazole followed by reaction with a primary amine gives the corresponding carbamates (534). Carbamates (535) can be formed by deprotinating the alcohol (528) with a suitable base followed by reaction with a carbamoyl chloride.

Benzyl alcohol (528) can be functionalized via alkylation or via Mitsunobu reaction as shown in Scheme XX. It will be appreciated that many of these functionalization reactions of the benzyl alcohol can also be applied to the corresponding phenolic alcohol. In the Schemes, $R^9$ can be methyl or ethyl.

Scheme XXI

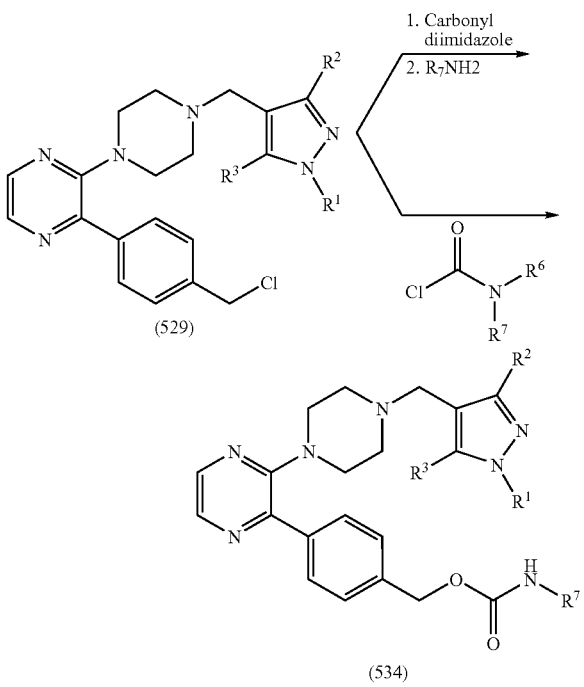

Scheme XX

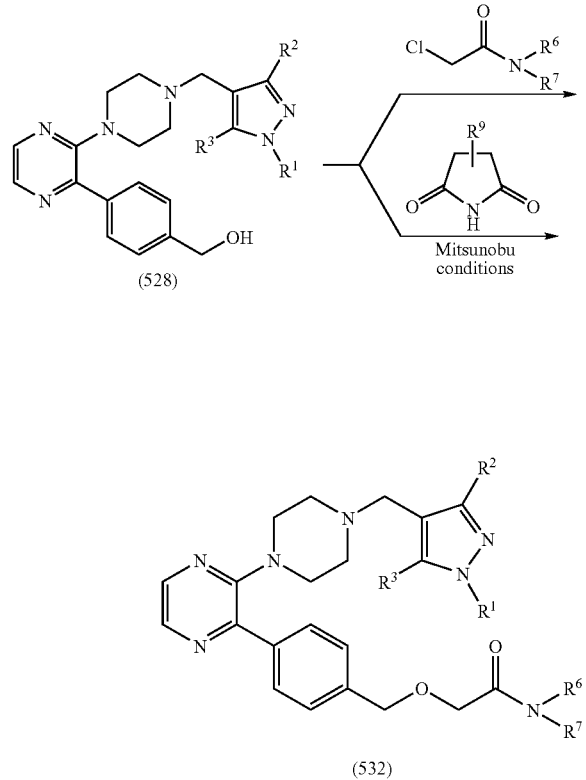

As with the benzyl alcohol, derivitization of a pendant primary benzyl amine can lead to a variety of additional functional groups such as ureas, thioureas, carbamates, and amides as shown in Scheme XXII. Amine (536) can be activated with carbonyl diimidazole and reacted with a primary amine to give ureas (537). Further, (536) may be reacted with a chloroformate to give carbamates (538). Ureas (539) can be realized via reaction of (536) with carbamoyl chlorides. Ureas or thioureas (540) can be obtained by reacting amine (536) with either isocyanates or thioisocyanates. Yet further, (536) can also be functionalized to give amides (541) via conventional amide coupling via acid chlorides or other commonly employed carboxylic acid coupling techniques. In Scheme XI, $R^{10}$ can be $(C_1\text{-}C_4)$alkyl, cyclopropyl, or $(C_1\text{-}C_2)$alkyl-O—$(C_1\text{-}C_2)$alkyl-.

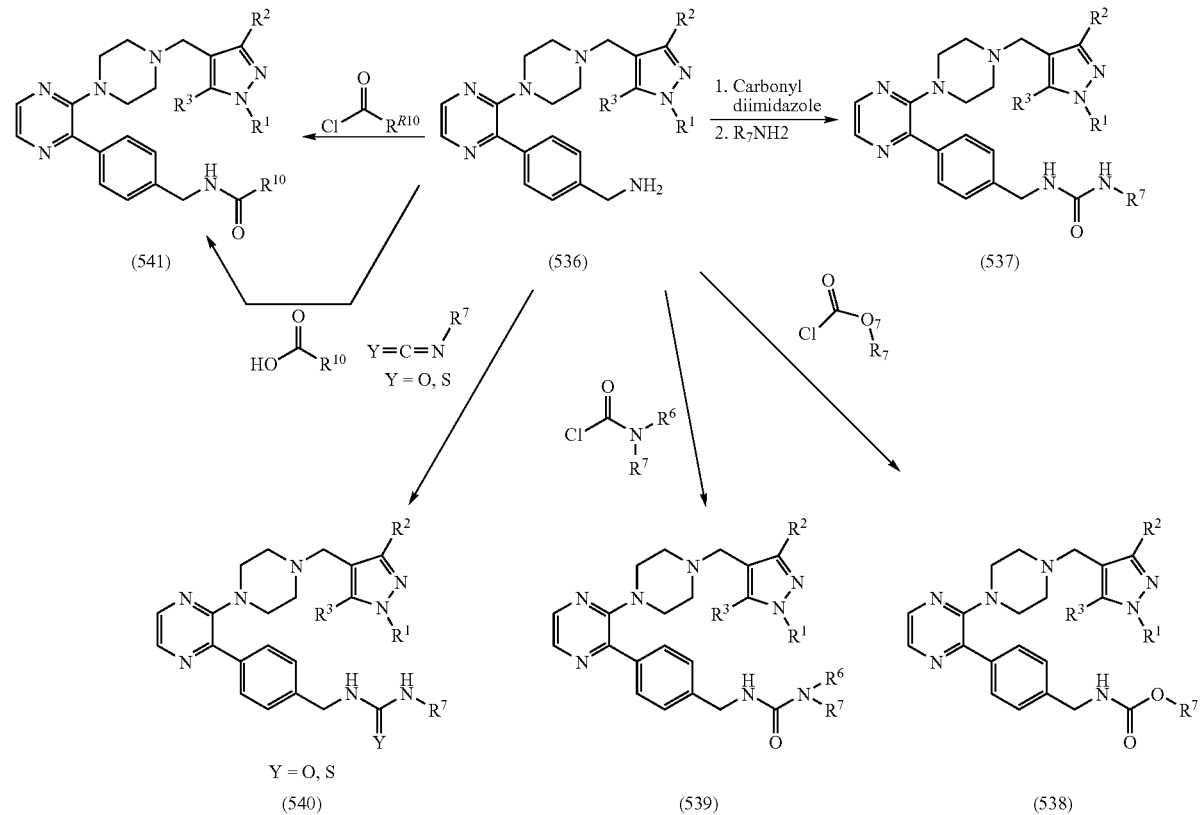

Additional functionalization can be realized via amidation of a pendant carboxylic acid (542) with an amine to give amide (543). This can occur via the acid chloride as in Scheme XXIII or via the carboxylic acid directly with traditional activation by amide bond forming reagents. $R^{11}$ is defined from the amine reagent which can alkyl or aryl and can be primary or secondary.

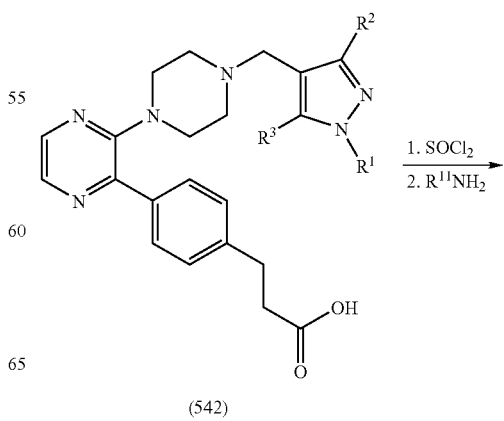

-continued

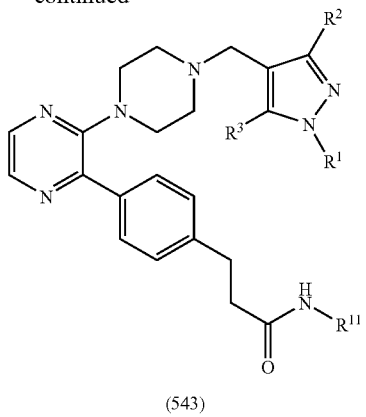

(543)

Mitsunobu functionalization can also occur on pendant reactive nitrogen functionality such as sulfonamide (544) to give alkylated products such as (545) in scheme XXIV.

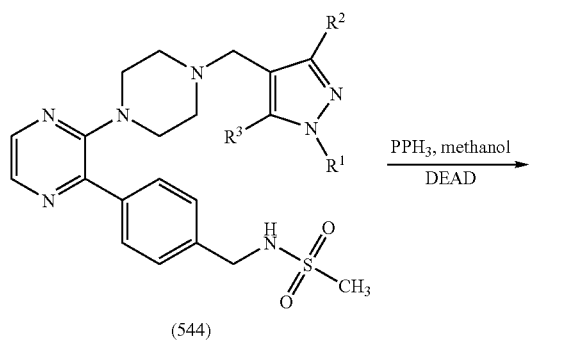

(544)

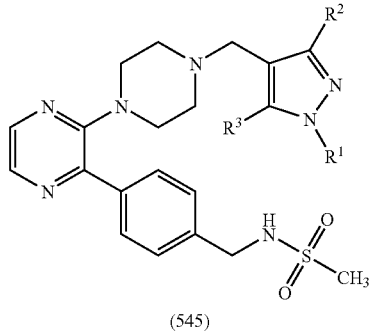

(545)

The following Preparations and Examples are illustrative of methods useful for the synthesis of the compounds of the present invention. The names for many of the compounds illustrated in the preparations and examples are provided from drawn structures with ChemDraw®, version 7.0 software or Autonom 2000 for ISIS/Draw.

PREPARATION 1

3'-Chloro-2,3,5,6-tetrahydro-[1,2']bipyrazinyl-4-carboxylic acid t-butyl ester

Charge a 2 L 3-neck round bottom flask with 2,3-dichloropyrazine (78.7 g, 0.532 mol), piperazine-1-carboxylic acid t-butyl ester (100 g, 0.537 mol), potassium carbonate (88.2 g, 0.638 mol) followed by DMA (0.780 L), and heat the resultant slurry to 110° C. under nitrogen with vigorous stirring. Cool to room temperature, add water (0.390 L) and MTBE (0.390 L), and stir the mixture for 60 min. Stop stirring and separate the layers. Wash the organic layer with water (2×200 mL), dry over MgSO$_4$, filter and concentrate to give the title preparation as a yellow syrup (145 g, 91% yield).

PREPARATION 2

3'-(4-Fluoro-phenyl)-3,4,5,6-tetrahydro-2H-[1,2']bipyrazine dihydrochloride

Charge a reactor with 2,3-dichloropyrazine (73.6 g, 0.497 mol, 1.0 equiv), piperazine-1-carboxylic acid t-butyl ester (101.9 g, 0.547 mol, 1.1 equiv) and powdered potassium carbonate (164.8 g, 1.19 mol, 2.4 equiv). Add N,N-dimethylacetamide (1.1 L) and heat to 110° C. under nitrogen for 5 hr. Cool the reaction to room temperature, and add 4-fluorophenylboronic acid (83.4 g, 0.596 mol, 1.2 equiv), tetrakis(triphenyl-phosphine)palladium(0) (2.87 g, 2.5 mmol, 0.005 equiv) and water (442 mL). Heat the reaction to 110° C. under a nitrogen atmosphere for 5 hr. Cool the reaction to 60° C. and dilute with water (800 mL) and methyl t-butyl ether (1.0 L). Cool to room temperature and separate the resulting layers. Wash the organic layer with 200 mL of water, separate the layers, and concentrate to give 3-(4-fluorophenyl)-2-[4-(t-butyloxycarbonyl)piperazin-1-yl]pyrazine as a light yellow solid that is taken into the next step without further purification.

Charge the crude 3-(4-fluorophenyl)-2-[4-(t-butyloxycarbonyl)piperazin-1-yl]pyrazine to a reactor along with n-butanol (1.67 L) and toluene (99 mL). Heat the reaction mixture to 60° C., and add a solution of HCl in n-butanol (835 mL, prepared by adding 2.33 moles of acetyl chloride to 668 mL of n-butanol at 0° C.) in situ to the reaction dropwise. After the addition is complete, stir at 60° C. for 2 hr. and cool to room temperature. Stir the resulting solids at room temperature, filter, wash with n-butanol (200 mL), and dry overnight in a vacuum oven at 70° C. to give the title intermediate as a yellow solid (148.95 g, 86% yield over four steps, correcting for n-butanol trapped in the solids). MS (ES): m/z=259 [M+H]$^+$.

PREPARATION 3

3'-m-Tolyl-3,4,5,6-tetrahydro-2H-[1,2']bipyrazine

Dissolve 3'-chloro-2,3,5,6-tetrahydro-[1,2']bipyrazinyl-4-carboxylic acid t-butyl ester (6.0 g, 20.2 mmol) and 3-methylbenzeneboronic acid (3.3 g, 24.0 mmol) in dimethoxyethane (20 mL) and water (10 mL). Add tetrakis(triphenylphosphine) palladium(0) (2.3 g, 2.0 mmol) and potassium carbonate (7.5 g, 54 mmol). Heat for 17 hr. at 102° C. and allow to cool about 1.5 hr. to room temperature. Partition reaction mixture between ethyl acetate and water. Separate layers. Wash organic layer with brine, dry (sodium sulfate), filter, concentrate and purify (silica gel chromatography eluting with 10:90 to 20:80 ethyl acetate:hexanes), to give 3'-m-tolyl-2,3,5,6-tetrahydro-[1,2']bipyrazinyl-4-carboxylic acid t-butyl ester (3.3 g, 47%). MS (ES): m/z=355 [M+H]$^+$.

Dissolve 3'-m-tolyl-2,3,5,6-tetrahydro-[1,2']bipyrazinyl-4-carboxylic acid t-butyl ester (3.3 g, 9.32 mmol) in DCM (10 mL). Add cold (from refrigerator) trifluoroacetic acid (42.6 g, 28.8 mL). Stir for 2 hr. at room temperature. Partition reaction mixture between methylene chloride and 5N NaOH (pH aqueous=14). Separate layers. Extract aqueous layer with methylene chloride (2×20 mL). Combine organic layers, dry over anh. sodium sulfate, filter and concentrate to give the title preparation (2.35 g, 99%). MS (ES): m/z=255 [M+H]+.

PREPARATION 4

3'-(3-Fluoro-phenyl)-3,4,5,6-tetrahydro-2H-[1,2'] bipyrazine

The title preparation is obtained using methods similar those in Preparation 3, using 3-fluorobenzeneboronic acid (89% yield). MS (ES): m/z=259 [M+H]+.

PREPARATION 5

3'-(2-Fluoro-phenyl)-3,4,5,6-tetrahydro-2H-[1,2'] bipyrazine dihydrochloride

3'-(2-Fluoro-phenyl)-2,3,5,6-tetrahydro-[1,2']bipyrazinyl-4-carboxylic acid t-butyl ester is prepared using the method of Preparation 3 using 2-fluorobenzeneboronic acid (82% yield, MS (ES): m/z=359 [M+H]+).

Add 4M HCl in dioxane (8 mL) to a solution of 3'-(2-fluorophenyl)-2,3,5,6-tetrahydro-[1,2']-bipyrazinyl-4-carboxylic acid t-butyl ester (1.48 g, 4.13 mmol) in 1,4-dioxane (8 mL), and stir the mixture at room temperature for 3 hr. then at 40° C. for 16 hr. Allow the reaction to cool, filter off the precipitated solid, wash with 1,4-dioxane and dry under reduced pressure at 60° C., to give the title preparation as a yellow solid (960 mg, 70%). MS (ES) m/z=259 [M+H].

PREPARATION 6

3'-Phenyl-3,4,5,6-tetrahydro-2H-[1,2']bipyrazine

Dissolve 3'-chloro-2,3,5,6-tetrahydro-[1,2']bipyrazinyl-4-carboxylic acid t-butyl ester (2.50 g, 8.40 mmol) and phenylboronic acid (1.23 g, 10.08 mmol) in N,N-dimethylacetamide (25 mL) and water (10 mL). Add tetrakis(triphenylphosphine) palladium(0) (0.49 g, 0.42 mmol) and potassium carbonate (2.80 g, 20.16 mmol). Heat for 4 hr. at 114° C. and allow to cool about 1.5 hr. to room temperature. Partition reaction mixture between MTBE and water. Separate layers. Dry organic layer (sodium sulfate), filter, concentrate and purify (silica gel chromatography eluting with 10:90 to 30:70 ethyl acetate:hexanes), to give 3'-(phenyl)-2,3,5,6-tetrahydro-[1,2']bipyrazinyl-4-carboxylic acid t-butyl ester (2.49 g, 87%). MS (ES): m/z=341 [M+H]+.

Deprotect using the procedure in preparation 3 to provide the title preparation (96% yield). MS (ES): m/z=241 [M+H]+.

PREPARATION 7

1-[4-(3,4,5,6-Tetrahydro-2H-[1,2']bipyrazinyl-3'-yl)-phenyl]-ethanone

Use the method of Preparation 6 using 4-acetylbenzeneboronic acid to obtain 3'-(phenyl)-2,3,5,6-tetrahydro-[1,2']bipyrazinyl-4-carboxylic acid t-butyl ester (91% yield). MS (ES): m/z=383 [M+H]+.

Deprotect using the method of Preparation 3 to obtain the title preparation (100% yield). MS (ES): m/z=283. [M+H]+.

PREPARATION 8

3'-(4-Chloro-phenyl)-3,4,5,6-tetrahydro-2H-[1,2'] bipyrazine

Couple 2,3-dichloropyrazine (0.302 g, 2.03 mmol) and 4-chlorophenylboronic acid (0.320 g, 2.05 mmol), using tetrakis(triphenylphosphine)palladium(0) (0.124 g, 0.107 mmol), and potassium fluoride (0.355 g, 6.11 mmol) in toluene (19 mL) and water (5 mL), at 100° C. for 17.5 hr. Cool the reaction, partition the layers and extract the aqueous layer with ethyl acetate. Wash the combined organic layers with saturated aqueous sodium chloride, dry (magnesium sulfate), concentrate and purify (silica gel chromatography, eluting with 0:100 to 35:65 ethyl acetate:hexanes), to give 2-chloro-3-(4-chlorophenyl)-pyrazine (0.199 g, 44%).

Couple 2-chloro-3-(4-chlorophenyl)-pyrazine (0.148 g, 0.710 mmol) and piperazine-1-carboxylic acid t-butyl ester (0.216 g, 1.16 mmol), using 2-(dicyclohexylphosphino)biphenyl (0.0321 g, 0.0916 mmol), tris(dibenzylideneacetone) dipalladium (0.0328 g, 0.0388 mmol), and the sodium salt of 2-methylpropan-2-ol (0.104 g, 1.09 mmol) in toluene (9 mL) at 82° C. for 17 hr. Cool the reaction to room temperature, dilute with diethyl ether (50 mL), filter through a 1 cm pad of silica gel, rinse the pad with diethyl ether (2×25 mL), combine the organic solutions, concentrate and purify (silica gel chromatography, eluting with 0:100 to 1:1 ethyl acetate:hexanes) to give 3'-(4-chloro-phenyl)-2,3,5,6-tetrahydro-[1,2'] bipyrazinyl-4-carboxylic acid t-butyl ester (0.143 g, 56%). MS (ES): m/z=303 [M+H-isobutylene]+.

Dissolve 3'-(4-chloro-phenyl)-2,3,5,6-tetrahydro-[1,2']bipyrazinyl-4-carboxylic acid t-butyl ester in DCM (10 mL), add 4 M aqueous HCl (5 equiv) and stir for 2 hr. at ambient temperature. Concentrate under reduced pressure, dissolve in methanol (2 mL) and purify by SCX, eluting the product from the ion-exchange resin using 2 M NH$_3$ in methanol, to give the title preparation (0.103 g, 100%). MS (ES): m/z=259 [M+H]+.

PREPARATION 9

3'-(4-Trifluoromethyl-phenyl)-3,4,5,6-tetrahydro-2H-[1,2']bipyrazine

Prepare 2-chloro-3-(4-trifluoromethylphenyl)-pyrazine in 30% according to the procedure used to make 2-chloro-3-(4-chlorophenyl)-pyrazine. Couple 2-chloro-3-(4-trifluoromethylphenyl)-pyrazine (0.570 g, 2.20 mmol) and piperazine (4.31 g, 50.0 mmol), at 125° C. for 111 min. Cool the reaction to about 70° C., add water (50 mL), stir until the reaction temperature is below 35° C. and dilute with DCM (70 mL). Separate the layers, extract the aqueous layer with DCM (2×70 mL), wash the combined organic layers with saturated aqueous sodium chloride, dry (magnesium sulfate), concentrate and purify (silica gel chromatography, eluting with 0:100 to 1:1 ethyl acetate:hexanes), to give the title preparation (0.384 g, 57%). MS (ES): m/z=309 [M+H]+.

PREPARATION 10

2-chloro-3-(3,4-dichloro-phenyl)-pyrazine

Dissolve 2,3-dichloropyrazine (2.42 g, 2.03 mmol) and 3,4-dichlorobenzene boronic acid (0.406 g, 2.13 mmol) in toluene (6 mL). Add a solution of potassium fluoride (0.36 g; 6.2 mmol) in deionized water (5 mL). Add tetrakis triphenylphosphine (0.124 gm; 0.11 mmol). Reflux the reaction for 17 hr.s, cool to ambient temperature, and add EtOAc (10 mL) and water (10 mL). Separate the organic layer, re-extract the aqueous layer with EtOAc (2×40 mL), and combine the organic layers. Wash the organic solution with saturated aq NaHCO$_3$ and brine (2×), dry over MgSO$_4$, filter and concentrate. Purify via chromatography on silica gel eluting 0-40% ethyl acetate/hexanes to give the title preparation (0.124 g, 23% yield). MS (ES) m/z: 274, 276 (M)+.

PREPARATION 11

3'-(3,4-dichloro-phenyl)-3,4,5,6-tetrahydro-2H-[1,2']bipyrazine

Combine 2-chloro-3-(3,4-dichloro-phenyl)-pyrazine (0.124 g, 0.477 mmol) and piperazine (1.40 gm; 16.3 mmol) and heat the mixture for 2 hr. at 120° C. Cool to room temperature, and add DCM (50 mL) and water (50 mL). Separate the layers and extract the aqueous layer with DCM (2×25 mL). Combine the organic layers, wash with brine, dry ($MgSO_4$) and concentrate. Purify via chromatography on silica gel eluting 0-15% methanol in DCM to give the title preparation (0.118 gm, 80%). MS (ES+) m/z: 310 (M+H)+.

PREPARATION 12

4-(3,4,5,6-Tetrahydro-2H-[1,2']bipyrazinyl-3'-yl)-benzonitrile

Dissolve 3'-chloro-2,3,5,6-tetrahydro-[1,2']bipyrazinyl-4-carboxylic acid t-butyl ester (9.19 g, 30.8 mmol) and 4-cyanobenzeneboronic acid (5.18 g, 35.2 mmol) in N,N-dimethylacetamide (90 mL) and water (35 mL), purge with nitrogen for 0.5 hr. and then add tetrakis(triphenylphosphine)palladium(0) (0.170 g, 0.15 mmol). Heat for 3 hr. at 110° C., allow to cool about 1.5 hr. to room temperature, filter and then dry the solid in an oven overnight to give 3'-(4-cyanophenyl)-2,3,5,6-tetrahydro-[1,2']bipyrazinyl-4-carboxylic acid t-butyl ester as a white solid (9.94 g, 88%). MS (ES): m/z=366 $[M+H]^+$. Add 4 M HCl in 1,4-dioxane (10 mL) to 3'-(4-cyanophenyl)-2,3,5,6-tetrahydro-[1,2']bipyrazinyl-4-carboxylic acid t-butyl ester (3.29 g, 9.0 mmol). Add more 4 M HCl in 1,4-dioxane (10 mL) to the reaction mixture and heat at 40° C. for 3 hr. Filter off the solid and wash with a mixture of 1,4-dioxane/isohexane to give the dihydrochloride salt as a yellow solid (4.2 g). MS (ES): m/z=266 $[M+H]^+$. Dissolve the dihydrochloride in water (20 mL), add 2 N sodium hydroxide (10 mL), extract with DCM and concentrate the DCM extract to give the title preparation as a yellow solid (1.8 g). MS (ES): m/z=266 $[M+H]^+$.

PREPARATION 13

3'-(4-Methanesulfonyl-phenyl)-3,4,5,6-tetrahydro-2H-[1,2']bipyrazine

Dissolve 3'-chloro-2,3,5,6-tetrahydro-[1,2']bipyrazinyl-4-carboxylic acid t-butyl ester (6.92 g, 30.75 mmol), potassium carbonate (7.34 g, 53.09 mmol) and 4-methanesulfonylbenzeneboronic acid (5.31 g, 26.55 mmol) in N,N-dimethylacetamide (90 mL) and purge for 15 min. Add water (35 mL) and the mixture further purged for 15 min. Add tetrakis(triphenylphosphine)palladium(0) (0.130 g, 0.11 mmol) and heat for 2 hr. 10 min. at 110° C. Allow to cool to 65° C., add water (30 mL) and t-butyl methyl ether (70 mL) and stir for 0.5 hr. Filter off the solid and dry in a vacuum oven to give 3'-(4-methanesulfonylphenyl)-2,3,5,6-tetrahydro-[1,2']bipyrazinyl-4-carboxylic acid t-butyl ester (8.3 g, 86%). MS (ES): m/z=419 $[M+H]^+$.

Deprotect using the method used in Preparation 12 to obtain the title preparation in essentially quantitative yield. MS (ES): m/z=319.1 $[M+H]^+$.

PREPARATION 14

3'-(4-Methoxyphenyl)-2,3,5,6-tetrahydro-[1,2']bipyrazine

Use the method used to make 2-chloro-3-(4-chlorophenyl)-pyrazine, using 4-methoxyphenylboronic acid to obtain 2-chloro-3-(4-methoxyphenyl)-pyrazine (54% yield).

Couple 2-chloro-3-(4-methoxyphenyl)-pyrazine (0.236 g, 1.07 mmol) and piperazine (3.10 g, 36.0 mmol) in tetrahydrofuran (5 mL) and heat at 120° C. for 2 hr. Purify using silica gel chromatography, eluting with 0:100 to 20:80 methanol:DCM, to give the title preparation (0.220 g, 76%). MS (ES): m/z=271 $[M+H]^+$.

PREPARATION 15

Alternative pathway for 3'-(4-methoxyphenyl)-2,3,5,6-tetrahydro-[1,2']bipyrazinyl Use the method of Preparation 3, using 4-methoxyphenylboronic acid, to obtain the title preparation (70% overall yield). MS (ES): m/z=271.2 $[M+H]^+$.

PREPARATION 16

3'-(4-Ethoxyphenyl)-3,4,5,6-tetrahydro-2H-[1,2']bipyrazine

Couple 3'-chloro-2,3,5,6-tetrahydro-[1,2']bipyrazinyl-4-carboxylic acid t-butyl ester (0.726 g, 2.43 mmol) and 4-ethoxyphenylboronic acid (0.95 g, 5.991 mmol), in the presence of triphenylphosphine (0.202 g, 0.770 mmol), palladium acetate (0.056 g, 0.243 mmol), sodium carbonate (3.8 mL of a 2 N solution in water) in a mixture of acetonitrile (42 mL) and water (8 mL). Reflux for 3 hr. Purify by silica gel chromatography, eluting with 0:100 to 25:75 ethyl acetate:hexanes, to give 3'-(4-ethoxyphenyl)-2,3,5,6-tetrahydro-[1,2']bipyrazinyl-4-carboxylic acid t-butyl ester (1.79 g, 96%).

Deprotect 3'-(4-ethoxyphenyl)-2,3,5,6-tetrahydro-[1,2']bipyrazinyl-4-carboxylic acid t-butyl ester (1.80 g, 4.7 mmol) using 4 M HCl in 1,4-dioxane (38 mL) in DCM (100 mL). Concentrate and dissolve the residue in DCM and 10% aqueous sodium carbonate. Separate the layers and extract the aqueous layer with DCM (2×150 mL). Combine the organic layers, wash with saturated aqueous sodium chloride, dry (magnesium sulfate) and concentrate to give the title preparation (1.12 g, 84%). MS (ES): m/z=285 $[M+H]^+$.

PREPARATION 17

3'-(4-Isopropoxyphenyl)-2,3,5,6-tetrahydro-2H-[1,2']bipyrazine

Couple 3'-chloro-2,3,5,6-tetrahydro-[1,2']bipyrazinyl-4-carboxylic acid t-butyl ester (0.135 g, 0.452 mmol) and 4-isopropoxyphenylboronic acid (0.134 g, 0.743 mmol), in the presence of triphenylphosphine (0.0482 g, 0.184 mmol), palladium acetate (0.0118 g, 0.0526 mmol), aqueous 2 N sodium carbonate (0.3 mL) in a mixture of n-propanol (4 mL) and water (0.3 mL). Reflux for 17.5 hr.s, cool to room temperature and extract with DCM. Purify by silica gel chromatography, eluting with 0:100 to 1:1 ethyl acetate:hexanes, to give 3'-(4-isopropoxyphenyl)-2,3,5,6-tetrahydro-[1,2']bipyrazinyl-4-carboxylic acid t-butyl ester (0.144 g, 80%).

PREPARATION 18

3'-(4-Trifluoromethoxyphenyl)-3,4,5,6-tetrahydro-2H-[1,2']bipyrazine

Dissolve 3'-chloro-2,3,5,6-tetrahydro-[1,2']bipyrazinyl-4-carboxylic acid t-butyl ester (0.400 g, 1.34 mmol) in toluene (2.68 mL). Add 4-(trifluoromethoxy)phenylboronic acid (0.303 g, 1.47 mmol), followed by tetrakis(triphenylphosphine)palladium(0) (0.077 g, 0.067 mmol). Add ethanol (2.68 mL), followed by a 2 N aqueous sodium carbonate solution (2.68 mL). Reflux reaction for 18 hr. Cool reaction to room temperature and concentrate. Add ethyl acetate and wash with water. Extract water layer one time with ethyl acetate. Dry (magnesium sulfate), filter, concentrate and purify (silica gel chromatography, eluting with 0:100 to 20:80 ethyl acetate:hexanes), to give 3'-(4-trifluoromethoxyphenyl)-2,3,5,6-tetrahydro-[1,2']bipyrazinyl-4-carboxylic acid t-butyl ester (534 mg, 94%). MS (ES): m/z=425 [M+H]$^+$.

Deprotect using the method in Preparation 16 to provide the title preparation (100% yield). MS (ES): m/z=271.2 [M+H]$^+$.

PREPARATION 19

3'-(2-Trifluoromethylphenyl)-3,4,5,6-tetrahydro-2H-[1,2']bipyrazine Dihydrochloride Dissolve 3'-chloro-2,3,5,6-tetrahydro-[1,2']bipyrazinyl-4-carboxylic acid t-butyl ester (1.00 g, 3.35 mmol) in N,N-dimethylacetamide (purged with nitrogen) (12 mL). Add potassium carbonate (1.11 g, 8.04 mmol) and 2-trifluoromethylbenzeneboronic acid (764 mg, 4.02 mmol) then purge with nitrogen for 15 min. Add deoxygenated water (6 mL) and tetrakis(triphenylphosphine)palladium(0) (0.039 g, 0.034 mmol) and purge with nitrogen for 15 min. Heat at 115° C. for 21 hr. under nitrogen. Cool to room temperature, add water (20 mL) and extract with DCM (4×20 mL). Concentrate the DCM extracts and purify (silica gel chromatography, eluting with 10:90 to 20:80 ethyl acetate:isohexane), to give 3'-(2-trifluoromethylphenyl)-2,3,5,6-tetrahydro-[1,2']bipyrazinyl-4-carboxylic acid t-butyl ester (408 mg, 29%). MS (ES): m/z=409 [M+H]$^+$.

Suspend 3'-(2-trifluoromethylphenyl)-2,3,5,6-tetrahydro-[1,2']bipyrazinyl-4-carboxylic acid t-butyl ester (408 mg, 1.00 mmol) in HCl in diethyl ether (1 M, 10 mL), stir for 2 hr. then concentrate in vacuo. Add more HCl in diethyl ether (1 M, 20 mL) and stir overnight at room temperature and concentrate. Add HCl in dioxane (4 M, 10 mL) and stir for 2 hr.s, then concentrate to give the title preparation as yellow solid (471 mg, 123%). MS (ES): m/z=309 [M+H]$^+$.

PREPARATION 20

3'-(2,6-Dimethylphenyl)-3,4,5,6-tetrahydro-2H-[1,2']bipyrazine dihydrochloride

Dissolve 3'-chloro-2,3,5,6-tetrahydro-[1,2']bipyrazinyl-4-carboxylic acid t-butyl ester (1.00 g, 3.35 mmol) in N,N-dimethylacetamide (purged with nitrogen) (12 mL). Add potassium carbonate (1.11 g, 8.04 mmol) then 2,6-dimethylbenzeneboronic acid (602 mg, 4.02 mmol) and purge with nitrogen for 10 min. Add deoxygenated water (6 mL) and tetrakis(triphenylphosphine)palladium(0) (0.039 g, 0.034 mmol) and purge with nitrogen for 10 min. Heat at 115° C. for 20 hr. under nitrogen. Cool to room temperature, add water (20 mL), extract with DCM (3×20 mL) and pass through an IST Phase Separator Frit® and concentrate. Dissolve in methanol, filter off solid and purify filtrate by SCX-2® chromatography washing with methanol then eluting with 2 M ammonia in methanol. Concentrate, then stir in HCl in dioxane (4 M, 50 mL) for 3 hr. at room temperature. Reduce solvent, add potassium carbonate (2 g), filter and concentrate filtrate. Purify by SCX-2® chromatography, washing with methanol then eluting with 4 M ammonia in methanol, and concentrate. Add HCl in diethyl ether (1 M, 20 mL) and concentrate, then dry under vacuum at 40° C. to give the title preparation as yellow crystals (650 mg, 57%). MS (ES): m/z=269 [M+H]$^+$.

PREPARATION 21

3'-(2-Fluoro-3-trifluoromethyl-phenyl)-3,4,5,6-tetrahydro-2H-[1,2']bipyrazine

Combine 1-bromo-2-fluoro-3-trifluoromethylbenzene (0.424 g, 1.77 mmol), 5,5,5',5'-tetramethyl-[2,2']bi[1,3,2]dioxaborinanyl] (0.458 g, 2.03 mmol), 1,1'-bis(diphenylphosphino)ferrocene dichloropalladium (0.0632 g, 0.0774 mmol), and potassium acetate (0.499 g, 5.08 mmol) in DMF (10 mL), and purge with nitrogen for 0.5 hr. Heat for 2 hr. at 80° C. and cool to room temperature. Add 3'-chloro-2,3,5,6-tetrahydro-[1,2']bipyrazinyl-4-carboxylic acid t-butyl ester (0.406 g, 1.36 mmol), sodium carbonate (4.0 mL of a 2M solution in water,) and bis(diphenylphosphino)ferrocene dichloropalladium (0.052 g, 0.0638 mmol). Heat the reaction at 80° C. for 20 hr. Purify by silica gel chromatography, eluting with 5:95 to 40:60 ethyl acetate:hexanes to give the 3'-(2-fluoro-3-trifluoromethyl-phenyl)-2,3,5,6-tetrahydro-[1,2']bipyrazinyl-4-carboxylic acid t-butyl ester (0.102 g, 18%).

Add 4 M HCl in 1,4-dioxane (5 mL) to a solution of 3'-(2-fluoro-3-trifluoromethyl-phenyl)-2,3,5,6-tetrahydro-[1,2']bipyrazinyl-4-carboxylic acid t-butyl ester (0.101 g, 0.237 mmol) in DCM (10 mL) and stir for 19 hr. Concentrate, dissolve the residue in methanol (20 mL) and purify by SCX chromatography (pre-wash column with methanol), load material, elute with 2 M ammonia in methanol, and concentrate to give the title preparation as a yellow solid (0.0985 g). MS (ES): m/z=327 [M+H]$^+$.

PREPARATION 22

3'-(4-Fluoro-3-trifluoromethyl-phenyl)-3,4,5,6-tetrahydro-2H-[1,2']bipyrazine

Use the procedure of Preparation 21, using 1-bromo-4-fluoro-3-trifluoromethylbenzene to obtain the title preparation (71% overall yield). MS (ES): m/z=327 [M+H]$^+$.

PREPARATION 23

1-[2-(4-Fluorophenyl)-pyridin-3-yl]-piperazine

Dissolve 2-chloro-3-iodopyridine (4.00 g, 16.74 mmol) in anhydrous toluene (25 mL). Add piperazine-1-carboxylic acid t-butyl ester (2.96 g, 15.90 mmol), followed by palladium acetate (0.113 g, 0.50 mmol), 2,2'-bis(diphenylphosphino)-1,1'-binaphthyl (0.313 g, 0.502 mmol), triethylamine (0.034 g, 0.047 mL, 0.335 mmol) and cesium carbonate (27.3 g, 83.7 mmol). Heat at reflux for 18 hr. Concentrate and partition the residue between DCM and a saturated solution of sodium bicarbonate. Extract the aqueous phase twice with DCM and once with ethyl acetate. Dry the combined organic extracts (sodium sulfate), filter, concentrate and purify (silica gel chromatography, eluting with 5:95 to 20:80 ethyl acetate: hexanes), to give 4-(2-Chloropyridin-3-yl)-piperazine-1-carboxylic acid t-butyl ester (54%). MS (ES): m/z=298 [M+H].

Dissolve 4-(2-chloropyridin-3-yl)-piperazine-1-carboxylic acid t-butyl ester (2.7 g, 9.1 mmol) in toluene (30 mL). Add 4-fluorophenylboronic acid (1.92 g, 13.70 mmol) followed by bis(dibenzylideneacetone)palladium(0) (0.42 g, 0.46 mmol), 1,2,3,4,5-pentaphenyl-1'-(di-t-butylphosphino)ferrocene (CTC-Q-PHOS) (0.65 g, 0.91 mmol) and potassium phosphate (5.8 g, 27.3 mmol). Heat the reaction mixture at 100° C. for 23 hr. Cool to room temperature, concentrate and partition the residue between ethyl acetate and 1 N sodium hydroxide (pH=11). Dry (sodium sulfate), filter, concentrate and purify (silica gel chromatography, eluting with 20:80 ethyl acetate: hexanes), to give 4-[2-(4-fluorophenyl)-pyridin-3-yl]-piperazine-1-carboxylic acid t-butyl ester (28%). MS (ES): m/z=358 [M+H].

Dissolve 4-[2-(4-fluorophenyl)-pyridin-3-yl]-piperazine-1-carboxylic acid t-butyl ester (0.9 g, 2.52 mmol) in DCM (25 mL). Add trifluoroacetic acid (8.6 g, 5.8 mL, 75.6 mmol). Stir the mixture at room temperature for 2 hr. Purify by a SCX ion-exchange column to give the title preparation. MS (ES): m/z=258 [M+H].

PREPARATION 24

1-[2-(2-Fluoro-phenyl)-pyridin-3-yl]-piperazine

Dissolve 2-chloro-3-iodopyridine (2.0 g, 8.37 mmol) in toluene (7 mL). Add piperazine-1-carboxylic acid t-butyl ester (1.2 g, 6.4 mmol), followed by the addition of tris(dibenzylideneacetone)dipalladium(0) (0.12 g, 0.13 mmol), 4,5-bis(diphenyl-phosphino)-9,9-dimethylxanthene (0.23 g, 0.39 mmol), and sodium t-butoxide (0.93 g, 9.7 mmol). Heat at 100° C. for 3.5 hr. Concentrate and partition the residue between EtOAc and water. Extract the aqueous phase twice with ethyl acetate. Wash combined organic layers with brine. Dry the organic extracts (sodium sulfate), filter, concentrate and purify (silica gel chromatography, eluting with 0:100 to 20:80 ethyl acetate:hexanes), to give 4-(2-Chloro-pyridin-3-yl)-piperazine-1-carboxylic acid t-butyl ester (95%). MS (ES): m/z=298 [M+H]+.

Dissolve 4-(2-chloropyridin-3-yl)-piperazine-1-carboxylic acid t-butyl ester (0.9 g, 3.0 mmol) in a mixture of 5 mL 1,2 dimethoxyethane and 4 mL water. Add 2-fluorophenylboronic acid (0.51 g, 3.64 mmol) followed by tetrakis(triphenylphosphine) palladium(0) (0.35 g, 0.30 mmol), and potassium carbonate (1.13 g, 8.2 mmol). Heat the reaction mixture at 100° C. for 22 hr. Cool to room temperature, concentrate and partition the residue between ethyl acetate and water. Extract water layer with ethyl acetate. Wash combined organic layers with brine. Dry organic extracts (sodium sulfate), filter, concentrate and purify (silica gel chromatography, eluting with 10:90 to 30:70 ethyl acetate:hexanes), to give 4-[2-(2-Fluoro-phenyl)-pyridin-3-yl]-piperazine-1-carboxylic acid t-butyl ester (91%). MS (ES): m/z=358 [M+H]+.

Deprotect using the method used in Preparation 21 to obtain the title preparation (100% yield). MS (ES): m/z=258 [M+H]+.

PREPARATION 25

1-[3-(4-Fluorophenyl)-pyridin-2-yl]-piperazine

Dissolve 2-bromopyridine (5 mL, 51.3 mmol) in tetrahydrofuran (125 mL). Cool to −78° C. and add lithium diisopropylamide (28.2 mL, 56.4 mmol, 2 M solution in heptane/tetrahydrofuran/ethylbenzene). Stir for 45 min. at −78° C., add zinc chloride (102.5 mL, 51.3 mmol, 0.5 M solution in tetrahydrofuran) and warm to 25° C. for one hr. Add 1-fluoro-4-iodobenzene (5.91 mL, 51.3 mmol) and tetrakis(triphenylphosphine)palladium(0) (2.96 g, 2.56 mmol) and reflux the mixture for 18 hr. Cool the mixture to room temperature, dilute with saturated aqueous sodium bicarbonate and extract 3 times with DCM. Combine the organic extracts, dry (sodium sulfate), filter and purify (silica gel chromatography, eluting with 20:80 ethyl acetate:hexanes) to give 2-bromo-3-(4-fluorophenyl)-pyridine (4.27 g, 33% yield).

Dissolve 2-bromo-3-(4-fluorophenyl)-pyridine (4.4 g, 17.5 mmol) in toluene (185 mL) and add piperazine (4.5 g, 52.4 mmol), tris(dibenzylideneacetone)dipalladium(0) (0.8 g, 0.873 mmol), sodium-t-butoxide (2.35 g, 24.4 mmol) and racemic-2,2'-bis(diphenylphosphino)-1,1'-binaphthyl (1.63 g, 2.62 mmol). Reflux the mixture for 18 hr.s, then cool to room temperature and filter through Celite®. Dilute the mixture with ethyl acetate and wash with saturated aqueous sodium bicarbonate, saturated aqueous sodium chloride, dry (sodium sulfate), filter, concentrate and purify (silica gel chromatography, eluting with 15:85 2 M ammonia in methanol:DCM) to give the title preparation as a yellow solid (3.9 g, 87%). MS (APCI): m/z=258 [M+H]+.

PREPARATION 26

1-(3-Phenyl-pyridin-2-yl)-piperazine

Add 3-bromo-2-chloro-pyridine (10.08 g, 52.4 mmol) to piperazine (45 g) and piperazine dihydrochloride (83.4 g). Heat the mixture to 190° C. with stirring for one hr. Allow the mixture to cool to about 80° C. then pour the material into water and extract 5 times with DCM. Dry the solution (sodium sulfate), filter and concentrate. Purify using silica gel chromatography, eluting with 15:85 methanol (with 2 M ammonia): DCM to give 1-(3-bromo-pyridin-2-yl)-piperazine as a white solid (8.98 g, 71%).

Dissolve 1-(3-bromo-pyridin-2-yl)-piperazine (0.579 g, 2.39 mmol) in ethylene glycol dimethyl ether (8 mL). Add sodium carbonate (2 M in water, 2.6 mL) then phenylboronic acid (0.321 g, 2.63 mmol). Add tetrakis(triphenylphosphine) palladium(0) (0.138 g, 0.120 mmol) and reflux for 18 hr. Cool to room temperature then dilute with saturated aqueous sodium bicarbonate and extract 3 times with ethyl acetate. Dry (sodium sulfate), filter, concentrate and purify (silica gel chromatography, eluting with 15:85 methanol (with 2 M ammonia:DCM), to give the title preparation as a yellow oil (0.404 g, 71%). MS (ES): m/z=240 [M+H]+.

Alternatively, 1-(3-Phenyl-pyridin-2-yl)-piperazine may be made as follows: 3-phenyl-pyridine 1-oxide: Dissolve 3-phenylpyridine (5.0 g, 32.2 mmol) in glacial acetic acid (20 mL). Add 30% hydrogen peroxide (3.25 mL, 28.6 mmol, 30% in water). Heat the reaction to 80° C. for 2.25 hours. Add 30% hydrogen peroxide (4.0 mL, 35.2 mmol, 30% in water). Heat the reaction at 80° C. for 1.75 hours. Add 30% hydrogen peroxide (1.0 mL, 8.8 mmol, 30% in water). Heat the reaction at 80° C. for 1.5 hours. Cool the reaction to ambient temperature over night. Concentrate the reaction mixture under reduced pressure but not to dryness. Purify the residue by silica gel chromatography. Elute with ethyl acetate-hexanes to remove impurities then elute with methanol-dichloromethane to give 4.4 g (80%) of 3-phenyl-pyridine 1-oxide as a white solid. MS (m/z): 172 (M+1).

2-chloro-3-phenyl-pyridine: Dissolve 3-phenyl-pyridine 1-oxide (1.0 g, 5.84 mmol) in phosphorus oxychloride (14 mL, 153 mmol). Heat the reaction to 105° C. for 6 hours, cool to ambient temperature and pour reaction mixture slowly onto ice with stirring to quench the excess phosphorus oxychloride. Basify with concentrated ammonium hydroxide and extract with dichloromethane. Wash the organic extract with brine, dry over sodium sulfate, filter and concentrate under reduced pressure. Purify the residue by silica gel chromatography (eluent: ethyl acetate-hexanes) to give 315 mg (28%) of 2-chloro-3-phenyl-pyridine as a yellow liquid. MS (m/z): 190 (M+1, 100), 192 (M+1, 60). $^1$H NMR (400 MHz, DMSO-$d_6$) δ 8.42 (dd, 1H, J=4.6, 2.0 Hz), 7.87 (dd, 1H, J=7.5, 1.8 Hz), 7.54-7.41 (m, 6H).

1-(3-phenyl-pyridin-2-yl)-piperazine: Heat a mixture of 2-chloro-3-phenyl-pyridine (1.12 g, 5.9 mmol) and piperazine (5.08 g, 59.0 mmol) in a sealed tube at 165° C. for 23 hours. Cool to ambient temperature. Dissolve the reaction mixture in water and ethyl acetate. Extract the aqueous layer with ethyl acetate (3×). Wash the organic extracts with water (2×) and brine. Re-extract the water washes with ethyl acetate. Combine all ethyl acetate extracts, dry over sodium sulfate, filter and concentrate under reduced pressure. Purify the residue by silica gel chromatography (eluent: 2N ammonia in methanol-dichloromethane) to give 1.36 g (96%) of the title preparation as a yellow oil. HRMS-FAB (m/z): [M+H]$^+$ calc'd for $C_{15}H_{18}N_3$, 240.1500; found, 240.1492.

PREPARATIONS 27-31

Are Prepared Essentially as Described for Preparation 26 Using the Appropriate Boronic Acid and 1-(3-bromo-pyridin-2-yl)-piperazine

| Prep | Compound | Yield (%) | MS (ES) [M + H]$^+$ |
|---|---|---|---|
| 27 | 1-[3-(4-Trifluoromethyl-phenyl)-pyridin-2-yl]-piperazine | 84 | 308 |
| 28 | 1-[3-(3-Trifluoromethyl-phenyl)-pyridin-2-yl]-piperazine | 60 | 308 |
| 29 | 1-[3-(2,5-Difluoro-phenyl)-pyridin-2-yl]-piperazine | 77 | 276 |
| 30 | 1-[3-(5-Fluoro-2-methoxy-phenyl)-pyridin-2-yl]-piperazine | 86 | 288 |
| 31 | 1-[3-(2-Fluoro-phenyl)-pyridin-2-yl]-piperazine | 92 | 258 |

PREPARATION 32

3-Methyl-4-(4,4,5,5-tetramethyl-[1,3,2]dioxaborolan-2-yl)-benzonitrile

Stir together 4-bromo-3-methylbenzonitrile (5.20 mmol, 1.02 g), bis(pinacolato) diboron (5.62 mmol, 1.43 g), potassium acetate (15.6 mmol, 1.53 g), and palladium acetate (0.16 mmol, 40 mg) in dry N,N-dimethylformamide (20 mL). Purge the reaction for 30 min. then heat to 85° C. overnight. Partition between water (100 mL) and ethyl acetate (100 mL), wash aqueous layer with ethyl acetate (100 mL). Combine ethyl acetate washings and dry over magnesium sulfate, filter and concentrate in vacuo. Purify (silica gel chromatography, eluting with 0:100 to 20:80 ethyl acetate:isohexane) to give the title preparation as a white powder (560 mg, 44% yield). MS (ES): m/z=244 [M+H]$^+$.

PREPARATION 33

1-Bromo-2-ethanesulfonyl-ethane

Dissolve 2-ethanesulfonyl-ethanol (1.06 g, 7.67 mmol) in DCM (18 mL) and add phosphorus tribromide (0.8 mL, 8.44 mmol). Stir the mixture at room temperature overnight then decant the solution away from the settled oil. Wash the solution with saturated aqueous sodium bicarbonate then dry (sodium sulfate), filter and concentrate to give the title preparation as a yellow oil (0.582 g, 38%). $^1$H-NMR (400 MHz, CDCl$_3$) δ 3.67 (t, J=7.6 Hz, 2H), 3.46 (t, J=7.6 Hz, 2H), 3.06 (q, J=7.5 Hz, 2H), 1.41 (t, J=7.5 Hz, 3H).

PREPARATION 34

4-(3-Bromo-propyl)-1-methyl-1H-pyrazole

Dissolve 3-(1-methyl-1H-pyrazol-4-yl)-propan-1-ol (0.250 g, 1.783 mmol) in dry chloroform (15 mL). Add PS-triphenylphosphine resin (1.824 g, 3.923 mmol) and carbon tetrabromide (0.650 g, 1.961 mmol). Stir at room temperature under nitrogen for 3 hr. Filter reaction over paper with DCM. Concentrate filtrate in vacuo to obtain the title preparation (0.362 g, 100% yield). GC-MS (m/z): 202/204(M+), 95.

PREPARATION 35

1-Methyl-3-trifluoromethyl-1H-pyrazole-4-carbaldehyde

Dissolve 3-trifluoromethyl-1H-pyrazole-4-carboxylic acid ethyl ester (2.0 g, 9.61 mmol) in N,N-dimethylformamide (20 mL) and cool to 0° C. Add sodium hydride (0.58 g, 14.42 mmol, 60% dispersion in oil) and stir at 0° C. for 20 min. Add iodomethane (0.90 mL, 14.42 mmol) and allow to warm to room temperature over 18 hr. Partition between ethyl acetate (100 mL) and water (50 mL). Separate the organic layer and wash with water (5×50 mL) and saturated aqueous sodium chloride solution (50 mL). Dry (sodium sulfate), filter, concentrate and purify (silica gel chromatography, eluting with 90:10 hexanes:ethyl acetate), to give 1-methyl-3-trifluoromethyl-1H-pyrazole-4-carboxylic acid ethyl ester (1.74 g, 81.7%). $^1$H-NMR (400 MHz, CDCl$_3$) δ 7.92 (s, 1H), 4.27 (q, 2H), 3.95 (s, 3H), 1.33 (t, 3H).

Dissolve 1-methyl-3-trifluoromethyl-1H-pyrazole-4-carboxylic acid ethyl ester (1.74 g, 7.83 mmol) in tetrahydrofuran (100 mL) and cool to 0° C. Add diisobutylaluminum hydride (47.0 mL, 47.0 mmol, 1 M in toluene) dropwise over 15 min. Allow the reaction mixture to warm to room temperature over 16 hr. Partition between ethyl acetate (100 mL) and saturated aqueous potassium sodium tartrate solution (50 mL) and stir at room temperature for another 16 hr. Separate the organic layer; dry (sodium sulfate), filter and concentrate to give (1-methyl-3-trifluoromethyl-1H-pyrazol-4-yl)-methanol (1.42 g, 100%). $^1$H-NMR (400 MHz, CDCl$_3$) δ 7.42 (s, 1H), 4.63 (s, 2H), 3.90 (s, 3H), 1.80 (bs, 1H).

Dissolve (1-methyl-3-trifluoromethyl-1H-pyrazol-4-yl)-methanol (1.41 g, 7.83 mmol) in DCM (25 mL) and dimethylsulfoxide (2.22 mL, 31.3 mmol) and cool to −78° C. Add oxalyl chloride (1.91 mL, 21.9 mmol) dropwise over 15 min. and stir at −78° C. for an additional 1 hr. Add triethylamine (6.55 mL, 47.0 mmol) dropwise and stir another 1 hr. Quench with water (20 mL) and dilute with DCM (50 mL) and warm to room temperature for 1 hr. Separate the organic layer; dry (sodium sulfate), filter, concentrate and purify (silica gel chromatography, eluting with 80:20 hexanes:ethyl acetate), to give the title preparation (0.98 g, 71%). $^1$H-NMR (400 MHz, CDCl$_3$) δ 9.94 (s, 1H), 7.97 (s, 1H), 3.99 (s, 3H).

PREPARATION 36

1,5-Dimethyl-3-trifluoromethyl-1H-pyrazole-4-carbaldehyde

Dissolve 5-methyl-3-(trifluoromethyl)pyrazole (1.00 g, 6.66 mmol) in 60% aqueous acetic acid (13 mL). Add sodium acetate (0.819 g, 9.99 mmol) and cool to 0° C. Add bromine (1.17 g, 7.33 mmol) dropwise over 10 min. Stir at 0° C. for 3 hr, then at room temperature for 18 hr. Add ethyl acetate and saturated aqueous sodium sulfite solution. Separate organics and wash one time with saturated aqueous sodium bicarbonate solution followed by saturated aqueous sodium chloride. Dry (magnesium sulfate), filter and concentrate to give 4-bromo-5-methyl-3-trifluoromethyl-1H-pyrazole (1.50 g, 100%). GC-MS: m/z=229 [M+].

Dissolve 4-bromo-5-methyl-3-trifluoromethyl-1H-pyrazole (1.53 g, 6.66 mmol) in acetone (20 mL). Add potassium carbonate (1.84 g, 13.3 mmol) followed by iodomethane (2.84 g, 19.9 mmol). Stir at 70° C. for 18 hr. Cool to room temperature and concentrate. Add water and ethyl acetate and separate organics. Extract water layer 2 times with ethyl acetate. Dry combined ethyl acetate layers (magnesium sulfate), filter and concentrate to 4-bromo-1,5-dimethyl-3-trifluoromethyl-1H-pyrazole (1.08 g, 67%). GC-MS: m/z=243 [M+].

Dissolve 4-bromo-1,5-dimethyl-3-trifluoromethyl-1H-pyrazole (0.30 g, 1.23 mmol) in tetrahydrofuran (14.7 mL). Cool to −78° C. and add 1.7 M t-butyllithium in pentane (2.9 mL) dropwise. Stir for 3 min. at −78° C. and then add dimethylformamide (669 µL, 8.64 mmol). Stir for thirty min. at −78° C., then warm to 0° C. over 2 hr. Add 2 N hydrochloric acid (12.3 mL) and stir at room temperature for one hr. Separate layers and extract aqueous layer 2 times with DCM. Dry combined organic layers (magnesium sulfate), filter, concentrate and purify (silica gel chromatography eluting with 0:100 to 15:85 ethyl acetate:hexanes), to give the title preparation (79 mg, 33%). GC-MS: m/z=192 [M+].

PREPARATION 37

(1,3,5-Trimethyl-1H-pyrazol-4-yl)-acetaldehyde

Add pentane-2,4-dione (2.0 g, 20.6 mmol) in tetrahydrofuran (30 mL) to a chilled (0° C.) suspension of 60% sodium hydride (0.99 g, 24.7 mmol) in tetrahydrofuran (40 mL). Stir for 1 hr. Then add bromoacetic acid ethyl ester (2.73 mL, 24.7 mmol) in tetrahydrofuran (30 mL) dropwise. Stir at 0° C. to room temperature for 16 hr. Partition between diethyl ether (100 mL) and saturated aqueous ammonium chloride solution (50 mL). Separate organic layer, dry (sodium sulfate), filter, concentrate and purify (silica gel chromatography, eluting with 9:1 hexanes:ethyl acetate), to give 3-acetyl-4-oxopentanoic acid ethyl ester (3.34 g, 94%). $^1$H NMR (CDCl$_3$) δ 5.15 (q, 2H), 5.1 (t, 1H), 2.84 (d, 2H), 2.23 (s, 6H), 1.22 (t, 3H).

Dissolve 3-acetyl-4-oxopentanoic acid ethyl ester (3.35 g, 19.5 mmol) in glacial acetic acid (20 mL) and add methylhydrazine (1.13 mL, 21.4 mmol) dropwise. Stir the resulting mixture at room temperature for 16 hr. Concentrate and partition the residue between ethyl acetate (100 mL) and saturated aqueous sodium bicarbonate solution (50 mL). Separate organic layer, dry (sodium sulfate), filter, concentrate and purify (silica gel chromatography, eluting with 7:3 hexanes: ethyl acetate) to give (1,3,5-trimethyl-1H-pyrazol-4-yl)-acetic acid ethyl ester (2.8 g, 73%) as an oil. $^1$H NMR (CDCl$_3$) δ 4.08 (q, 2H), 3.67 (s, 3H), 3.29 (s, 2H), 2.18 (s, 6H), 1.21 (t, 3H).

Dissolve (1,3,5-trimethyl-1H-pyrazol-4-yl)-acetic acid ethyl ester (2.8 g, 14.3 mmol) in tetrahydrofuran (200 mL) and cool to −78° C. Add diisobutylaluminum hydride (42.8 mL, 42.8 mmol, 1 M in toluene) dropwise over 30 min. Stir an additional 2 hr. at −78° C. Partition between saturated aqueous potassium sodium tartrate solution (150 mL) and ethyl acetate (500 mL) and stir for 16 hr. at room temperature. Separate organic layer, dry (sodium sulfate), filter, concentrate and purify (silica gel chromatography, eluting with 1:1 hexanes:ethyl acetate), to give the title preparation (0.26 g, 12%). $^1$H NMR (CDCl$_3$) δ 9.54 (t, 1H), 3.71 (s, 3H), 3.38 (d, 2H), 2.15 (s, 3H), 2.14 (s, 3H).

PREPARATION 38

(1,3,5-Triethyl-1H-pyrazol-4-yl)-acetaldehyde

Combine 4-oxo-3-propionylhexanoic acid ethyl ester (2.49 g, 11.6 mmol) and hydrazine hydrate (0.70 g, 13.9 mmol) in glacial acetic acid (20 mL) and stir at room temperature for 88 hr. Concentrate to an oil. Partition this residue between ethyl acetate (100 mL) and saturated aqueous sodium bicarbonate solution (50 mL). Separate the organic layer; dry (sodium sulfate), filter and concentrate to provide (3,5-diethyl-1H-pyrazol-4-yl)-acetic acid ethyl ester (2.4 g, 98%). $^1$H-NMR (400 MHz, CDCl$_3$) δ 8.64 (bs, 1H), 4.08 (q, 2H), 3.35 (s, 2H), 2.61 (q, 4H), 1.21 (m, 9H).

Suspend sodium hydride (0.23 g, 5.71 mol, 60% dispersion in oil) in tetrahydrofuran (10 mL) and cool to 0° C. Add a solution of (3,5-diethyl-1H-pyrazol-4-yl)-acetic acid ethyl ester (1.0 g, 4.76 mmol) in tetrahydrofuran (10 mL) dropwise. After stirring at 0° C. for 30 min., add iodoethane (0.46 mL, 5.71 mmol). Allow the reaction mixture to warm to room temperature while stirring for 18 hr. Partition between ethyl acetate (100 mL) and saturated aqueous ammonium chloride solution (50 mL). Separate the organic layer, dry (sodium sulfate), filter and concentrate to give (1,3,5-triethyl-1H-pyrazol-4-yl)-acetic acid ethyl ester as an oil (0.92 g, 81%). $^1$H-NMR (400 MHz, CDCl$_3$) δ 4.09 (q, 2H), 4.01 (q, 2H), 3.33 (s, 2H), 2.58 (m, 4H), 1.38 (t, 3H), 1.20 (m, 9H).

Cool a solution of (1,3,5-triethyl-1H-pyrazol-4-yl)-acetic acid ethyl ester (0.92 g, 3.86 mmol) in tetrahydrofuran (50 mL) to −78° C. and add diisobutylaluminum hydride (16.2 mL, 16.2 mmol, 1 M in toluene) dropwise. Stir the resulting mixture for 5 hr. at −78° C. Quench the reaction mixture with saturated aqueous potassium sodium tartrate solution (30 mL) and ethyl acetate (100 mL) and stir at room temperature for 16 hr. Separate the organic layer; dry (sodium sulfate), filter and concentrate to give the title preparation as an oil (0.65 g, 87%). $^1$H-NMR (400 MHz, CDCl$_3$) δ 9.57 (t, 1H), 4.01 (q, 2H), 3.38 (d, 2H), 2.57 (q, 4H), 1.39 (t, 3H), 1.20 (t, 3H), 1.15 (t, 3H).

PREPARATION 39

3-(1,3,5-Trimethyl-1H-pyrazol-4-yl)-propionaldehyde

Dissolve ethyl 4-acetyl-5-oxohexanoate (2.00 g, 9.99 mmol) in acetic acid (21 mL). Add methyl hydrazine (589 µL, 10.99 mmol) and stir at room temperature for 18 hr. Concentrate and dissolve residue in ethyl acetate. Wash ethyl acetate layer with saturated aqueous sodium bicarbonate solution. Extract aqueous layer twice with ethyl acetate, dry (magnesium sulfate), filter, concentrate and purify (silica gel chromatography, eluting with 0:100 to 100% ethyl acetate:hexanes) to give 3-(1,3,5-trimethyl-1H-pyrazol-4-yl)-propionic acid ethyl ester (1.95 g, 93%). MS (ES): m/z=211 [M+H]$^+$.

Dissolve 3-(1,3,5-trimethyl-1H-pyrazol-4-yl)-propionic acid ethyl ester (1.94 g, 9.23 mmol) in tetrahydrofuran (78 mL). Cool to −78° C. in a dry ice/acetone bath and treat dropwise with 1 M diisobutylaluminum hydride in toluene (10.15 mL). Stir reaction mixture at −78° C. for one hr. and add 1 M diisobutylaluminum hydride in toluene (10.15 mL). Stir reaction mixture at −78° C. for one hr. and add 1 M diisobutylaluminum hydride in toluene (10.15 mL). Stir reaction mixture at −78° C. for 1 hr. and add 1 M diisobutylaluminum hydride in toluene (10.15 mL). Stir reaction mixture at −78° C. for 1 hr. and quench with aqueous saturated potassium sodium tartrate tetrahydrate solution. Add ethyl acetate (150 mL), and stir for 3 hr. at room temperature. Separate organic layer, extract aqueous layer 3 times with ethyl acetate, dry (magnesium sulfate), filter, concentrate and purify (silica gel chromatography, eluting with 1:1 to 100% ethyl acetate: hexanes), to give the title preparation (760 mg, 51%). GC-MS m/z=166 [M+].

PREPARATION 40

1-Benzyl-3,5-dimethyl-1H-pyrazole-4-carbaldehyde

Dissolve 2,4-pentanedione (5.09 g, 50.8 mmol) and benzylhydrazine dihydrochloride (10.91 g, 55.9 mmol) in acetic acid (40 mL). Slowly add triethylamine (15.6 mL, 0.112 mol) and stir the mixture for 18 hr. Concentrate the solution then dilute the residue with saturated aqueous sodium bicarbonate and extract 3 times with ethyl acetate. Dry (sodium sulfate), filter, concentrate and purify (silica gel chromatography, eluting with 40:60 hexanes:ethyl acetate), to give 1-benzyl-3,5-dimethyl-1H-pyrazole as a yellow oil (8.703 g, 92%).

Dissolve 1-benzyl-3,5-dimethyl-1H-pyrazole (3.088 g, 16.6 mmol) in N,N-dimethylformamide (12.8 mL) and heat the mixture to 95° C., then add phosphorus oxychloride (13.4 mL) dropwise. Stir the mixture for 3 hr. at 95° C. then cool and add ice water very slowly. Adjust the mixture to approximately pH=4 using 5 N sodium hydroxide, extract the black mixture with diethyl ether 3 times, dry (sodium sulfate) and filter to give the title preparation as a yellow solid (2.65 g, 75%). $^1$H-NMR (400 MHz, DMSO-d6) δ 2.282 (s, 3H); 2.433 (s, 3H); 5.233 (s, 2H); 7.13 (m, 2H); 7.21-7.34 (m, 3H); 9.800 (s, 1H).

PREPARATION 41

1-Benzyl-3,5-diethyl-1H-pyrazole-4-carbaldehyde

Use the methods of Preparation 40, using 3,5-heptanedione, to obtain the title preparation. $^1$H-NMR (400 MHz, DMSO-d6) δ 0.952 (t, J=7.6 Hz, 3H), 1.128 (t, J=7.5 Hz, 3H), 2.734 (q, J=7.6 Hz, 2H), 2.873 (q, J=7.5 Hz, 2H), 5.298 (s, 2H), 7.12 (m, 2H), 7.21-7.33 (m, 3H), 9.844 (s, 1H).

PREPARATION 42

3-Ethyl-1-phenyl-1H-pyrazole-4-carbaldehyde

Add acetic acid (1.00 mL, 17.45 mmol) and phenyl hydrazine (1.98 mL, 20.00 mmol) to a solution of 2-butanone (2.15 mL, 24.00 mmol) in ethanol (90 mL) at room temperature. Stir the reaction for 1 hr., then remove the solvents in vacuo to give N-[1-methyl-prop-(E)-ylidene]-N'-phenyl-hydrazine as a crude orange oil (3.21 g, 99%). MS (ES): m/z=163 [M+H]+.

To an ice cold solution of N,N-dimethylformamide (4.59 mL, 59.36 mmol) and phosphoryl chloride (5.52 mL, 59.36 mmol) add a solution of N-[1-methyl-prop-(E)-ylidene]-N'-phenyl-hydrazine (3.21 g, 19.79 mmol) in N,N-dimethylformamide (2 mL) dropwise. Warm to room temperature, then heat to 75° C. for 5 hr. Cool to room temperature and pour into an ice-cold solution of saturated potassium carbonate. Extract with DCM (3×20 mL), pass through an IST Phase Separator Frit® and concentrate. Purify (silica gel chromatography, eluting with 0:100 to 20:80 ethyl acetate:isohexane), to give the title compound as a brown solid (600 mg, 15%). MS (ES): m/z=201 [M+H]+.

PREPARATION 43

1-(4-Methoxybenzyl)-3,5-dimethyl-1H-pyrazole-4-carbaldehyde

Dissolve 3,5-dimethylpyrazole (0.331 g, 3.44 mmol) in N,N-dimethylformamide (7 mL) and add sodium hydride (0.165 g, 4.13 mmol). After 10 min., cool to 0° C. and add 4-methoxybenzyl chloride (0.654 mL, 4.82 mmol) dropwise. Stir the mixture at 25° C. for 18 hr. then dilute with saturated ammonium chloride. Extract with ethyl acetate 3 times, dry (sodium sulfate), filter, concentrate and purify (silica gel chromatography, eluting with 40:60 hexanes:ethyl acetate), to give 1-(4-methoxybenzyl)-3,5-dimethyl-1H-pyrazole as a colorless oil (0.682 g, 92%). MS (APCI): m/z=217 [M+H].

Use the method in Preparation 39 using 1-(4-methoxybenzyl)-3,5-dimethyl-1H-pyrazole to obtain the title preparation (46% yield). $^1$H-NMR (400 MHz, DMSO-d6) δ 2.27 (s, 3H), 2.43 (s, 3H), 3.67 (s, 3H), 5.15 (s, 2H), 6.85 (m, 2H), 7.10 (m, 2H), 9.79 (s, 1H).

PREPARATION 44

3,5-Dimethyl-1-pyridin-4-yl-1H-pyrazole-4-carbaldehyde

Use the method of Preparation 43 using pyridin-4-ylhydrazine to obtain the title preparation (62% yield for 4-(3,5-dimethylpyrazol-1-yl)-pyridine, MS (ES): m/z=174 [M+H]; then 60% yield for 3,5-dimethyl-1-pyridin-4-yl-1H-pyrazole-4-carbaldehyde, $^1$H-NMR (400 MHz, DMSO-d6) δ 2.15 (s, 3H), 2.40 (s, 3H), 7.61 (m, 2H), 8.69 (m, 2H), 9.95 (s, 1H).

PREPARATION 45

3,5-Dimethyl-1-pyridin-2-yl-1H-pyrazole-4-carbaldehyde

Dissolve 2-acetyl-3-oxobutyric acid ethyl ester (20.74 g, 0.120 mol) and 2-pyridylhydrazine (14.5 mL, 0.133 mol) in acetic acid (160 mL) and stir the mixture for 18 hr. Concentrate, dilute with DCM, wash with saturated sodium bicarbonate, dry (sodium sulfate), filter and concentrate to give 3,5-dimethyl-1-pyridin-2-yl-1H-pyrazole-4-carboxylic acid ethyl ester as an oil (28.6 g, 97%). MS (APCI): m/z=246 [M+H]$^+$.

Suspend lithium aluminum hydride (0.359 g, 9.46 mmol) in tetrahydrofuran (25 mL) at −10° C. and add 3,5-dimethyl-1-pyridin-2-yl-1H-pyrazole-4-carboxylic acid ethyl ester (1.160 g, 4.73 mmol) dropwise in tetrahydrofuran (5 mL). Allow the mixture to warm to 25° C. and stir for 4 hr. Cool the mixture to 0° C. then quench carefully with saturated sodium sulfate solution (1 mL). Allow the mixture to stir at room temperature for 2 hr. then filter off the precipitate, dry the solution and concentrate to give (3,5-dimethyl-1-pyridin-2-yl-1H-pyrazol-4-yl)-methanol as a yellow solid (0.821 g, 86%). $^1$H-NMR (400 MHz, DMSO) 8.408 (m, 1H); 7.889 (m, 1H); 7.738 (m, 1H); 7.256 (m, 1H); 4.269 (s, 2H); 2.459 (s, 3H); 2.181 (s, 3H)

Dissolve dimethylsulfoxide (0.324 mL, 4.56 mmol) in DCM (10 mL) and cool the solution to −78° C. Add oxalyl chloride (0.239 mL, 2.74 mmol) to the mixture dropwise and stir at −78° C. for 20 min. Add (3,5-dimethyl-1-pyridin-2-yl-1H-pyrazol-4-yl)-methanol (0.369 g, 1.82 mmol) in DCM (10 mL) and stir the mixture at −78° C. for one hr. Add triethylamine (1.27 mL, 9.12 mmol) to the mixture and warm to room temperature then stir for 18 hr. Add saturated aqueous sodium bicarbonate and extract the aqueous 3 times with DCM, dry organic solution then filter and concentrate. Purify using silica gel chromatography, eluting with 20:80 hexanes: ethyl acetate to give the title preparation as a yellow solid (0.358 g, 97%). MS (APCI): m/z=202 [M+H]$^+$.

PREPARATION 46

(3-Isobutyl-5-methyl-1-pyridin-2-yl-1H-pyrazol-4-yl)-acetaldehyde

Add a solution of 6-methylheptane-2,4-dione (5.0 g, 35.16 mmol) in tetrahydrofuran (50 mL) dropwise to a cooled suspension (0° C.) of sodium hydride (1.69 g, 42.2 mmol, 60% dispersion in oil) in tetrahydrofuran (50 mL). After 1 hr., add bromoacetic acid ethyl ester (4.28 mL, 38.68 mmol) dropwise and stir at 0° C. to room temperature over 88 hr. Partition the reaction mixture between ethyl acetate (200 mL) and saturated aqueous ammonium chloride solution (100 mL). Separate the organic layer, dry (sodium sulfate), filter and concentrate. Purify using silica gel chromatography (95:5 hexanes: ethyl acetate) to give 3-acetyl-6-methyl-4-oxoheptanoic acid ethyl ester (5.81 g, 73%). $^1$H-NMR (400 MHz, CDCl$_3$) δ 4.10 (m, 4H), 2.81 (d, 2H), 2.41 (t, 1H), 2.22 (s, 3H), 1.23 (m, 4H), 0.92 (m, 6H).

Combine 3-acetyl-6-methyl-4-oxoheptanoic acid ethyl ester (3.0 g, 13.1 mmol) and pyridin-2-yl-hydrazine (1.72 g, 15.72 mmol) in glacial acetic acid (25 mL) and stir at room temperature for 68 hr. Concentrate to an oil and partition the residue between ethyl acetate (150 mL) and saturated aqueous sodium bicarbonate solution (50 mL). Separate the organic layer, dry (sodium sulfate), filter and concentrate. Purify using silica gel chromatography, eluting with 90:10 hexanes:ethyl acetate, to give (3-isobutyl-5-methyl-1-pyridin-2-yl-1H-pyrazol-4-yl)-acetic acid ethyl ester (3.35 g, 85%). $^1$H-NMR (400 MHz, CDCl$_3$) δ 8.38 (m, 1H), 7.77 (m, 2H), 7.13 (m, 1H), 4.12 (q, 2H), 3.41 (s, 2H), 2.98 (d, 2H), 2.27 (s, 3H), 1.82 (m, 1H), 1.22 (t, 3H), 0.80 (d, 6H).

Dissolve (3-isobutyl-5-methyl-1-pyridin-2-yl-1H-pyrazol-4-yl)-acetic acid ethyl ester (3.35 g, 11.11 mmol) in tetrahydrofuran (50 mL) and cool to −78° C. Add diisobutylaluminum hydride (33.3 mL, 33.3 mmol, 1 M in toluene) dropwise. Continue stirring at −78° C. for 6 hr. Quench with saturated aqueous potassium sodium tartrate solution (50 mL) and warm to room temperature over 16 hr. Extract with ethyl acetate (2×100 mL). Combine organic layers, dry (sodium sulfate), filter and concentrate. Purify using silica gel chromatography, eluting with 90:10 hexanes:ethyl acetate, to give the title preparation (1.60 g, 56%). $^1$H-NMR (400 MHz, CDCl$_3$) δ 9.62 (t, 1H), 8.39 (m, 1H), 7.77 (m, 2H), 7.15 (m, 1H), 3.45 (d, 2H), 2.96 (d, 2H), 2.22 (s, 3H), 1.80 (m, 1H), 0.81 (d, 6H).

PREPARATION 47

3,5-Dimethyl-1-pyrimidin-2-yl-1H-pyrazole-4-carbaldehyde

Dissolve 2-chloropyrimidine (10.04 g, 87.7 mmol) in pyridine (200 mL) and add hydrazine (35.8 mL, 1.14 mol) to the mixture followed by pyridine (100 mL). Stir the mixture for 3 hr. at room temperature then concentrate. Suspend the residue in water and filter. Wash the cake with cold methanol. Collect the powder and dry under vacuum to give pyrimidin-2-ylhydrazine as a white powder (8.05 g, 83%).

Dissolve 2,4-pentanedione (0.81 mL, 7.85 mmol) and pyrimidin-2-yl-hydrazine (1.037 g, 9.42 mmol) in acetic acid (10 mL). Stir the mixture for 69 hr. at room temperature then concentrate. Dilute the residue with saturated aqueous sodium bicarbonate, extract 3 times with DCM, dry (sodium sulfate), filter and concentrate to give 2-(3,5-dimethylpyrazol-1-yl)-pyrimidine as a white solid (1.333 g, 97%). MS (ES): m/z=175 [M+H]$^+$.

Use the method of Preparation 43, using 2-(3,5-dimethylpyrazol-1-yl)-pyrimidine to obtain the title preparation (13% yield). $^1$H-NMR (400 MHz, DMSO-d6) δ 2.38 (s, 3H), 2.77 (s, 3H), 6.10 (m, 1H), 7.55 (m, 1H), 8.92 (m, 1H), 9.98 (s, 1H).

PREPARATION 48

5-Methyl-1-pyridin-2-yl-1H-pyrazole-4-carbaldehyde

Add ethyl acetoacetate (15 mL, 0.118 mol) to dimethoxymethyl-dimethyl-amine (19 mL, 0.142 mol) and reflux the mixture for one hr. Evaporate the mixture to give 2-dimethylaminomethylene-3-oxo-butyric acid ethyl ester (21.7 g, 99%).

Dissolve 2-dimethylaminomethylene-3-oxo-butyric acid ethyl ester (0.662 g, 3.57 mmol) and pyridin-2-yl-hydrazine (0.410 g, 3.75 mmol) in ethanol (15 mL) and reflux for 2 hr. Evaporate the mixture then dilute with saturated sodium bicarbonate and extract 3 times with ethyl acetate. Dry the solution (sodium sulfate), filter and concentrate. Purify using silica gel chromatography, eluting with 50:50 ethyl acetate: hexane to give 5-methyl-1-pyridin-2-yl-1H-pyrazole-4-carboxylic acid ethyl ester as a white solid (0.700 g, 85%). MS (ES): m/z=232 [M+H]$^+$.

Add lithium aluminum hydride (0.225 g, 5.92 mmol) to tetrahydrofuran (15 mL) at 0° C. then slowly add 5-methyl-1-pyridin-2-yl-1H-pyrazole-4-carboxylic acid ethyl ester (0.685 g, 2.96 mmol) in tetrahydrofuran (5 mL) dropwise. Warm the mixture to room temperature and stir for 2 hr. then cool the solution to 0° C. Add saturated aqueous sodium sulfate (0.5 mL), warm to room temperature then stir for 2 hr. Filter off the solid materials then dry the solution (sodium sulfate), filter and concentrate to give (5-methyl-1-pyridin-2-yl-1H-pyrazol-4-yl)-methanol as a white solid (0.501 g, 89%).

Dissolve dimethyl sulfoxide (0.751 mL, 10.6 mmol) in DCM (20 mL) and cool to −78° C. Add oxalyl chloride (0.577 mL, 6.62 mmol) dropwise in DCM (8 mL) and stir for 15 min. Add (5-methyl-1-pyridin-2-yl-1H-pyrazol-4-yl)-methanol (0.501 g, 2.65 mmol) in DCM (20 mL) dropwise and stir for one hr. at −78° C. Add triethylamine (1.85 mL, 13.2 mmol) and warm the mixture to room temperature for one hr. Dilute the mixture with saturated sodium bicarbonate and extract 3 times with DCM. Dry (sodium sulfate) the solution, filter and concentrate to give the title preparation as a white solid (0.496 g, 100%). MS (ES): m/z=188 [M+H]+.

PREPARATION 49

5-Methyl-1-pyridin-4-yl-1H-pyrazole-4-carbaldehyde

Dissolve 2-dimethylaminomethylene-3-oxo-butyric acid ethyl ester (0.550 g, 2.96 mmol), pyridin-4-yl-hydrazine hydrochloride (0.454 g, 3.12 mmol) and triethylamine (0.435 mL, 3.12 mmol) in ethanol (12 mL) and reflux for 2 hr. Evaporate the mixture then dilute with saturated sodium bicarbonate and extract 3 times with ethyl acetate. Dry (sodium sulfate) the solution, filter and concentrate. Purify using silica gel chromatography, eluting with 50:50 ethyl acetate:hexane to give 5-methyl-1-pyridin-4-yl-1H-pyrazole-4-carboxylic acid ethyl ester as a tan solid (0.520 g, 76%). MS (ES): m/z=232 [M+H]+.

Using the method of Preparation 48 using 5-methyl-1-pyridin-4-yl-1H-pyrazole-4-carboxylic acid ethyl ester, prepare the title preparation in essentially quantitative yield. $^1$H-NMR (400 MHz, DMSO-d6) δ 9.93 (s, 1H), 8.73 (m, 2H), 8.21 (d, 1H), 7.66 (m, 2H), 2.67 (s, 3H).

PREPARATION 50

1-(3,5-Dimethylisoxazol-4-ylmethyl)-1H-pyrazole-4-carbaldehyde

Add N,N-dimethylformamide (3 mL) to sodium hydride (0.092 g, 2.29 mmol) and stir at 0° C. Add 1-H-pyrazole-4-carboxaldehyde (0.200 g, 2.08 mmol) and stir at 0° C. for 20 min. Dissolve 4-chloromethyl-3,5-dimethylisoxazole (0.318 g, 2.18 mmol) in N,N-dimethylformamide (4 mL) and add to reaction mixture. Stir reaction at room temperature for 18 hr. Quench with aqueous saturated sodium bicarbonate solution. Add ethyl acetate and separate organic layer. Extract aqueous layer twice with ethyl acetate. Dry combined organic layers (magnesium sulfate), filter, concentrate and purify (silica gel chromatography, eluting with 25:75 to 75:25 ethyl acetate:hexanes), to give the title preparation (387 mg, 91%). GC-MS: m/z=205 [M+].

PREPARATION 51

1-(2-methylthiazol-4-ylmethyl)-1H-pyrazole-4-carbaldehyde

Prepare the title preparation using the method of Preparation 50 using 4-chloromethyl-2-methyl-1,3-thiazole, (350 mg, 81%). GC-MS: m/z=207 [M+].

PREPARATION 52

1-(2-Hydroxy-ethyl)-1H-pyrazole-4-carbaldehyde

Combine 1H-pyrazole-4-carbaldehyde (0.110 g, 1.14 mmol), 2-bromoethanol (0.172 g, 1.37 mmol), and potassium carbonate (0.236 g, 1.71 mmol) in acetonitrile (2 mL). Heat in microwave at 150° C. for 20 min. Cool to room temperature and filter, washing with acetonitrile. Concentrate filtrate to give the title preparation (0.155 g, 97%). GC-MS: m/z=140 [M+].

PREPARATION 53

1-Cyclopropylmethyl-1H-pyrazole-4-carbaldehyde

Add 1H-pyrazole-4-carbaldehyde (0.200 g, 2.08 mmol) to a suspension of sodium hydride (0.092 g, 2.29 mmol) in DMF (3 mL) at 0° C. Stir for 20 min. at 0° C. Add a solution of 1-(bromomethyl)cyclopropane (0.295 g, 2.18 mmol) in DMF (4 mL) dropwise to the reaction mixture. Stir reaction to ambient temperature for 18 hr. Quench with aqueous saturated sodium bicarbonate solution and add ethyl acetate. Separate organic layer. Extract aqueous layer twice with ethyl acetate, dry combined organics (magnesium sulfate), filter, concentrate and purify (silica gel chromatography, eluting with 0:100 to 60:40 ethyl acetate:hexanes) to give the title preparation (175 mg, 56%). GC-MS: m/z=150 [M+].

PREPARATION 54

1-Cyclopropyl-1H-pyrazole-4-carbaldehyde

Dissolve 1H-pyrazole-4-carboxaldehyde in N,N-dimethylformamide (1.9 mL). Add potassium carbonate (0.539 g, 3.90 mmol) and cyclopropylbromide (0.346 g, 2.86 mmol). Heat in a pressure tube to 130° C. for 18 hr. Cool to ambient temperature and add DCM and water. Separate layers and extract water layer 3 times with DCM. Wash combined DCM layers with brine, dry (magnesium sulfate), filter, and concentrated to give the free base of the title preparation. GC-MS: m/z=136 [M+].

PREPARATION 55

1-(2,2,2-Trifluoro-ethyl)-1H-pyrazole-4-carbaldehyde

Add 1H-pyrazole-4-carbaldehyde (0.400 g, 4.16 mmol) as a solution in DMF (2 mL) dropwise to a suspension of sodium hydride (0.333 g, 8.32 mmol) in DMF (5 mL) at 0° C. Stir for 15 min. at 0° C. Add 2,2,2-trifluoroethyl-p-toluenesulfonate (1.27 g, 5.00 mmol) and DMF (3 mL) to the reaction mixture. Heat to 60° C. for 18 hr. Quench with aqueous saturated sodium bicarbonate solution and add ethyl acetate. Separate organic layer. Extract aqueous layer twice with ethyl acetate, wash combined organics with brine, dry (magnesium sulfate), filter, concentrate and purify (silica gel chromatography, eluting with 0:100 to 100:0 ethyl acetate:hexanes) to give the title preparation (309 mg, 42%). GC-MS: m/z=178 [M+].

PREPARATION 56

Racemic 1-(2-Hydroxy-propyl)-1H-pyrazole-4-carbaldehyde

Combine 1H-pyrazole-4-carbaldehyde (0.150 g, 1.56 mmol), racemic 1-bromo-2-propanol (0.260 g, 1.87 mmol), and potassium carbonate (0.323 g, 2.34 mmol) in acetonitrile (2 mL). Heat in microwave at 150° C. for 20 min. Filter, wash with acetonitrile and concentrate filtrate. Purify via silica gel chromatography, eluting with 0:100 to 100:0 ethyl acetate:hexanes) to give the title preparation (177 mg, 73%). GC-MS: m/z=154 [M+].

PREPARATIONS 57-60

Are Prepare Essentially as Described for Preparation 55 Using the Appropriate Alkyl Halide

| Prep | Compound | Yield (%) | MS (ES) [M + H]+ |
|---|---|---|---|
| 57 | 1-(3,3,3-Trifluoro-2-hydroxy-propyl)-1H-pyrazole-4-carbaldehyde | 74 | 208 |
| 58 | 1-(2-Methoxy-ethyl)-1H-pyrazole-4-carbaldehyde | 100 | 154 |
| 59 | 1-Methoxymethyl-1H-pyrazole-4-carbaldehyde | 49 | 140 |
| 60 | 1-(3-Hydroxy-propyl)-1H-pyrazole-4-carbaldehyde | 62 | 154 |

PREPARATION 61

1-(1,2-Dimethyl-1H-imidazole-4-sulfonyl)-1H-pyrazole-4-carbaldehyde

Dissolve 1H-pyrazole-4-carboxaldehyde (0.150 g, 1.56 mmol) in DCM (5 mL). Add triethylamine (240 µL, 1.72 mmol) and 1,2-dimethyl-1H-imidazole-4-sulfonyl chloride (0.334 g, 1.72 mmol). Stir at ambient temperature for 18 hr. Concentrate, and purify via silica gel chromatography, eluting with 50:50 to 100:0 ethyl acetate:hexanes to give the title preparation (317 mg, 80%). GC-MS: m/z=254 [M+].

PREPARATION 62

1-(1-Methyl-1H-imidazol-4-yl)-1H-pyrazole-4-carbaldehyde

In an oven-dried flask, combine 4-bromo-1-methyl-1H-imidazole (0.200 g, 1.24 mmol), copper (I) iodide (0.022 g, 0.113 mmol), N,N-dimethylglycine (0.023 g, 0.226 mmol), and potassium carbonate (0.312 g, 2.26 mmol). Purge with nitrogen 3 times. Add 1-H-pyrazole-4-carboxaldehyde (0.109 g, 1.13 mmol), and DMSO (1.7 mL). Heat to 110° C. for 48 hr. Cool to ambient temperature and partition between ethyl acetate and water. Separate organic layer and extract aqueous layer twice with ethyl acetate. Dry combined organic layers (magnesium sulfate), filter and concentrate. Add copper (I) iodide (0.022 g, 0.113 mmol), N,N-dimethylglycine (0.023 g, 0.226 mmol), potassium carbonate (0.312 g, 2.26 mmol), and DMSO (1.7 mL). Purge with nitrogen 3 times. Heat to 110° C. for 18 hr. Cool to ambient temperature and partition between ethyl acetate and water. Separate organic layer and extract aqueous layer twice with ethyl acetate. Dry combined organic layers (magnesium sulfate), filter, concentrate, and purify (silica gel chromatography, eluting with 50:50 to 100:0 ethyl acetate:hexanes) to give the title preparation (39 mg, 20%). GC-MS: m/z=176 [M+].

PREPARATION 63

2-[4-(2-Bromoethyl)-3,5-diethylpyrazol-1-yl]-pyridine

Dissolve heptane-3,5-dione (2.5 g, 19.5 mmol) in dry tetrahydrofuran (10 mL) and add the resulting solution dropwise to a chilled (0° C.) suspension of sodium hydride (0.94 g, 23.4 mmol, 60% dispersion in oil) in tetrahydrofuran (20 mL). Stir at 0° C. for 1 hr., then add bromoacetic acid ethyl ester (2.6 mL, 23.4 mmol) dropwise. Stir for 16 hr. at 0° C. and warm to room temperature. Partition the reaction mixture between diethyl ether (100 mL) and saturated aqueous ammonium chloride solution (50 mL). Separate the organic layer and wash with saturated aqueous sodium chloride solution (50 mL), dry (sodium sulfate), filter and concentrate. Purify using silica gel chromatography, eluting with 10:1 hexanes:ethyl acetate, to give 4-oxo-3-propionyl-hexanoic acid ethyl ester as an oil (3.2 g, 77%). $^1$H-NMR (400 MHz, CDCl$_3$) δ 4.08 (m, 3H), 2.83 (d, 2H), 2.55 (q, 2H), 1.21 (t, 3H), 1.02 (t, 6H).

Using the method in Preparation 43, using 4-oxo-3-propionylhexanoic acid ethyl ester, prepare (3,5-diethyl-1-pyridin-2-yl-1H-pyrazol-4-yl)-acetic acid ethyl ester (95% yield). $^1$H-NMR (400 MHz, CDCl$_3$) δ 8.39 (m, 1H), 7.80 (d, 1H), 7.73 (m, 1H), 7.09 (m, 1H), 4.12 (q, 2H), 3.40 (s, 2H), 3.07 (q, 2H), 2.63 (q, 2H), 1.22 (m, 6H), 1.15 (t, 3H).

Dissolve (3,5-diethyl-1-pyridin-2-yl-1H-pyrazol-4-yl)-acetic acid ethyl ester (0.54 g, 1.88 mmol) in tetrahydrofuran (20 mL) and cool to −78° C. Add diisobutyl-aluminum hydride (7.52 mL, 7.52 mmol, 1 M in toluene) dropwise and continue to stir for 2.5 hr. Warm to room temperature over 1 hr. then quench with saturated aqueous potassium sodium tartrate solution (50 mL). Add ethyl acetate (100 mL) and stir at room temperature for 16 hr. Separate the organic layer, dry (sodium sulfate), filter and concentrate. Purify using silica gel chromatography, eluting with 80:20 hexanes:ethyl acetate, to give 2-(3,5-diethyl-1-pyridin-2-yl-1H-pyrazol-4-yl)-ethanol as a white solid (0.30 g, 66%). $^1$H-NMR (400 MHz, CDCl$_3$) δ 8.39 (m, 1H), 7.80 (d, 1H), 7.73 (m, 1H), 7.12 (m, 1H), 3.72 (m, 2H), 3.08 (q, 2H), 2.67 (m, 4H), 1.58 (bs, 1H), 1.28 (t, 3H), 1.15 (t, 3H).

Combine 2-(3,5-diethyl-1-pyridin-2-yl-1H-pyrazol-4-yl)-ethanol (0.68 g, 2.78 mmol) and triphenylphosphine (1.09 g, 4.18 mmol) in DCM (20 mL) and cool to 0° C. Add a solution of carbon tetrabromide (1.39 g, 4.18 mmol) and triethylamine (0.77 mL, 5.56 mmol) in DCM (5 mL) dropwise. Warm the reaction mixture to room temperature and stir for 3 hr. Dilute with diethyl ether (20 mL) and filter. Concentrate filtrate and purify using silica gel chromatography, eluting with 90:10 hexanes:ethyl acetate, to give the title preparation as an oil (0.8 g, 93%): $^1$H-NMR (400 MHz, CDCl$_3$) δ 8.39 (m, 1H), 7.80 (m, 1H), 7.75 (m, 1H), 7.15 (m, 1H), 3.39 (m, 2H), 3.08 (q, 2H), 2.98 (m, 2H), 2.64 (q, 2H), 1.28 (t, 3H), 1.15 (t, 3H).

PREPARATION 64

3'-Chloro-4-(1,3-dimethyl-1H-pyrazol-4-ylmethyl)-3,4,5,6-tetrahydro-2H-[1,2']bipyrazine To a solution of 3'-chloro-2,3,5,6-tetrahydro-[1,2']bipyrazinyl-4-carboxylic acid t-butyl ester (10 g, 33.4 mmol, 1 eq) in 1,4-dioxane (160 mL) add a 4 M solution of hydrochloric acid in 1,4-dioxane (80 mL, 0.3 mol, 10 eq) and stir under nitrogen at room temperature overnight. Dilute with DCM (600 mL) then basify with 50% aqueous sodium hydroxide. Add water (100 mL), separate the layers and extract the aqueous twice with DCM (200 mL). Combine the organic extracts, wash with saturated aqueous sodium chloride, dry (magnesium sulfate), filter, and concentrate to give 3'-chloro-3,4,5,6-tetrahydro-2H-[1,2']bipyrazinyl as a viscous oil which solidifies on standing (6.39 g, 96%). MS (ES): m/z=199.1, 201.1 [M+H]+.

To a solution of 3'-chloro-3,4,5,6-tetrahydro-2H-[1,2']bipyrazinyl (3 g, 15.1 mmol, 1 eq) and 1,3-dimethyl-1H-pyrazole-4-carbaldehyde (2.0 g, 16.6 mmol, 1.1 eq) in DCE (75 mL) add sodium triacetoxyborohydride (4.8 g, 22.6 mmol, 1.5 eq) and stir at room temperature over the weekend. Add 2 N sodium hydroxide (100 mL), separate the layers, extract the aqueous layer twice with DCM (75 mL), dry (magnesium sulfate), filter, concentrate and purify (silica gel chromatography, eluting with 0:100 to 10:90 methanol:DCM). Combine only the fractions which contain the main component and concentrate to give the title preparation as a viscous yellow oil (2.14 g, 46%). Combine all other fractions which contain main component plus impurities, concentrate then repeat the chromatography step to recover further material (1.6 g, 35%, total yield 81%). MS (ES): m/z=307.1 [M+H]+.

PREPARATION 65

3'-Chloro-4-(1-methyl-1H-pyrazol-4-ylmethyl)-3,4,5,6-tetrahydro-2H-[1,2']bipyrazine Dissolve 3'-chloro-3,4,5,6-tetrahydro-2H-[1,2']bipyrazinyl (3.43 g, 17.3 mmol) in tetrahydrofuran (100 mL). Add 1-methyl-1H-pyrazole-4-carbaldehyde (2.244 g, 20.38 mmol) in dry tetrahydrofuran (5 mL), stir for 10 min. at room temperature, add sodium triacetoxyborohydride (4.32 g, 20.4 mmol) and subject the reaction to ultrasound stirring for 6 hr. at room temperature. Add saturated aqueous sodium hydrogen carbonate (100 mL) then 2 N sodium hydroxide (10 mL) to the mixture and extract with DCM (2×200 mL). Pass the combined DCM extracts through an IST Phase Separator Frit®, concentrate and purify (silica gel chromatography, eluting with 0:100 to 8:92 methanol:DCM), to give the title preparation as a crystalline solid (5.21 g, 92%). MS (ES): m/z=293.1 [M+H]+.

PREPARATION 66

3'-Chloro-4-(1,3,5-trimethyl-1H-pyrazol-4-ylmethyl)-3,4,5,6-tetrahydro-2H-[1,2']bipyrazine To 3'-chloro-2,3,5,6-tetrahydro-[1,2']bipyrazinyl-4-carboxylic acid t-butyl ester (3.00 g, 10.0 mmol, 1 eq) add a 4 M solution of hydrochloric acid in 1,4-dioxane (100 mL, 400 mmol, 40 eq) and stir at room temperature for 3 hr. Filter precipitate and wash with diethyl ether. Dry the powder in vacuum oven over night to give 3'-chloro-3,4,5,6-tetrahydro-2H-[1,2']bipyrazinyl dihydrochloride as a pale yellow powder (2.11 g, 78%). MS (ES): m/z=199 [M+H]+.

To a suspension of 3'-chloro-3,4,5,6-tetrahydro-2H-[1,2'] bipyrazinyl dihydrochloride (2.11 g, 7.77 mmol, 1 eq) in tetrahydrofuran (20 mL) add 1,3,5-trimethyl-1H-pyrazole-4-carbaldehyde (1.61 g, 11.65 mmol, 1.5 eq). Stir for 10 min and add sodium triacetoxyborohydride (4.20 g, 19.40 mmol, 2.5 eq) in one portion. Stir at room temperature under nitrogen for 1 hr., then add further 1,3,5-trimethyl-1H-pyrazole-4-carbaldehyde (0.50 g, 3.6 mmol, 0.47 eq). Stir for 30 min., add saturated aqueous sodium hydrogen carbonate (100 mL) slowly, and then extract with DCM (3×50 mL). Pass the combined DCM extracts through an IST Phase Separator Frit®, concentrate and purify (silica gel chromatography, eluting with 2:98 to 5:95 methanol:DCM), to give the title preparation as a white powder (2.468 g, 98%). MS (ES): m/z=321 [M+H]+.

PREPARATION 67

2-[4-(3'-Chloro-2,3,5,6-tetrahydro-[1,2']bipyrazinyl-4-ylmethyl)-pyrazol-1-yl]-ethanol To a solution of 3'-chloro-3,4,5,6-tetrahydro-2H-[1,2']bipyrazinyl (0.789 g, 4.01 mmol) and 1-(2-hydroxy-ethyl)-1H-pyrazole-4-carbaldehyde (0.562 g, 4.01 mmol) in DCE (35 mL) add sodium triacetoxyborohydride (1.28 g, 6.02 mmol) and acetic acid (0.382 mL) and stir at room temperature for 20 hr. Add saturated aqueous sodium bicarbonate, separate the layers, extract the aqueous layer twice with DCM, dry (sodium sulfate), filter and concentrate. Purify using silica gel chromatography, eluting with 6:94 methanol (with 2N ammonia):DCM to give the title preparation as a yellow oil (1.16 g, 90%). MS (ES): m/z=323 [M+H]+.

PREPARATION 68

[3'-(4-Fluorophenyl)-2,3,5,6-tetrahydro-[1,2']bipyrazinyl-4-yl]-(1-isopropyl-1H-pyrazol-4-yl)-methanone Dissolve 1-isopropyl-1H-pyrazole-4-carboxylic acid (0.120 g, 0.780 mmol) in DCM (5 mL). Add HOBt (0.088 g, 0.650 mmol) followed by 1-(3-dimethyl-aminopropyl)-3-ethylcarbodiimide hydrochloride (0.125 g, 0.650 mmol). Add 3'-(4-fluorophenyl)-3,4,5,6-tetrahydro-2H-[1,2']bipyrazinyl (0.168 g, 0.650 mmol) and stir at room temperature for 18 hr. Add DCM and water and separate layers. Extract aqueous layer 3 times with DCM, dry (magnesium sulfate), filter, concentrate and purify (silica gel chromatography, eluting with 25:75 to 100:0 ethylacetate/hexanes), to give the title preparation (211 mg, 82%). MS (ES): m/z=395 [M+H]+.

Preparations 69-71 may be prepared essentially as described in Preparation 68 using either 3'-(4-fluorophenyl)-3,4,5,6-tetrahydro-2H-[1,2']bipyrazinyl or the appropriate (phenyl-pyridin-2-yl)-piperazine, and the appropriate carboxylic acid.

| Prep | Compound | Yield (%) | MS (ES) [M + H]+ |
|---|---|---|---|
| 69 | [3'-(4-Fluorophenyl)-2,3,5,6-tetrahydro-[1,2']bipyrazinyl-4-yl]-(3-methyl-1-propyl-1H-pyrazol-4-yl)-methanone | 87 | 409 |
| 70 | {4-[3-(4-Fluoro-phenyl)-pyridin-2-yl]-piperazin-1-yl}-(1-isopropyl-1H-pyrazol-4-yl)-methanone | 95 | 394 |
| 71 | (1-Isopropyl-1H-pyrazol-4-yl)-{4-[3-(4-trifluoromethyl-phenyl)-pyridine-2-yl]piperazin-1-yl}-methanone | 90 | 444 |

EXAMPLE 1

4-(3,5-Dimethyl-1-phenyl-1H-pyrazol-4-ylmethyl)-3'-(4-fluorophenyl)-3,4,5,6-tetrahydro-2H-[1,2']bipyrazine hydrochloride

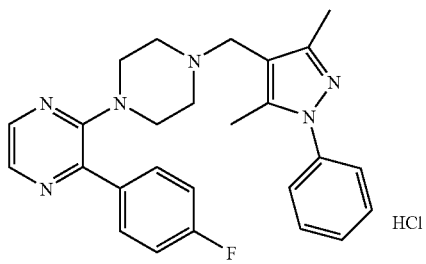

Dissolve 3'-(4-fluorophenyl)-3,4,5,6-tetrahydro-2H-[1,2']bipyrazinyl (0.200 g, 0.774 mmol) in DCE (10 mL). Add 3,5-dimethyl-1-phenylpyrazole-4-carboxaldehyde (0.186 g, 0.929 mmol), and stir at room temperature for 10 min. Add sodium triacetoxyborohydride (0.247 g, 1.16 mmol) followed by acetic acid (47 μL, 0.813 mmol). Stir at room temperature for 18 hr. Purify via SCX chromatography, followed by silica gel chromatography, eluting with 0:100 to 10:90 methanol:DCM, followed by reverse phase chromatography to give the free base of the title compound (221 mg, 65%). Dissolve the free base (0.099 g, 0.225 mmol) in methanol and add a solution of ammonium chloride (0.012 g, 0.225 mmol) in a minimal volume of methanol. Shake for 1 hr. at room temperature and concentrate to give the title compound (108 mg, 100%). MS (ES): m/z=443 [M+H]$^+$.

EXAMPLE 2

3'-(4-fluoro-phenyl)-4-(1-phenyl-1H-pyrazol-4-ylmethyl)-3,4,5,6-tetrahydro-2H-[1,2']bipyrazine hydrochloride salt

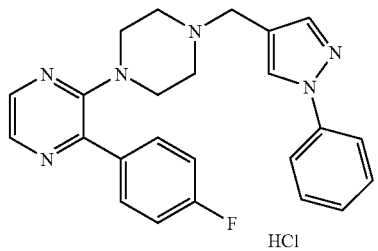

Form the free base of 3'-(4-fluoro-phenyl)-3,4,5,6-tetrahydro-2H-[1,2']bipyrazinyl dihydrochloride by SCX-2® chromatography washing with methanol then eluting with 2M ammonia in methanol. Dissolve 3'-(4-fluoro-phenyl)-3,4,5,6-tetrahydro-2H-[1,2']bipyrazinyl (0.200 g, 0.774 mmol) in DCE (5 mL). Add 1-phenyl-1H-pyrazole-4-carbaldehyde (0.200 g, 1.16 mmol, 1.5 eq.). Stir at room temperature for 20-30 min. Add sodium triacetoxyborohydride (0.33 g, 1.55 mmol, 2 eq.) followed by acetic acid (0.048 g, 0.81 mmol, 1.05 eq.). Stir the reaction mixture at room temperature for 48 hr. Purify by SCX cartridge, followed by reverse phase chromatography to obtain the freebase of the title compound (0.360 g, 0.87 mmol, 100% yield). MS (ES): m/z=415.3[M+H]. Dissolve in methanol (5 mL). Add ammonium chloride (0.047 g, 0.87 mmol, 1 eq.). Stir the reaction mixture at room temperature for 2 hr. and concentrate to give the title compound (0.327 g, 83% yield for salt formation). MS (ES): m/z=415.3[M+H]$^+$.

EXAMPLE 3

3'-(4-Fluorophenyl)-4-(1,3,5-trimethyl-1H-pyrazol-4-ylmethyl)-3,4,5,6-tetrahydro-2H-[1,2']bipyrazine hydrochloride

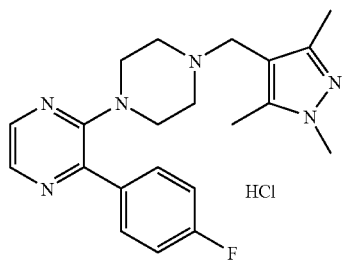

Prepare the title compound using the method of Example 1 using 1,3,5-trimethyl-1H-pyrazole-4-carbaldehyde (182 mg, 62%). MS (ES): m/z=381 [M+H]$^+$.

EXAMPLE 4

4-(1-Ethyl-5-methyl-1H-pyrazol-4-ylmethyl)-3'-phenyl-3,4,5,6-tetrahydro-2H-[1,2']bipyrazine hydrochloride

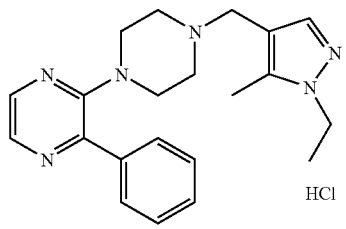

Dissolve 3'-phenyl-3,4,5,6-tetrahydro-2H-[1,2']bipyrazinyl (0.28 g, 1.18 mmol) in DCE (5 mL). Add 1-ethyl-5-methyl-1H-pyrazole-4-carbaldehyde (0.24 g, 1.76 mmol) and stir at room temperature for 20 min. Add sodium triacetoxyborohydride (0.5 g, 2.36 mmol) followed by acetic acid (0.07 mL, 1.24 mmol). Stir at room temperature for 16 hr. Purify via SCX chromatography, followed by silica gel chromatography, eluting with 3:97 to 7:93 7 N ammonia in methanol:ethyl acetate, to give the free base of the title compound (0.22 g, 52%). MS (ES): m/z=363.3 [M+H]$^+$.

Dissolve the free base (0.22 g, 0.61 mmol) in acetonitrile (1 mL) and water (2 mL). Add aqueous 1M HCl (1 eq, 0.61 mmol, 0.61 mL) and lyophilize for 48 hr. to give the title compound (0.26 g, 100%). MS (ES): m/z=363.3 [M+H]$^+$.

The compounds of Examples 5-13 may be prepared essentially as described in Example 4 using the appropriate 3,4,5,6-tetrahydro-2h-[1,2']bipyrazine and aldehyde.

| Ex | Structure | Compound | Yield (%) | MS (ES) [M + H]+ |
|---|---|---|---|---|
| 5 | 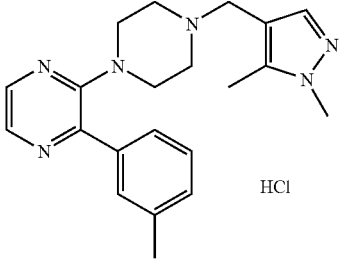 | 4-(1,5-Dimethyl-1H-pyrazol-4-ylmethyl)-3'-m-tolyl-3,4,5,6-tetrahydro-2H-[1,2']bipyrazine hydrochloride | 64 | 363 |
| 6 | 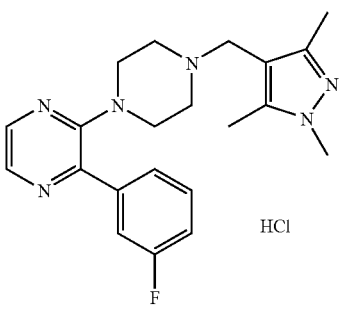 | 3'-(3-Fluoro-phenyl)-4-(1,3,5-trimethyl-1H-pyrazol-4-ylmethyl)-3,4,5,6-tetrahydro-2H-[1,2']bipyrazine hydrochloride | 51 | 381 |
| 7 | 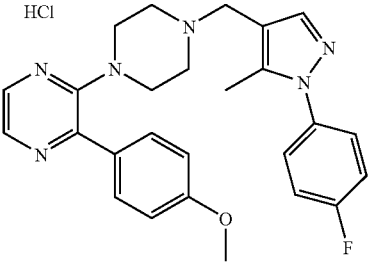 | 4-[1-(4-Fluoro-phenyl)-5-methyl-1H-pyrazol-4-ylmethyl]-3'-(4methoxy-phenyl)-3,4,5,6-tetrahydro-2H-[1,2']bipyrazine hydrochloride | 35 | 459 |
| 8 | 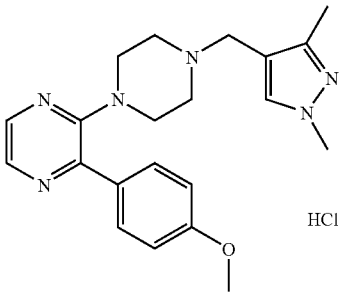 | 4-(1,3-Dimethyl-1H pyrazol-4-ylmethyl-3'-(4-methoxy-phenyl)-3,4,5,6 tetrahydro-2H [1,2']bipyrazine hydrochloride | 24 | 379 |
| 9 | 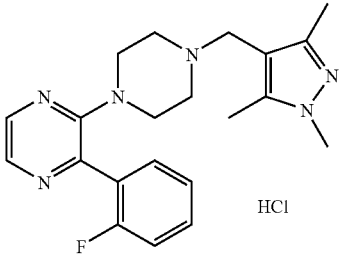 | 3'-(2-Fluoro-phenyl)-4-(1,3,5-trimethyl-1H-pyrazol-4-ylmethyl)-3,4,5,6-tetrahydro-2H-[1,2']bipyrazine hydrochloride | 57 | 381 |

-continued

| Ex | Structure | Compound | Yield (%) | MS (ES) [M + H]⁺ |
|---|---|---|---|---|
| 10 | 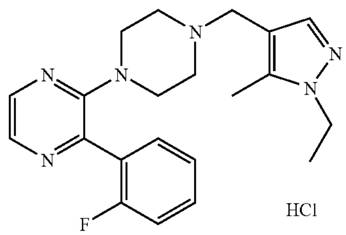 | 4-(1-Ethyl-5-methyl-1H-pyrazol-4-ylmethyl)-3'-(2-fluoro-phenyl)-3,4,5,6-tetrahydro-2H-[1,2']bipyrazine hydrochloride | 35 | 381 |
| 11 | 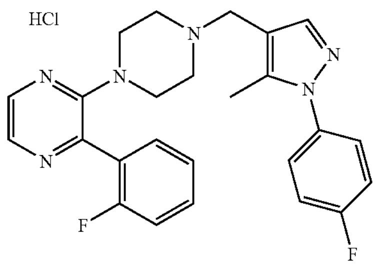 | 3'-(2-Fluoro-phenyl)-4-[1-(4-fluoro-phenyl)-5-methyl-1H-pyrazol-4-ylmethyl]-3,4,5,6-tetrahydro-2H-[1,2']bipyrazine hydrochloride | 41 | 447 |
| 12 | 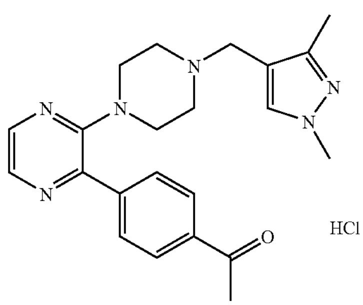 | 1-{4-[4-(1,3-Dimethyl-1H-pyrazol-4-ylmethyl)-3,4,5,6-tetrahydro-2H-[1,2']bipyrazinyl-3'-yl]-phenyl}-ethanone hydrochloride | 58 | 391 |
| 13 | 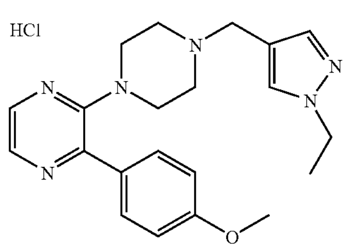 | 4-(1-Ethyl-1H-pyrazol-4-ylmethyl)-3'-(4-Methoxy-phenyl)-3,4,5,6-tetrahydro-2H-[1,2']bipyrazine hydrochloride | 60 | 379 |

EXAMPLE 14

3'-(4-Fluorophenyl)-4-[2-(1,3,5-trimethyl-1H-pyrazol-4-yl)-ethyl]-3,4,5,6-tetrahydro-2H-[1,2']bipyrazine hydrochloride

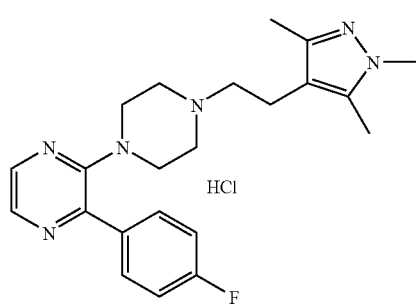

Combine (1,3,5-trimethyl-1H-pyrazol-4-yl)-acetaldehyde (0.35 g, 2.27 mmol) and 3'-(4-fluorophenyl)-3,4,5,6-tetrahydro-2H-[1,2']bipyrazinyl (0.71 g, 2.76 mmol) in DCM (10 mL) and stir at room temperature for 10 min. Add glacial acetic acid (0.21 mL, 3.44 mmol) followed by sodium triacetoxyborohydride (0.73 g, 3.44 mmol). Stir at room temperature for 2 hr. Concentrate, dissolve in methanol (5 mL) and load on a 10 g SCX column. Wash with methanol (2×50 mL). Elute with 2 M ammonia in methanol (2×30 mL). Concentrate the eluent and purify (silica gel chromatography, eluting with 45:45:10 hexanes:DCM:ethanol), to give the free base of the title compound (48 mg, 5%). Dissolve the free base (0.041 g, 0.104 mmol) in methanol and add a solution of ammonium chloride (0.006 g, 0.104 mmol) in a minimal volume of methanol. Shake for 18 hr. at room temperature and concentrate to give the title compound (50 mg, 95%). MS (ES): m/z=395 [M+H]$^+$.

EXAMPLE 15

3'-(4-Fluorophenyl)-4-[3-(1,3,5-trimethyl-1H-pyrazol-4-yl)-propyl]-3,4,5,6-tetrahydro-2H-[1,2']bipyrazine hydrochloride

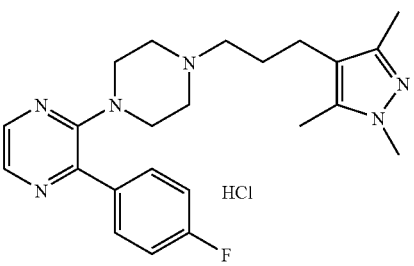

Dissolve 3'-(4-fluorophenyl)-3,4,5,6-tetrahydro-2H-[1,2'] bipyrazinyl (0.300 g, 1.16 mmol) in DCE (15 mL). Add 3-(1,3,5-trimethyl-1H-pyrazol-4-yl)-propionaldehyde (0.232 g, 1.39 mmol), and stir at room temperature for 10 min. Add sodium triacetoxyborohydride (0.369 g, 1.74 mmol) and stir at room temperature for 18 hr. Purify by SCX chromatography, followed by silica gel chromatography, eluting with 45:45:10 DCM:hexanes:ethanol, to give the free base of the title compound (368 mg, 78%). Dissolve the free base (0.362 g, 0.888 mmol) in methanol and add a solution of ammonium chloride (0.047 g, 0.888 mmol) in a minimal volume of methanol. Shake for 3 hr. at room temperature and concentrate to give the title compound (395 mg, 100%). MS (ES): m/z=409 [M+H]$^+$.

The free base compounds of Examples 16-41 may be prepared essentially as described in Example 15 using the appropriate 3'-phenyl-3,4,5,6-tetrahydro-2H-[1,2']bipyrazinyl and aldehyde. The HCl salt of each may be prepared either by the method described in Example 5, or by stirring the free base with an equimolar amount of 2M HCl/diethyl ether in IPA and diethyl ether, followed by precipitation of the HCl salt.

| EX | Structure | Compound | Yield (%) | MS (ES) [M + H]+ |
|---|---|---|---|---|
| 16 | 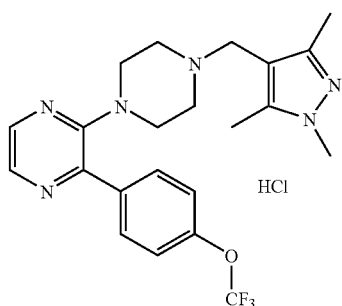 | 3'-(4-Trifluoromethoxyphenyl)-4-(1,3,5-trimethyl-1H-pyrazol-4-ylmethyl)-3,4,5,6-tetrahydro-2H-[1,2']bipyrazine hydrochloride | 92 | 447 |
| 17 | 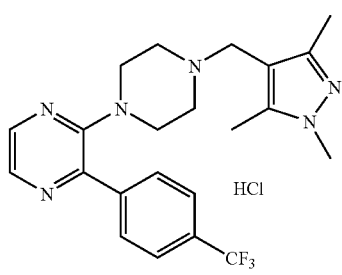 | 3'-(4-Trifluoromethylphenyl)-4-(1,3,5-trimethyl-1H-pyrazol-4-ylmethyl)-3,4,5,6-tetrahydro-2H-[1,2']bipyrazine hydrochloride | 86 | 431 |
| 18 | 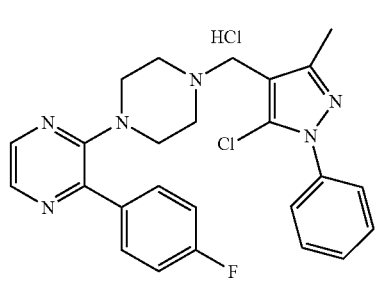 | 4-(5-Chloro-3-methyl-1-phenyl-1H-pyrazol-4-ylmethyl)-3'-(4-fluorophenyl)-3,4,5,6-tetrahydro-2H-[1,2']bipyrazine hydrochloride | 89 | 463 |
| 19 | 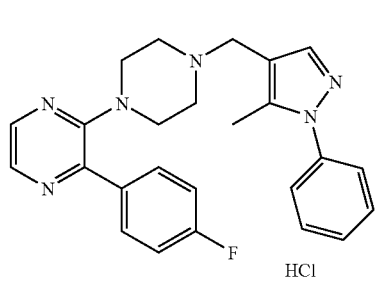 | 4-(5-methyl-1-phenyl-1H-pyrazol-4-ylmethyl)-3'-(4-fluorophenyl)-3,4,5,6-tetrahydro-2H-[1,2']bipyrazine hydrochloride | 89 | 429 |
| 20 | 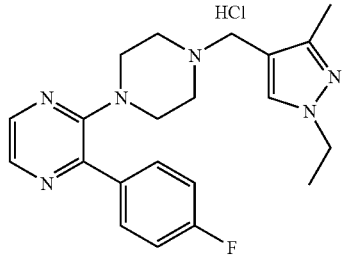 | 4-(1-Ethyl-3-methyl-1H-pyrazol-4-ylmethyl)-3'-(4-fluorophenyl)-3,4,5,6-tetrahydro-2H-[1,2']bipyrazine hydrochloride | 89 | 381 |

-continued

| EX | Structure | Compound | Yield (%) | MS (ES) [M + H]+ |
|---|---|---|---|---|
| 21 | 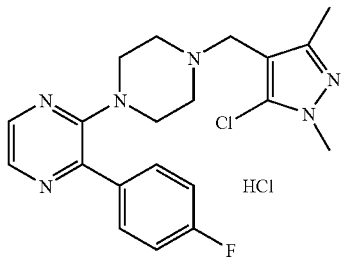 | 4-(5-Chloro-1,3-dimethyl-1H-pyrazol-4-ylmethyl)-3'-(4-fluorophenyl)-3,4,5,6-tetrahydro-2H-[1,2']bipyrazine hydrochloride | 91 | 401 |
| 22 | 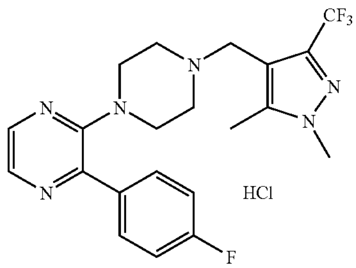 | 4-(1,5-Dimethyl-3-trifluoromethyl-1H-pyrazol-4-ylmethyl)-3'-(4-fluorophenyl)-3,4,5,6-tetrahydro-2H-[1,2']bipyrazine hydrochloride | 61 | 435 |
| 23 | 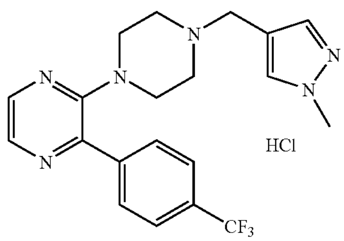 | 4-(1-Methyl-1H-pyrazol-4-ylmethyl)-3'-(4-trifluoromethylphenyl)-3,4,5,6-tetrahydro-2H-[1,2']bipyrazine hydrochloride | 40 | 403 |
| 24 | 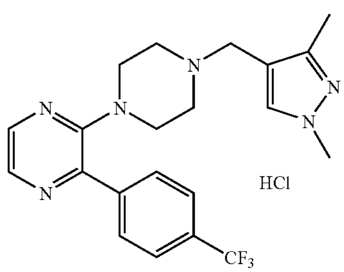 | 4-(1,3-Dimethyl-1H-pyrazol-4-ylmethyl)-3'-(4-trifluoromethylphenyl)-3,4,5,6-tetrahydro-2H-[1,2']bipyrazine hydrochloride | 41 | 417 |
| 25 | 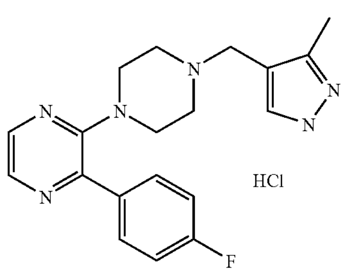 | 3'-(4-Fluorophenyl)-4-(3-methyl-1H-pyrazol-4-ylmethyl)-3,4,5,6-tetrahydro-2H-[1,2']bipyrazine hydrochloride | 100 | 353 |
| 26 | 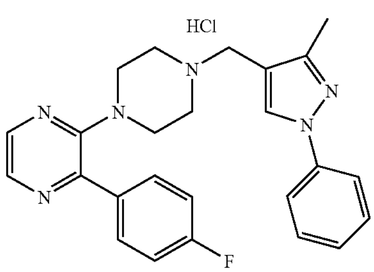 | 3'-(4-Fluorophenyl)-4-(3-methyl-1-phenyl-1H-pyrazol-4-ylmethyl)-3,4,5,6-tetrahydro-2H-[1,2']bipyrazine hydrochloride | 94 | 429 |

-continued

| EX | Structure | Compound | Yield (%) | MS (ES) [M + H]+ |
|---|---|---|---|---|
| 27 | 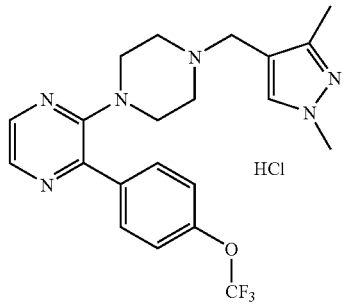 | 4-(1,3-Dimethyl-1H-pyrazol-4-ylmethyl)-3'-(4-trifluoromethoxyphenyl)-3,4,5,6-tetrahydro-2H-[1,2']bipyrazine hydrochloride | 88 | 433 |
| 28 | 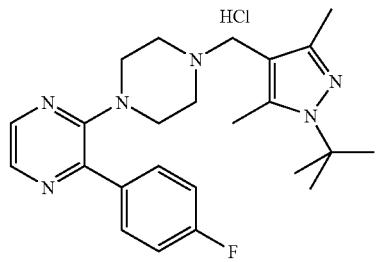 | 4-(1-t-Butyl-3,5-dimethyl-1H-pyrazol-4-ylmethyl)-3'-(4-fluorophenyl)-3,4,5,6-tetrahydro-2H-[1,2']bipyrazine hydrochloride | 84 | 423 |
| 29 | 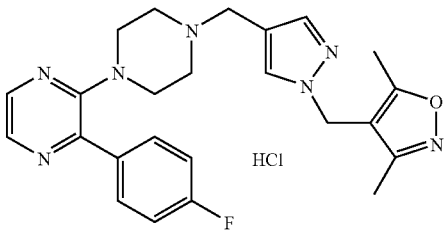 | 4-[1-(3,5-Dimethylisoxazol-4-ylmethyl)-1H-pyrazol-4-ylmethyl]-3'-(4-fluorophenyl)-3,4,5,6-tetrahydro-2H-[1,2']bipyrazine hydrochloride | 72 | 448 |
| 30 | 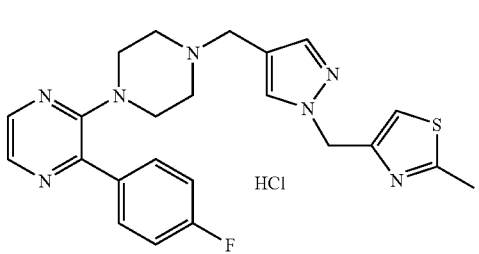 | 3'-(4-Fluorophenyl)-4-[1-(2-methylthiazol-4-ylmethyl)-1H-pyrazol-4-ylmethyl]-3,4,5,6-tetrahydro-2H-[1,2']bipyrazine hydrochloride | 40 | 450 |
| 31 | 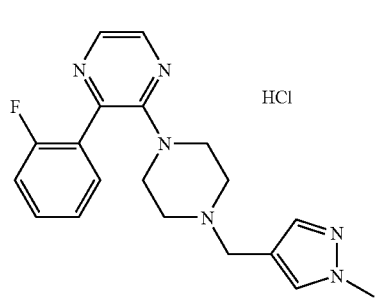 | 3'-(2-Fluorophenyl)-4-(1-methyl-1H-pyrazole-4ylmethyl)-3,4,5,6-tetrahydro-2H-[1,2']bipyrazine hydrochloride | 44 | 353 |

| EX | Structure | Compound | Yield (%) | MS (ES) [M + H]+ |
|---|---|---|---|---|
| 32 | 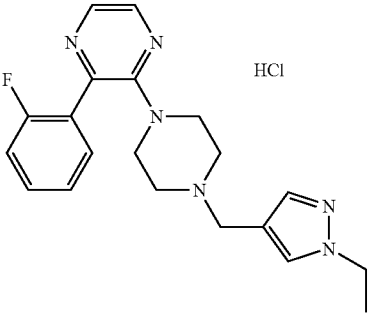 | 4-(1-Ethyl-1H-pyrazol-4-ylmethyl)-3'-(2-fluorophenyl)-3,4,5,6-tetrahydro-2H-[1,2']-bipyrazine hydrochloride | 27 | 367 |
| 33 | 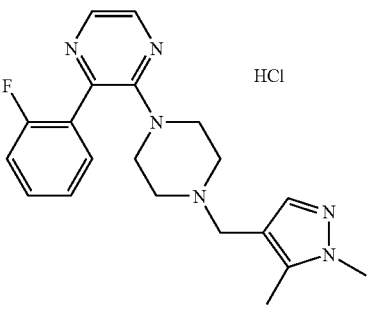 | 4-(1,5-Dimethyl-1H-pyrazol-4-ylmethyl)-3'-(2-fluorophenyl)-3,4,5,6-tetrahydro-2H-[1,2']-bipyrazine hydrochloride | 48 | 367 |
| 34 | 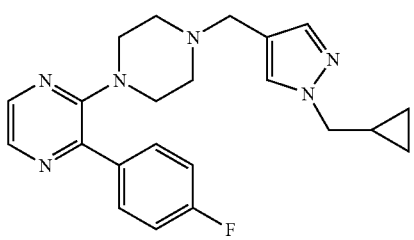 | 4-(1-Cyclopropylmethyl-1H-pyrazol-4-ylmethyl)-3'-(4-fluoro-phenyl)-3,4,5,6-tetrahydro-2H-[1,2']bipyrazine | 50 | 393 |
| 35 | 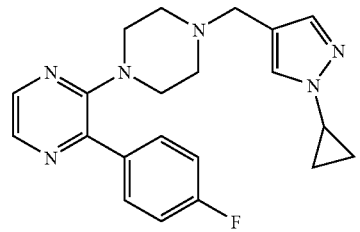 | 4-(1-Cyclopropyl-1H-pyrazol-4-ylmethyl)-3'-(4-fluoro-phenyl)-3,4,5,6-tetrahydro-2H-[1,2']bipyrazine | 7 | 379 |
| 36 | 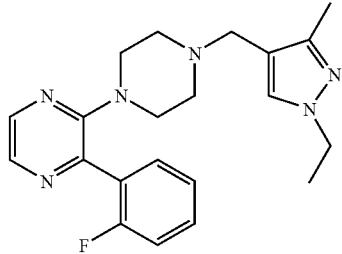 | 4-(1-Ethyl-3-methyl-1H-pyrazol-4-ylmethyl)-3'-(2-fluoro-phenyl)-3,4,5,6-tetrahydro-2H-[1,2']bipyrazine | 36 | 381 |

-continued

| EX | Structure | Compound | Yield (%) | MS (ES) [M + H]+ |
|---|---|---|---|---|
| 37 | 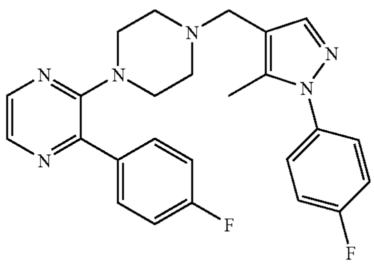 | 3'-(4-Fluoro-phenyl)-4-[1-(4-fluoro-phenyl)-5-methyl-1H-pyrazol-4-ylmethyl]-3,4,5,6-tetrahydro-2H-[1,2']bipyrazine | 93 | 447 |
| 38 | 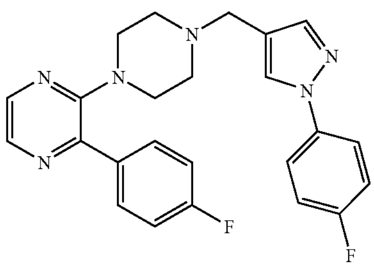 | 3'-(4-Fluoro-phenyl)-4-[1-(4-fluoro-phenyl)-1H-pyrazol-4-ylmethyl]-3,4,5,6-tetrahydro-2H-[1,2']bipyrazine | 89 | 433 |
| 39 | 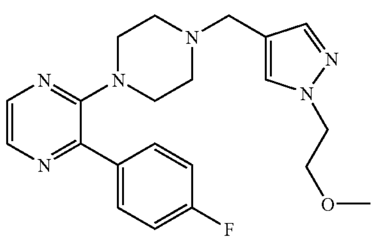 | 3'-(4-Fluoro-phenyl)-4-[1-(2-methoxy-ethyl)-1H-pyrazol-4-ylmethyl]-3,4,5,6-tetrahydro-2H-[1,2']bipyrazine | 45 | 397 |
| 40 | 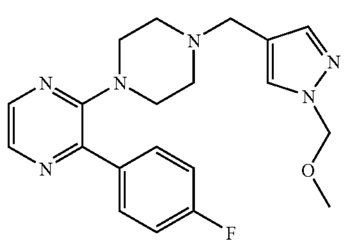 | 3'-(4-Fluoro-phenyl)-4-(1-methoxymethyl-1H-pyrazol-4-ylmethyl)-3,4,5,6-tetrahydro-2H-[1,2']bipyrazine | 44 | 383 |
| 41 | 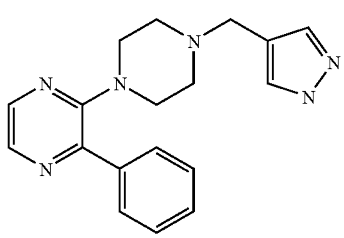 | 3'-Phenyl-4-(1H-pyrazol-4-ylmethyl)-3,4,5,6-tetrahydro-2H-[1,2']bipyrazine | 78 | 321 |

EXAMPLE 42

3'-(3,4-Dichloro-phenyl)-4-(3,5-dimethyl-1-phenyl-1H-pyrazol-4-ylmethyl)-3,4,5,6-tetrahydro-2H-[1,2']bipyrazinyl hydrochloride

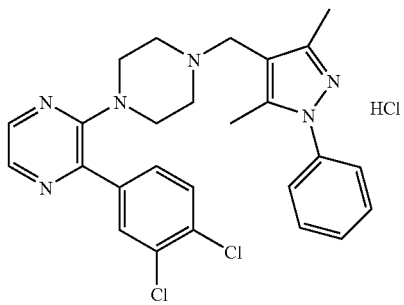

Combine 3'-(3,4-dichloro-phenyl)-3,4,5,6-tetrahydro-2H-[1,2']bipyrazinyl (0.0590 g, 0.191 mmol) and 3,5-dimethyl-1-phenyl-1H-pyrazole-4-carbaldehyde (0.0592 gm, 0.300 mmol) in DCE (5 mL), stir 10 min, and add sodium triacetoxyborohydride (0.838 gm, 0.400 mmol). Stir at ambient temperature for 44 hr. and purify by SCX chromatography, followed by silica gel chromatography, eluting with 0-50% THF in hexanes to give the free base of the title compound (0.017 gm, 18%). Convert the free base to the hydrochloride salt by addition of 0.17 mL of a 0.2 M solution of ammonium chloride in methanol to give the title compound (0.017 gm). MS (ES+) m/z: 494 [M+H]$^+$.

EXAMPLE 43

3'-(4-Fluorophenyl)-4-[2-(1,3,5-triethyl-1H-pyrazol-4-yl)-ethyl]-3,4,5,6-tetrahydro-2H-[1,2']bipyrazine hydrochloride

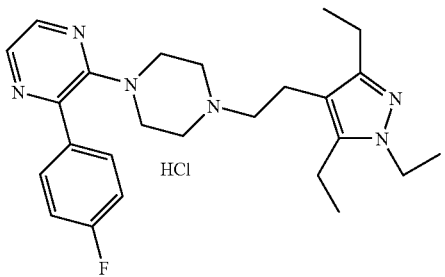

Combine (1,3,5-triethyl-1H-pyrazol-4-yl)-acetaldehyde (0.16 g, 0.82 mmol) and 3'-(4-fluoro-phenyl)-3,4,5,6-tetrahydro-2H-[1,2']bipyrazinyl (0.24 g, 0.91 mmol) in DCM (10 mL) and stir at room temperature for 15 min. Then add glacial acetic acid (0.07 mL, 1.23 mmol) and sodium triacetoxyborohydride (0.26 g, 1.23 mmol) and stir for 3 hr. at room temperature. Purify using SCX chromatography and further purify using silica gel chromatography (5% 7 M ammonia in methanol/DCM). Dissolve the free base in methanol (5 mL) and treat with ammonium chloride (0.037 g). Concentrate the resulting solution to give the title compound (0.032 g, 83%). MS: m/z=437.3[M+H]$^+$.

EXAMPLE 44

3'-(4-Fluorophenyl)-4-[2-(3-isobutyl-5-methyl-1-pyridin-2-yl-1H-pyrazol-4-yl)-ethyl]-3,4,5,6-tetrahydro-2H-[1,2']bipyrazine hydrochloride

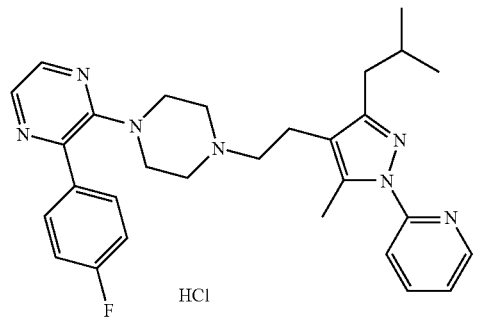

Combine (3-isobutyl-5-methyl-1-pyridin-2-yl-1H-pyrazol-4-yl)-acetaldehyde (0.21 g, 0.82 mmol), 3'-(4-fluorophenyl)-3,4,5,6-tetrahydro-2H-[1,2']bipyrazinyl (0.21 g, 0.82 mmol) in DCM (10 mL) and stir at room temperature for 15 min. Add glacial acetic acid (0.07 mL, 1.23 mmol) then sodium triacetoxyborohydride (0.26 g, 1.23 mmol). Stir at room temperature for 20 hr. Concentrate, then purify using SCX chromatography and further purify using silica gel chromatography, eluting with 5% 7 M ammonia in methanol: DCM. Dissolve the free base in methanol (5 mL) and treat with ammonium chloride (0.022 g). Concentrate the resulting solution to give the title compound as a white powder (0.22 g, 50%). MS: m/z=500.3 [M+H]$^+$.

EXAMPLE 45

3'-(4-Fluorophenyl)-4-(1-methyl-3-trifluoromethyl-1H-pyrazol-4-ylmethyl)-3,4,5,6-tetrahydro-2H-[1,2']bipyrazine dihydrochloride

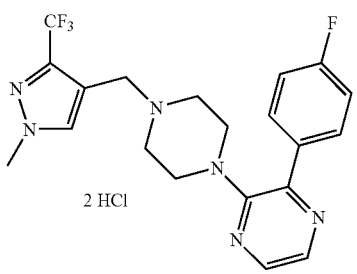

Combine 1-methyl-3-trifluoromethyl-1H-pyrazole-4-carbaldehyde (0.17 g, 0.97 mmol) and 3'-(4-fluorophenyl)-3,4,5,6-tetrahydro-2H-[1,2']bipyrazinyl dihydrochloride (0.35 g, 1.06 mmol) in DCM (20 mL) and treat with triethylamine (0.30 mL, 2.12 mmol). After stirring for 15 min, add glacial acetic acid (0.08 mL, 1.46 mmol) then sodium triacetoxyborohydride (0.31 g, 1.46 mmol). Stir at room temperature for 18 hr. Concentrate and purify using SCX chromatography and further purify using silica gel chromatography (5% 7 M ammonia in methanol/DCM). Dissolve the free base in methanol (5 mL) and treat with ammonium chloride (0.107 g). Concentrate the resulting solution to give the title compound (0.39 g, 81%). MS: m/z=421.3 [M+H]$^+$.

EXAMPLE 46

2-{4-[3'-(4-Fluoro-phenyl)-2,3,5,6-tetrahydro-[1,2'] bipyrazinyl-4-ylmethyl]-pyrazol-1-yl}-ethanol hydrochloride

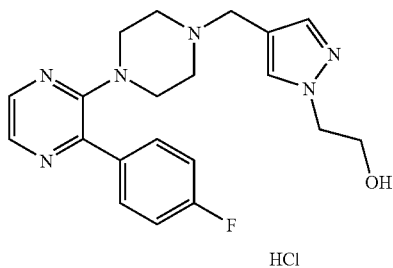

Dissolve 3'-(4-fluoro-phenyl)-3,4,5,6-tetrahydro-2H-[1,2']bipyrazinyl (0.320 g, 1.24 mmol) in DCE (5 mL). Add 1-(2-hydroxy-ethyl)-1H-pyrazole-4-carbaldehyde (0.243 g, 1.73 mmol), and stir at room temperature. Add sodium triacetoxyborohydride (0.394 g, 1.86 mmol) and stir at room temperature for 18 hr. Purify via SCX chromatography, followed by silica gel chromatography, eluting with 20:80 then 0:100 hexanes:ethyl acetate then 5:95 methanol:ethyl acetate then 10:90 methanol:ethyl acetate, to give the free base of the title compound (296 mg, 62%). Dissolve the free base (0.290 g, 0.760 mmol) in acetonitrile and add 1N aqueous HCl solution (913 μL, 0.913 mmol) and shake at ambient temperature for 30 min. Freeze and lyophilize to give the title compound (315 mg, 99%). MS (ES): m/z=383 [M+H]$^+$.

EXAMPLE 47

4-(1-Ethyl-5-methyl-1H-pyrazol-4-ylmethyl)-3'-(4-fluoro-phenyl)-3,4,5,6-tetrahydro-2H-[1,2']bipyrazine hydrochloride

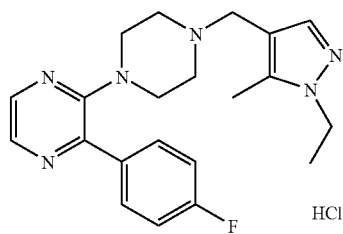

Dissolve 3'-(4-fluoro-phenyl)-3,4,5,6-tetrahydro-2H-[1,2']bipyrazinyl (0.183 g, 0.708 mmol) in DCE (8.5 mL). Add 1-ethyl-5-methyl-1H-pyrazole-4-carbaldehyde (0.117 g, 0.850 mmol) followed by sodium triacetoxyborohydride (0.225 g, 1.06 mmol) and stir at room temperature for 18 hr. Purify via SCX chromatography, followed by silica gel chromatography, eluting with 50:50 then 0:100 hexanes:ethyl acetate then 10:90 methanol:ethyl acetate, followed by reverse phase chromatography to give the free base of the title compound (149 mg, 55%). Dissolve the free base (0.138 g, 0.363 mmol) in methanol and add a solution of ammonium chloride (0.019 g, 0.363 mmol) in a minimal volume of methanol. Shake for 18 hr. at ambient temperature and concentrate to give the title compound (149 mg, 99%). MS (ES): m/z=381 [M+H]$^+$.

EXAMPLE 48

3'-(4-Fluoro-phenyl)-4-[1-(2,2,2-trifluoro-ethyl)-1H-pyrazol-4-ylmethyl]-3,4,5,6-tetrahydro-2H-[1,2'] bipyrazine hydrochloride

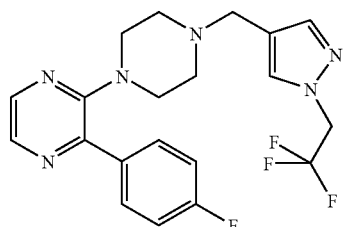

Dissolve 3'-(4-fluoro-phenyl)-3,4,5,6-tetrahydro-2H-[1,2']bipyrazinyl (0.150 g, 0.581 mmol) in DCE (5 mL). Add 1-(2,2,2-trifluoro-ethyl)-1H-pyrazole-4-carbaldehyde (0.124 g, 0.697 mmol) followed by sodium triacetoxyborohydride (0.185 g, 0.872 mmol) and stir at ambient temperature for 18 hr. Add 1-(2,2,2-trifluoro-ethyl)-1H-pyrazole-4-carbaldehyde (0.062 g, 0.349 mmol) and stir at ambient temperature for 2 hr. Add sodium triacetoxyborohydride (0.092 g, 0.436 mmol) and stir at ambient temperature for 72 hr. Purify via SCX chromatography. Add resin-bound-isocyanate (0.796 g, 1.16 mmol) and DCM (8 mL) and shake at ambient temperature for 4 hr. Filter, concentrate and purify (silica gel chromatography, eluting with 100:0 to 0:100 hexanes:ethyl acetate, then 10:90 methanol:ethyl acetate) to give the free base of the title compound (103 mg, 42%). Dissolve the free base (0.099 g, 0.237 mmol) in methanol and add a solution of ammonium chloride (0.013 g, 0.237 mmol) in a minimal volume of methanol. Shake for 18 hr. at ambient temperature and concentrate to give the title compound (108 mg, 100%). MS (ES): m/z=421[M+H]$^+$.

EXAMPLE 49

2-{4-[3'-(2-Fluoro-phenyl)-2,3,5,6-tetrahydro-[1,2'] bipyrazinyl-4-ylmethyl]-pyrazol-1-yl}-ethanol hydrochloride

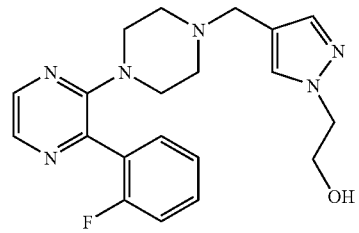

Dissolve 3'-(2-fluoro-phenyl)-3,4,5,6-tetrahydro-2H-[1,2']bipyrazinyl (0.213 g, 0.825 mmol) in DCE (5 mL). Add 1-(2-hydroxy-ethyl)-1H-pyrazole-4-carbaldehyde (0.137 g, 0.990 mmol) followed by sodium triacetoxyborohydride (0.262 g, 1.24 mmol) and stir at ambient temperature for 18 hr. Add additional 1-(2-hydroxy-ethyl)-1H-pyrazole-4-carbaldehyde (0.093 g, 0.663 mmol) and stir at ambient temperature for 18 hr. Purify via SCX chromatography followed by silica gel chromatography, (eluting with 100:0 to 0:100 hexanes:ethyl acetate, then 10:90 methanol:ethyl acetate), to give the free base of the title compound (116 mg, 37%). Dissolve the free base (0.114 g, 0.298 mmol) in methanol and add a solution of ammonium chloride (0.016 g, 0.298 mmol) in a minimal volume of methanol. Shake for 18 hr. at ambient temperature and concentrate to give the title compound (125 mg, 100%). MS (ES): m/z=383[M+H]$^+$.

EXAMPLE 50

3-{4-[3'-(4-Fluoro-phenyl)-2,3,5,6-tetrahydro-[1,2']bipyrazinyl-4-ylmethyl]-pyrazol-1-yl}-propan-1-ol hydrochloride

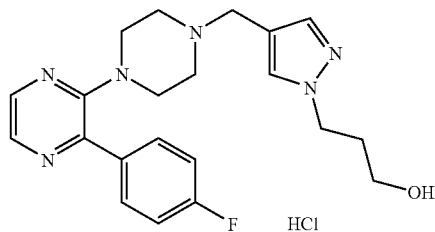

Dissolve 3'-(4-fluoro-phenyl)-3,4,5,6-tetrahydro-2H-[1,2']bipyrazinyl (0.150 g, 0.581 mmol) in DCE (5 mL). Add 1-(3-hydroxy-propyl)-1H-pyrazole-4-carbaldehyde (0.107 g, 0.697 mmol) followed by sodium triacetoxyborohydride (0.185 g, 0.872 mmol) and stir at room temperature for 18 hr. Purify via SCX chromatography, followed by silica gel chromatography (0:100 hexanes:ethyl acetate then 10:90 methanol:ethyl acetate), followed by reverse phase chromatography, SCX chromatography and silica gel chromatography (100:0 to 0:100 hexanes:ethyl acetate then 10:90 methanol:ethyl acetate to 20:80 methanol:ethyl acetate), to give the free base of the title compound (103 mg, 45%). Dissolve the free base (0.099 g, 0.251 mmol) in methanol and add a solution of ammonium chloride (0.013 g, 0.251 mmol) in a minimal volume of methanol. Shake for 18 hr. at ambient temperature and concentrate to give the title compound (105 mg, 97%). MS (ES): m/z=397 [M+H]$^+$.

EXAMPLE 51

4-[1-(1,2-Dimethyl-1H-imidazole-4-sulfonyl)-1H-pyrazol-4-ylmethyl]-3'-(4-fluoro-phenyl)-3,4,5,6-tetrahydro-2H-[1,2']bipyrazine

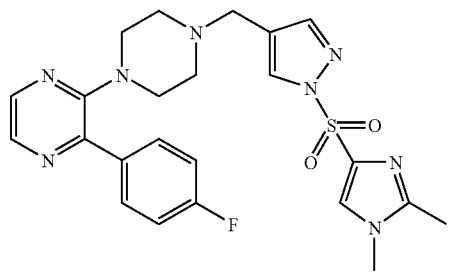

Use the method of Example 50, using 1-(1,2-dimethyl-1H-imidazole-4-sulfonyl)-1H-pyrazole-4-carbaldehyde to prepare the title compound (100 mg, 35%). MS (ES): m/z=497 [M+H]$^+$.

EXAMPLE 52

3'-(4-Fluoro-phenyl)-4-[1-(1-methyl-1H-imidazol-4-yl)-1H-pyrazol-4-ylmethyl]-3,4,5,6-tetrahydro-2H-[1,2']bipyrazinyl hydrochloride

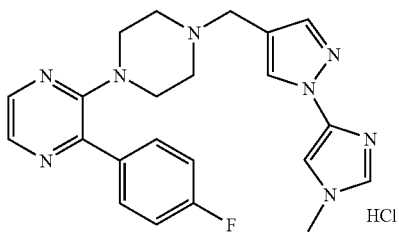

Dissolve 3'-(4-fluoro-phenyl)-3,4,5,6-tetrahydro-2H-[1,2']bipyrazinyl (0.053 g, 0.204 mmol) in DCE (2.1 mL). Add 1-(1-methyl-1H-imidazol-4-yl)-1H-pyrazole-4-carbaldehyde (0.036 g, 0.204 mmol) and stir at ambient temperature for 1 hr. Add sodium triacetoxyborohydride (0.065 g, 0.306 mmol) and acetic acid (19 μL) and stir at room temperature for 72 hr. Purify via SCX chromatography, followed by silica gel chromatography (50:50 to 0:100 hexanes:ethyl acetate then 10:90 to 20:80 methanol:ethyl acetate) to give the free base of the title compound (61 mg, 71%).

Dissolve the free base (0.059 g, 0.141 mmol) in acetonitrile (169 μL), add aqueous 1 N HCl solution (169 μL, 0.169 mmol), and shake for 15 min at ambient temperature. Freeze-dry to give the title compound (64 mg, 100%). MS (ES): m/z=419 [M+H]$^+$.

EXAMPLES 53 AND 54

1-{4-[3'-(4-Fluoro-phenyl)-2,3,5,6-tetrahydro-[1,2']bipyrazinyl-4-ylmethyl]-pyrazol-1-yl}-propan-2-ol hydrochloride, Isomer 1 and 2 respectively

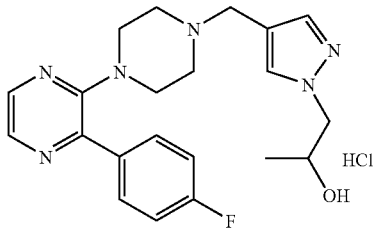

Dissolve 3'-(4-fluoro-phenyl)-3,4,5,6-tetrahydro-2H-[1,2']bipyrazinyl (0.160 g, 0.619 mmol) in DCE (5 mL). Add racemic 1-(2-hydroxy-propyl)-1H-pyrazole-4-carbaldehyde (0.175 g, 1.14 mmol) followed by sodium triacetoxyborohydride (0.262 g, 1.24 mmol) and stir at room temperature for 72 hr. Purify via SCX chromatography, followed by silica gel chromatography, eluting with 100:0 to 0:100 hexanes:ethyl acetate then 10:90 methanol:ethyl acetate, to give the racemic mixture of the free bases of the title compounds (223 mg, 91%).

Chirally purify the racemic title free bases on a Chiralpak AD-H 4.6×150 mm column with eluant 100% 3A+0.2% DMEA (0.6 mL/min flow). Separately dissolve each free base (Isomer 1: 0.080 g, 0.202 mmol, Isomer 2: 0.010 g, 0.187 mmol) in methanol and add a solution of ammonium chloride (equimolar in each case) in a minimal volume of methanol. Shake for 18 hr. at ambient temperature and concentrate to give the title compounds. (Isomer 1: 85 mg, 98% MS (ES): m/z=397 [M+H]$^+$, R$_f$=6.00; Isomer 2: (81 mg, 100%). MS (ES): m/z=397 [M+H]$^+$, R$_f$=–12.00.)

EXAMPLES 55 AND 56

1,1,1-Trifluoro-3-{4-[3'-(4-fluoro-phenyl)-2,3,5,6-tetrahydro-[1,2']bipyrazinyl-4-ylmethyl]-pyrazol-1-yl}-propan-2-ol hydrochloride, Isomers 1 and 2 Respectively

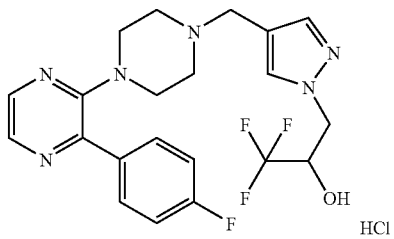

Dissolve 3'-(4-fluoro-phenyl)-3,4,5,6-tetrahydro-2H-[1,2']bipyrazinyl (0.143 g, 0.554 mmol) in DCE (5 mL). Add racemic 1-(3,3,3-trifluoro-2-hydroxy-propyl)-1H-pyrazole-4-carbaldehyde (0.236 g, 1.13 mmol) followed by sodium triacetoxyborohydride (0.235 g, 1.11 mmol) and stir at room temperature for 18 hr. Purify via SCX chromatography, followed by silica gel chromatography (eluting with 100:0 to 0:100 hexanes:ethyl acetate then 3:97 methanol:ethyl acetate), to give a racemic mixture of the free bases of the racemic title compounds (166 mg, 67%).

Chirally purify the free bases on a Chiralpak AD-H 4.6×150 mm column with eluant 100% 3A+0.2% DMEA (0.6 mL/min flow). Separately dissolve each free base (Isomer 1: 0.064 g, 0.142 mmol; Isomer 2: 0.060 g, 0.133 mmol) in methanol and add a solution of ammonium chloride (equimolar) in a minimal volume of methanol. Shake for 18 hr. at ambient temperature and concentrate to give the title compound. (Isomer 1: 69 mg, 100%, MS (ES): m/z=451 [M+H]$^+$, R$_f$=4.00; Isomer 2: 65 mg, 100%, MS (ES): m/z=451 [M+H]$^+$, R$_f$=–10.00.)

EXAMPLE 57

3'-(4-Fluoro-phenyl)-4-(2-methylphenyl-1H-pyrazol-4-ylmethyl)-3,4,5,6-tetrahydro-2H-[1,2']bipyrazine hydrochloride

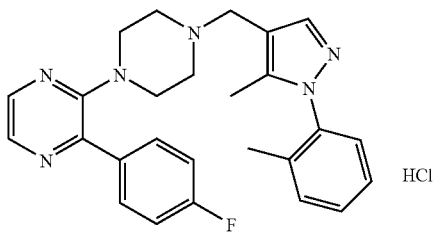

Dissolve 3'-(4-fluoro-phenyl)-3,4,5,6-tetrahydro-2H-[1,2']bipyrazinyl (0.151 g, 0.585 mmol) in DCE (5 mL). Add 5-methyl-1-(2-methylphenyl)-1H-pyrazole-4-carbaldehyde (0.140 g, 0.702 mmol) followed by sodium triacetoxyborohydride (0.186 g, 0.878 mmol) and stir at room temperature for 72 hr. Purify via SCX chromatography, followed by silica gel chromatography (eluting with 100:0 to 0:100 hexanes: ethyl acetate then 10:90 methanol:ethyl acetate), to give the free base of the title compound (222 mg, 86%). Dissolve the free base (0.217 g, 0.490 mmol) in methanol and add a solution of ammonium chloride (0.026 g, 0.490 mmol) in a minimal volume of methanol. Shake for 18 hr. at ambient temperature and concentrate to give the title compound (235 mg, 100%). MS (ES): m/z=443 [M+H]$^+$.

EXAMPLE 58

4-(1-Ethyl-5-methyl-1H-pyrazol-4-ylmethyl)-3'-(4-fluoro-phenyl)-3,4,5,6-tetrahydro-2H-[1,2']bipyrazinyl hydrochloride

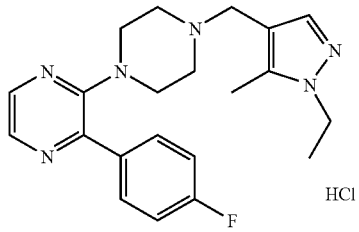

Dissolve 3'-(4-Fluoro-phenyl)-3,4,5,6-tetrahydro-2H-[1,2']bipyrazinyl (0.183 g, 0.708 mmol) in DCE (8.5 mL). Add 1-ethyl-5-methyl-1H-pyrazole-4-carbaldehyde (0.117 g, 0.850 mmol) followed by sodium triacetoxyborohydride (0.225 g, 1.06 mmol) and stir at room temperature for 18 hr. Purify via SCX chromatography, followed by silica gel chromatography (eluting with 50:50 then 0:100 hexanes:ethyl acetate then 10:90 methanol:ethyl acetate), followed by reverse phase chromatography to give the free base of the title compound (149 mg, 55%). Dissolve the free base (0.138 g, 0.363 mmol) in methanol and add a solution of ammonium chloride (0.019 g, 0.363 mmol) in a minimal volume of methanol. Shake for 18 hr. at ambient temperature and concentrate to give 4-(1-Ethyl-5-methyl-1H-pyrazol-4-ylmethyl)-3'-(4-fluoro-phenyl)-3,4,5,6-tetrahydro-2H-[1,2']bipyrazinyl hydrochloride (149 mg, 99%). MS (ES): m/z=381 [M+H]⁺.

EXAMPLE 59

4-(1-Cyclopropyl-1H-pyrazol-4-ylmethyl)-3'-(4-fluoro-phenyl)-3,4,5,6-tetrahydro-2H-[1,2']bipyrazinyl hydrochloride

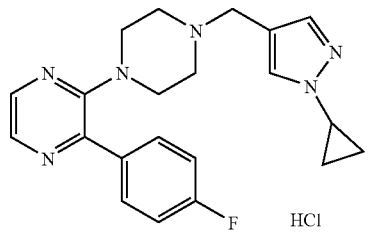

Dissolve 3'-(4-Fluoro-phenyl)-3,4,5,6-tetrahydro-2H-[1,2']bipyrazinyl (0.157 g, 0.608 mmol) in DCE (5 mL). Add 1-cyclopropyl-1H-pyrazole-4-carbaldehyde (0.354 g, 2.60 mmol) followed by sodium triacetoxyborohydride (0.193 g, 0.912 mmol) and stir at room temperature for 18 hr. Purify via SCX chromatography, followed by silica gel chromatography (eluting with 100:0 to 0:100 hexanes:ethyl acetate then 10:90 methanol:ethyl acetate), to give the free base of the title compound (16 mg, 7%). Dissolve this free base (0.014 g, 0.038 mmol) in methanol and add a solution of ammonium chloride (0.002 g, 0.038 mmol) in a minimal volume of methanol. Shake for 18 hr. at ambient temperature and concentrate to give the title compound (15 mg, 100%). MS (ES): m/z=379 [M+H]+.

EXAMPLE 60

1-{4-[4-(5-Methyl-1-phenyl-1H-pyrazol-4-ylmethyl)-3,4,5,6-tetrahydro-2H-[1,2']bipyrazinyl-3'-yl]-phenyl}-ethanone hydrochloride

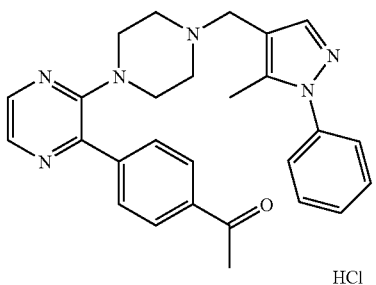

Dissolve 1-[4-(3,4,5,6-tetrahydro-2H-[1,2']bipyrazinyl-3'-yl)-phenyl]-ethanone (0.250 g, 0.885 mmol) in 1,2 dichloroethane (4 mL). Add 5-methyl-1-phenyl-1H-pyrazole-4-carbaldehyde (1.5 eq., 0.250 g, 1.33 mmol). Stir for 30 min. Add sodium triacetoxyborohydride (2.0 eq., 0.375 g, 1.77 mmol). Stir at room temperature for 48 hr. Purify by SCX column followed by normal phase chromatography with a gradient of 100% EtOAc to 5% 7N ammonia in methanol/ EtOAc to give the freebase of the title compound, (0.312 g, 78% yield). MS (ES): m/z=453.2[M+H]. Dissolve in a mixture of acetonitrile (2 mL) and water (3 mL). Add aq. 1N HCl (1 eq., 0.69 mmol, 0.69 mL). Freeze the solution to −78° C. in a dry-ice/acetone bath. Place the solution in the lyophilizer for 48 hr. to give the title compound (0.268 g, 80% yield). MS (ES): m/z=453.2 [M+H]⁺.

EXAMPLE 61

1-{4-[4-(5-Methyl-1-pyridin-2-yl-1H-pyrazol-4-ylmethyl)-3,4,5,6-tetrahydro-2H-[1,2']bipyrazinyl-3'-yl]-phenyl}-ethanone hydrochloride

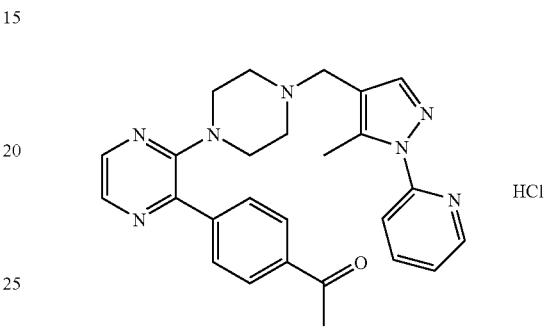

Dissolve 1-[4-(3,4,5,6-tetrahydro-2H-[1,2']bipyrazinyl-3'-yl)-phenyl]-ethanone (0.200 g, 0.710 mmol) in 1,2 dichloroethane (4 mL). Add 5-methyl-1-pyridin-2-yl-1H-pyrazole-4-carbaldehyde (1.5 eq., 0.200 g, 1.07 mmol). Stir for 30 min. Add sodium triacetoxyborohydride (2.0 eq., 0.300 g, 1.42 mmol). Stir at room temperature for 48 hr. Purify by SCX column followed by normal phase chromatography with a gradient of 100% EtOAc to 5% 7N NH₃ in methanol/EtOAc to give the free base of the title compound (0.273 g, 85% yield). MS (ES): m/z=454.2[M+H]⁺. Dissolve this free base (0.273 g, 0.60 mmol) in a mixture of acetonitrile (2 mL) and water (3 mL). Add aqueous 1N HCl (1 eq., 0.60 mmol, 0.60 mL). Freeze the solution to −78° C. in a dry-ice/acetone bath. Place the solution in the lyophilizer for 48 hr. to give the title compound (0.295 g, 100% yield). MS (ES): m/z=454.2 [M+H]⁺.

EXAMPLE 62

1-{4-[4-(3-Methyl-1-phenyl-1H-pyrazol-4-ylmethyl)-3,4,5,6-tetrahydro-2H-[1,2']bipyrazinyl-3'-yl]-phenyl}-ethanone hydrochloride

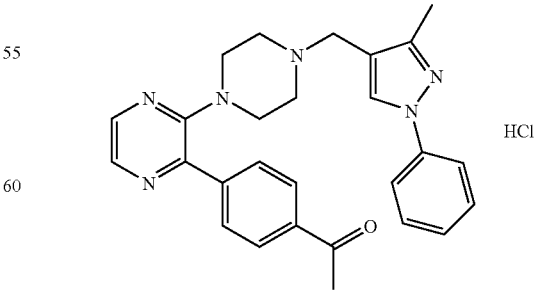

Dissolve 1-[4-(3,4,5,6-tetrahydro-2H-[1,2']bipyrazinyl-3'-yl)-phenyl]-ethanone (0.5 g, 1.77 mmol) in 1,2 dichloroethane (4 mL). Add 3-methyl-1-phenyl-1H-pyrazole-4-carbaldehyde (1.5 eq., 0.495 g, 2.66 mmol). Stir for 30 min. Add sodium triacetoxyborohydride (2.0 eq., 0.75 g, 3.54 mmol). Stir at room temperature for 48 hr. Purify by SCX column followed by normal phase chromatography with a gradient of 100% EtOAc-5% 7N $NH_3$ in methanol/EtOAc to give the freebase of the title compound (0.15 g, 18% yield). MS (ES): m/z=453.2 $[M+H]^+$. Dissolve (0.15 g, 0.33 mmol) in a mixture of acetonitrile (2 mL) and water (3 mL). Add aq. 1N HCl (1 eq., 0.33 mmol, 0.33 mL). Freeze the solution to −78° C. in a dry-ice/acetone bath. Place the solution in the lyophilizer for 48 hr. to give the title compound (0.156 g, 97% yield). MS (ES): m/z=453.2$[M+H]^+$.

EXAMPLE 63

3'-(4-Fluoro-phenyl)-4-[1-(4-methoxy-phenyl)-5-methyl-1H-pyrazol-4-ylmethyl]-3,4,5,6-tetrahydro-2H-[1,2']bipyrazine hydrochloride

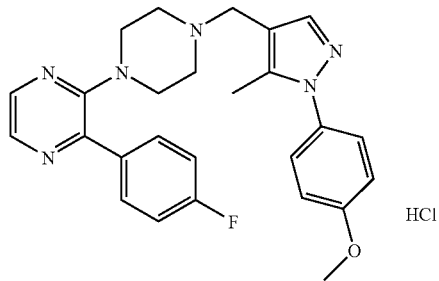

Use the methods of Example 55 using 5-methyl-1-(4-methoxyphenyl)-1H-pyrazole-4-carbaldehyde to prepare the title compound (240 mg, 91%). MS (ES): m/z=459 $[M+H]^+$.

EXAMPLE 64

3'-(4-Chlorophenyl)-4-(3,5-dimethyl-1-phenyl-1H-pyrazol-4-ylmethyl)-3,4,5,6-tetrahydro-2H-[1,2']bipyrazine hydrochloride

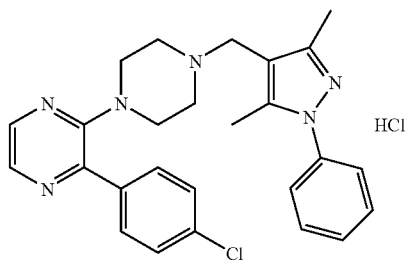

Couple 3'-(4-chlorophenyl)-3,4,5,6-tetrahydro-2H-[1,2']bipyrazinyl (0.103 g, 0.400 mmol) and 3,5-dimethyl-1-phenyl 1H-pyrazole-4-carbaldehyde (0.083 g, 0.679 mmol) in the presence of acetic acid (0.035 mL, 0.61 mmol) and sodium triacetoxy-borohydride (0.105 g, 0.491 mmol) in DCE (5 mL) for 44 hr. Purify by silica gel chromatography, eluting with 0:100 to 10:90 methanol:DCM. Dissolve the free base in methanol and add ammonium chloride (6.0 mg, 0.2 mmol). Stir overnight, concentrate under reduced pressure, add diethyl ether and stir overnight. Isolate the solid product by filtration and vacuum dry overnight to give the title compound (0.0637 g, 46%). MS (ES): m/z=460 $[M+H]^+$.

EXAMPLE 65

3'-(4-Methoxyphenyl)-4-(1,3,5-trimethyl-1H-pyrazol-4-ylmethyl)-3,4,5,6-tetrahydro-2H-[1,2']bipyrazine hydrochloride

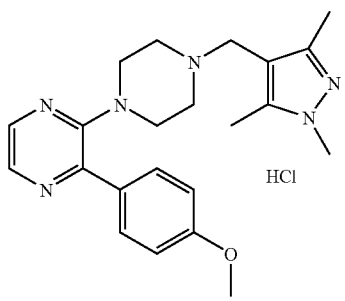

Couple 3'-(4-methoxyphenyl)-3,4,5,6-tetrahydro-2H-[1,2']bipyrazinyl (0.103 g, 0.400 mmol) and 1,3,5-trimethyl-1H-pyrazole-4-carbaldehyde (0.0727 g, 0.526 mmol) using sodium triacetoxyborohydride (0.167 g, 0.788 mmol) in DCE (5 mL). Stir at room temperature for 18 hr, and add the reaction mixture to an SCX column. Elute with 2 M ammonia in methanol. Purify by silica gel chromatography, eluting with 0:100 to 20:80 methanol:DCM. Dissolve the residue in methanol and add ammonium chloride (1.3 mL of a 0.2 M solution of ammonium chloride in methanol, 0.26 mmol). Stir overnight, concentrate, add diethyl ether and stir overnight. Isolate the solid product by filtration and vacuum dry overnight to give the title compound (100 mg, 58%). MS (ES): m/z=393 $[M+H]^+$.

EXAMPLE 66

3'-(4-Ethoxyphenyl)-4-(1,3,5-trimethyl-1H-pyrazol-4-ylmethyl)-3,4,5,6-tetrahydro-2H-[1,2']bipyrazine succinate

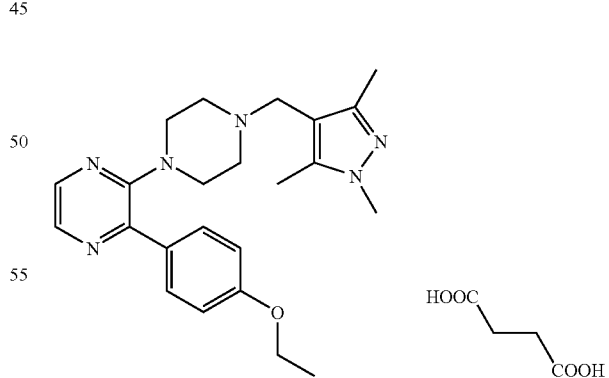

Couple (4-ethoxyphenyl)-3,4,5,6-tetrahydro-2H-[1,2']bipyrazinyl (0.745 g, 2.50 mmol) and 3,5-dimethyl-1-phenyl-1H-pyrazole-4-carbaldehyde (0.368 g, 2.66 mmol) in DCE (42 mL) using sodium triacetoxyborohydride (0.820 g, 3.87 mmol). Stir at room temperature for 43 hr, add 1 N sodium hydroxide (20 mL), and extract with DCM. Purify by silica gel chromatography, eluting with 0:100 to 7:93 methanol:

DCM, to give the free base (0.839 g, 83%). Dissolve a portion of the free base (0.160 g, 0.39 mmol) in methanol (5 mL), add succinic acid (0.0459 g, 0.39 mmol) and stir overnight. Concentrate, dissolve the residue in methanol (1 mL), add ethyl acetate, concentrate to a volume of about 1-2 mL and cool to −25° C. overnight. Isolate the solid product by filtration, wash with cold diethyl ether, and vacuum dry overnight to give the title compound (0.111 g, 54%). MS (ES): m/z=407 [M+H]$^+$.

EXAMPLE 67

3'-(4-Isopropoxyphenyl)-4-(1,3,5-trimethyl-1H-pyrazol-4-ylmethyl)-3,4,5,6-tetrahydro-2H-[1,2']bipyrazine succinate

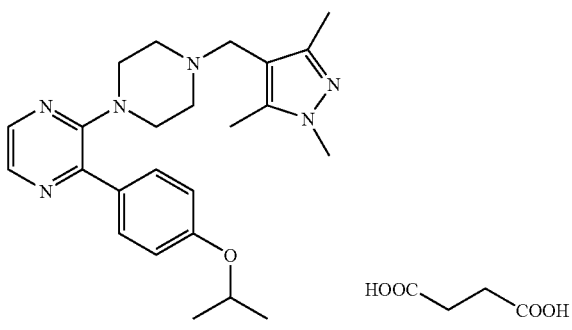

Combine (4-isopropoxyphenyl)-3,4,5,6-tetrahydro-2H-[1,2']bipyrazinyl (0.158 g, 0.557 mmol) and 1,3,5-trimethyl-1-1H-pyrazole-4-carbaldehyde (0.0853 g, 0.617 mmol) in DCE (12 mL), and add sodium triacetoxyborohydride (0.239 g, 1.13 mmol). Stir at room temperature for 24 hr. and add directly to an SCX cartridge (pre-wash column with methanol, then DCM), and elute with 2 M ammonia in methanol and concentrate. Purify by silica gel chromatography, eluting with 0:100 to 1:1 tetrahydrofuran:hexanes, to give the free base (0.158 g, 68%). GC-MS: m/z=421 [M+H]$^+$. Prepare the salt essentially as described for 3'-(4-ethoxyphenyl)-4-(1,3,5-trimethyl-1H-pyrazol-4-ylmethyl)-3,4,5,6-tetrahydro-2H-[1,2']bipyrazinyl succinate (0.0700 g, 23%). GC-MS: m/z=421 [M+H]$^+$.

EXAMPLE 68

4-(1,3-Dimethyl-1H-pyrazol-4-ylmethyl)-3'-(2-fluoro-phenyl)-3,4,5,6-tetrahydro-2H-[1,2']bipyrazinyl hydrochloride

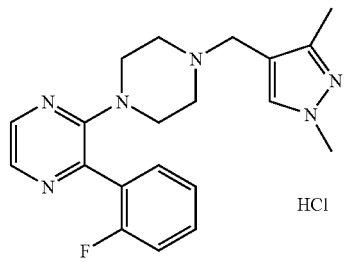

Charge a reaction tube with 3'-(2-fluoro-phenyl)-3,4,5,6-tetrahydro-2H-[1,2']bipyrazinyl (595 μmoles; 154 mg) in 3.5 mL of dry MeOH, followed by 10 mL of a 10% solution of trimethylacetic anhydride (TMAA) in dioxane, and 1,3-dimethyl-1H-pyrazole-4-carbaldehyde (396 μmoles; 50 mg). To the reaction mixture, add silica-bound cyanoborohydride (1200 μmoles; 1000 mg), seal the suspension and stir at room temperature overnight. Filter the crude material, wash with MeOH, and evaporate to dryness. Dissolve the residue in 50 mL of DCM, treat with water, brine, and evaporate the combined organics to give a pale yellow oil. Dissolve the crude material in DCM and pour onto a SCX column prewashed with 10 mL MeOH. Wash the material with 10 mL MeOH, and release the product with 20 mL of a 2N—NH$_3$/MeOH solution. Evaporate to give a white powder. Subject the crude material to reverse phase purification (22% isocratic CH$_3$CN/0.01 M NH$_4$HCO$_3$ in water, 80 mL/min, for 8 min, on a 30×75 mm, C$^{18}$ Xterra column) to provide the free base as a white solid (0.088 g, 40% yield, MS ES+(m/z) 367 [M+H]$^+$). Convert the purified material to the hydrochloride salt by dissolving in CH$_3$CN at room temperature and adding 1 eq. 1N HCl in water. After 5 min, lyophilize the solution to give the title compound as a white solid in quantitative yield, MS ES+(m/z) 367 [M+H]$^+$).

EXAMPLE 69

3'-(2-Fluoro-3-trifluoromethyl-phenyl)-4-(1,5-dimethyl-1H-pyrazol-4-ylmethyl)-3,4,5,6-tetrahydro-2H-[1,2']bipyrazine hydrochloride

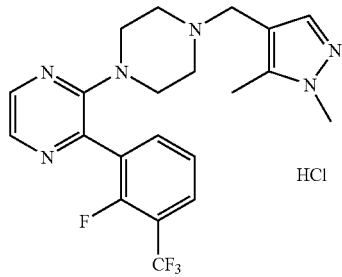

Dissolve 3'-(2-fluoro-3-trifluoromethyl-phenyl)-2,3,5,6-tetrahydro-[1,2']bipyrazinyl (0.0910 g, 0.279 mmol) and 1,5-dimethyl-1H-pyrazole-4-carbaldehyde (0.0591 g, 0.476 mmol) in DCE (10 mL) and stir at room temperature for 10 min. Add this mixture to a suspension of polystyrene-bound sodium cyanoborohydride (Biotage-Argonaut; 2.3 mmol/gm loading; 0.29 g, 0.67 mmol) followed by acetic acid (0.5 mL). Stir at room temperature for 18 hr. Purify via SCX chromatography, followed by silica gel chromatography (eluting with 0:100 to 10:90 methanol:DCM), to give the free base (120 mg, 99%). Dissolve the free base (0.119 g, 0.274 mmol)

in acetonitrile (6 mL), add 0.30 mL of 1M HCl (aq), and lyophilize to give the title compound (127 mg, 100%). MS (ES): m/z=435 [M+H]+.

EXAMPLE 70

3'-(4-Fluoro-3-trifluoromethyl-phenyl)-4-(1,5-dimethyl-1H-pyrazol-4-ylmethyl)-3,4,5,6-tetrahydro-2H-[1,2']bipyrazine succinate

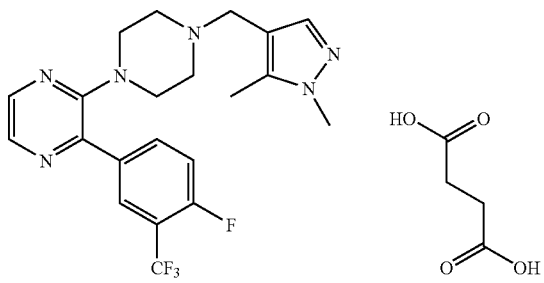

Use the methods of Example 69 using 3'-(4-fluoro-3-trifluoromethyl-phenyl)-2,3,5,6-tetrahydro-[1,2']bipyrazinyl to obtain title compound (54% overall yield). MS (ES): m/z=327 [M+H]+.

EXAMPLE 71

1-[2-(4-Fluorophenyl)-pyridin-3-yl]-4-(1H-pyrazol-4-ylmethyl)-piperazine hydrochloride

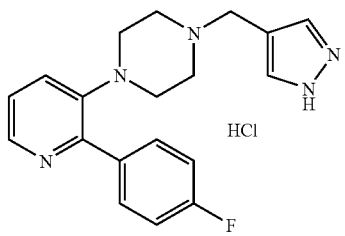

Dissolve 1-[2-(4-fluoro-phenyl)-pyridin-3-yl]-piperazine (0.140 g, 0.54 mmol) in DCE (5 mL). Add 1H-pyrazole-4-carbaldehyde (0.106 g, 1.10 mmol). Stir at room temperature for 20-30 min. Add sodium triacetoxyborohydride (0.233 g, 1.10 mmol) followed by acetic acid (0.049 g, 0.81 mmol). Stir the reaction mixture at room temperature for 48 hr. Check reaction mixture by LC-MS. Add DMSO (3 mL) as a cosolvent. Stir at ambient temperature for 72 hr. Purify by SCX cartridge, followed by reverse phase chromatography and normal phase chromatography (elute with a gradient of 20:80 to 0:100 5% 7N NH3 in methanol/EtOAc:EtOAc) to obtain the free base (0.099 g, 54%). Dissolve the free base (0.099 g, 0.293 mmol) in methanol (5 mL). Add ammonium chloride (0.016 g, 0.293 mmol, 1 eq.). Stir the reaction mixture at room temperature for 2 hr. and concentrate to give the title compound (0.103 g, 94%). MS (ES): m/z=338 [M+H]+.

EXAMPLE 72

1-(1,3-Dimethyl-1H-pyrazol-4-ylmethyl)-4-[2-(4-fluorophenyl)-pyridin-3-yl]-piperazine hydrochloride

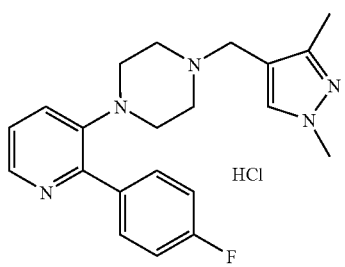

Dissolve 1-[2-(4-fluoro-phenyl)-pyridin-3-yl]-piperazine (0.140 g, 0.54 mmol) in DCE (5 mL). Add 1,3-dimethyl-1H-pyrazole-4-carbaldehyde (0.137 g, 1.10 mmol). Stir at room temperature for 20-30 min. Add sodium triacetoxyborohydride (0.233 g, 1.10 mmol) followed by acetic acid (0.049 g, 0.81 mmol). Stir the reaction mixture at room temperature for 48 hr. Purify by SCX cartridge, followed by reverse phase chromatography to obtain the free base (0.103 g, 52%). Dissolve the free base in methanol (5 mL). Add ammonium chloride (0.015 g, 0.282 mmol, 1 eq.). Stir the reaction mixture at room temperature for 2 hr. and concentrate to give the title compound (0.100 g, 88%). MS (ES): m/z=366 [M+H]+.

EXAMPLE 73

1-(1-Ethyl-1H-pyrazol-4-ylmethyl)-4-[2-(4-fluorophenyl)-pyridin-3-yl]-piperazine hydrochloride

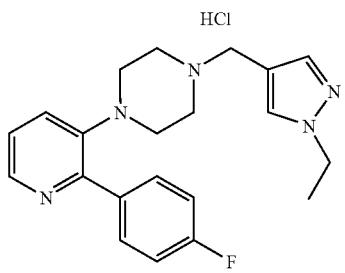

Prepared according to the methods of Example 72 using 1-ethyl-1H-pyrazole-4-carbaldehyde (51%). MS (ES): m/z=366 [M+H]+.

EXAMPLE 74

1-[2-(4-Fluoro-phenyl)-pyridin-3-yl]-4-(1-methyl-1H-pyrazol-4-ylmethyl)-piperazine hydrochloride

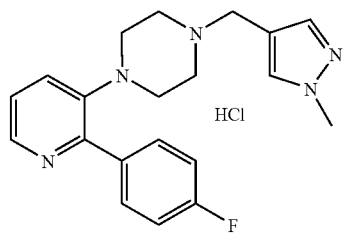

Dissolve 1-[2-(4-fluoro-phenyl)-pyridin-3-yl]-piperazine (0.150 g, 0.63 mmol) in DCE (5 mL). Add 1-methyl-1H-pyrazole-4-carbaldehyde (0.139 g, 1.26 mmol). Stir at room temperature for 20-30 min. Add sodium triacetoxyborohydride (0.267 g, 1.26 mmol) followed by acetic acid (0.040 g, 0.66 mmol). Stir the reaction mixture at room temperature for 14 hr. Partition crude reaction mixture between DCM and aqueous sat. NaHCO$_3$. Dry organic layer over anhydrous Na$_2$SO$_4$, filter and concentrate. Purify by normal phase chromatography (elute with a gradient of 100:0 to 80:20 EtOAc:7 N NH$_3$ in CH$_3$OH) to obtain the free base (0.157 g, 71%). Dissolve the free base in methanol (5 mL). Add ammonium chloride (0.024 g, 0.450 mmol, 1 eq.). Stir the reaction mixture at room temperature for 2 hr. and concentrate to give the title compound (0.150 g, 86%). MS (ES): m/z=352 [M+H]+.

Examples 75-81 are prepared essentially as described in Example 74 using the appropriate pyrazole-4-carbaldehyde.

| EX | Structure | Compound | Yield (%) | MS (ES) [M + H]+ |
|---|---|---|---|---|
| 75 | 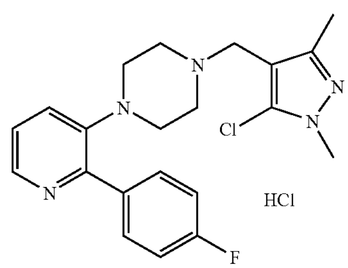 | 1-(5-Chloro-1,3-dimethyl-1H-pyrazol-4-ylmethyl)-4-[2-(4-fluorophenyl)-pyridin-3-yl]-piperazine hydrochloride | 91 | 400 |
| 76 | 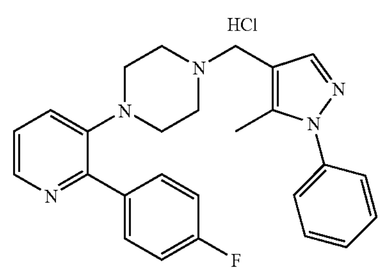 | 1-[2-(4-Fluorophenyl)-pyridin-3-yl]-4-(5-methyl-1-phenyl-1H-pyrazol-4-ylmethyl)-piperazine hydrochloride | 74 | 428 |
| 77 | 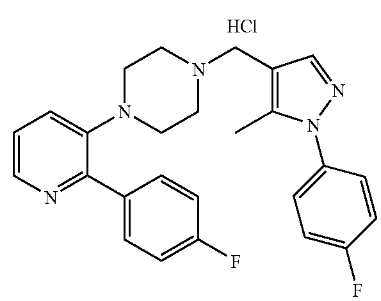 | 1-[1-(4-Fluorophenyl)-5-methyl-1H-pyrazol-4-ylmethyl]-4-[2-(4-fluorophenyl)-pyridin-3-yl]-piperazine hydrochloride | 100 | 446 |

| EX | Structure | Compound | Yield (%) | MS (ES) [M + H]+ |
|---|---|---|---|---|
| 78 | 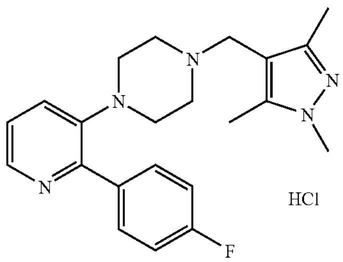 | 1-[2-(4-Fluoro-phenyl)-pyridin-3-yl]-4-(1,3,5-trimethyl-1H-pyrazol-4-ylmethyl)-piperazine hydrochloride | 81 | 380 |

EXAMPLE 79

1-[1-(4-Fluoro-phenyl)-5-methyl 1H-pyrazol-4-ylmethyl]-4-[2-(2-fluoro-phenyl)-pyridin-3-yl]-piperazine hydrochloride

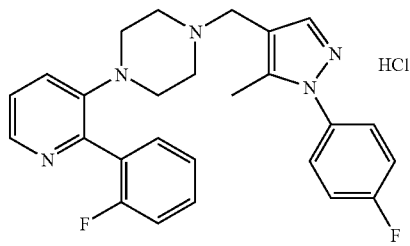

Prepare the title compound using methods similar to Example 4 using 2-(2-fluorophenyl)-3-piperazinylpyridine and 1-(4-fluorophenyl)-5-methyl-1H-pyrazole-4-carbaldehyde. 52% Yield, MS (ES) m/z=446 [M+H].

EXAMPLE 80

1-(1,5-Dimethyl-1H-pyrazol-4-ylmethyl)-4-[2-(4-fluoro-phenyl)-pyridin-3-yl]-piperazine hydrochloride

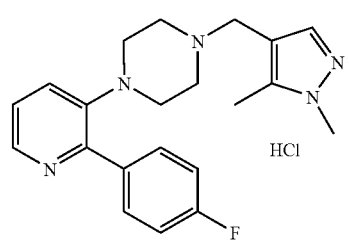

Prepare the title compound using methods similar to Example 4 using 2-(4-fluorophenyl)-3-piperazinylpyridine and 1,5-dimethyl-1H-pyrazole-4-carbaldehyde. 92% Yield, MS (ES) m/z=336 [M+H].

EXAMPLE 81

2-(4-{4-[2-(2-Fluoro-phenyl)-pyridin-3-yl]-piperazin-1-ylmethyl}-pyrazol-1-yl)-ethanol hydrochloride

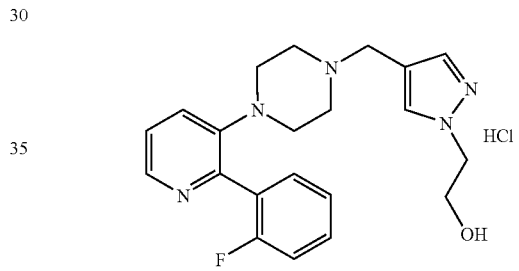

Prepare the title compound using methods similar to Example 72 using 1-[2-(2-fluoro-phenyl)-pyridin-3-yl]-piperazine and 1-(2-hydroxyethyl)-1H-pyrazole-4-carbaldehyde. 86% Yield, MS (ES) m/z=382 [M+H].

EXAMPLE 82

4-(1-Benzyl-3,5-dimethyl-1H-pyrazol-4-ylmethyl)-3'-(4-fluorophenyl)-3,4,5,6-tetrahydro-2H-[1,2']bipyrazine dihydrochloride

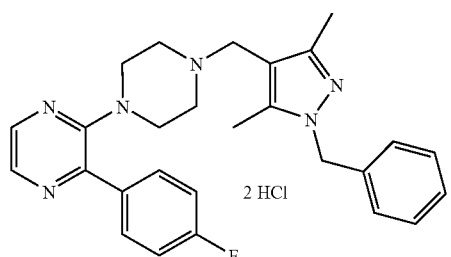

Dissolve 3'-(4-fluorophenyl)-3,4,5,6-tetrahydro-2H-[1,2']bipyrazinyl (1.834 g, 7.10 mmol) in dichloroethane (85 mL) and add 1-benzyl-3,5-dimethyl-1H-pyrazole-4-carbaldehyde (1.521 g, 7.10 mmol), sodium triacetoxyborohydride (2.257 g, 10.7 mmol) and acetic acid (0.60 mL). Stir the mixture for 18 hr. then dilute with ethyl acetate and wash with saturated aqueous sodium bicarbonate and saturated aqueous sodium chloride. Dry (sodium sulfate), filter, concentrate and purify (silica gel chromatography, eluting with ethyl acetate) to give the free base as a yellow glass (1.83 g, 56%). Dissolve the free base in methanol, add ammonium chloride and sonicate the mixture for 10 min. Concentrate the solution to give the title compound as a yellow solid. MS (ES): m/z=457 [M+H]$^+$.

The compounds of Examples 83-109 may be prepared essentially as described in Example 82 using the appropriate phenyl-3,4,5,6-tetrahydro-2H-[1,2']bipyrazine or phenyl-pyridin-2-yl-piperazine and pyrazole-4-carbaldehyde. The calculated yield is based on the free base. The mass spectroscopy data is based on the final compound as the mono or dihydrochloride salt.

| EX | Structure | Compound | Yield (%) | MS (ES) [M + H] |
|---|---|---|---|---|
| 83 | 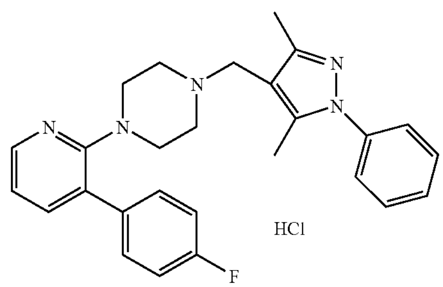 | 1-(3,5-Dimethyl-1-phenyl-1H-pyrazol-4-ylmethyl)-4-[3-(4-fluorophenyl)-pyridin-2-yl]-piperazine hydrochloride | 79 | 442 |
| 84 | 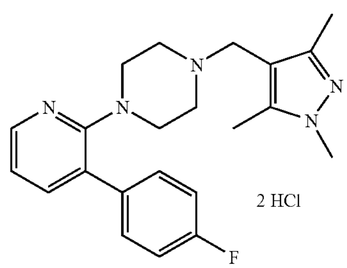 | 1-[3-(4-Fluorophenyl)-pyridin-2-yl]-4-(1,3,5-trimethyl-1H-pyrazol-4-ylmethyl)-piperazine dihydrochloride | 35 | 380 |
| 85 | 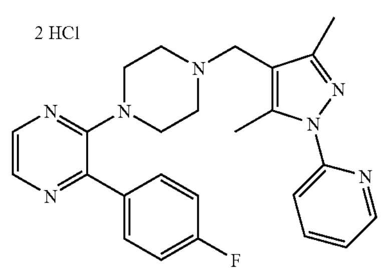 | 4-(3,5-Dimethyl-1-pyridin-2-yl-1H-pyrazol-4-ylmethyl)-3'-(4-fluorophenyl)-3,4,5,6-tetrahydro-2H-[1,2']bipyrazine dihydrochloride | 52 | 444 |
| 86 | 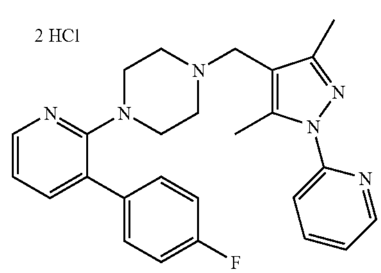 | 1-(3,5-Dimethyl-1-pyridin-2-yl-1H-pyrazol-4-ylmethyl)-4-[3-(4-fluorophenyl)-pyridin-2-yl]-piperazine dihydrochloride | 46 | 443 |

-continued

| EX | Structure | Compound | Yield (%) | MS (ES) [M + H] |
|---|---|---|---|---|
| 87 | 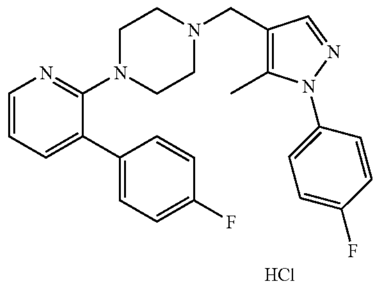 | 1-[1-(4-Fluoro-phenyl)-5-methyl-1H-pyrazol-4-ylmethyl]-4-[3-(4-fluoro-phenyl)-pyridin-2-yl]-piperazine hydrochloride | 80 | 446 |
| 88 | 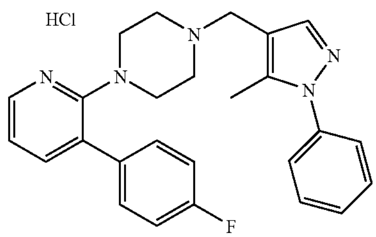 | 1-[3-(4-Fluoro-phenyl)-pyridin-2-yl]-4-(5-methyl-1-phenyl-1H-pyrazol-4-ylmethyl)-piperazine hydrochloride | 82 | 428 |
| 89 | 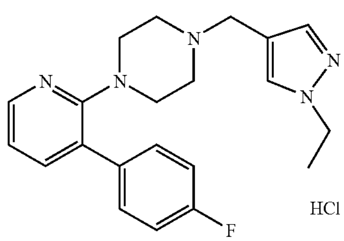 | 1-(1-Ethyl-1H-pyrazol-4-ylmethyl)-4-[3-(4-fluoro-phenyl)-pyridin-2-yl]-piperazine hydrochloride | 92 | 366 |
| 90 | 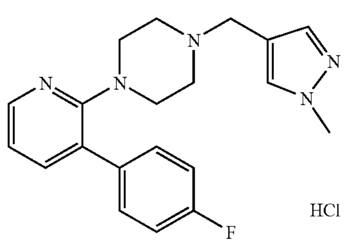 | 1-[3-(4-Fluoro-phenyl)-pyridin-2-yl]-4-(1-methyl-1H-pyrazol-4-ylmethyl)-piperazine hydrochloride | 86 | 352 |
| 91 | 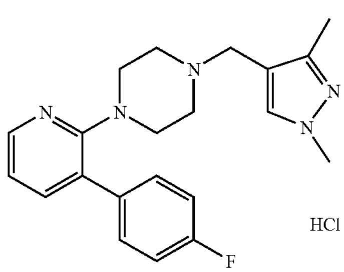 | 1-(1,3-Dimethyl-1H-pyrazol-4-ylmethyl)-4-[3-(4-fluoro-phenyl)-pyridin-2-yl]-piperazine hydrochloride | 93 | 366 |
| 92 | 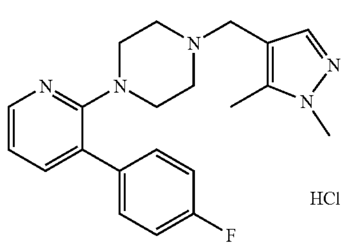 | 1-(1,5-Dimethyl-1H-pyrazol-4-ylmethyl)-4-[3-(4-fluoro-phenyl)-pyridin-2-yl]-piperazine hydrochloride | 96 | 366 |

-continued

| EX | Structure | Compound | Yield (%) | MS (ES) [M + H] |
|---|---|---|---|---|
| 93 | 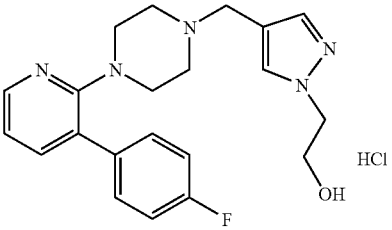 | 2-(4-{4-[3-(4-Fluoro-phenyl)-pyridin-2-yl]-piperazin-1-ylmethyl}-pyrazol-1-yl)-ethanol hydrochloride | 35 | 382 |
| 94 | 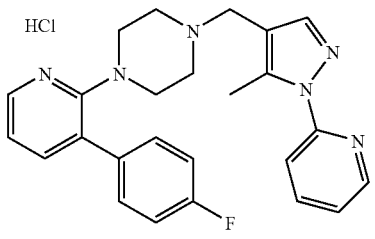 | 1-[3-(4-Fluoro-phenyl)-pyridin-2-yl]-4-(5-methyl-1-pyridin-2-yl-1H-pyrazol-4-ylmethyl)-piperazine hydrochloride | 57 | 429 |
| 95 | 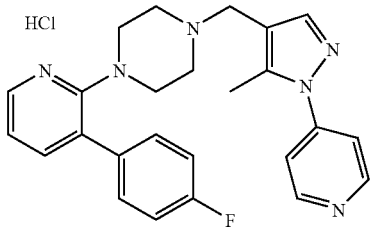 | 1-[3-(4-Fluoro-phenyl)-pyridin-2-yl]-4-(5-methyl-1-pyridin-4-yl-1H-pyrazol-4-ylmethyl)-piperazine hydrochloride | 53 | 429 |
| 96 | 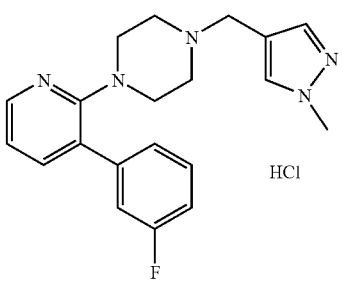 | 1-[3-(3-Fluoro-phenyl)-pyridin-2-yl]-4-(1-methyl-1H-pyrazol-4-ylmethyl)-piperazine hydrochloride | 94 | 352 |
| 97 | 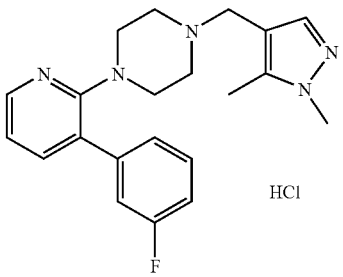 | 1-[3-(3-Fluoro-phenyl)-pyridin-2-yl]-4-(1,5-dimethyl-1H-pyrazol-4-ylmethyl)-piperazine hydrochloride | 84 | 366 |
| 98 | 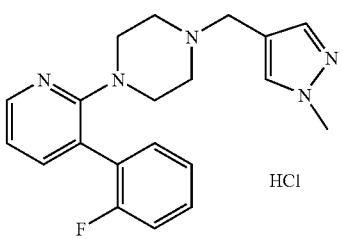 | 1-[3-(2-Fluoro-phenyl)-pyridin-2-yl]-4-(1-methyl-1H-pyrazol-4-ylmethyl)-piperazine hydrochloride | 89 | 352 |

-continued

| EX | Structure | Compound | Yield (%) | MS (ES) [M + H] |
|---|---|---|---|---|
| 99 | 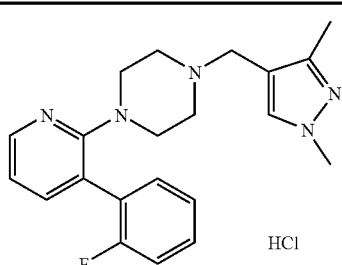 | 1-(1,3-Dimethyl-1H-pyrazol-4-ylmethyl)-4-[3-(2-fluoro-phenyl)-pyridin-2-yl]-piperazine hydrochloride | 84 | 366 |
| 100 | 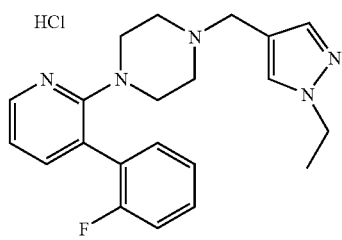 | 1-(1-Ethyl-1H-pyrazol-4-ylmethyl)-4-[3-(2-fluoro-phenyl)-pyridin-2-yl]-piperazine hydrochloride | 88 | 366 |
| 101 | 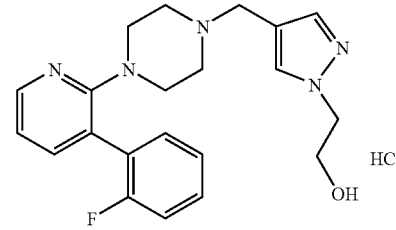 | 2-(4-{4-[3-(2-Fluoro-phenyl)-pyridin-2-yl]-piperazin-1-ylmethyl}-pyrazol-1-yl)-ethanol hydrochloride | 46 | 382 |
| 102 | 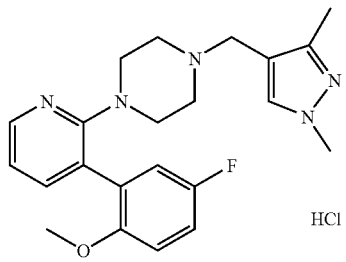 | 1-(1,3-Dimethyl-1H-pyrazol-4-ylmethyl)-4-[3-(5-fluoro-2-methoxy-phenyl)-pyridin-2-yl]-piperazine hydrochloride | 95 | 396 |
| 103 | 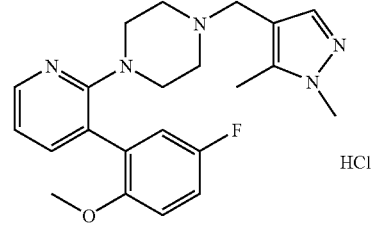 | 1-(1,5-Dimethyl-1H-pyrazol-4-ylmethyl)-4-[3-(5-fluoro-2-methoxy-phenyl)-pyridin-2-yl]-piperazine hydrochloride | 90 | 396 |
| 104 | 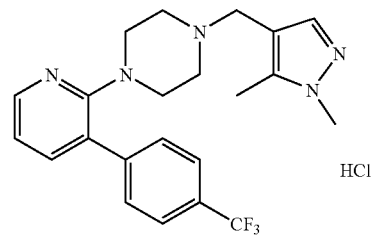 | 1-(1,5-Dimethyl-1H-pyrazol-4-ylmethyl)-4-[3-(4-trifluoromethyl-phenyl)-pyridin-2-yl]-piperazine hydrochloride | 86 | 416 |

-continued

| EX | Structure | Compound | Yield (%) | MS (ES) [M + H] |
|---|---|---|---|---|
| 105 | 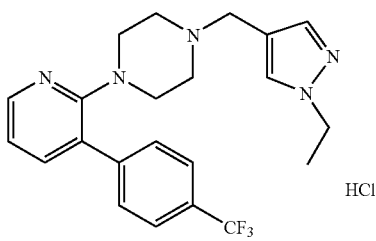 | 1-(1-Ethyl-1H-pyrazol-4-ylmethyl)-4-[3-(4-trifluoromethyl-phenyl)-pyridin-2-yl]-piperazine hydrochloride | 86 | 416 |
| 106 | 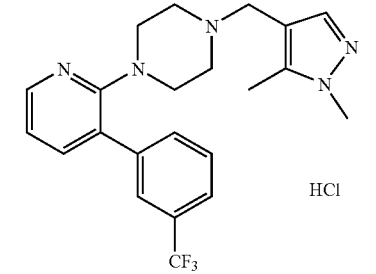 | 1-(1,5-Dimethyl-1H-pyrazol-4-ylmethyl)-4-[3-(3-trifluoromethyl-phenyl)-pyridin-2-yl]-piperazine hydrochloride | 98 | 416 |
| 107 | 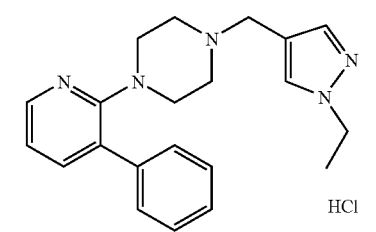 | 1-(1-Ethyl-1H-pyrazol-4-ylmethyl)-4-[3-phenyl-pyridin-2-yl]-piperazine hydrochloride | 93 | 348 |
| 108 | 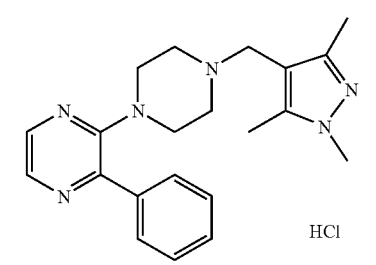 | 3'-Phenyl-4-(1,3,5-trimethyl-1H-pyrazol-4-ylmethyl)-3,4,5,6-tetrahydro-2H-[1,2']bipyrazine hydrochloride | 72 | 363 |
| 109 | 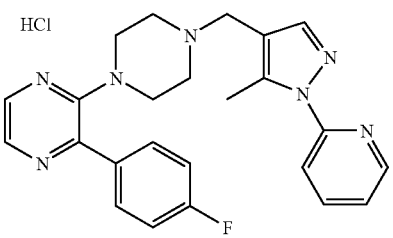 | 3'-(4-Fluoro-phenyl)-4-(5-methyl-1-pyridin-2-yl-1H-pyrazol-4-ylmethyl)-3,4,5,6-tetrahydro-2H-[1,2']bipyrazine hydrochloride | 51 | 430 |

EXAMPLE 110

4-(1-Benzyl-3,5-diethyl-1H-pyrazol-4-ylmethyl)-3'-(4-fluorophenyl)-3,4,5,6-tetrahydro-2H-[1,2']bipyrazine dihydrochloride

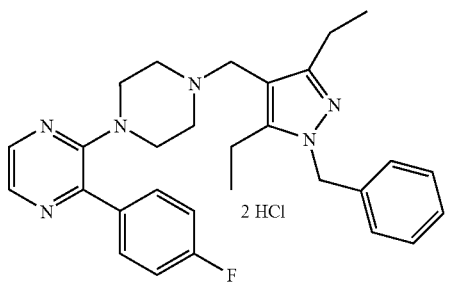

Dissolve 3'-(4-fluorophenyl)-3,4,5,6-tetrahydro-2H-[1,2']bipyrazinyl (1.082 g, 4.19 mmol) in dichloroethane (50 mL) and add 1-benzyl-3,5-diethyl-1H-pyrazole-4-carbaldehyde (1.015 g, 4.19 mmol), sodium triacetoxyborohydride (1.332 g, 6.28 mmol) and acetic acid (0.35 mL). Stir the mixture for 18 hr. then dilute with ethyl acetate and wash with saturated aqueous sodium bicarbonate, saturated aqueous sodium chloride, dry (sodium sulfate), filter, concentrate and purify (silica gel chromatography, eluting with 25:75 hexanes:ethyl acetate) to give the free base as a yellow oil (1.36 g, 67%). Dissolve the free base in methanol and add ammonium chloride (0.300 g, 5.61 mmol) then sonicate the mixture for 10 min. Concentrate the solution to give the title compound as a yellow solid. MS (ES): m/z=485 [M+H]+.

EXAMPLE 111

3'-(4-Fluorophenyl)-4-[1-(4-methoxybenzyl)-3,5-dimethyl-1H-pyrazol-4-ylmethyl]-3,4,5,6-tetrahydro-2H-[1,2']bipyrazine dihydrochloride

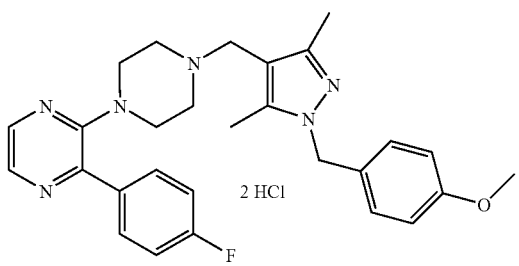

Dissolve 3'-(4-fluorophenyl)-3,4,5,6-tetrahydro-2H-[1,2']bipyrazinyl (0.344 g, 1.33 mmol) in DCM (15 mL) and add 1-(4-methoxybenzyl)-3,5-dimethyl-1H-pyrazole-4-carbaldehyde (0.325 g, 1.33 mmol), sodium triacetoxyborohydride (0.422 g, 2.00 mmol) and acetic acid (0.12 mL). Stir the mixture for 18 hr. then dilute with ethyl acetate, wash with saturated aqueous sodium bicarbonate, saturated aqueous sodium chloride, dry (sodium sulfate), filter, concentrate and purify (silica gel chromatography, eluting with 25:75 hexanes:ethyl acetate), to give the free base as a colorless oil (0.281 g, 43%). Dissolve the free base in methanol and add ammonium chloride then sonicate the mixture for 10 min. Concentrate the solution to give the title compound as a white solid. MS (ES): m/z=487 [M+H]+.

EXAMPLE 112

4-(3,5-Dimethyl-1-pyridin-4-yl-1H-pyrazol-4-ylmethyl)-3'-(4-fluorophenyl)-3,4,5,6-tetrahydro-2H-[1,2']bipyrazine dihydrochloride

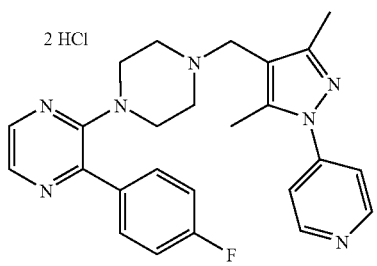

Dissolve 3'-(4-fluorophenyl)-3,4,5,6-tetrahydro-2H-[1,2']bipyrazinyl dihydrochloride (0.271 g, 0.870 mmol) in dichloroethane (11 mL) and add 3,5-dimethyl-1-pyridin-4-yl-1H-pyrazole-4-carbaldehyde (0.210 g, 1.04 mmol), sodium triacetoxyborohydride (0.332 g, 1.57 mmol), triethylamine (0.320 mL, 2.30 mmol) and acetic acid (0.090 mL). Stir for 18 hr, dilute with ethyl acetate, wash with saturated aqueous sodium bicarbonate, saturated aqueous sodium chloride, dry (sodium sulfate), filter, concentrate and purify (silica gel chromatography, eluting with ethyl acetate), to give the free base as a yellow oil (0.124 g, 32%). Dissolve the free base in methanol and add ammonium chloride then sonicate the mixture for 10 min. Concentrate the solution to give the title compound as a yellow solid. MS (ES): m/z=444 [M+H]+.

EXAMPLE 113

4-(5-Chloro-1-phenyl-1H-pyrazol-4-ylmethyl)-3'-(4-fluorophenyl)-3,4,5,6-tetrahydro-2H-[1,2']bipyrazine dihydrochloride

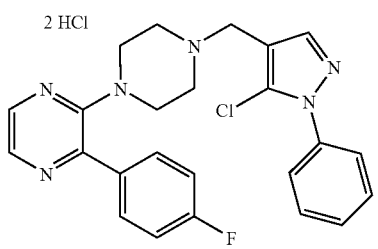

Dissolve 3'-(4-fluorophenyl)-3,4,5,6-tetrahydro-2H-[1,2']bipyrazinyl dihydrochloride (0.426 g, 1.29 mmol) in dichloroethane (13 mL) and add 5-chloro-1-phenyl-1H-pyrazole-4-carbaldehyde (0.319 g, 1.54 mmol), sodium triacetoxyborohydride (0.409 g, 1.93 mmol), triethylamine (0.394 mL, 2.83 mmol) and acetic acid (0.108 mL). Stir the mixture for 18 hr, dilute with ethyl acetate, wash with saturated aqueous sodium bicarbonate and saturated aqueous sodium chloride, dry (sodium sulfate), filter, concentrate and purify (silica gel chromatography, eluting with ethyl acetate), to give the free base as a yellow oily foam (0.279 g, 48%).

Dissolve the free base in methanol and add ammonium chloride then sonicate the mixture for 10 min. Concentrate the solution to give the title compound as a yellow solid. MS (ES): m/z=449,451 [M+H]+.

EXAMPLE 114

4-(3,5-Dimethyl-1-pyrimidin-2-yl-1H-pyrazol-4-ylmethyl)-3'-(4-fluorophenyl)-3,4,5,6-tetrahydro-2H-[1,2']bipyrazine dihydrochloride

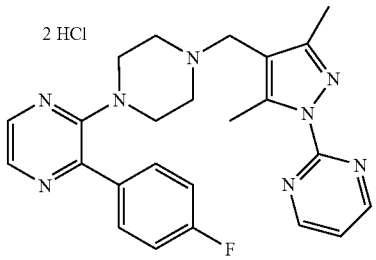

Dissolve 3'-(4-fluorophenyl)-3,4,5,6-tetrahydro-2H-[1,2'] bipyrazinyl dihydrochloride (0.257 g, 0.776 mmol) in dichloroethane (8 mL) and add 3,5-dimethyl-1-pyrimidin-2-yl-1H-pyrazole-4-carbaldehyde (0.157 g, 0.776 mmol), sodium triacetoxyborohydride (0.247 g, 1.16 mmol), triethylamine (0.238 mL, 1.71 mmol) and acetic acid (0.065 mL). Stir the mixture for 18 hr, then dilute with ethyl acetate. Wash with saturated aqueous sodium bicarbonate, saturated aqueous sodium chloride, dry (sodium sulfate), filter, concentrate and purify (silica gel chromatography, eluting with ethyl acetate), to give the free base as a yellow solid (0.211 g, 61%). Dissolve the free base in methanol and add ammonium chloride then sonicate the mixture for 10 min. Concentrate the solution to give the title compound as a yellow solid. MS (ES): m/z=445 [M+H]+.

EXAMPLE 115

1-[3-(2,5-Difluoro-phenyl)-pyridin-2-yl]-4-(1-methyl-1H-pyrazol-4-ylmethyl)-piperazine hydrochloride

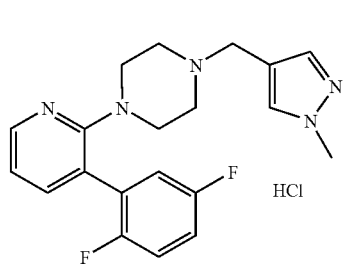

Combine 1-methyl-1H-pyrazole-4-carbaldehyde (0.090 g, 0.726 mmol) and 1-[3-(2,5-difluoro-phenyl)-pyridin-2-yl]-piperazine (0.200 g, 0.726 mmol) in dichloroethane (7 mL). Add glacial acetic acid (68 μL) followed by sodium triacetoxyborohydride (0.231 g, 1.09 mmol). Stir at room temperature for 20 hr. Dilute with saturated aqueous sodium bicarbonate then extract 3 times using DCM. Dry (sodium sulfate), filter, concentrate and purify (silica gel chromatography, (eluting with 4.5:95.5 2 M ammonia in methanol: DCM), to give a brown oil. Purify the oil using HPLC, (eluting with 40:60 acetonitrile:water (with 0.25% TFA) to give a clear oil. Dissolve the oil in methanol and apply to a 10 g SCX column. Wash the column with methanol then elute with 2N ammonia in methanol to give the free base as a clear oil. Dissolve the oil in methanol, add ammonium chloride and sonicate the mixture for 10 min. Evaporate the solution to give the title compound as a white solid (0.053 g, 18%). MS (ES): m/z=370 [M+H]+.

EXAMPLE 116

1-[3-(2,5-Difluoro-phenyl)-pyridin-2-yl]-4-(1,5-dimethyl-1H-pyrazol-4-ylmethyl)-piperazine hydrochloride

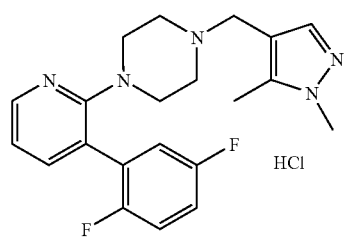

Use the methods of Example 115 using 1,5-dimethyl-1H-pyrazole-4-carbaldehyde to obtain the title compound (37%), MS (ES): m/z=384 [M+H]+.

EXAMPLE 117

4-(1,3,5-Trimethyl-1H-pyrazol-4-ylmethyl)-3'-(4-cyanophenyl)-3,4,5,6-tetrahydro-2H-[1,2']bipyrazine

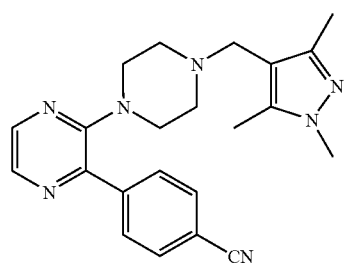

Suspend 4-(3,4,5,6-tetrahydro-2H-[1,2']bipyrazinyl-3'-yl)-benzonitrile (0.179 g, 0.675 mmol) in tetrahydrofuran (4 mL). Add 1,3,5-trimethyl-1H-pyrazole-4-carbaldehyde (0.098 g, 0.71 mmol) in tetrahydrofuran (490 μL), then sodium triacetoxyborohydride (0.15 g, 0.071 mmol) and stir under nitrogen at room temperature for 3 hr. Add saturated aqueous sodium hydrogen carbonate (10 mL) followed by 2 N sodium hydroxide (1 mL) to the mixture and extract with DCM (3×20 mL). Pass the combined DCM extracts through an IST Phase Separator Frit®, concentrate, and purify (silica gel chromatography, eluting with 0:100 to 12:88 methanol:DCM), to give the title compound (153.5 mg, 59%). MS (ES): m/z=388 [M+H]+.

EXAMPLE 118

3'-(4-Methanesulfonylphenyl)-4-(1,3,5-trimethyl-1H-pyrazol-4-ylmethyl)-3,4,5,6-tetrahydro-2H-[1,2']bipyrazine

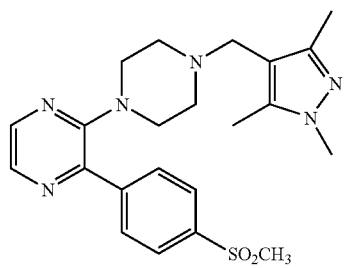

Suspend 3'-(4-methanesulfonylphenyl)-3,4,5,6-tetrahydro-2H-[1,2']bipyrazinyl (0.191 g, 0.60 mmol) in tetrahydrofuran (4 mL). Add 1,3,5-trimethyl-1H-pyrazole-4-carbaldehyde (0.087 g, 0.63 mmol) in tetrahydrofuran (435 µL), then sodium triacetoxyborohydride (0.13 g, 0.63 mmol). Subject reaction to ultrasound for 30 sec. then stir under nitrogen at room temperature for 7 hr. Add saturated aqueous sodium hydrogen carbonate (10 mL) followed by 2 N sodium hydroxide (1 mL) to the mixture and extract with DCM (3×20 mL). Pass the combined DCM extracts through an IST Phase Separator Frit®, concentrate and purify (silica gel chromatography, eluting with 0:100 to 12:88 methanol:DCM), to give the title compound (241.9 mg, 91%). MS (ES): m/z=441.2 [M+H]+.

EXAMPLE 119

3'-(2,6-Dimethyl-phenyl)-4-(1,5-dimethyl-1H-pyrazol-4-ylmethyl)-3,4,5,6-tetrahydro-2H-[1,2']bipyrazinyl (E)-but-2-enedioic acid fumarate

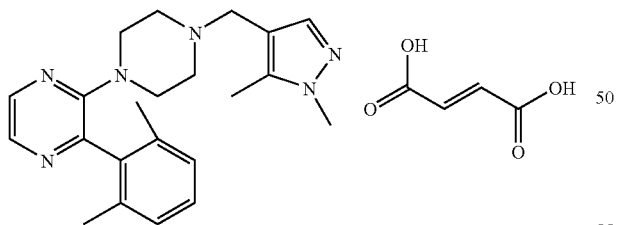

Stir 3'-(2,6-dimethyl-phenyl)-3,4,5,6-tetrahydro-2H-[1,2']bipyrazinyl dihydrochloride (156 mg, 0.46 mmol) in dry tetrahydrofuran (3 mL), and add 1,5-dimethyl-1H-pyrazole-4-carbaldehyde (86 mg, 0.69 mmol). Stir at room temperature for 10 min, and then add sodium triacetoxyborohydride (146 mg, 0.69 mmol). Stir reaction for 18 hr. at room temperature, then at 50° C. for 5 hr. under nitrogen. Pour reaction mixture into saturated aqueous sodium bicarbonate (10 mL), extract with DCM (3×10 mL) and pass through an IST Phase Separator Frit®. Concentrate and purify using silica gel chromatography, eluting with 0:100 to 10:90 methanol:DCM to give the free base as an oil. Dissolve the oil in ethanol and add 1 equivalent fumaric acid. Recrystallise to give the title compound as a white powder (67 mg, 30%). MS (ES): m/z=377 [M+H]+.

EXAMPLE 120

4-(1,5-Dimethyl-1H-pyrazol-4-ylmethyl)-3'-(3-trifluoromethyl-phenyl)-3,4,5,6-tetrahydro-2H-[1,2']bipyrazinyl (E)-but-2-enedioic acid fumarate

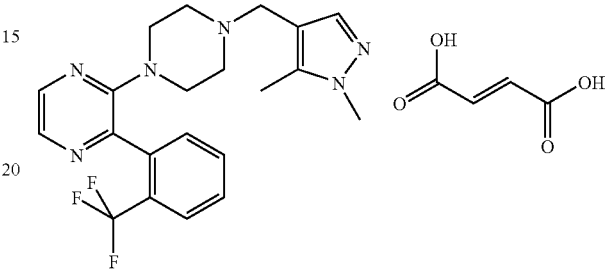

Stir 3'-(3-trifluoromethyl-phenyl)-3,4,5,6-tetrahydro-2H-[1,2']bipyrazinyl dihydrochloride (157 mg, 0.41 mmol) in dry tetrahydrofuran (3 mL), and add 1,5-dimethyl-1H-pyrazole-4-carbaldehyde (76 mg, 0.615 mmol). Stir at room temperature for 10 min, and then add sodium triacetoxyborohydride (130 mg, 0.615 mmol). Stir reaction for 18 hr. at room temperature, then quench with saturated aqueous sodium bicarbonate (10 mL), extract with DCM (3×10 mL) and pass through an IST Phase Separator Frit®. Concentrate and purify using silica gel chromatography, eluting with 0:100 to 10:90 methanol:DCM to obtain the free base as an oil. Dissolve the oil in ethanol and add 1 equivalent fumaric acid. Remove solvent to give the title compound as a white/cream colored powder (137 mg, 68%). MS (ES): m/z=417 [M+H]+.

EXAMPLE 121

4-(1-Ethyl-1H-pyrazol-4-ylmethyl)-3'-(4-fluorophenyl)-3,4,5,6-tetrahydro-2H-[1,2']bipyrazine hydrochloride

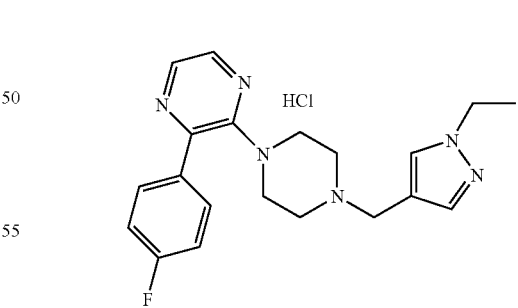

Add sodium triacetoxyborohydride (636 mg, 3 mmol) to a stirred suspension of 3'-(4-fluorophenyl)-3,4,5,6-tetrahydro-2H-[1,2']bipyrazinyl dihydrochloride (497 mg, 1.5 mmol) and 1-ethyl-1H-pyrazole-4-carboxaldehyde (279 mg, 2.25 mmol) in tetrahydrofuran (5 mL). The thick yellow suspension becomes mobile within 10 min. Quench after 30 min by addition of saturated aqueous sodium bicarbonate (10 mL), 2 N sodium hydroxide (3 mL), water (3 mL) and extract with DCM (10 mL). Separate the organic extract via a hydrophobic frit and concentrate to give a brown oil (740 mg). Purify using silica gel chromatography, eluting with 2:98 to 7:93 methanol:DCM, to give the free base as a yellow oil (577 mg). Redissolve in warm isopropanol (12 mL) and add a solution of 2 M HCl in diethyl ether (0.8 mL) to crystallize a white solid on standing. Filter and dry in vacuo at 60° C. to give the title compound (456 mg, 75%). MS (ES): m/z=367 [M+H]$^+$.

EXAMPLE 122

4-(1,5-Dimethyl-1H-pyrazol-4-ylmethyl)-3'-(4-fluorophenyl)-3,4,5,6-tetrahydro-2H-[1,2']bipyrazine hydrochloride

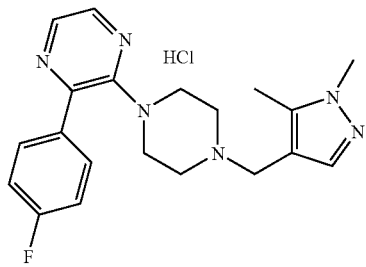

Add sodium triacetoxyborohydride (233 mg, 1.1 mmol) to a stirred mixture of 3'-(4-fluorophenyl)-3,4,5,6-tetrahydro-2H-[1,2']bipyrazinyl (190 mg, 0.74 mmol) and 1,5-dimethyl-1H-pyrazole-4-carboxaldehyde (137 mg, 1.1 mmol) in tetrahydrofuran (4 mL). Quench after 4 hr. by addition of saturated aqueous sodium bicarbonate (10 mL), 2 N sodium hydroxide (1 mL) and extract with DCM (10 mL). Separate the organic extract via a hydrophobic frit and concentrate to give a yellow oil (321 mg). Purify using silica gel chromatography, eluting with 2:92 to 20:90 methanol:DCM, to give the free base as a colorless oil (234 mg). Redissolve in isopropanol (3 mL) and add a solution of 2 M HCl in diethyl ether (0.5 mL) to crystallize a yellow solid on standing. Filter and dry in vacuo at 60° C. to give the title compound (217 mg, 73%). MS (ES): m/z=273 [M+H]$^+$.

Compounds of Examples 123-132 are prepared essentially as described in Example 122 using the appropriate aldehyde and sodium triacetoxyborohydride in tetrahydrofuran.

| EX | Structure | Compound | Yield (%) | MS (ES) [M + H]$^+$ |
|---|---|---|---|---|
| 123 | 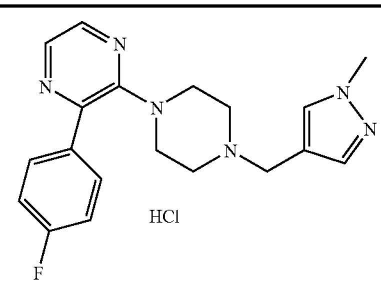 | 4-(1-Methyl-1H-pyrazol-4-ylmethyl)-3'-(4-fluorophenyl)-3,4,5,6-tetrahydro-2H-[1,2']bipyrazine hydrochloride | 65 | 353 |
| 124 | 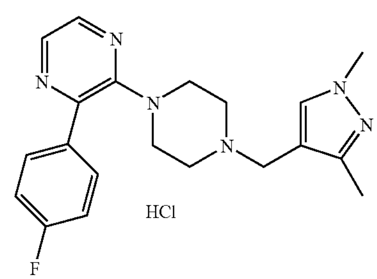 | 4-(1,3-Dimethyl-1H-pyrazol-4-ylmethyl)-3'-(4-fluorophenyl)-3,4,5,6-tetrahydro-2H-[1,2']bipyrazine hydrochloride | 88 | 367 |
| 125 | 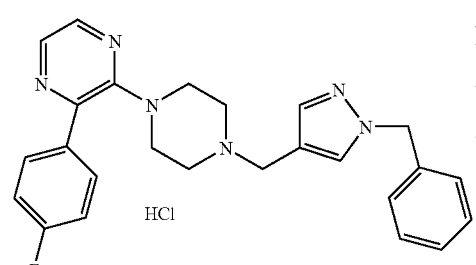 | 4-(1-Benzyl-1H-pyrazol-4-ylmethyl)-3'-(4-fluorophenyl)-3,4,5,6-tetrahydro-2H-[1,2']bipyrazine hydrochloride | 73 | 429 |

| EX | Structure | Compound | Yield (%) | MS (ES) [M + H]+ |
|---|---|---|---|---|
| 126 | 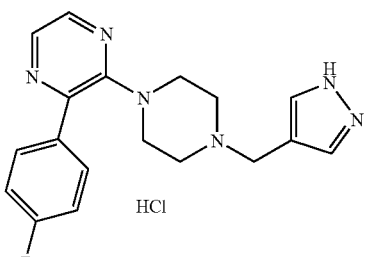 | 3'-(4-Fluorophenyl)-4-(1H-pyrazol-4-ylmethyl)-3,4,5,6-tetrahydro-2H-[1,2']bipyrazine hydrochloride | 24 | 339 |
| 127 | 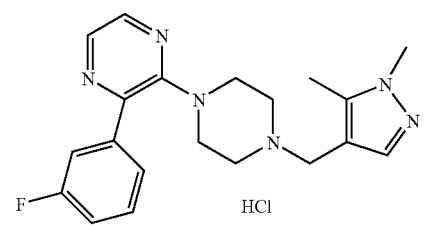 | 4-(1,5-Dimethyl-1H-pyrazol-4-ylmethyl)-3'-(3-fluoro-phenyl)-3,4,5,6-tetrahydro-2H-[1,2']bipyrazinyl hydrochloride | 64 | 367 |
| 128 | 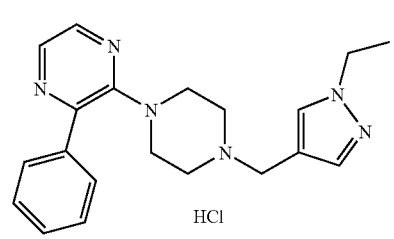 | 4-(1-Ethyl-1H-pyrazol-4-ylmethyl)-3'-phenyl-3,4,5,6-tetrahydro-2H-[1,2']bipyrazinyl hydrochloride | 71 | 349 |
| 129 | 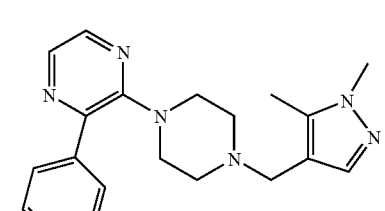 | 4-(1,5-Dimethyl-1H-pyrazol-4-ylmethyl)-3'-phenyl-3,4,5,6-tetrahydro-2H-[1,2']bipyrazinyl hydrochloride | 61 | 349 |
| 130 | 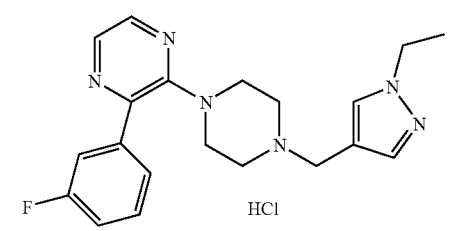 | 4-(1-Ethyl-1H-pyrazol-4-ylmethyl)-3'-(3-fluoro-phenyl)-3,4,5,6-tetrahydro-2H-[1,2']bipyrazinyl hydrochloride | 48 | 367 |

EXAMPLE 131

4-(3-Ethyl-1-phenyl-1H-pyrazol-4-ylmethyl)-3'-(4-fluoro-phenyl)-3,4,5,6-tetrahydro-2H-[1,2']bipyrazinyl hydrochloride

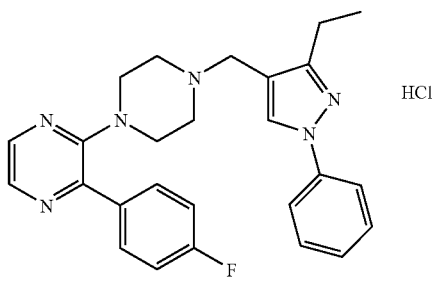

Dissolve 3'-(4-fluoro-phenyl)-3,4,5,6-tetrahydro-2H-[1,2']bipyrazinyl dihydrochloride (400 mg, 1.208 mmol) in methanol and form the free base by passing through an SCX-2® ion exchange cartridge, washing with methanol then eluting with 2M ammonia in methanol and concentrate to give a yellow oil (320 mg, 100%). Stir 3'-(4-fluoro-phenyl)-3,4,5,6-tetrahydro-2H-[1,2']bipyrazinyl (160 mg, 0.60 mmol) and 3-ethyl-1-phenyl-1H-pyrazole-4-carbaldehyde (120 mg, 0.60 mmol) in dry tetrahydrofuran (5 mL) at room temperature for 10 min. Add sodium triacetoxyborohydride (152 mg, 0.719 mmol) and stir reaction for 1 hr. under nitrogen. Pour reaction mixture into saturated aqueous sodium bicarbonate (10 mL), extract with DCM (3×20 mL) and pass through an IST Phase Separator Frit®. Concentrate and purify using silica gel chromatography (eluting with 5:95 methanol: DCM). Further purify by high pH reverse phase HPLC and concentrate. Dissolve the oil in acetonitrile and convert to the hydrochloride salt by adding 2 M aq HCl solution. Add water and lyophilize to give the title compound as a white powder (52 mg, 18%). MS (ES): m/z=443.2 [M+H]+.

EXAMPLE 132

1-(3,5-Dimethyl-1-phenyl-1H-pyrazol-4-ylmethyl)-4-(3-phenyl-pyridin-2-yl)-piperazine dihydrochloride

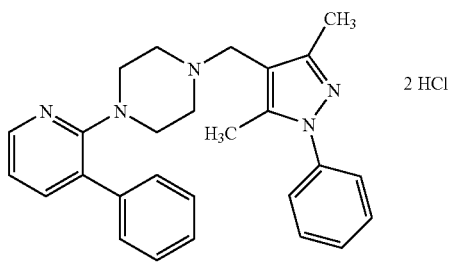

Add glacial acetic acid (81 µL, 1.38 mmol) to a solution of 1-(3-phenyl-pyridin-2-yl)-piperazine (275 mg, 1.15 mmol) and 3,5-dimethyl-1-phenyl-1H-pyrazole-4-carbaldehyde (276 mg, 1.38 mmol) in tetrahydrofuran (6 mL). Stir the reaction mixture at ambient temperature for 1.17 hr. Add sodium triacetoxyborohydride (365 mg, 1.72 mmol) and rinse with tetrahydrofuran (3 mL). Stir the reaction mixture at ambient temperature for 18 hr. Dilute the reaction mixture with diethyl ether and saturated sodium bicarbonate solution. Separate layers and extract the aqueous layer with diethyl ether. Combine the diethyl ether extracts and wash with water and brine, dry over sodium sulfate, filter and concentrate under reduced pressure. Purify the residue by silica gel chromatography. Elute with methanol-DCM to give the free base of the title compound (370 mg, 76%) HRMS-FAB (m/z): [M+H]+ calc'd for $C_{27}H_{30}N_5$, 424.2501; found, 424.2531.

Add acetyl chloride (126 µL, 1.77 mmol) to ethanol (10 mL) and stir the solution at ambient temperature for 10 min. Dissolve this free base (375 mg, 0.88 mmol) in diethyl ether and filter. Add an ethanolic hydrochloric acid solution to the free base solution. Concentrate the mixture under reduced pressure and concentrate twice more from diethyl ether. Dry the residue under reduced pressure for 18 hr. to give the title compound as a white foam (415 mg, 94%). HRMS-FAB (m/z): [M+H]+ calc'd for $C_{27}H_{30}N_5$, 424.2501; found, 424.2504.

EXAMPLE 133

4-(3-Methyl-1H-pyrazol-4-ylmethyl)-3'-phenyl-3,4,5,6-tetrahydro-2H-[1,2']bipyrazinyl hydrochloride

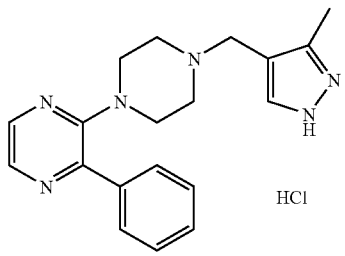

To a stirred suspension of 3'-phenyl-3,4,5,6-tetrahydro-2H-[1,2']bipyrazinyl dihydrochloride (0.4 g, 1.28 mmol, 1 eq) and 3-methyl-1H-pyrazole-4-carbaldehyde (0.27 g, 2.45 mmol, 1.92 eq) in tetrahydrofuran (20 mL) add sodium triacetoxyborohydride (0.88 g, 4.15 mmol, 3 eq) in one portion as a solid. Stir the mixture at room temperature under nitrogen for 70 hr. Add a further portion of 3-methyl-1H-pyrazole-4-carbaldehyde (70 mg, 0.639 mmol, 0.5 eq) and sodium triacetoxyborohydride (271 mg, 1.28 mmol, 1 eq) and stir for a further 21 hr. Add 2M aqueous sodium hydroxide solution (10 ml) and DCM (20 ml) separate and extract the aqueous layer with DCM (20 ml). Combine the organics, dry over magnesium sulfate, filter and concentrate. Purify by flash chromatography on silica gel column, eluting with 5% methanol in DCM, and then 5-10% methanol in DCM. Dissolve this material (157 mg, 0.47 mmol) in the minimum quantity of 50% aqueous acetonitrile. Add 2M aqueous hydrogen chloride (235 µL, 0.47 mmol) and lyophilize to give the title compound (159 mg, 34%). MS (ES): m/z=335.2 [M+H]⁺.

EXAMPLE 134

4-(1-Ethyl-3,5-dimethyl-1H-pyrazol-4-ylmethyl)-3'-(4-fluoro-phenyl)-3,4,5,6-tetrahydro-2H-[1,2']bipyrazinyl hydrochloride

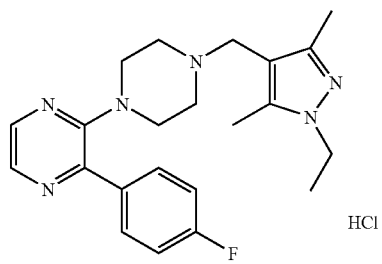

To a stirred suspension of 3'-(4-fluoro-phenyl)-3,4,5,6-tetrahydro-2H-[1,2']bipyrazinyl dihydrochloride (0.3 g, 0.906 mmol, 1 eq) and 1-ethyl-3,5-dimethyl-1H-pyrazole-4-carbaldehyde (207 mg, 1.36 mmol, 1.5 eq) in tetrahydrofuran (10 mL) add sodium triacetoxyborohydride (480 mg, 2.26 mmol, 2.5 eq) in one portion as a solid. Stir the mixture at room temperature under nitrogen for 19 hr. Add 2M aqueous sodium hydroxide solution (10 ml) and DCM (20 ml) separate and extract the aqueous layer with DCM (20 ml). Combine the organics, dry over magnesium sulfate, filter and concentrate. Purify by high pH reverse phase HPLC. Dissolve this material (49 mg, 0.12 mmol), in the minimum quantity of 50% aqueous acetonitrile. Add 2M aqueous hydrogen chloride (60 µL, 0.12 mmol) and lyophilize to give the title compound (58 mg, 15%). MS (ES): m/z=395.2 [M+H]⁺.

EXAMPLE 135

3'-(4-Fluorophenyl)-4-(3-methyl-1-propyl-1H-pyrazol-4-ylmethyl)-3,4,5,6-tetrahydro-2H-[1,2']bipyrazine hydrochloride

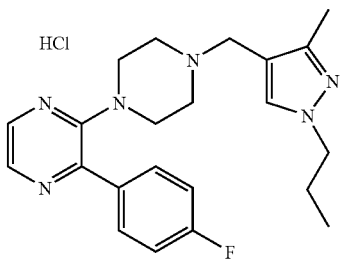

Dissolve [3'-(4-fluoro-phenyl)-2,3,5,6-tetrahydro-[1,2']bipyrazinyl-4-yl]-(3-methyl-1-propyl-1H-pyrazol-4-yl)-methanone (0.190 g, 0.465 mmol) in tetrahydrofuran (5 mL). Add 2 M borane-dimethylsulfide complex (349 µL, 0.697 mmol). Reflux at 75° C. for 18 hr. Cool to ambient temperature, and quench with methanol. Add 5 N sodium hydroxide solution (5 mL) and reflux for 1.5 hr. Cool to ambient temperature and concentrate under reduced pressure. Add ethyl acetate and water and separate layers. Extract aqueous layer 3 times with ethyl acetate. Dry organics over magnesium sulfate, filter and concentrate under reduced pressure. Purify with chromatography on silica gel eluting 50-100% ethyl acetate/hexanes then 10% methanol/ethyl acetate to give the free base (66 mg, 36% yield). Dissolve the free base (0.061 g, 0.156 mmol) in methanol and add a solution of ammonium chloride (0.008 g, 0.156 mmol) in a minimal volume of methanol. Shake for 18 hr. at room temperature and concentrate to give the title compound (67 mg, 100%). MS (ES): m/z=395 [M+H]⁺.

EXAMPLE 136

3'-(4-Fluorophenyl)-4-(1-isopropyl-1H-pyrazol-4-ylmethyl)-3,4,5,6-tetrahydro-2H-[1,2']bipyrazine hydrochloride

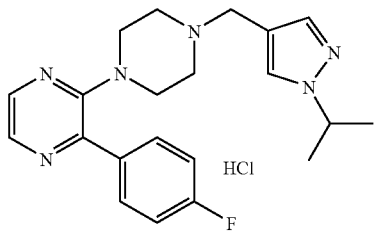

Prepare the title compound using the methods of Example 135 starting with [3'-(4-fluorophenyl)-2,3,5,6-tetrahydro-[1,2']bipyrazinyl-4-yl]-(1-isopropyl-1H-pyrazol-4-yl)-methanone (94 mg, 47%). Dissolve the free base (0.087 g, 0.229 mmol) in methanol and add a solution of ammonium chloride (0.012 g, 0.229 mmol) in a minimal volume of methanol. Shake for 18 hr. at room temperature and concentrate to give the title compound (94 mg, 99%). MS (ES): m/z=381 [M+H]⁺.

EXAMPLE 137

1-[3-(4-Fluoro-phenyl)-pyridin-2-yl]-4-(1-isopropyl-1H-pyrazol-4-ylmethyl)-piperazine hydrochloride

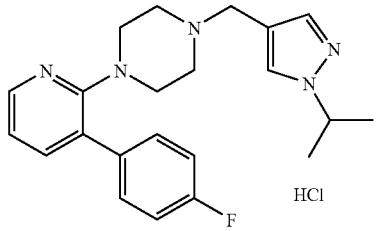

Dissolve {4-[3-(4-fluoro-phenyl)-pyridin-2-yl]-piperazin-1-yl}-(1-isopropyl-1H-pyrazol-4-yl)-methanone (0.280 g, 0.712 mmol) in tetrahydrofuran (5 mL). Add borane dimethylsulfide (2 M in tetrahydrofuran, 0.64 mL, 1.28 mmol), and reflux the mixture for 18 hr. Cool the mixture to room temperature and carefully add a small amount of methanol then 2N sodium hydroxide (5 mL). Reflux the mixture for 2 hr. then cool and evaporate the organics. Add water and extract the mixture 3 times with ethyl acetate. Dry (sodium sulfate), filter, concentrate and purify (silica gel chromatography, eluting with 6:94 2 M ammonia in methanol:DCM), to give the free base white solid. Dissolve the free base in methanol and add ammonium chloride then sonicate the mixture for 10 min. Evaporate the solution to give the title compound as a white solid (0.127 g, 43%). MS (ES): m/z=380 [M+H]⁺.

EXAMPLE 138

1-(1-Isopropyl-1H-pyrazol-4-ylmethyl)-4-[3-(4-trifluoromethyl-phenyl)-pyridin-2-yl]-piperazine hydrochloride

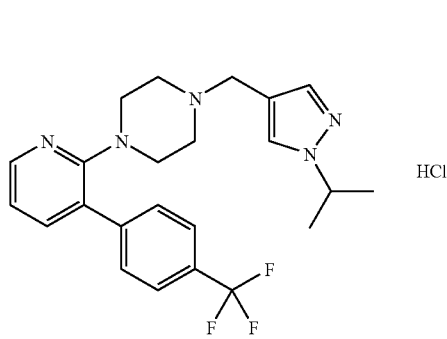

Use the methods of Example 137 starting with [3'-(4-trifluoromethyl-phenyl)-2,3,5,6-tetrahydro-[1,2']bipyrazinyl-4-yl]-(1-isopropyl-1H-pyrazol-4-yl)-methanone to obtain the title compound (52%). MS (ES): m/z=430 [M+H]⁺.

EXAMPLE 139

4-(5-Chloro-1-methyl-1H-pyrazol-4-ylmethyl)-3'-(4-fluoro-phenyl)-3,4,5,6-tetrahydro-2H-[1,2']bipyrazine hydrochloride

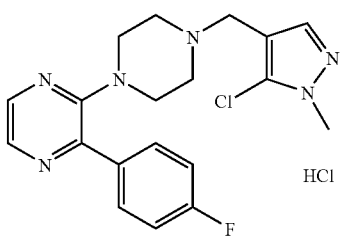

To a solution of 1M lithium aluminum hydride in tetrahydrofuran (1.97 mL, 1.97 mmol) under nitrogen add dropwise a solution of 3'-(4-fluoro-phenyl)-3,4,5,6-tetrahydro-2H-[1,2']bipyrazinyl (0.255 g, 0.99 mmoles) in tetrahydrofuran (5 mL). After stirring for 30 min heat the solution to reflux, then add dropwise a solution of 5-chloro-1-methyl-1H-pyrazole-4-carboxylic acid ethyl ester (223 mg, 1.18 mmol) in tetrahydrofuran (2 mL) over 45 min. After 30 min cool the reaction to room temperature and then cool to 0° C. Cautiously quench with water (10 mL), add DCM (10 mL) and then pass through a phase separator. Wash the aqueous layer twice with DCM (10 mL) and pass through the separator. Combine the organic extracts and concentrate then purify by flash chromatography (silica gel column, eluting with 0-15% methanol in methylene chloride). Further purify by reverse phase HPLC to obtain the free base. Dissolve the free base (59 mg, 0.16 mmol) in the minimum quantity of 50% aqueous acetonitrile. Add 2M aqueous HCl (80 μL, 0.16 mmol) and lyophilize to give the title compound (52 mg, 12%). MS (ES): m/z=387.1 [M+H]⁺.

EXAMPLE 140

3'-(4-Chloro-phenyl)-4-(1,3-dimethyl-1H-pyrazol-4-ylmethyl)-3,4,5,6-tetrahydro-2H-[1,2']bipyrazinyl

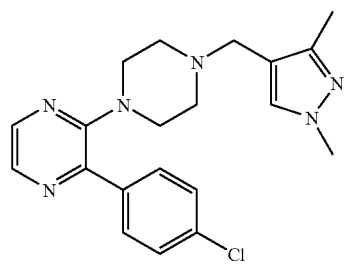

Add 4-chlorobenzeneboronic acid (64 mg, 0.41 mmol) to a mixture 3'-chloro-4-(1,3-dimethyl-1H-pyrazol-4-ylmethyl)-3,4,5,6-tetrahydro-2H-[1,2']bipyrazinyl (104 mg, 0.34 mmol), potassium carbonate (113 mg, 0.82 mmol) and tetrakis(triphenylphosphine) palladium(0) (0.002 g, 0.002 mmol) in N,N-dimethylacetamide (2 mL) and water (1 mL). Purge with nitrogen and heat overnight at 110° C. Cool to room temperature add water (10 mL), extract with DCM (3×20 mL) combine and purify using high pH reverse phase HPLC to give 3'-(4-chloro-phenyl)-4-(1,3-dimethyl-1H-pyrazol-4-ylmethyl)-3,4,5,6-tetrahydro-2H-[1,2']bipyrazinyl (68 mg, 54.2%). MS (ES): m/z=383 [M+H]⁺.

EXAMPLE 141

3'-(3-Chloro-4-fluorophenyl)-4-(1-methyl-1H-pyrazol-4-ylmethyl)-3,4,5,6-tetrahydro-2H-[1,2']bipyrazinyl

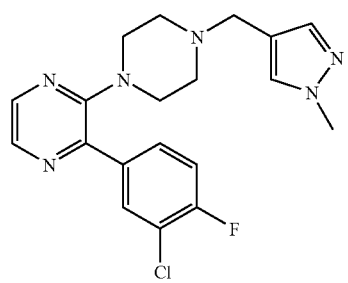

Add 3-chloro-4-fluorobenzeneboronic acid (71 mg, 0.41 mmol) to a mixture of 3'-chloro-4-(1-methyl-1H-pyrazol-4-ylmethyl)-3,4,5,6-tetrahydro-2H-[1,2']bipyrazinyl (104 mg, 0.34 mmol), potassium carbonate (113 mg, 0.82 mmol) and tetrakis(triphenyl-phosphine)palladium(0) (0.002 g, 0.002 mmol) in N,N-dimethylacetamide (2 mL) and water (1 mL). Purge with nitrogen and heat overnight at 110° C. Cool to room temperature, add water (10 mL), extract with DCM (3×20 mL), combine and purify using high pH reverse phase HPLC to give title compound (76 mg, 57.7%). MS (ES): m/z=387 [M+H]⁺.

EXAMPLE 142

4-(1-Methyl-1H-pyrazol-4-ylmethyl)-3'-(2,3-difluorophenyl)-3,4,5,6-tetrahydro-2H-[1,2']bipyrazine

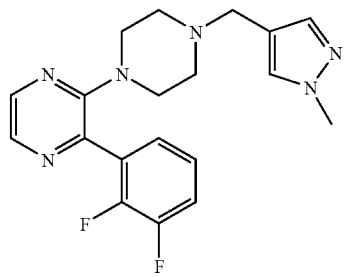

Dissolve 3'-chloro-4-(1-methyl-1H-pyrazol-4-ylmethyl)-3,4,5,6-tetrahydro-2H-[1,2']bipyrazinyl (160 mg, 0.55 mmol) in N,N-dimethylacetamide (4 mL) and water (2 mL) and purge with nitrogen for 0.5 hr. Add potassium carbonate (180 mg, 1.30 mmol) then 2,3-difluorobenzeneboronic acid (100 mg, 0.66 mmol) and purge with nitrogen for 0.5 hr. Add tetrakis(triphenylphosphine)palladium(0) (0.01 g, 0.0086 mmol) and heat at 110° C. for 3.25 hr. Cool to room temperature and purify (silica gel chromatography, eluting with 0:100 to 30:70 methanol:DCM), followed by reverse phase HPLC to give the title compound (52.69 mg, 26%). MS (ES): m/z=371 [M+H]$^+$.

The compounds of Examples 143-145 are prepared essentially as described in Example 142 using the appropriate boronic acid.

| EX | Structure | Compound | Yield (%) | MS (ES) [M + H]$^+$ |
|---|---|---|---|---|
| 143 | 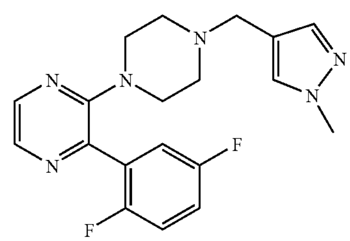 | 4-(1-Methyl-1H-pyrazol-4-ylmethyl)-3'-(2,5-difluorophenyl)-3,4,5,6-tetrahydro-2H-[1,2']bipyrazine | 26 | 371 |
| 144 | 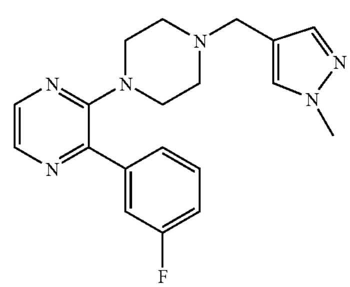 | 4-(1-Methyl-1H-pyrazol-4-ylmethyl)-3'-(3-fluorophenyl)-3,4,5,6-tetrahydro-2H-[1,2']bipyrazine | 50 | 353 |
| 145 | 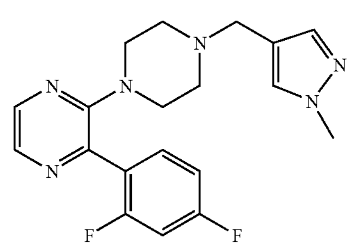 | 4-(1-Methyl-1H-pyrazol-4-ylmethyl)-3'-(2,4-difluorophenyl)-3,4,5,6-tetrahydro-2H-[1,2']bipyrazine | 53 | 371 |

EXAMPLE 146

4-(1-Methyl-1H-pyrazol-4-ylmethyl)-3'-(3-trifluoromethylphenyl)-3,4,5,6-tetrahydro-2H-[1,2']bipyrazine

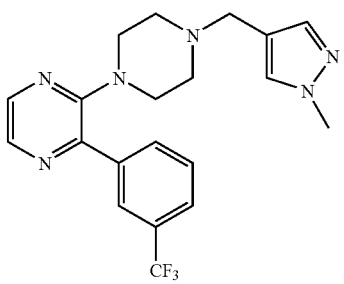

Charge a carousel tube with 3-trifluoromethylbenzeneboronic acid (136 mg, 0.66 mmol), 3'-chloro-4-(1-methyl-1H-pyrazol-4-ylmethyl)-3,4,5,6-tetrahydro-2H-[1,2']bipyrazinyl (160 mg, 0.55 mmol) and N,N-dimethylacetamide (1 mL). Add N,N-dimethylacetamide (3 mL) and potassium carbonate (185 mg, 1.32 mmol) and purge with nitrogen for about 45 min. Add water (2 mL, purged with nitrogen for 1 hr.) then tetrakis(triphenylphosphine)palladium(0) (0.003 g, 0.0025 mmol) and purge the reaction vessel for about 30 min. Heat at 110° C. overnight. Cool to room temperature, add water and extract with DCM (3×30 mL), and then concentrate the combined DCM extracts. Purify using silica gel chromatography, followed by reverse phase HPLC, to give the title compound (128 mg, 58%). MS (ES): m/z=403.1 [M+H]$^+$.

Compounds of Examples 147-154 are prepared essentially as described in Example 146 using the appropriate boronic acid and 3'-chloro-4-(1-methyl-1H-pyrazol-4-ylmethyl)-3,4,5,6-tetrahydro-2H-[1,2']bipyrazinyl.

| EX | Structure | Compound | Yield (%) | MS (ES) [M + H]$^+$ |
|---|---|---|---|---|
| 147 | 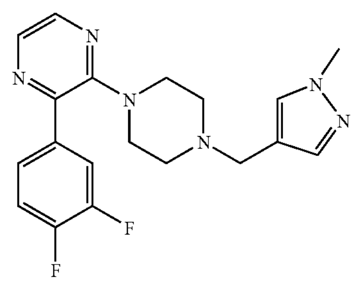 | 4-(1-Methyl-1H-pyrazol-4-ylmethyl)-3'-(3,4-difluorophenyl)-3,4,5,6-tetrahydro-2H-[1,2']bipyrazine | 29 | 371 |
| 148 | 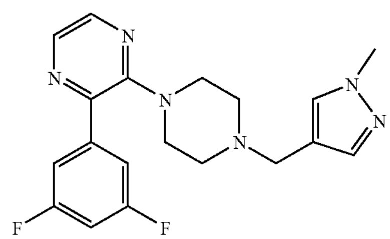 | 4-(1-Methyl-1H-pyrazol-4-ylmethyl)-3'-(3,5-difluorophenyl)-3,4,5,6-tetrahydro-2H-[1,2']bipyrazine | 54 | 371 |
| 149 | 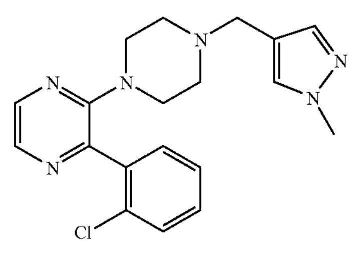 | 4-(1-Methyl-1H-pyrazol-4-ylmethyl)-3'-(2-chlorophenyl)-3,4,5,6-tetrahydro-2H-[1,2']bipyrazine | 53 | 36 |
| 150 | 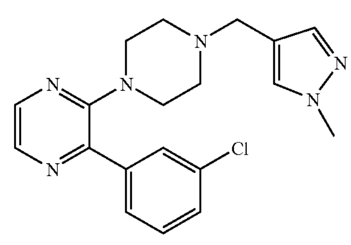 | 4-(1-Methyl-1H-pyrazol-4-ylmethyl)-3'-(3-chlorophenyl)-3,4,5,6-tetrahydro-2H-[1,2']bipyrazine | 47 | 369 |

-continued

| EX | Structure | Compound | Yield (%) | MS (ES) [M + H]+ |
|---|---|---|---|---|
| 151 | 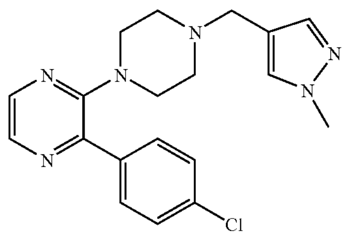 | 4-(1-Methyl-1H-pyrazol-4-ylmethyl)-3'-(4-chlorophenyl)-3,4,5,6-tetrahydro-2H-[1,2']bipyrazine | 25 | 369 |
| 152 | 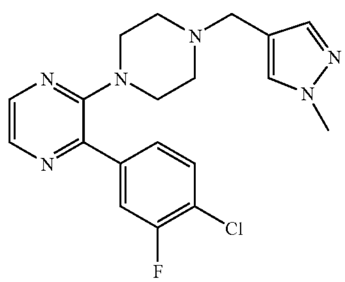 | 4-(1-Methyl-1H-pyrazol-4-ylmethyl)-3'-(4-chloro-3-fluorophenyl)-3,4,5,6-tetrahydro-2H-[1,2']bipyrazine | 54 | 387 |
| 153 | 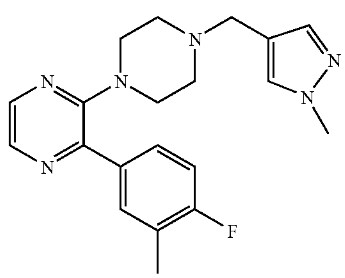 | 4-(1-Methyl-1H-pyrazol-4-ylmethyl)-3'-(4-fluoro-3-methylphenyl)-3,4,5,6-tetrahydro-2H-[1,2']bipyrazine | 56 | 367 |
| 154 | 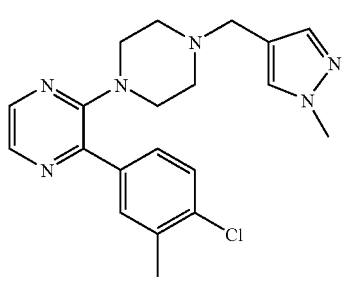 | 4-(1-Methyl-1H-pyrazol-4-ylmethyl)-3'-(4-chloro-3-methylphenyl)-3,4,5,6-tetrahydro-2H-[1,2']bipyrazine | 50 | 383 |

EXAMPLE 155

4-(1,3-Dimethyl-1H-pyrazol-4-ylmethyl)-3'-(3-trifluoromethoxyphenyl)-3,4,5,6-tetrahydro-2H-[1,2']bipyrazine

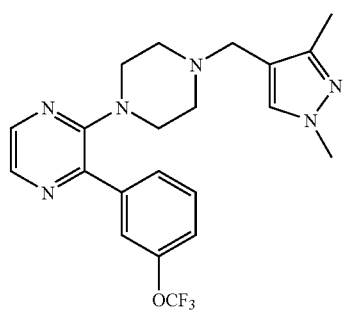

Charge a carousel tube with 3-(trifluoromethoxy)benzeneboronic acid (140 mg, 0.68 mmol), 3'-chloro-4-(1,3-dimethyl-1H-pyrazol-4-ylmethyl)-3,4,5,6-tetrahydro-2H-[1,2']bipyrazinyl (173 mg, 0.56 mmol) and N,N-dimethylacetamide (1 mL). Add N,N-dimethylacetamide (3 mL) and potassium carbonate (190 mg, 1.35 mmol) and purge with nitrogen for about 45 min. Add water (2 mL, purged with nitrogen for 1 hr.), then tetrakis(triphenylphosphine)palladium(0) (0.004 g, 0.0034 mmol), purge the reaction for about 30 min., and then heat overnight at 110° C. Cool to room temperature, add water and extract with DCM (3×30 mL). Concentrate the combined DCM extracts and purify using silica gel chromatography followed by reverse phase HPLC to give the title compound (0.087 g, 30%). MS (ES): m/z=433.1 [M+H]$^+$.

Compounds of Examples 156-162 are prepared essentially as described in Example 155 using the appropriate boronic acid.

| EX | Structure | Compound | Yield (%) | MS (ES) [M + H]$^+$ |
|---|---|---|---|---|
| 156 | 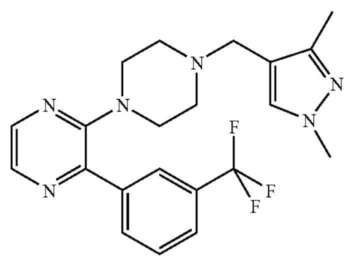 | 4-(1,3-Dimethyl-1H-pyrazol-4-ylmethyl)-3'-(3-trifluoromethylphenyl)-3,4,5,6-tetrahydro-2H-[1,2']bipyrazine | 44 | 417 |
| 157 | 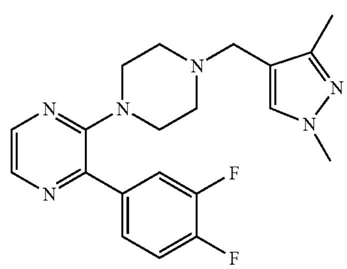 | 4-(1,3-Dimethyl-1H-pyrazol-4-ylmethyl)-3'-(3,4-difluorophenyl)-3,4,5,6-tetrahydro-2H-[1,2']bipyrazine | 38 | 385 |
| 158 | 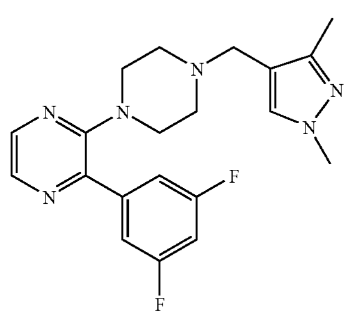 | 4-(1,3-Dimethyl-1H-pyrazol-4-ylmethyl)-3'-(3,5-difluorophenyl)-3,4,5,6-tetrahydro-2H-[1,2']bipyrazine | 38 | 385 |

-continued

| EX | Structure | Compound | Yield (%) | MS (ES) [M + H]+ |
|----|-----------|----------|-----------|------------------|
| 159 | 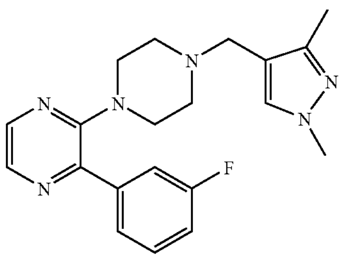 | 4-(1,3-Dimethyl-1H-pyrazol-4-ylmethyl)-3'-(3-fluorophenyl)-3,4,5,6-tetrahydro-2H-[1,2']bipyrazine | 51 | 367 |
| 160 | 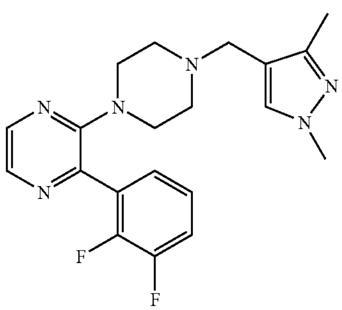 | 4-(1,3-Dimethyl-1H-pyrazol-4-ylmethyl)-3'-(2,3-difluorophenyl)-3,4,5,6-tetrahydro-2H-[1,2']bipyrazine | 9 | 385 |
| 161 | 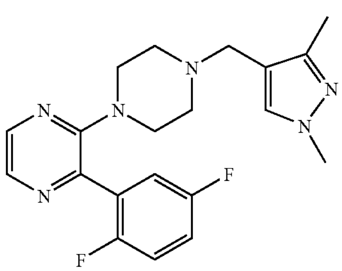 | 4-(1,3-Dimethyl-1H-pyrazol-4-ylmethyl)-3'-(2,5-difluorophenyl)-3,4,5,6-tetrahydro-2H-[1,2']bipyrazine | 9 | 385 |
| 162 | 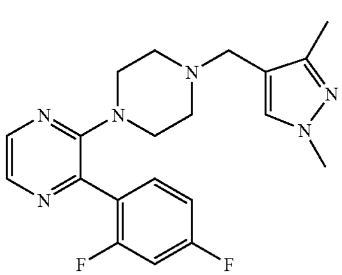 | 4-(1,3-Dimethyl-1H-pyrazol-4-ylmethyl)-3'-(2,4-difluorophenyl)-3,4,5,6-tetrahydro-2H-[1,2']bipyrazine | 27 | 385 |

EXAMPLE 163

4-(1,3-Dimethyl-1H-pyrazol-4-ylmethyl)-3'-(3-chloro-4-fluorophenyl)-3,4,5,6-tetrahydro-2H-[1,2']bipyrazine

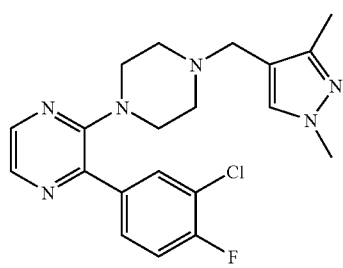

Add 2-chloro-4-fluorobenzeneboronic acid (71 mg, 0.41 mmol) to a nitrogen purged solution of 3'-chloro-4-(1,3-dimethyl-1H-pyrazol-4-ylmethyl)-3,4,5,6-tetrahydro-2H-[1,2'] bipyrazinyl (104 mg, 0.34 mmol) in dry N,N-dimethylacetamide (2 mL) and deoxygenated water (1 mL). Add potassium carbonate (113 mg, 0.82 mmol) then tetrakis(triphenylphosphine)palladium(0) (0.002 g, 0.0017 mmol) and stir at 110° C. overnight. Cool to room temperature, add water (10 mL) and extract with DCM (3×20 mL). Concentrate the combined DCM extracts and purify by reverse phase HPLC to give the title compound (0.075 g, 20%). MS (ES): m/z=401 [M+H]$^+$.

The compounds of Examples 164-167 may be prepared essentially as described in Example 163, using the appropriate boronic acid.

| EX | Structure | Compound | Yield (%) | MS (ES) [M + H]$^+$ |
|---|---|---|---|---|
| 164 | 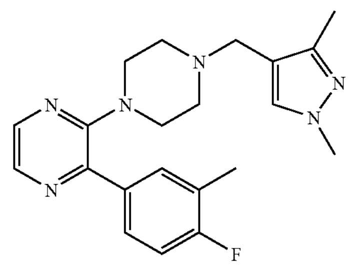 | 4-(1,3-Dimethyl-1H-pyrazol-4-ylmethyl)-3'-(4-fluoro-3-methylphenyl)-3,4,5,6-tetrahydro-2H-[1,2']bipyrazine | 18 | 381 |
| 165 | 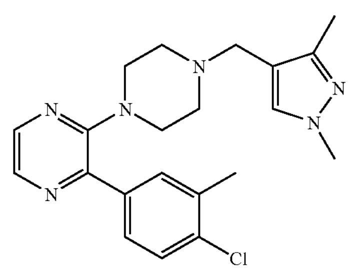 | 4-(1,3-Dimethyl-1H-pyrazol-4-ylmethyl)-3'-(4-chloro-3-methylphenyl)-3,4,5,6-tetrahydro-2H-[1,2']bipyrazine | 23 | 397 |
| 166 | 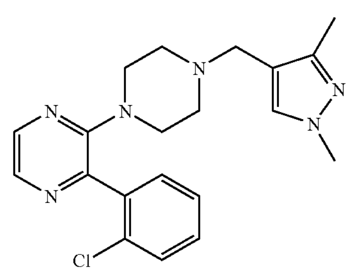 | 4-(1,3-Dimethyl-1H-pyrazol-4-ylmethyl)-3'-(2-chlorophenyl)-3,4,5,6-tetrahydro-2H-[1,2']bipyrazine | 11 | 383 |

| EX | Structure | Compound | Yield (%) | MS (ES) [M + H]+ |
|---|---|---|---|---|
| 167 | 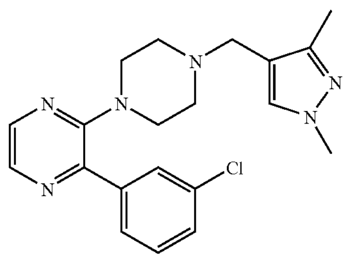 | 4-(1,3-Dimethyl-1H-pyrazol-4-ylmethyl)-3'-(3-chlorophenyl)-3,4,5,6-tetrahydro-2H-[1,2']bipyrazine | 41 | 383 |

EXAMPLE 168

4-(1,3-Dimethyl-1H-pyrazol-4-ylmethyl)-3'-(4-chloro-3-fluorophenyl)-3,4,5,6-tetrahydro-2H-[1,2']bipyrazine

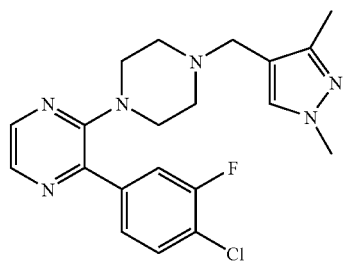

Add 4-chloro-3-fluorobenzeneboronic acid (125 mg, 0.72 mmol) to a nitrogen purged solution of 3'-chloro-4-(1,3-dimethyl-1H-pyrazol-4-ylmethyl)-3,4,5,6-tetrahydro-2H-[1,2']bipyrazinyl (200 mg, 0.65 mmol) in dry N,N-dimethylacetamide (4 mL) and deoxygenated water (2 mL). Add potassium carbonate (215 mg, 1.72 mmol) then tetrakis(triphenylphosphine)palladium(0) (0.004 g, 0.0035 mmol) and stir at 110° C. for 6 hr. Cool to room temperature, add water (10 mL) and extract with DCM (3×20 mL). Concentrate the combined DCM extracts and purify by reverse phase HPLC to give the title compound (0.036 g, 14%). MS (ES): m/z=401 [M+H]+

EXAMPLE 169

4-(1,3-Dimethyl-1H-pyrazol-4-ylmethyl)-3'-(2-fluorophenyl)-3,4,5,6-tetrahydro-2H-[1,2']bipyrazine

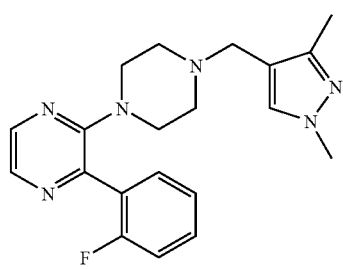

Add 2-fluorobenzeneboronic acid (215 mg, 1.5 mmol) to a nitrogen purged solution of 3'-chloro-4-(1,3-dimethyl-1H-pyrazol-4-ylmethyl)-3,4,5,6-tetrahydro-2H-[1,2']bipyrazinyl (200 mg, 0.65 mmol) in dry N,N-dimethylacetamide (4 mL), deoxygenated water (2 mL), potassium carbonate (215 mg, 1.72 mmol), tetrakis(triphenylphosphine)palladium(0) (0.004 g, 0.0035 mmol) and stir at 110° C. for 16 hr. Cool to room temperature, add water (10 mL) and extract with DCM (3×20 mL). Concentrate the combined DCM extracts and purify by reverse phase HPLC to give the title compound (0.130 g, 54%). MS (ES): m/z=367 [M+H]+.

EXAMPLE 170

3'-(2,5-Difluoro-phenyl)-4-(1,5-dimethyl-1H-pyrazol-4-ylmethyl)-3,4,5,6-tetrahydro-2H-[1,2']bipyrazine hydrochloride

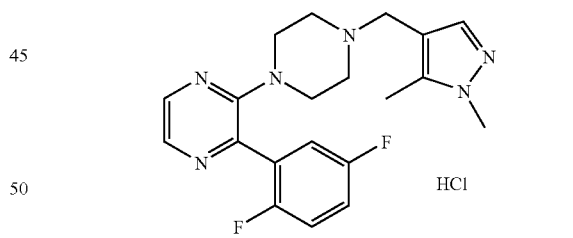

Dissolve 3'-chloro-4-(1,5-dimethyl-1H-pyrazol-4-ylmethyl)-3,4,5,6-tetrahydro-2H-[1,2']bipyrazinyl (153 mg, 0.50 mmol) in N,N-dimethylacetamide (2 mL, nitrogen purged) under nitrogen. Add potassium carbonate (166 mg, 1.20 mmol) then 2,5-difluorobenzeneboronic acid (95 mg, 0.60 mmol) and purge with nitrogen for 10 min. Add deoxygenated water (1 mL) and tetrakis(triphenylphosphine)palladium (0) (0.003 g, 0.003 mmol) then purge with nitrogen for 10 min. Heat at 115° C. for between 24 and 42 hr. Cool to room temperature, add water (5 mL) and extract with DCM (4×5 mL). Pass the combined DCM extracts through an IST Phase Separator Frit®. Concentrate the filtrate and purify by SCX-2® chromatography washing with methanol then eluting with approximately 2 M ammonia in methanol. Purify (silica gel chromatography, eluting with 0:100 to 10:90 methanol:DCM). Further purify by low pH reverse phase HPLC, followed by passage through an SCX-2® ion exchange cartridge (wash with methanol, elute with 7M ammonia in methanol). Concentrate to provide the free base. Dissolve the free base in acetonitrile and add 2M aqueous HCl solution. Add water and lyophilize to give the title compound as a yellow solid (25 mg, 12%). MS (ES): m/z=385 [M+H]$^+$.

EXAMPLE 171

3'-(5-Chloro-2-methyl-phenyl)-4-(1,5-dimethyl-1H-pyrazol-4-ylmethyl)-3,4,5,6-tetrahydro-2H-[1,2']bipyrazine hydrochloride

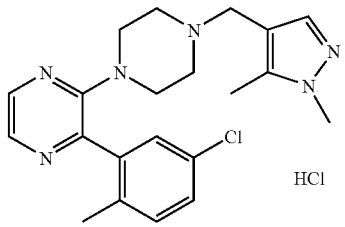

Dissolve 3'-chloro-4-(1,5-dimethyl-1H-pyrazol-4-ylmethyl)-3,4,5,6-tetrahydro-2H-[1,2']bipyrazinyl (307 mg, 1.0 mmol) in N,N-dimethylacetamide (5 mL). Add potassium carbonate (332 mg, 2.40 mmol), then 5-chloro-2-methyl benzene boronic acid (204 mg, 1.20 mmol), tetrakis(triphenylphosphine)palladium(0) (0.012 g, 0.01 mmol), then water (1 mL) and purge with nitrogen for 30 min. Heat at 110° C. for 18 hr. Cool to room temperature, add water (5 mL) and extract with DCM (3×5 mL). Pass the combined DCM extracts through an IST Phase Separator Frit®. Concentrate the filtrate and purify (silica gel chromatography, eluting with 0:100 to 10:90 methanol:DCM), to give the free base as a yellow oil. Dissolve the oil in acetonitrile and add 2M aqueous HCl solution. Add water and lyophilize, then purify by SCX-2® chromatography (wash with methanol, elute with 4 M ammonia in methanol). Concentrate and further purify by high pH reverse phase HPLC followed by passage through an SCX-2® ion exchange cartridge (wash with methanol, elute with 2M ammonia in methanol) to provide the free base. Dissolve the free base crystals in acetonitrile and add 2M aqueous HCl solution. Add water and lyophilize to give the title compound as cream colored powder (278 mg, 64%). MS (ES): m/z=397 [M+H]$^+$.

EXAMPLE 172

4-(1,5-Dimethyl-1H-pyrazol-4-ylmethyl)-3'-(4-methoxy-phenyl)-3,4,5,6-tetrahydro-2H-[1,2']bipyrazine hydrochloride

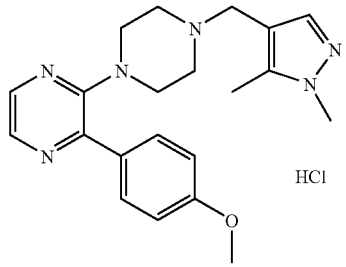

Dissolve 3'-chloro-4-(1,5-dimethyl-1H-pyrazol-4-ylmethyl)-3,4,5,6-tetrahydro-2H-[1,2']bipyrazinyl (614 mg, 2.0 mmol) in N,N-dimethylacetamide (20 mL). Add potassium carbonate (662 mg, 4.80 mmol), 4-methoxybenzene boronic acid (334 mg, 2.40 mmol), tetrakis(triphenylphosphine)palladium(0) (0.023 g, 0.02 mmol), then water (10 mL) and purge with nitrogen for 30 min. Heat at 110° C. for 6 hr, then cool to room temperature, add water (10 mL) and extract with DCM (3×10 mL). Pass the combined DCM extracts through an IST Phase Separator Frit®. Concentrate the filtrate and purify by SCX-2® chromatography (wash with methanol, elute with 2 M ammonia in methanol). Further purify (silica gel chromatography, eluting with 0:100 to 10:90 methanol:DCM), to give the free base as a yellow oil. Dissolve the oil in acetonitrile and add 2M aqueous HCl solution. Add water and lyophilize to give the title compound as a dark yellow powder (754 mg, 92%). MS (ES): m/z=379 [M+H]$^+$.

The compounds of Example 173-176 may be prepared essentially as described in Example 172, using the appropriate boronic acid and 3'-chloro-4-(1,5-dimethyl-1H-pyrazol-4-ylmethyl)-3,4,5,6-tetrahydro-2H-[1,2']bipyrazinyl or 3'-chloro-4-(1,3,5-trimethyl-1H-pyrazol-4-ylmethyl)-3,4,5,6-tetrahydro-2H-[1,2']bipyrazinyl.

| EX | Structure | Compound | Yield (%) | MS (ES) [M + H]$^+$ |
|---|---|---|---|---|
| 173 | 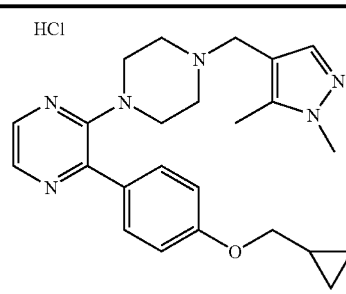 | 3'-(4-Cyclopropylmethoxy-phenyl)-4-(1,5-dimethyl-1H-pyrazol-4-ylmethyl)-3,4,5,6-tetrahydro-2H-[1,2']bipyrazine hydrochloride | 86 | 419 |

| EX | Structure | Compound | Yield (%) | MS (ES) [M + H]+ |
|---|---|---|---|---|
| 174 | HCl | 1-{4-[4-(1,5-Dimethyl-1H-pyrazol-4-ylmethyl)-3,4,5,6-tetrahydro-2H-[1,2']bipyrazinyl-3'-yl]-phenyl}-ethanone hydrochloride | 97 | 391 |
| 175 | HCl | 1-{4-[4-(1,3,5-Trimethyl-1H-pyrazol-4-ylmethyl)-3,4,5,6-tetrahydro-2H-[1,2']bipyrazinyl-3'-yl]-phenyl}-ethanone hydrochloride | 89 | 405 |
| 176 | HCl | 4-(1,5-Dimethyl-1H-pyrazol-4-ylmethyl)-3'-(4-ethoxyphenyl)-3,4,5,6-tetrahydro-2H-[1,2']bipyrazine hydrochloride | 43 | 393 |

EXAMPLE 177

4-(1-Methyl-1H-pyrazol-4-ylmethyl)-3-(2-methylphenyl)-3,4,5,6-tetrahydro-2H-[1,2]bipyrazine hydrochloride

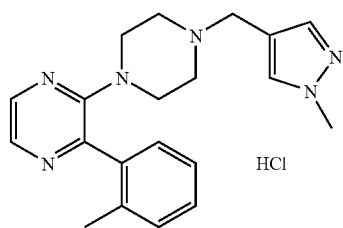

Add a solution of 3'-chloro-4-(1-methyl-1H-pyrazol-4-ylmethyl)-3,4,5,6-tetrahydro-2H-[1,2']bipyrazinyl (208 mg, 0.7 mmol) in dry, deoxygenated N,N-dimethyl-acetamide (4 mL) to 2-methylphenylboronic acid (116 mg, 0.85 mmol) and potassium carbonate (236 mg, 1.7 mmol). Add deoxygenated water (1.5 mL) and further purge the mixture with nitrogen for 10 min. Add palladium tetrakis(triphenylphosphine) (82 mg, 0.07 mmol) and stir the mixture at 110° C. under nitrogen for 16 hr. Quench the reaction with water (50 mL) and extract with DCM (3×). Wash the combined organic extracts with water, brine, separate the organic extract via a hydrophobic frit, and evaporate under reduced pressure to give a brown oil (800 mg). Purify by chromatography on silica gel eluting with 2-8% methanol gradient in DCM to give the free base as an amber oil (168 mg). Redissolve the free base in IPA (3 mL) and diethyl ether (3 mL) and add HCl in diethyl ether (2M, 0.33 mL) to precipitate a yellow solid. Dry the solid at 60° C. under reduced pressure to give the title compound as a yellow glassy solid (60 mg, 22%). MS (ES): m/z=349 [M+H]+.

The compounds of Examples 178-183 may be prepared essentially as described in Example 177, using the appropriate boronic acid and 3'-chloro-4-(1-methyl-1H-pyrazol-4-ylmethyl)-3,4,5,6-tetrahydro-2H-[1,2']bipyrazinyl or 3'-chloro-4-(1,5-dimethyl-1H-pyrazol-4-ylmethyl)-3,4,5,6-tetrahydro-2H-[1,2']bipyrazinyl.

| EX | Structure | Compound | Yield (%) | MS (ES) [M + H]+ |
|----|-----------|----------|-----------|------------------|
| 178 | 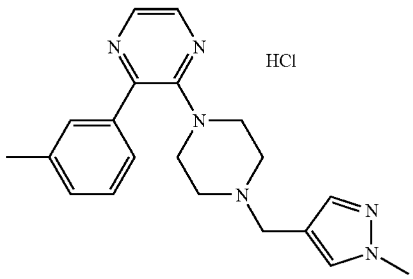 | 4-(1-Methyl-1H-pyrazol-4-ylmethyl)-3'-m-tolyl-3,4,5,6-tetrahydro-2H-[1,2']bipyrazine hydrochloride | 38 | 349 |
| 179 | 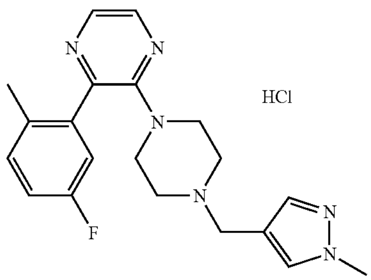 | 3'-(5-Fluoro-2-methylphenyl)-4-(1-methyl-1H-pyrazol-4-ylmethyl)-3,4,5,6-tetrahydro-2H-[1,2']-bipyrazine hydrochloride | 25 | 367 |
| 180 | 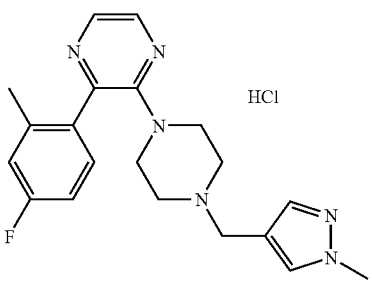 | 3'-(4-Fluoro-2-methylphenyl)-4-(1-methyl-1H-pyrazol-4-ylmethyl)-3,4,5,6-tetrahydro-2H-[1,2']-bipyrazine hydrochloride | 42 | 367 |
| 181 | 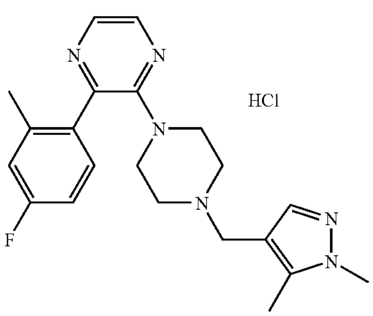 | 4-(1,5-dimethyl-1H-pyrazol-4-ylmethyl)-3'-(4-fluoro-2-methylphenyl)-3,4,5,6-tetrahydro-2H-[1,2']-bipyrazine hydrochloride | 45 | 381 |
| 182 | 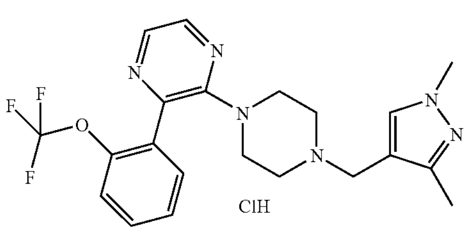 | 4-(1,3-Dimethyl-1H-pyrazol-4-ylmethyl)-3'-(2-trifluoromethoxy-phenyl)-3,4,5,6-tetrahydro-2H-[1,2']bipyrazinyl hydrochloride | 46 | 433 |

| EX | Structure | Compound | Yield (%) | MS (ES) [M + H]+ |
|---|---|---|---|---|
| 183 | 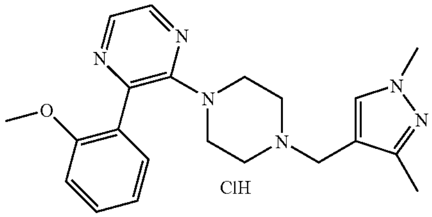 | 4-(1,3-Dimethyl-1H-pyrazol-4-ylmethyl)-3'-(2-methoxy-phenyl)-3,4,5,6-tetrahydro-2H-[1,2']bipyrazinyl hydrochloride | 43 | 379 |

EXAMPLE 184

3'-(2-Chloro-phenyl)-4-(1,5-dimethyl-1H-pyrazol-4-ylmethyl)-3,4,5,6-tetrahydro-2H-[1,2']bipyrazine fumarate

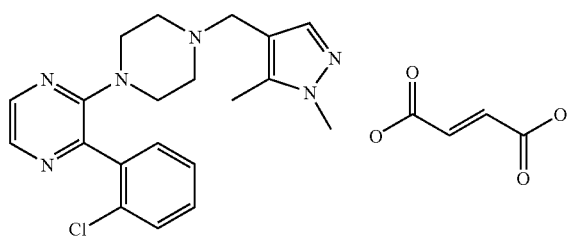

Dissolve 3'-chloro-4-(1,5-dimethyl-1H-pyrazol-4-ylmethyl)-3,4,5,6-tetrahydro-2H-[1,2']bipyrazinyl (153 mg, 0.50 mmol) in N,N-dimethylacetamide (2 mL, nitrogen purged) under nitrogen. Add potassium carbonate (166 mg, 1.20 mmol) then 2-chlorobenzeneboronic acid (94 mg, 0.60 mmol) and purge with nitrogen for 10 min. Add deoxygenated water (1 mL) and tetrakis(triphenylphosphine)palladium (0) (0.003 g, 0.003 mmol) then purge with nitrogen for 10 min. Heat at 115° C. for 20 hr. Cool to room temperature, add water (5 mL) and extract with DCM (4×5 mL). Pass the combined DCM extracts through an IST Phase Separator Frit®. Concentrate the filtrate and purify by SCX-2® chromatography (wash with methanol, elute with 2 M ammonia in methanol). Purify (silica gel chromatography, eluting with 0:100 to 10:90 methanol:DCM), to give the free base as an oil (140 mg). Dissolve the oil in methanol and add fumaric acid (1.0 eq), concentrate and wash the solid with diethyl ether and DCM. Sonicate material with diethyl ether (30 mL) and decant solvent and dry in vacuum oven to give the title compound as beige powder (185 mg, 74%). MS (ES): m/z=383 [M+H]+.

The compounds of Examples 185-192 may be prepared essentially as described in Example 184, using the appropriate boronic acid and 3'-chloro-4-(1,3-dimethyl-1H-pyrazol-4-ylmethyl)-3,4,5,6-tetrahydro-2H-[1,2']bipyrazine, 3'-chloro-4-(1,5-dimethyl-1H-pyrazol-4-ylmethyl)-3,4,5,6-tetrahydro-2H-[1,2']bipyrazine or 3'-chloro-4-(1-methyl-1H-pyrazol-4-ylmethyl)-3,4,5,6-tetrahydro-2H-[1,2']bipyrazine.

| EX | Structure | Compound | Yield (%) | MS (ES) [M + H]+ |
|---|---|---|---|---|
| 185 | 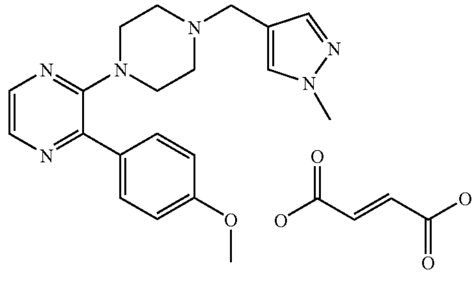 | 4-(1-Methyl-1H-pyrazol-4-ylmethyl)-3'-(4-methoxyphenyl)-3,4,5,6-tetrahydro-2H-[1,2']bipyrazine fumarate | 79 | 365 |

-continued

| EX | Structure | Compound | Yield (%) | MS (ES) [M + H]+ |
|---|---|---|---|---|
| 186 | 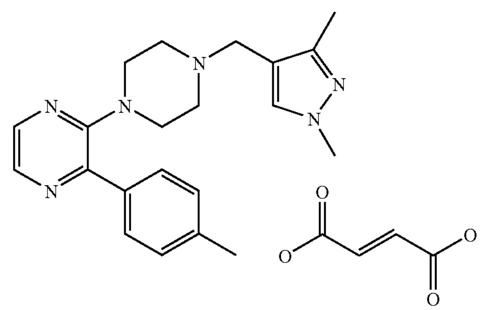 | 4-(1,3-Dimethyl-1H-pyrazol-4-ylmethyl)-3'-(4-methylphenyl)-3,4,5,6-tetrahydro-2H-[1,2']bipyrazine fumarate | 80 | 363 |
| 187 | 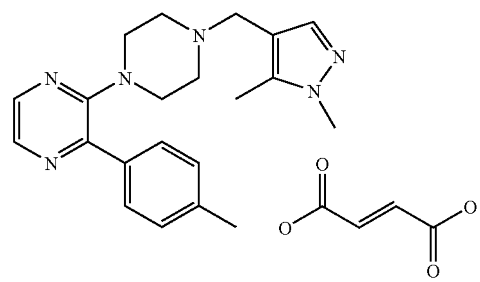 | 4-(1,5-Dimethyl-1H-pyrazol-4-ylmethyl)-3'-(4-methylphenyl)-3,4,5,6-tetrahydro-2H-[1,2']bipyrazine fumarate | 75 | 363 |
| 188 | 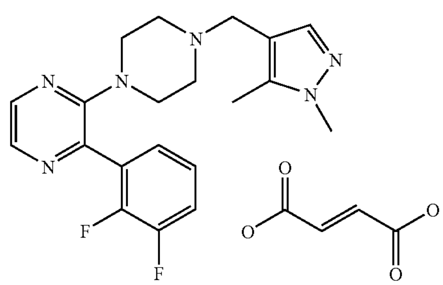 | 3'-(2,3-Difluoro-phenyl)-4-(1,5-dimethyl-1H-pyrazol-4-ylmethyl)-3,4,5,6-tetrahydro-2H-[1,2']bipyrazine fumarate | 64 | 385 |
| 189 | 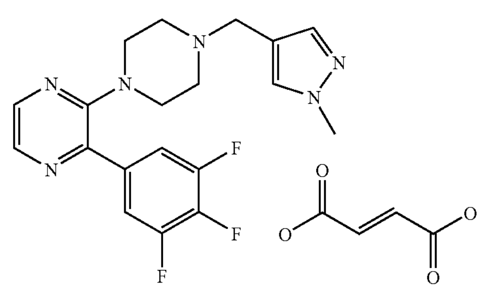 | 4-(1-Methyl-1H-pyrazol-4-ylmethyl)-3'-(3,4,5-trifluorophenyl)-3,4,5,6-tetrahydro-2H-[1,2']bipyrazinefumarate | 77 | 389 |
| 190 | 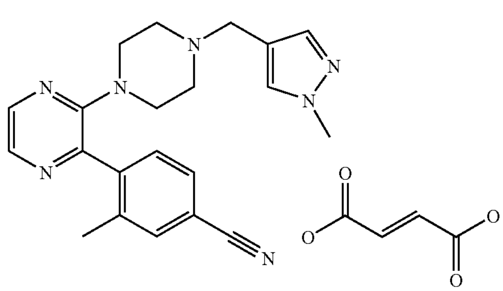 | 3-Methyl-4-[4-(1-methyl-1H-pyrazol-4-ylmethyl)-3,4,5,6-tetrahydro-2H-[1,2']bipyrazinyl-3'-yl]-benzonitrile fumarate | 76 | 374 |

| EX | Structure | Compound | Yield (%) | MS (ES) [M + H]+ |
|---|---|---|---|---|
| 191 | 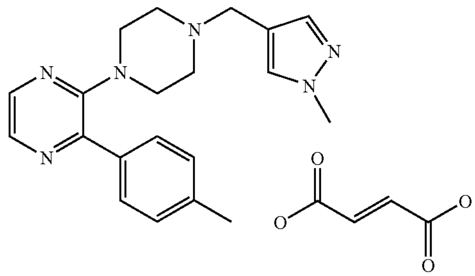 | 4-(1-Methyl-1H-pyrazol-4-ylmethyl)-3'-(4-methylphenyl)-3,4,5,6-tetrahydro-2H-[1,2']bipyrazine fumarate | 69 | 349 |
| 192 | 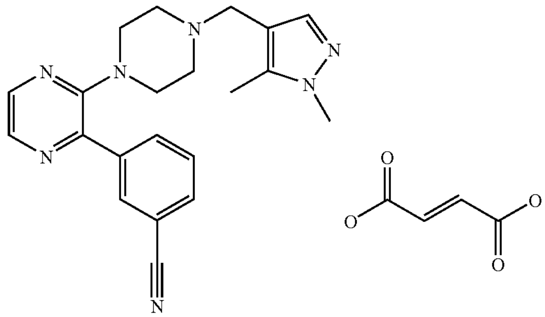 | 3-[4-(1,5-Dimethyl-1H-pyrazol-4-ylmethyl)-3,4,5,6-tetrahydro-2H-[1,2']bipyrazinyl-3'-yl]-benzonitrile fumarate | 55 | 374 |

EXAMPLE 193

4-(1-Methyl-1H-pyrazol-4-ylmethyl)-3'-phenyl-3,4,5,6-tetrahydro-2H-[1,2']bipyrazine hydrochloride

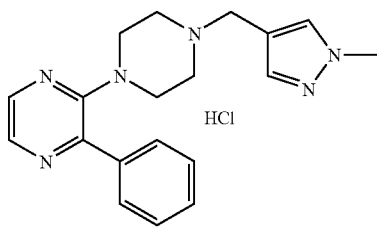

Nitrogen-purge a stirred mixture of 3'-chloro-4-(1-methyl-1H-pyrazol-4-ylmethyl)-3,4,5,6-tetrahydro-2H-[1,2']bipyrazinyl (208 mg, 0.7 mmol), phenylboronic acid (104 mg, 1.2 equiv) and potassium carbonate (236 mg, 2.4 equiv) in N,N-dimethylacetamide (4 mL) and water (1.5 mL). Add under nitrogen tetrakis(triphenylphospine)palladium(0) (82 mg, 0.1 equiv) and heat to 110° C. for 4 hr. Dilute with water (1.5 mL) and t-butyl methyl ether (3.5 mL) and then extract with DCM (3×). Wash the combined extracts with water, dry and concentrate the solution to give a yellow oil (450 mg). Purify by silica gel chromatography, eluting with 2:98 to 8:92 methanol:DCM, to give the free base as a clear gum (144 mg). Dissolve the free base in isopropanol (3 mL) and diethyl ether (3 mL), treat with HCl (0.3 mL, 2 M in diethyl ether). Filter to give the title compound (62 mg, 26%). MS (ES.): m/z=335 [M+H]+.

EXAMPLE 194

4-(1,3-Dimethyl-1H-pyrazol-4-ylmethyl)-3'-phenyl-3,4,5,6-tetrahydro-2H-[1,2']bipyrazine hydrochloride

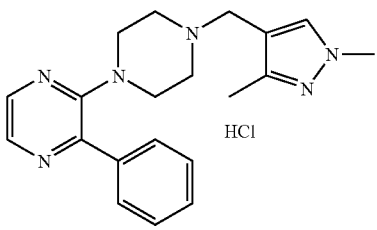

Prepare 4-(1,3-dimethyl-1H-pyrazol-4-ylmethyl)-3'-phenyl-3,4,5,6-tetrahydro-2H-[1,2']bipyrazinyl hydrochloride essentially as described in Example 196 using 3'-chloro-4-(1,3-dimethyl-1H-pyrazol-4-ylmethyl)-3,4,5,6-tetrahydro-2H-

[1,2']bipyrazinyl (200 mg, 0.65 mmol) and phenylboronic acid (96 mg, 1.2 equiv) at 110° C. for 20 hr. (83 mg). MS (ES): m/z=349 [M+H]⁺.

EXAMPLE 195

2-{4-[3'-(3-Fluoro-phenyl)-2,3,5,6-tetrahydro-[1,2'] bipyrazinyl-4-ylmethyl]-pyrazol-1-yl}-ethanol hydrochloride

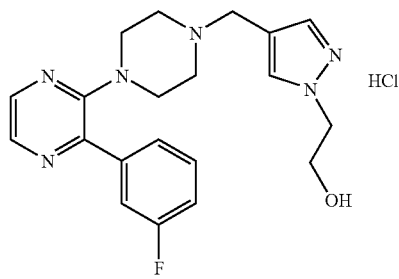

Dissolve 2-[4-(3'-chloro-2,3,5,6-tetrahydro-[1,2']bi-pyrazinyl-4-ylmethyl)-pyrazol-1-yl]-ethanol (187 mg, 0.579 mmol) in tetrahydrofuran (1.6 mL) and water (0.8 mL). Add potassium carbonate (176 mg, 1.27 mmol) then 3-fluorobenzeneboronic acid (113 mg, 0.811 mmol) and purge with nitrogen for 15 min. Add tri-n-butylphospine tetrafluoroborate (6.7 mg, 0.0231 mmol) and tris(dibenzylideneacetone)dipalladium(0) (10.5 mg, 0.0115 mmol) and microwave at 150° C. for 15 min. Cool to room temperature then dilute with saturated aqueous sodium bicarbonate and extract 6 times with ethyl acetate. Dry (sodium sulfate), filter, concentrate and purify by silica gel chromatography, (eluting with 6:94 2 M ammonia in methanol:DCM), to give the free base as a yellow oil. Dissolve the oil in methanol, add ammonium chloride, then sonicate the mixture for 10 min. Evaporate the solution to give the title compound as a yellow solid (0.177 g, 73%). MS (ES): m/z=383 [M+H]⁺.

The compounds of Examples 196-198 are prepared essentially as described in Example 195 using the appropriate boronic acid and 2-[4-(3'-chloro-2,3,5,6-tetrahydro-[1,2']bipyrazinyl-4-ylmethyl)-pyrazol-1-yl]-ethanol.

| EX | Structure | Compound | Yield (%) | MS (ES) [M + H]⁺ |
|---|---|---|---|---|
| 196 | 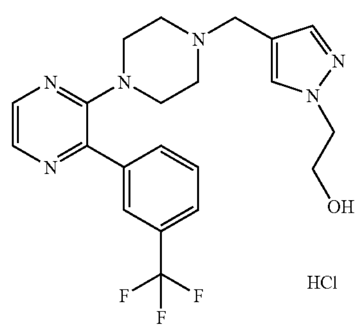 | 2-{4-[3'-(3-Trifluoromethyl-phenyl)-2,3,5,6-tetrahydro-[1,2']bipyrazinyl-4-ylmethyl]-pyrazol-1-yl}-ethanol hydrochloride | 83 | 433 |
| 197 | 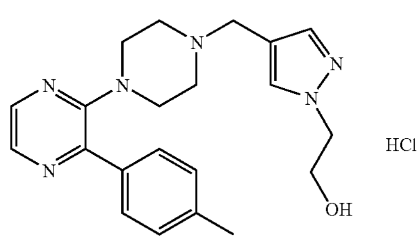 | 2-[4-[3'-p-Tolyl-2,3,5,6-tetrahydro-[1,2']bipyrazinyl-4-ylmethyl)-pyrazol-1-yl}-ethanol hydrochloride | 70 | 379 |
| 198 | 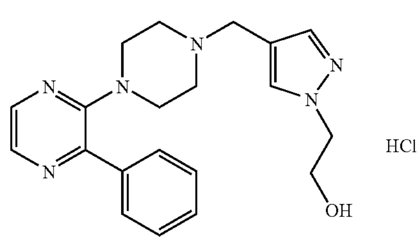 | 2-[4-[3'-Phenyl-2,3,5,6-tetrahydro-[1,2']bipyrazinyl-4-ylmethyl)-pyrazol-1-yl]-ethanol hydrochloride | 71 | 365 |

EXAMPLE 199

1-(3-(3-(4-((1,3-Dimethyl-1H-pyrazol-4-yl)methyl)piperazin-1-yl)pyrazin-2-yl)phenyl)ethanone hydrochloride

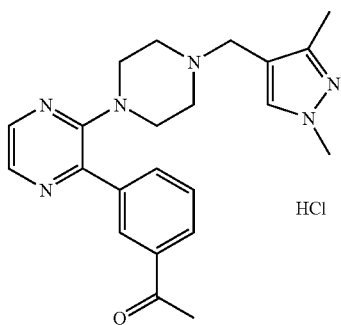

Charge a microwave tube with 3'-chloro-4-(1,3-dimethyl-1H-pyrazol-4-ylmethyl)-3,4,5,6-tetrahydro-2H-[1,2']bipyrazinyl (0.150 g, 0.490 mmoles), 10 mol % of bis[(diphenylphosphinyl)methyl]-amine palladium (II) dichloride polymer bound (0.032 g, 0.049 mmoles), 3-acetylphenylboronic acid (0.096 g, 0.588 mmoles), $NaHCO_3$ (0.182 g, 1.72 mmoles) and 3 mL of MeOH. Seal the tube, heat in microwave at 140° C. for 30 min, then cool to room temperature. Pour the reaction mixture onto a SCX column prewashed with 10 mL MeOH. Wash with 10 mL of MeOH, and elute with 20 mL 2N—$NH_3$ in MeOH. The desired fraction is evaporated to give a brown oil. Further purify with reverse phase chromatography (22% isocratic $CH_3CN$/0.01 M $NH_4HCO_3$ in water, 80 mL/min, for 8 min, on a 30×75 mm, $C^{18}$ Xterra column) to provide the free base as a white solid (0.115 g, 60% yield, ES+(m/z) 391 [M+H]). Dissolve the free base in $CH_3CN$ (5 mL), add 1N HCl in water (0.294 mL, 0.294 mmoles). After 5 min, freeze the solution and lyophilize to give the title compound as a white solid (126 mg, quantitative yield, MS ES+(m/z) 391 [M+H]$^+$).

EXAMPLE 200

2-[4-(1,3-Dimethyl-1H-pyrazol-4-ylmethyl)-3,4,5,6-tetrahydro-2H-[1,2']bipyrazinyl-3'-yl]-benzonitrile (E)-but-2-enedioic acid

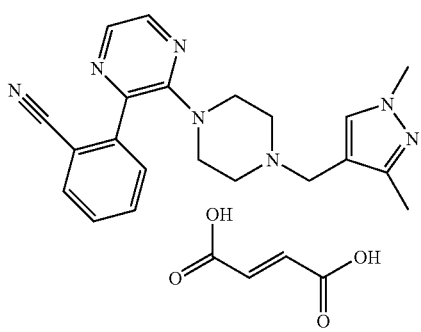

Using 2-cyanophenyl boronic acid and 3'-chloro-4-(1,3-dimethyl-1H-pyrazol-4-ylmethyl)-3,4,5,6-tetrahydro-2H-[1,2']bipyrazinyl, prepare 2-[4-(1,3-dimethyl-1H-pyrazol-4-ylmethyl)-3,4,5,6-tetrahydro-2H-[1,2']bipyrazinyl-3'-yl]-benzamide using the method described for the preparation of 4-(1-methyl-1H-pyrazol-4-ylmethyl)-3'-o-tolyl-3,4,5,6-tetrahydro-2H-[1,2']bipyrazinyl hydrochloride. Note that partial hydrolysis of the nitrile group occurs under the Suzuki reaction conditions. MS (ES.): m/z=392 [M+H]$^+$. Heat a stirred suspension of 2-[4-(1,3-dimethyl-1H-pyrazol-4-ylmethyl)-3,4,5,6-tetrahydro-2H-[1,2']bipyrazinyl-3'-yl]-benzamide (120 mg, 0.3 mmol), triphenylphosphine (314 mg, 1.2 mmol), carbon tetrachloride (92 mg, 0.6 mmol) in dry acetonitrile (1 ml) to 60° C. for 30 min. Quench with methanol (1 ml) and apply to SCX-2® cartridge (10 g). Wash with methanol then elute with 2M ammonia in methanol to give a yellow oil (167 mg). Purify by chromatography on silica gel eluting with 3-8% methanol in DCM to give an oil (59 mg). Dissolve in ethanol (1 ml) and add a hot solution of fumaric acid (18 mg) in ethanol (1 ml). After allowing to crystallize in an atmosphere of diethyl ether, filter the white crystals and dry in vacuo at 60° C. to give the title compound (62 mg, 43%). MS (ES.): m/z=374 [M+H]$^+$.

EXAMPLE 201

4-(3,5-Dimethyl-1H-pyrazol-4-ylmethyl)-3'-(4-fluorophenyl)-3,4,5,6-tetrahydro-2H-[1,2']bipyrazine dihydrochloride

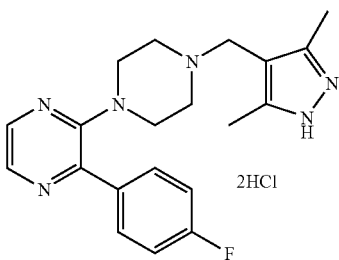

Dissolve 4-(1-benzyl-3,5-dimethyl-1H-pyrazol-4-ylmethyl)-3'-(4-fluorophenyl)-3,4,5,6-tetrahydro-2H-[1,2']bipyrazinyl (1.69 g, 3.70 mmol) in ethanol (25 mL) and add 10% palladium on carbon (0.325 g) and ammonium formate (2.334 g, 37.0 mmol). Reflux the mixture for 24 hr. Filter off the catalyst then add more palladium on carbon (0.325 g) and reflux for another 24 hr. Filter off the catalyst, concentrate and purify (silica gel chromatography, eluting with 9:91 2 M ammonia in methanol:DCM), to give the free base as a white solid (0.390 g, 29%). Dissolve the free base in methanol and add ammonium chloride then sonicate the mixture for 10 min. Concentrate the solution to give the title compound as a white solid. MS (ES): m/z=367 [M+H]$^+$.

EXAMPLE 202

4-(3,5-Dimethyl-1-pyridin-3-yl-1H-pyrazol-4-ylmethyl)-3'-(4-fluorophenyl)-3,4,5,6-tetrahydro-2H-[1,2']bipyrazine dihydrochloride

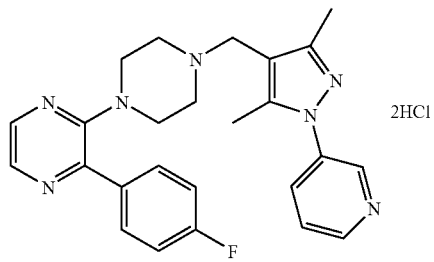

Dissolve 4-(3,5-dimethyl-1H-pyrazol-4-ylmethyl)-3'-(4-fluorophenyl)-3,4,5,6-tetrahydro-2H-[1,2']bipyrazinyl (0.141 g, 0.385 mmol) and 3-iodopyridine (0.158 g, 0.769 mmol) in a sealed tube with xylenes (1.5 mL) then add copper (1)trifluoromethane-sulfonate benzene complex (11 mg, 0.0192 mmol), 1,10-phenanthroline (69 mg, 0.385 mmol), 1,5-diphenyl-1,4-pentadien-3-one (4.5 mg, 0.0192 mmol) and cesium carbonate (138, mg 0.423 mmol). Heat to 110° C. for 18 hr. then cool and dilute with saturated aqueous ammonium chloride. Extract the mixture with DCM 3 times, dry (sodium sulfate), filter, concentrate and purify (silica gel chromatography, eluting with 5:95 2 M ammonia in methanol:DCM), to give the free base as a white solid (0.130 g, 76%). Dissolve the free base in methanol and add ammonium chloride then sonicate the mixture for 10 min. Concentrate the solution to give the title compound as a white solid. MS (ES): m/z=444 [M+H]$^+$.

EXAMPLE 203

3'-(4-Fluorophenyl)-4-(1-isobutyl-3,5-dimethyl-1H-pyrazol-4-ylmethyl)-3,4,5,6-tetrahydro-2H-[1,2'] bipyrazine dihydrochloride

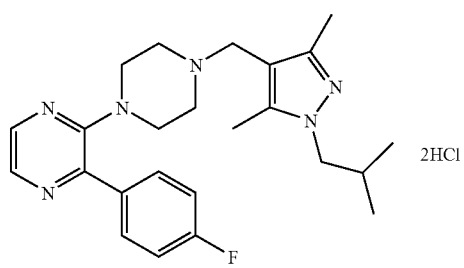

Dissolve 4-(3,5-dimethyl-1H-pyrazol-4-ylmethyl)-3'-(4-fluorophenyl)-3,4,5,6-tetrahydro-2H-[1,2']bipyrazinyl (0.139, 0.379 mmol) in N,N-dimethylformamide (5 mL) and add sodium hydride (0.018 g, 0.455 mmol). Stir the mixture for 10 min at 25° C., then cool to 0° C. Add the 1-bromo-2-methylpropane (0.058 mL, 0.531 mmol) dropwise then warm the mixture to 25° C. and stir for 18 hr. Dilute the mixture with saturated ammonium chloride and extract 3 times with ethyl acetate. Wash the combined organics with saturated aqueous sodium chloride six times, dry (sodium sulfate), filter, concentrate and purify (silica gel chromatography, eluting with 6:94 2 M ammonia in methanol:DCM), to give the free base as a colorless oil (0.043 g, 27%). Dissolve the free base in methanol, add ammonium chloride, then sonicate the mixture for 10 min. Concentrate the solution to give the title compound as a white solid. MS (ES): m/z=423 [M+H]$^+$.

EXAMPLE 204

4-[1-(4-Fluorobenzyl)-3,5-dimethyl-1H-pyrazol-4-ylmethyl]-3'-(4-fluorophenyl)-3,4,5,6-tetrahydro-2H-[1,2']bipyrazine dihydrochloride

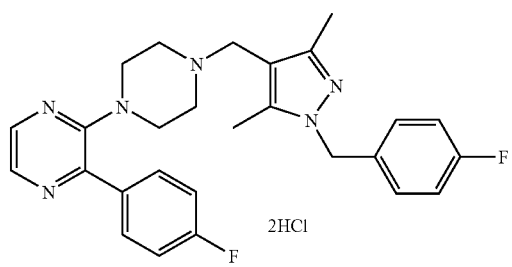

Prepare the title compound essentially as described in Example 203 using 1-bromomethyl-4-fluorobenzene. MS (ES): m/z=475 [M+H]$^+$.

EXAMPLE 205

4-(1-Cyclohexylmethyl-3,5-dimethyl-1H-pyrazol-4-ylmethyl)-3'-(4-fluorophenyl)-3,4,5,6-tetrahydro-2H-[1,2']bipyrazine dihydrochloride

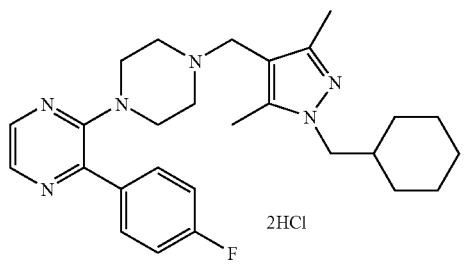

Prepare the title compound essentially as described in Example 204 using bromomethyl-cyclohexane. MS (ES): m/z=463 [M+H]⁺.

EXAMPLE 206

4-(3,5-Dimethyl-1-thiazol-2-yl-1H-pyrazol-4-ylmethyl)-3'-(4-fluorophenyl)-3,4,5,6-tetrahydro-2H-[1,2']bipyrazine dihydrochloride

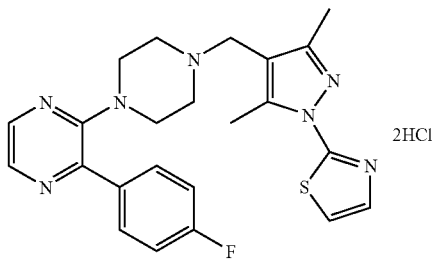

Dissolve 4-(3,5-dimethyl-1H-pyrazol-4-ylmethyl)-3'-(4-fluorophenyl)-3,4,5,6-tetrahydro-2H-[1,2']bipyrazinyl (0.106 g, 0.289 mmol) and 2-bromothiazole (0.052 mL, 0.578 mmol) in a sealed tube with xylenes (3 mL). Add copper(I) trifluoromethane-sulfonate benzene complex (8 mg, 0.0114 mmol), 1,10-phenanthroline (52 mg, 0.289 mmol), 1,5-diphenyl-1,4-pentadien-3-one (3.4 mg, 0.0114 mmol) and cesium carbonate (104 mg, 0.318 mmol). Heat the mixture to 110° C. for 44 hr, cool and dilute with saturated ammonium chloride. Extract the mixture with DCM 3 times, dry (sodium sulfate), filter, concentrate and purify (silica gel chromatography, eluting with 5:95 2 M ammonia in methanol:DCM), to give the free base as a white solid (0.088 g, 68%). Dissolve the free base in methanol and add ammonium chloride then sonicate the mixture for 10 min. Concentrate the solution to give the title compound as a white solid. MS (ES): m/z=450 [M+H]⁺.

EXAMPLE 207

4-[2-(3,5-Diethyl-1-pyridin-2-yl-1H-pyrazol-4-yl)-ethyl]-3'-(4-fluorophenyl)-3,4,5,6-tetrahydro-2H-[1,2']bipyrazine dihydrochloride

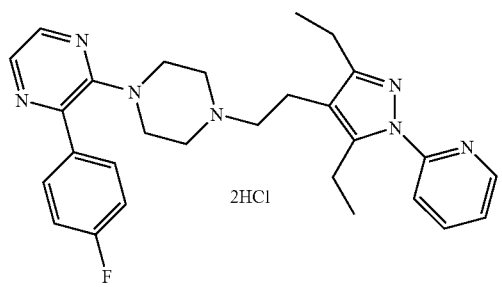

Combine 2-[4-(2-bromoethyl)-3,5-diethylpyrazol-1-yl]-pyridine (0.15 g, 0.49 mmol), 3'-(4-fluorophenyl)-3,4,5,6-tetrahydro-2H-[1,2']bipyrazinyl (0.12 g, 0.46 mmol), potassium iodide (0.01 g, 0.05 mmol), potassium carbonate (0.10 g, 0.74 mmol) and acetonitrile (10 mL) and heat to reflux for 18 hr. Cool the reaction mixture to room temperature. Purify using SCX chromatography followed by silica gel chromatography, eluting with 1:1 hexanes:ethyl acetate and convert to the dihydrochloride salt with 1 M HCl in diethyl ether to give the title compound (0.07 g, 22%). LC-MS: m/z=486.2 [M+H]⁺.

EXAMPLE 208

4-[2-(3,5-Dimethyl-1H-pyrazol-4-yl)-ethyl]-3'-(4-fluoro-phenyl)-3,4,5,6-tetrahydro-2H-[1,2']bipyrazinyl hydrochloride

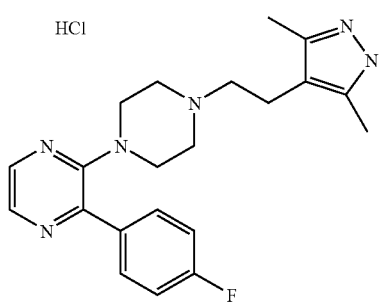

Dissolve 3'-(4-fluoro-phenyl)-3,4,5,6-tetrahydro-2H-[1,2']bipyrazinyl dihydrochloride (0.200 g, 0.604 mmol) in acetonitrile (12 mL). Add potassium carbonate (0.334 g, 2.415 mmol), potassium iodide (0.005 g, 0.030 mmol), and 4-(2-bromo-ethyl)-3,5-dimethyl-1H-pyrazole (0.135 g, 0.664 mmol). Heat reaction at reflux for 14 hr. under nitrogen. Cool to room temperature and filter over celite. Concentrate filtrate in vacuo and purify residue by flash chromatography eluting with DCM:acetone 6:4 to afford the freebase as a mixture. Purify by reverse phase chromatography (43 g C-18, CH3CN: 1% aqueous TFA 5 to 95% over 20 min.) to afford a mixture. Purify by flash chromatography eluting with chloroform:methanol 0-10% to afford 4-[2-(3,5-dimethyl-1H-pyrazol-4-yl)-ethyl]-3'-(4-fluoro-phenyl)-3,4,5,6-tetrahydro-2H-[1,2']bipyrazinyl (0.150 mg). Dissolve the free base (0.150 g, 0.394 mmol) in acetonitrile (1 mL) and add aqueous 1N HCl (0.433 mL, 0.433 mmol). Stir for 1 h at room temperature. Remove organics and lyophilize to afford the title compound (0.144 g, 77% yield). MS (m/z)=381 [M+H]⁺.

EXAMPLE 209

3'-(4-Fluoro-phenyl)-4-[3-(1-methyl-1H-pyrazol-4-yl)-propyl]-3,4,5,6-tetrahydro-2H-[1,2']bipyrazinyl hydrochloride

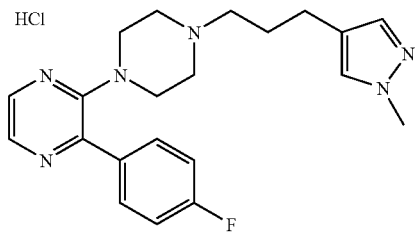

Dissolve 3'-(4-fluoro-phenyl)-3,4,5,6-tetrahydro-2H-[1,2']bipyrazinyl dihydrochloride (0.200 g, 0.604 mmol) in acetonitrile (10 mL). Add potassium carbonate (0.334 g, 2.415 mmol), potassium iodide (0.005 g, 0.030 mmol), and 4-(3-bromo-propyl)-1-methyl-1H-pyrazole (0.184 g, 0.906 mmol). Heat reaction at reflux for 14 hr. under nitrogen. Cool to room temperature and partition between water and ethyl acetate. Separate and extract aqueous with ethyl acetate. Combine organic portions, dry over sodium sulfate, filter, and concentrate in vacuo. Purify residue by flash chromatography eluting with chloroform:methanol 19:1 to afford 3'-(4-fluorophenyl)-4-[3-(1-methyl-1H-pyrazol-4-yl)-propyl]-3,4,5,6-tetrahydro-2H-[1,2']bipyrazinyl (0.194 g). Dissolve in acetonitrile (1 mL) and add aqueous 1N HCl (0.561 mL, 0.561 mmol). Stir for 1 h at room temperature. Remove organics and lyophilize to afford the title compound (0.189 g, 75% yield). MS (m/z)=381[M+H]+.

EXAMPLE 210

4-(1-Benzenesulfonyl-3,5-dimethyl-1H-pyrazol-4-ylmethyl)-3'-(4-fluorophenyl)-3,4,5,6-tetrahydro-2H-[1,2']bipyrazine

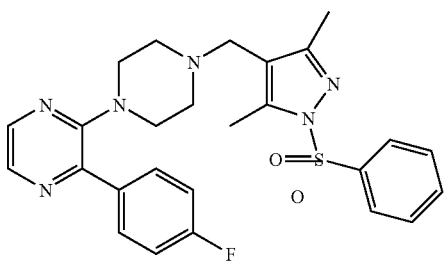

To a solution of 4-(3,5-dimethyl-1H-pyrazol-4-ylmethyl)-3'-(4-fluorophenyl)-3,4,5,6-tetrahydro-2H-[1,2']bipyrazinyl (0.160 g, 0.4 mmol, 1 eq) add benzenesulfonyl chloride (56 μL, 0.4 mmol) followed by pyridine (1 mL). Heat to 120° C. with stirring for 4 hr. Add water and extract 3 times with ethyl acetate (20 mL), dry (magnesium sulfate), concentrate and purify (silica gel chromatography, eluting with 25:75 to 75:25 ethyl acetate:DCM). Lyophilize from a 50% acetonitrile/water solution to give the title compound as a white solid (138 mg, 68%). MS (ES): m/z=507.1 [M+H]+.

EXAMPLE 211

3'-(4-Fluorophenyl)-4-(1-methanesulfonyl-3,5-dimethyl-1H-pyrazol-4-ylmethyl)-3,4,5,6-tetrahydro-2H-[1,2']bipyrazine

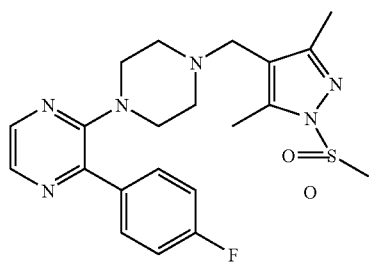

To a solution of 4-(3,5-dimethyl-1H-pyrazol-4-ylmethyl)-3'-(4-fluorophenyl)-3,4,5,6-tetrahydro-2H-[1,2']bipyrazinyl (0.250 g, 0.7 mmol, 1 eq) add methanesulfonyl chloride (63 μL, 0.8 mmol) followed by pyridine (2 mL). Stir at room temperature for 3 hr. then add a further portion of methanesulfonyl chloride (100 μL, 1.4 mmol, 2 eq). Stir for 2 hr. at room temperature then add yet a further portion of methanesulfonyl chloride (63 μL, 0.8 mmol, 1.2 eq) and then stir at room temperature overnight. Add water (10 mL) and ethyl acetate (10 mL), separate and extract the aqueous layer twice with ethyl acetate (10 mL), dry the combined organic extracts (magnesium sulfate), concentrate and purify (silica gel chromatography, eluting with a gradient of 0:100 to 10:90 methanol:DCM), to give the title compound (207 mg, 66%). MS (ES): m/z=445.1 [M+H]+.

EXAMPLE 212

3-{4-[3'-(4-Fluoro-phenyl)-2,3,5,6-tetrahydro-[1,2']bipyrazinyl-4-ylmethyl]-pyrazol-1-yl}-propionitrile hydrochloride

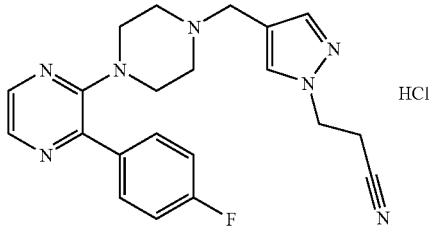

Combine 3'-(4-fluoro-phenyl)-4-(1H-pyrazol-4-ylmethyl)-3,4,5,6-tetrahydro-2H-[1,2']bipyrazinyl (0.125 g, 0.369 mmol), 3-bromopropionitrile (0.059 g, 0.443 mmol), and potassium carbonate (0.076 g, 0.554 mmol) in acetonitrile (2 mL). Heat in microwave at 150° C. for 20 min. Cool to room temperature and filter, washing with acetonitrile. Concentrate filtrate and purify via silica gel chromatography (50:50 hexanes:ethyl acetate then 0:100 hexanes:ethyl acetate, then 10:90 methanol:ethyl acetate) to give the free base (0.144 g, 100%). Dissolve the free base (0.143 g, 0.365 mmol) in methanol and add a solution of ammonium chloride (0.019 g, 0.365 mmol) in a minimal volume of methanol. Shake for 18 hr. at ambient temperature and concentrate to give the title compound (156 mg, 100%). MS (ES): m/z=392 [M+H]+.

EXAMPLE 213

{4-[3'-(4-Fluoro-phenyl)-2,3,5,6-tetrahydro-[1,2']bipyrazinyl-4-ylmethyl]-pyrazol-1-yl}-acetonitrile hydrochloride

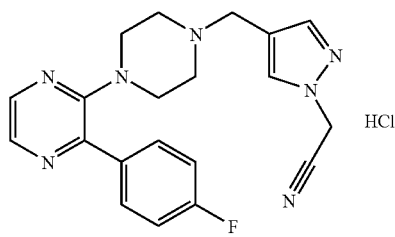

Prepare the title compound essentially as described in Example 212 using bromoacetonitrile (14%). MS (ES): m/z=378 [M+H]⁺.

EXAMPLE 214

5-{4-[3'-(4-Fluoro-phenyl)-2,3,5,6-tetrahydro-[1,2']bipyrazinyl-4-ylmethyl]-pyrazol-1-ylmethyl}-oxazolidin-2-one

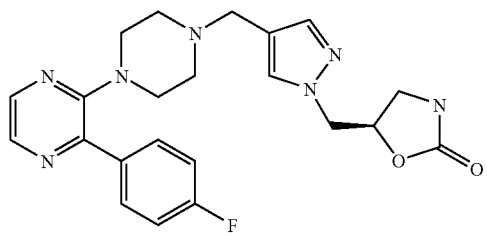

Combine 3'-(4-fluoro-phenyl)-4-(1H-pyrazol-4-ylmethyl)-3,4,5,6-tetrahydro-2H-[1,2']bipyrazinyl (0.125 g, 0.369 mmol), 5-chloromethyl-2-oxazolidinone (0.060 g, 0.443 mmol), and potassium carbonate (0.077 g, 0.554 mmol) in acetonitrile (2 mL). Heat in microwave at 145° C. for 25 min. Add 5-chloromethyl-2-oxazolidinone (0.060 g, 0.443 mmol), and heat in microwave at 145° C. for 25 min. Cool to room temperature and filter, washing with acetonitrile. Concentrate filtrate and purify via silica gel chromatography (0:100 methanol:ethyl acetate then 10:90 methanol:ethyl acetate then 20:80 methanol: ethyl acetate) to give the free base (0.045 g, 28%). Dissolve the free base (0.043 g, 0.099 mmol) in methanol and add a solution of ammonium chloride (0.005 g, 0.099 mmol) in a minimal volume of methanol. Shake for 18 hr. at ambient temperature and concentrate to give the title compound (47 mg, 100%). MS (ES): m/z=438 [M+H]⁺.

EXAMPLE 215

2-{4-[3'-(4-Fluoro-phenyl)-2,3,5,6-tetrahydro-[1,2']bipyrazinyl-4-ylmethyl]-5-methyl-pyrazol-1-yl}-ethanol

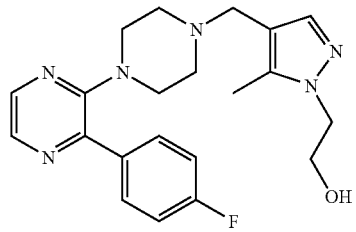

Combine 3'-(4-fluoro-phenyl)-3,4,5,6-tetrahydro-2H-[1,2']bipyrazinyl (0.500 g, 1.94 mmol) with (5-methyl-pyrazol-1-yl)-acetic acid ethyl ester (0.416 g, 2.48 mmol) in ethanol (8 mL). Add acetic acid (801 µL, 14 mmol) and a 37% aqueous solution of formaldehyde (401 µL). Heat in microwave at 120° C. for 5 hr. Add acetic acid (801 µL, 14 mmol) and a 37% aqueous solution of formaldehyde (401 µL). Heat in microwave at 120° C. for 3 hr. Concentrate, add ethyl acetate and saturated aqueous sodium bicarbonate solution. Separate organic layer. Extract aqueous layer twice with ethyl acetate, dry (magnesium sulfate), filter, concentrate and purify (silica gel chromatography, eluting with 50:50 to 100:0 ethyl acetate:hexanes then 10:90 methanol:ethyl acetate) to give {4-[3'-(4-fluoro-phenyl)-2,3,5,6-tetrahydro-[1,2']bipyrazinyl-4-ylmethyl]-5-methyl-pyrazol-1-yl}-acetic acid ethyl ester (139 mg, 16%). MS (ES): m/z=439 [M+H]⁺.

Dissolve this intermediate (0.134 g, 0.306 mmol) in THF (2.7 mL). Cool to −42° C. in acetonitrile/dry ice bath. Treat dropwise with 1 M diisobutylaluminum hydride in toluene (1.22 mL, 1.22 mmol). Stir at −42° C. for 1 hr, then ambient temperature for 2 hr. Quench with saturated aqueous potassium sodium tartrate solution. Add ethyl acetate, and separate organic layer. Extract aqueous layer 3 times with ethyl acetate. Wash combined organic layers with brine, dry (magnesium sulfate), filter, concentrate and purify (silica gel chromatography, eluting with 80:20 to 100:0 ethyl acetate:hexanes then 10:90 to 20:80 methanol:ethyl acetate) to give the title compound (37 mg, 31%). MS (ES): m/z=397 [M+H]⁺.

EXAMPLE 216

2-{4-[3'-(4-Fluoro-phenyl)-2,3,5,6-tetrahydro-[1,2']bipyrazinyl-4-ylmethyl]-pyrazol-1-yl}-1-pyrrolidin-1-yl-ethanone

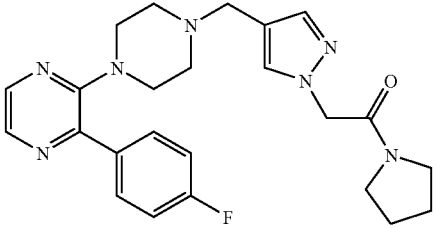

Combine 3'-(4-fluoro-phenyl)-4-(1H-pyrazol-4-ylmethyl)-3,4,5,6-tetrahydro-2H-[1,2']bipyrazinyl (0.150 g, 0.443 mmol), 2-chloro-1-pyrrolidin-1-yl-ethanone (0.092 g, 0.621 mmol), and potassium carbonate (0.092 g, 0.665 mmol) in acetonitrile (2 mL). Heat in microwave at 150° C. for 25 min. Cool to room temperature and filter, washing with acetonitrile. Concentrate filtrate and purify via silica gel chromatography (0:100 methanol:ethyl acetate to 20:80 methanol: ethyl acetate) to give the free base (127 mg, 64%). Dissolve the free base (0.120 g, 0.268 mmol) in acetonitrile (300 µL) and add aqueous 1 N HCl solution (322 µL, 0.322 mmol).

Shake for 0.5 hr. at ambient temperature. Freeze-dry to give the title compound (130 mg, 100%). MS (ES): m/z=450 [M+H]$^+$.

EXAMPLE 217

(2-{4-[3'-(4-Fluoro-phenyl)-2,3,5,6-tetrahydro-[1,2']bipyrazinyl-4-ylmethyl]-pyrazol-1-yl}-ethyl)-methyl-amine dihydrochloride

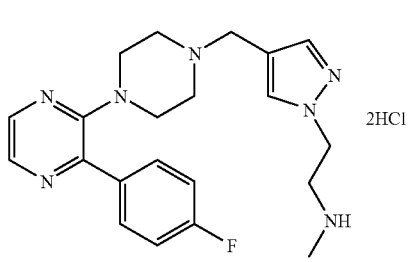

Dissolve 3'-(4-fluoro-phenyl)-4-(1H-pyrazol-4-ylmethyl)-3,4,5,6-tetrahydro-2H-[1,2']bipyrazinyl (0.450 g, 1.33 mmol) in acetonitrile (3 mL) and add solid sodium hydroxide (0.186 g, 4.65 mmol). After 30 min. add (2-chloro-ethyl)-methyl-amine hydrochloride (0.190 g, 1.46 mmol) and tetrabutylammonium bisulfate (18 mg, 0.0531 mmol) then reflux the mixture for 20 hr. Cool and filter the mixture then evaporate. Purify using silica gel chromatography, eluting with 6:94 2N ammonia in methanol:DCM to give a yellow oil. Dissolve the solid in methanol and add ammonium chloride then sonicate the mixture for 10 min. Evaporate the solution to give the title compound as a white solid (0.139 g, 23%). MS (ES): m/z=396 [M+H]$^+$.

EXAMPLE 218

N-(2-{4-[3'-(4-Fluoro-phenyl)-2,3,5,6-tetrahydro-[1,2']bipyrazinyl-4-ylmethyl]-pyrazol-1-yl}-ethyl)-N-methyl-methanesulfonamide hydrochloride

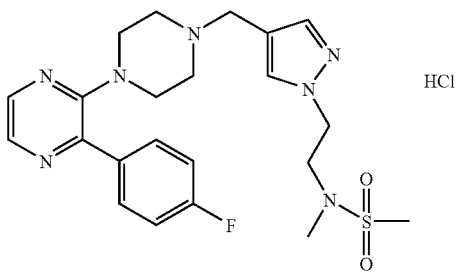

Dissolve (2-{4-[3'-(4-fluoro-phenyl)-2,3,5,6-tetrahydro-[1,2']bipyrazinyl-4-ylmethyl]-pyrazol-1-yl}-ethyl)-methyl-amine (0.124 g, 0.314 mmol) in DCM (3 mL) with triethylamine (66 µL, 0.470 mmol). Add methanesulfonyl chloride (26 µL, 0.329 mmol) dropwise in DCM (1 mL). Stir the mixture for 20 hr. Dilute with saturated aqueous sodium bicarbonate then extract 3 times with DCM. Dry (sodium sulfate), filter, concentrate and purify (silica gel chromatography, eluting with 4.5:95.5 2 M ammonia in methanol:DCM), to give a yellow oil. Dissolve the oil in methanol and add ammonium chloride then sonicate the mixture for 10 min. Evaporate the solution to give the title compound as a yellow solid (0.154 g, 97%). MS (ES): m/z=474 [M+H]$^+$.

EXAMPLE 219

N-(2-{4-[3'-(4-Fluoro-phenyl)-2,3,5,6-tetrahydro-[1,2']bipyrazinyl-4-ylmethyl]-pyrazol-1-yl}-ethyl)-N-methyl-methanesulfonamide hydrochloride

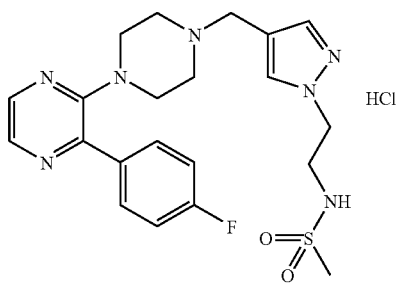

Prepare 2-{4-[3'-(4-Fluoro-phenyl)-2,3,5,6-tetrahydro-[1,2']bipyrazinyl-4-ylmethyl]-pyrazol-1-yl}-ethylamine using the methods in Example 217 using 2-chloro-ethylamine hydrochloride (76%). MS (ES): m/z=382 [M+H]$^+$. Then, using the methods of Example 218, convert the ethylamine intermediate to the title compound (83%). MS (ES): m/z=460 [M+H]$^+$.

EXAMPLE 220

3'-(4-Fluoro-phenyl)-4-[1-(2-methanesulfonyl-ethyl)-1H-pyrazol-4-ylmethyl]-3,4,5,6-tetrahydro-2H-[1,2']bipyrazine hydrochloride

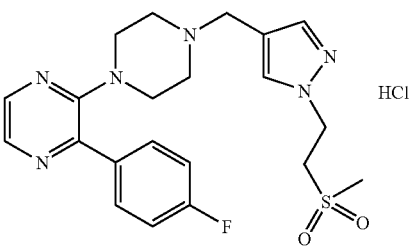

Dissolve 3'-(4-fluoro-phenyl)-4-(1H-pyrazol-4-ylmethyl)-3,4,5,6-tetrahydro-2H-[1,2']bipyrazinyl (0.192 g, 0.567 mmol) in acetonitrile (2 mL). Add 1-bromo-2-methanesulfonyl-ethane (0.375 g, 1.99 mmol) and potassium carbonate (0.118 g, 0.851 mmol) and microwave the mixture for 15 min at 150° C. Dilute with saturated aqueous sodium bicarbonate then extract 3 times with ethyl acetate. Dry (sodium sulfate), filter, concentrate and purify (silica gel chromatography, eluting with 4.5:95.5 2 M ammonia in methanol:DCM), to give the free base as a yellow oil. Dissolve the oil in methanol and add ammonium chloride then sonicate the mixture for 10 min. Evaporate the solution to give the title compound as a yellow solid (0.174 g, 64%). MS (ES): m/z=445 [M+H]$^+$.

The compounds of Examples 221-223 are prepared essentially as described for Example 223 using the appropriate chloride or bromide and 3'-(4-fluoro-phenyl)-4-(1H-pyrazol-4-ylmethyl)-3,4,5,6-tetrahydro-2H-[1,2']bipyrazinyl.

| EX | Structure | Compound | Yield (%) | MS (ES) [M + H]+ |
|---|---|---|---|---|
| 221 | 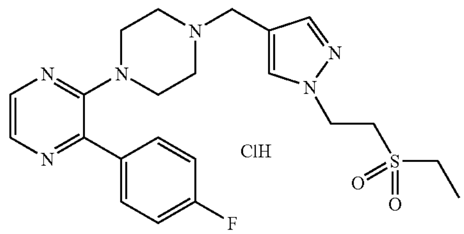 | 4-[1-(2-Ethanesulfonyl-ethyl)-1H-pyrazol-4-ylmethyl]-3'-(4-fluoro-phenyl)-3,4,5,6-tetrahydro-2H-[1,2']bipyrazine hydrochloride 2529768 | 60 | 459 |
| 222 | 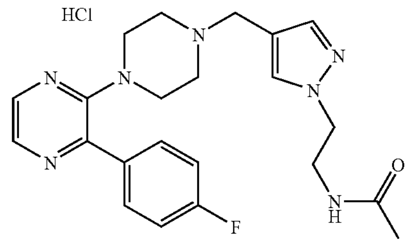 | N-(2-{4-[3'-(4-Fluoro-phenyl)-2,3,5,6-tetrahydro-[1,2']bipyrazinyl-4-ylmethyl]-pyrazol-1-yl}-ethyl)-acetamide hydrochloride | 34 | 424 |
| 223 | 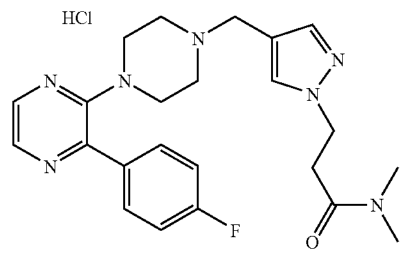 | 3-{4-[3'-(4-Fluoro-phenyl)-2,3,5,6-tetrahydro-[1,2']bipyrazinyl-4-ylmethyl]-pyrazol-1-yl}-N,N-dimethyl-propionamide hydrochloride | 18 | 438 |

EXAMPLE 224

4-[3'-(4-Fluoro-phenyl)-2,3,5,6-tetrahydro-[1,2']bipyrazinyl-4-ylmethyl]-pyrazole-1-carboxylic acid dimethylamide hydrochloride

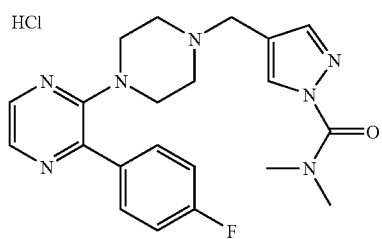

Dissolve 3'-(4-fluoro-phenyl)-4-(1H-pyrazol-4-ylmethyl)-3,4,5,6-tetrahydro-2H-[1,2']bipyrazinyl (0.200 g, 0.591 mmol) in DCM (1.6 mL). Add triethylamine (115 μL, 0.827 mmol) and cool in ice/methanol bath. Add dimethylcarbamyl chloride (65 μL, 0.709 mmol). Stir at ambient temperature for 18 hr. Add dimethylcarbamyl chloride (130 μL, 1.42 mmol), triethylamine (115 μL, 0.827 mmol), and DCM (2 mL) and reflux for 18 hr. Cool to room temperature, concentrate, and purify via silica gel chromatography (0:100 methanol:ethyl acetate to 10:90 methanol:ethyl acetate) to give the free base (166 mg, 69%). Dissolve the free base (0.164 g, 0.401 mmol) in acetonitrile (481 μL) and add aqueous 1 N HCl (481 μL, 0.481 mmol). Shake for 0.5 hr. at ambient temperature. Freeze dry to give the title compound (150 mg, 84%). MS (ES): m/z=410 [M+H]+.

EXAMPLE 225

(1R,2R)-2-(4#4-(3-(4-Fluorophenyl)pyrazin-2-yl)piperazin-1-yl)methyl)-1H-pyrazol-1-yl)cyclopentanol hydrochloride

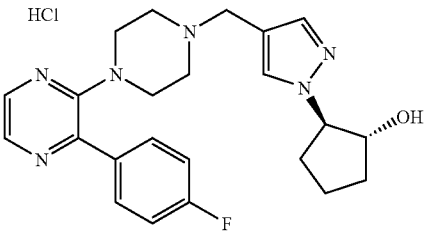

Dissolve 2-(4-((1H-pyrazol-4-yl)methyl)piperazin-1-yl)-3-phenylpyrazine (100 mg, 0.30 mmol) in 1 mL of acetonitrile in a 7 mL vial. Add cis-1,2-epoxycyclopentane (390 mg 4.58 mmol) followed by cesium carbonate (200 mg, 610 mmol). Add a stir bar, seal the vial and heat and stir at 90° C. for 4 hr. At the end of this time cool the mixture, add methylene chloride and filter. Wash the solid with more methylene chloride, combine the filtrates and pass through a 5 g SCX cartridge, washing well with methanol. Elute the product with 2 N ammonia/methanol and evaporate the solvent to yield 116 mg (89%) of the free base. Convert the free base to the HCl salt and lyophilize to obtain the title compound. MS (ES): m/z=423 [M+H]+.

The compounds of Examples 226-234 are obtained using the methods of Example 225 and the appropriate epoxide:

| Ex. | Structure | Name | Yield | MS (ES) [M + H]+ |
|---|---|---|---|---|
| 226 | 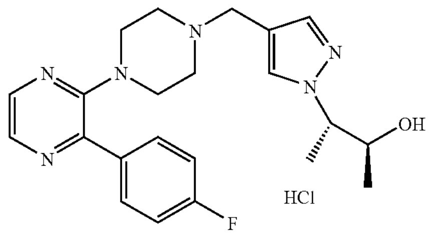 | (2S,3S)-3-(4-((4-(3-(4-fluorophenyl)pyrazin-2-yl)piperazin-1-yl)methyl)-1H-pyrazol-1-yl)butan-2-ol hydrochloride | 68 | 411 |
| 227 | 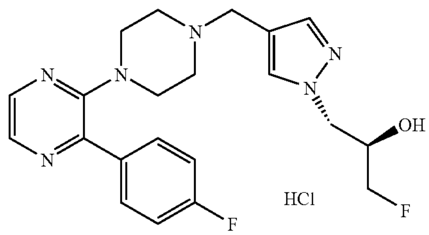 | (R)-1-fluoro-3-(4-((4-(3-phenylpyrazin-2-yl)piperazin-1-yl)methyl)-1H-pyrazol-1-yl)propan-2-ol hydrochloride | 50 | 415 |
| 228 | 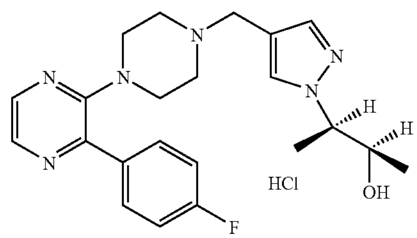 | (2R,3R)-3-(4-((4-(3-(4-fluorophenyl)pyrazin-2-yl)piperazin-1-yl)methyl)-1H-pyrazol-1-yl)butan-2-ol hydrochloride | 74 | 411 |
| 229 | 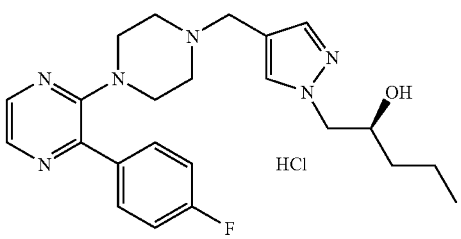 | (R)-1-(4-((4-(3-(4-fluorophenyl)pyrazin-2-yl)piperazin-1-yl)methyl)-1H-pyrazol-1-yl)pentan-2-ol hydrochloride | 82 | 425 |
| 230 | 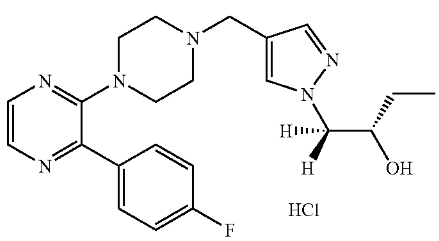 | (S)-1-(4-((4-(3-(4-fluorophenyl)pyrazin-2-yl)piperazin-1-yl)methyl)-1H-pyrazol-1-yl)butan-2-ol hydrochloride | 89 | 411 |
| 231 | 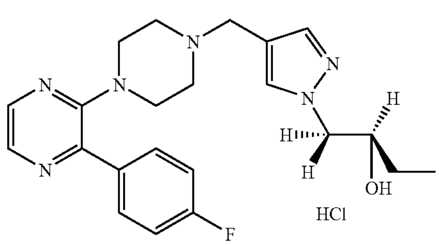 | (R)-1-(4-((4-(3-(4-fluorophenyl)pyrazin-2-yl)piperazin-1-yl)methyl)-1H-pyrazol-1-yl)butan-2-ol hydrochloride | 86 | 411 |

| Ex. | Structure | Name | Yield | MS (ES) [M + H]+ |
|---|---|---|---|---|
| 232 | 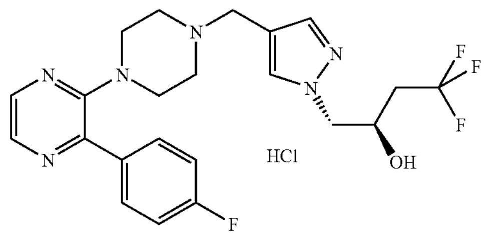 | (R)-4,4,4-trifluoro-1-(4-((4-(3-(4-fluorophenyl)pyrazin-2-yl)piperazin-1-yl)methyl)-1H-pyrazol-1-yl)butan-2-ol hydrochloride | 95 | 465 |
| 233 | 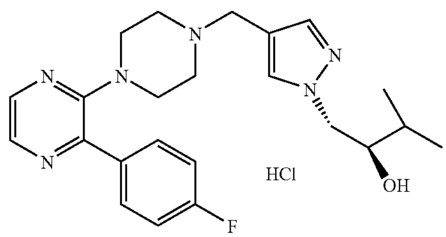 | (R)-1-(4-((4-(3-(4-fluorophenyl)pyrazin-2-yl)piperazin-1-yl)methyl)-1H-pyrazol-1-yl)-3-methylbutan-2-ol hydrochloride | 72 | 425 |
| 234 | 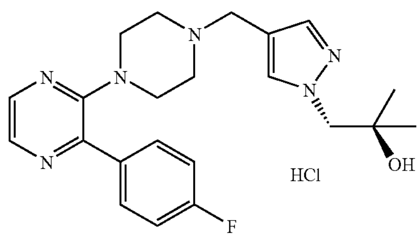 | 1-(4-((4-(3-(4-fluorophenyl)pyrazin-2-yl)piperazin-1-yl)methyl)-1H-pyrazol-1-yl)-2-methylpropan-2-ol hydrochloride | 96 | 411 |

EXAMPLE 235

{4-[3'-(4-Fluoro-phenyl)-2,3,5,6-tetrahydro-[1,2']bipyrazinyl-4-ylmethyl]-1,5-dimethyl-1H-pyrazol-3-yl}-methanol hydrochloride

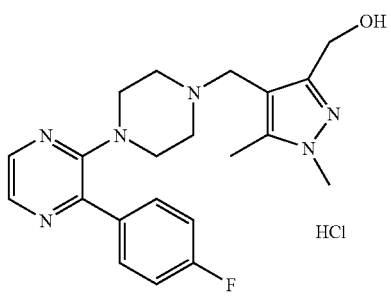

Dissolve 3'-(4-fluoro-phenyl)-3,4,5,6-tetrahydro-2H-[1,2']bipyrazinyl dihydrochloride (120 mg, 0.465 mmol) and (1,5-dimethyl-1H-pyrazol-3-yl)methanol (64 mg, 0.511 mmol, 1.1 eq) in ethanol (2 mL) in a microwave vial. Add acetic acid (150 μL) followed by dropwise addition of formaldehyde (125 μL of 37% wt. % in water) and cap. Heat in a microwave oven at 120° C. for 1 hr. Cool the reaction mixture and concentrate in vacuo. Partition the residue between ethyl acetate and saturated aqueous sodium hydrogen carbonate solution. Separate the organics and wash with brine and dry (sodium sulfate) and evaporate. Purify by silica gel chromatography (1:1 to 2:1 acetone-hexane) to give the free base (25 mg, 14% yield). Dissolve in a minimum amount of 1:1 acetonitrile-water, add 1M HCl (171 μL, 0.171 mmol) and lyophilize to give the title compound (25 mg). MS (ES): m/z=397 [M+H]+.

EXAMPLE 236

3'-(4-Fluoro-phenyl)-4-(3-methoxymethyl-1,5-dimethyl-1H-pyrazol-4-ylmethyl)-3,4,5,6-tetrahydro-2H-[1,2']bipyrazine hydrochloride

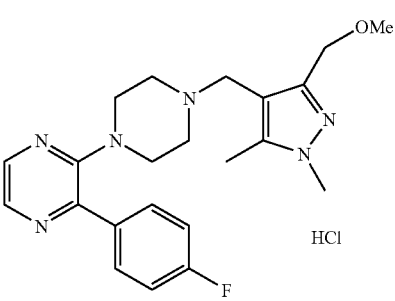

Prepare the title compound essentially as described for Example 235 using (1,5-dimethyl-1H-pyrazol-3-yl)methoxymethylether and 3'-(4-fluoro-phenyl)-3,4,5,6-tetrahydro-2H-[1,2']bipyrazinyl (14%). MS (ES): m/z=411 [M+H]+.

PREPARATION 1M

3'-Chloro-2,3,5,6-tetrahydro-[1,2']bipyrazinyl-4-carboxylic acid tert-butyl ester Charge a 2 L 3-neck round bottom flask with 2,3-dichloropyrazine (78.7 g, 0.532 mol), piperazine-1-carboxylic acid t-butyl ester (100 g, 0.537 mol), potassium carbonate (88.2 g, 0.638 mol) followed by N,N-dimethylacetamide (0.780 L), and heat the resultant slurry to 110° C. under nitrogen with vigorous stirring. Cool to room temperature, add water (0.390 L) and methyl t-butyl ether (0.390 L), and stir the mixture for 60 min. Stop stirring and separate the layers. Wash the organic layer with water (2×200 mL), dry over MgSO$_4$, filter and concentrate to give 145 g of 3'-chloro-2,3,5,6-tetrahydro-[1,2']bipyrazinyl-4-carboxylic acid t-butyl ester as a yellow syrup (91% yield). $^1$H NMR (400 MHz, chloroform-d) δ ppm-8.10 (s, 1H), 7.91 (s, 1H), 3.59 (m, 4H), 3.40 (m, 4H), 1.48 (s, 9H)

PREPARATION 2M

3'-Chloro-3,4,5,6-tetrahydro-2H-[1,2']bipyrazinyl

Add 4 M HCl in 1,4-dioxane (10 mL) to 3'-chloro-2,3,5,6-tetrahydro-[1,2']bipyrazinyl-4-carboxylic acid t-butyl ester (6.80 g, 22.76 mmol). Add 1,4-dioxane (40 mL) and subject the reaction to ultrasound then stir at room temperature under nitrogen for 3 hr. Add further HCl in 1,4-dioxane (40 mL) and stir for 1 hr. Add chloroform (400 mL), wash with 2 N sodium hydroxide (200 mL), saturated aq. sodium chloride (100 mL), dry (magnesium sulfate) and concentrate to give 3'-chloro-3,4,5,6-tetrahydro-2H-[1,2']bipyrazinyl as a yellow oil which crystallized on standing to give a solid (4.0 g, 88%). MS (ES): m/z=199.1 [M+H]$^+$.

PREPARATION 3M

3'-Chloro-3,4,5,6-tetrahydro-2H-[1,2']bipyrazinyl dihydrochloride

To 3'-chloro-2,3,5,6-tetrahydro-[1,2']bipyrazinyl-4-carboxylic acid t-butyl ester (3.00 g, 10.0 mmol, 1 eq) add a 4 M solution of hydrochloric acid in 1,4-dioxane (100 mL, 400 mmol, 40 eq) and stir at room temperature for 3 hr. Filter precipitate and wash with diethyl ether. Dry the powder in vacuum oven over night to give 3'-chloro-3,4,5,6-tetrahydro-2H-[1,2']bipyrazinyl dihydrochloride as a pale yellow powder (2.11 g, 78%). MS (ES): m/z=199 [M+H]$^+$.

PREPARATION 4M

3'-Chloro-4-(1,5-dimethyl-1H-pyrazol-4-ylmethyl)-3,4,5,6-tetrahydro-2H-[1,2']bipyrazinyl Charge a 2 L 3-neck round bottom flask with 3'-chloro-3,4,5,6-tetrahydro-2H-[1,2']bipyrazinyl (39 g, 0.196 mol), 1,2-dichloroethane (780 mL), followed by 1,5-dimethyl-1H-pyrazole-4-carbalehyde (25.5 g, 0.206 mol) and stir for 15 min. under nitrogen with vigorous stirring. Add sodium triacetoxyborohydride (45.77 g, 215 mmol) in three portions, 10 min. apart. Add methanol (100 mL) slowly and stir for 20 min. and then concentrate to a white foam. Dissolve the foam in methylene chloride and add to a 1 kg silica plug. Elute the product with 5-10% isopropyl alcohol/DCM and concentrate the product containing fractions to give 3'-chloro-4-(1,5-dimethyl-1H-pyrazol-4-ylmethyl)-3,4,5,6-tetrahydro-2H-[1,2']bipyrazinyl as a yellow oil (37 g, 60%). MS (ES): m/z=307.0 [M+H]$^+$.

PREPARATION 5M

3'-Chloro-4-(1,5-dimethyl-1H-pyrazol-4-ylmethyl)-3,4,5,6-tetrahydro-2H-[1,2']bipyrazinyl hydrochloride Charge a 2 L 3-neck round bottom flask with methanol (95 mL) and chill to 2° C. and slowly add acetyl chloride (7.62 mL, 0.107 mol) dropwise under nitrogen. In a separate 1 L 3-neck flask, dissolve 3'-chloro-4-(1,5-dimethyl-1H-pyrazol-4-ylmethyl)-3,4,5,6-tetrahydro-2H-[1,2']bipyrazinyl (36.5 g, 0.107 mol) in toluene (365 mL). Add this solution to the methanolic HCl solution in one portion. Stir vigorously for 1 hr. and concentrate to one half volume and filter to give 3'-chloro-4-(1,5-dimethyl-1H-pyrazol-4-ylmethyl)-3,4,5,6-tetrahydro-2H-[1,2']bipyrazinyl hydrochloride as a white solid (25.5 g, 87%). MS (ES): m/z=307.0 [M+H]$^+$.

PREPARATION 6M

3'-Chloro-4-(1-methyl-1H-pyrazol-4-ylmethyl)-3,4,5,6-tetrahydro-2H-[1,2']bipyrazinyl Dissolve 3'-chloro-3,4,5,6-tetrahydro-2H-[1,2']bipyrazinyl (3.43 g, 17.3 mmol) in tetrahydrofuran (100 mL). Add 1-methyl-1H-pyrazole-4-carbaldehyde (2.244 g, 20.38 mmol) in dry tetrahydrofuran (5 mL), stir for 10 min. at room temperature, add sodium triacetoxyborohydride (4.32 g, 20.4 mmol), subject the reaction to ultrasound and stir for 6 hr. at room temperature. Add saturated aq. sodium hydrogen carbonate (100 mL) then 2 N sodium hydroxide (10 mL) to the mixture and extract with DCM (2×200 mL). Pass the combined DCM extracts through an IST Phase Separator Frit®, concentrate and purify (silica gel chromatography, eluting with 0:100 to 8:92 methanol:DCM), to give 3'-chloro-4-(1-methyl-1H-pyrazol-4-ylmethyl)-3,4,5,6-tetrahydro-2H-[1,2']bipyrazinyl as a crystalline solid (5.21 g, 92%). MS (ES): m/z=293.1 [M+H]$^+$.

PREPARATION 7M

3'-Chloro-4-(1,3-dimethyl-1H-pyrazol-4-ylmethyl)-3,4,5,6-tetrahydro-2H-[1,2']bipyrazinyl To a solution of 3'-chloro-3,4,5,6-tetrahydro-2H-[1,2']bipyrazinyl (3 g, 15.1 mmol, 1 eq) and 1,3-dimethyl-1H-pyrazole-4-carbaldehyde (2.0 g, 16.6 mmol, 1.1 eq) in 1,2-dichloroethane (75 mL) add sodium triacetoxyborohydride (4.8 g, 22.6 mmol, 1.5 eq) and stir at room temperature over the weekend. Add 2 N sodium hydroxide (100 mL), separate the layers, extract the aq. layer twice with DCM (75 mL), dry (magnesium sulfate), filter, concentrate and purify (silica gel chromatography, eluting with 0:100 to 10:90 methanol:DCM). Combine only the fractions which contain the main component and concentrate to give 3'-chloro-4-(1,3-dimethyl-1H-pyrazol-4-ylmethyl)-3,4,5,6-tetrahydro-2H-[1,2']bipyrazinyl as a viscous yellow oil (2.14 g, 46%). Combine all other fractions which contain main component plus impurities, concentrate then repeat the chromatography step to recover further material (1.6 g, 35%, total yield 81%). MS (ES): m/z=307.1 [M+H]$^+$.

PREPARATION 8M

3'-Chloro-4-(1,3,5-trimethyl-1H-pyrazol-4-ylmethyl)-3,4,5,6-tetrahydro-2H-[1,2']bipyrazinyl To a suspension of 3'-chloro-3,4,5,6-tetrahydro-2H-[1,2'] bipyrazinyl dihydrochloride (2.11 g, 7.77 mmol, 1 eq) in tetrahydrofuran (20 mL) add 1,3,5-trimethyl-1H-pyrazole-4-carbaldehyde (1.61 g, 11.65 mmol, 1.5 eq). Stir for 10 min and add sodium triacetoxyborohydride (4.20 g, 19.40 mmol, 2.5 eq) in one portion. Stir at room temperature under nitrogen for 1 hr., then add additional 1,3,5-trimethyl-1H-pyrazole-4-carbaldehyde (0.50 g, 3.6 mmol, 0.47 eq). Stir for 30 min., add saturated aq. sodium hydrogen carbonate (100 mL) slowly, and then extract with DCM (3×50 mL). Pass the combined DCM extracts through an IST Phase Separator Frit®, concentrate and purify (silica gel chromatography, eluting with 2:98 to 5:95 methanol:DCM), to give 3'-chloro-4-(1,3,5-trimethyl-1H-pyrazol-4-ylmethyl)-3,4,5,6-tetrahydro-2H-[1,2']bipyrazinyl as a white powder (2.468 g, 98%). MS (ES): m/z=321 [M+H]$^+$.

PREPARATION 9M

3'-Chloro-4-(1-phenyl-1H-pyrazol-4-ylmethyl)-3,4,5,6-tetrahydro-2H-[1,2']bipyrazinyl Stir together 3'-chloro-3,4,5,6-tetrahydro-2H-[1,2']bipyrazinyl (1.6 g, 8.43 mmol) and 1-phenyl-1H-pyrazole-4-carbaldehyde (2.17 g, 12.6 mmol) in dry tetrahydrofuran (10 mL) at room temperature for 15 min., under nitrogen. Add sodium triacetoxyborohydride (2.68 g, 12.6 mmol) and stir reaction for 1 hr. Quench reaction mixture with saturated aq. sodium bicarbonate (50 mL), then extract with DCM (3×50 mL) and pass through an IST Phase Separator Frit®. Concentrate and purify (silica gel chromatography, eluting with 5:95 methanol:DCM) and concentrate all fractions containing product. Pass the mixture through a CBA column to retain the product, wash with methanol and then elute with 2 M ammonia in methanol. Evaporate the ammonia methanol solution and purify (silica gel chromatography, eluting with 0:100 then 5:95 methanol:DCM). Concentrate, wash with diethyl ether and dry in vacuum oven to give 3'-chloro-4-(1-phenyl-1H-pyrazol-4-ylmethyl)-3,4,5,6-tetrahydro-2H-[1,2']bipyrazinyl as brown powder (2.25 g, 76%). MS (ES): m/z=355 [M+H]$^+$.

PREPARATION 10M

3'-Chloro-4-(5-methyl-1-phenyl-1H-pyrazol-4-ylmethyl)-3,4,5,6-tetrahydro-2H-[1,2']bipyrazinyl Stir together 3'-chloro-3,4,5,6-tetrahydro-2H-[1,2']bipyrazinyl (1.6 g, 8.43 mmol) and 5-methyl-1-phenyl-1H-pyrazole-4-carbaldehyde (2.35 g, 12.6 mmol) in dry tetrahydrofuran (10 mL) at room temperature for 15 min., under nitrogen. Add sodium triacetoxyborohydride (2.68 g, 12.6 mmol) and stir reaction for 1 hr. Quench reaction mixture with saturated aq. sodium bicarbonate (50 mL), then extract with DCM (3×50 mL) and pass through an IST Phase Separator Frit®. Concentrate and purify (silica gel chromatography, eluting with 5:95 methanol:DCM) and concentrate all fractions containing product. Pass the mixture through a CBA column to retain the product, wash with methanol and then elute with 2 M ammonia in methanol. Recrystallize from hot ethanol and dry in vacuum oven to give 3'-chloro-4-(5-methyl-1-phenyl-1H-pyrazol-4-ylmethyl)-3,4,5,6-tetrahydro-2H-[1,2']bipyrazinyl as white crystals (2.08 g, 65%). MS (ES): m/z=369 [M+H]$^+$.

PREPARATION 11M

2-[4-(3'-Chloro-2,3,5,6-tetrahydro-[1,2']bipyrazinyl-4-ylmethyl)-pyrazol-1-yl]-ethanol To a solution of 3'-chloro-3,4,5,6-tetrahydro-2H-[1,2']bipyrazinyl (0.789 g, 4.01 mmol) and 1-(2-hydroxy-ethyl)-1H-pyrazole-4-carbaldehyde (0.562 g, 4.01 mmol) in 1,2-dichloroethane (35 mL) add sodium triacetoxyborohydride (1.28 g, 6.02 mmol) and acetic acid (0.382 mL) and stir at room temperature for 20 hr. Add saturated aq. sodium bicarbonate, separate the layers, extract the aq. layer twice with DCM, dry (sodium sulfate), filter and concentrate. Purify using silica gel chromatography, eluting with 6:94 methanol (with 2 N ammonia): DCM to give 2-[4-(3'-chloro-2,3,5,6-tetrahydro-[1,2']bipyrazinyl-4-ylmethyl)-pyrazol-1-yl]-ethanol as a yellow oil (1.16 g, 90%). MS (ES): m/z=323 [M+H]$^+$.

PREPARATION 12M

3'-Chloro-4-(1-ethyl-5-methyl-1H-pyrazol-4-ylmethyl)-3,4,5,6-tetrahydro-2H-[1,2']bipyrazinyl Dissolve 1-ethyl-5-methyl-1H-pyrazole-4-carbaldehyde (2.92 g, 21.1 mmol) in 1,2-dichloroethane (184 mL). Add 3'-chloro-3,4,5,6-tetrahydro-2H-[1,2']bipyrazinyl dihydrochloride (4.97 g, 18.3 mmol), triethylamine (5.9 mL, 42.3 mmol), sodium triacetoxyborohydride (6.72 g, 31.7 mmol) and acetic acid (1.98 mL) and stir at room temperature for 18 hr. Add aq. saturated sodium bicarbonate and extract four times with DCM. Dry combined organic layers (magnesium sulfate), filter, concentrate, and purify (silica gel chromatography, eluting with 50:50 to 100:0 ethyl acetate:hexanes then 10:90 to 20:80 methanol:ethyl acetate) to give 3'-chloro-4-(1-ethyl-5-methyl-1H-pyrazol-4-ylmethyl)-3,4,5,6-tetrahydro-2H-[1,2']bipyrazinyl (5.2 g, 88%). MS (ES): m/z=321 [M+H]$^+$.

PREPARATION 13M

3'-Chloro-4-(5-methyl-1-phenyl-1H-pyrazol-4-ylmethyl)-3,4,5,6-tetrahydro-2H-[1,2']bipyrazinyl Dissolve 3'-chloro-3,4,5,6-tetrahydro-2H-[1,2']bipyrazinyl dihydrochloride (0.500 g, 1.84 mmol) in 1,2-dichloroethane (19 mL). Add 5-methyl-1-phenyl-1H-pyrazole-4-carbaldehyde (0.396 g, 2.13 mmol), triethylamine (594 µL, 4.26 mmol), sodium triacetoxyborohydride (0.677 g, 3.20 mmol) and acetic acid (200 µL) and stir at room temperature for 18 hr. Add aq. saturated sodium bicarbonate and extract four times with DCM. Dry combined organic layers (magnesium sulfate), filter, concentrate, and purify (silica gel chromatography, eluting with 0:100 to 100:0 ethyl acetate:hexanes) to give 3'-chloro-4-(5-methyl-1-phenyl-1H-pyrazol-4-ylmethyl)-3,4,5,6-tetrahydro-2H-[1,2']bipyrazinyl (597 mg, 88%) MS (ES): m/z=369[M+H]$^+$.

PREPARATION 14M

3'-Chloro-4-(1-ethyl-3-methyl-1H-pyrazol-4-ylmethyl)-3,4,5,6-tetrahydro-2H-[1,2']bipyrazinyl Combine 3'-chloro-3,4,5,6-tetrahydro-2H-[1,2']bipyrazinyl dihydrochloride (2.21 g, 8.18 mmol), 1-ethyl-3-methyl- 1H-pyrazole-4-carbaldehyde (1.3 g, 9.40 mmol) and triethylamine (1.31 mL, 9.40 mmol) in dichloroethane (50 mL). Add glacial acetic acid (0.85 mL) followed by sodium triacetoxyborohydride (2.99 g, 14.1 mmol). Stir at room temperature for 20 hr. Dilute with saturated aq. sodium bicarbonate then extract three times using DCM. Dry (sodium sulfate), filter, concentrate and purify (silica gel chromatography, eluting with 4.5:95.5 methanol (with 2 M ammonia):DCM), to give 3'-chloro-4-(1-ethyl-3-methyl-1H-pyrazol-4-ylmethyl)-3,4,5,6-tetrahydro-2H-[1,2']bipyrazinyl as a yellow oil (1.702 g, 65%). MS (ES): m/z=321 [M+H]$^+$.

PREPARATION 15M

3'-Chloro-4-(3-methyl-1-phenyl-1H-pyrazol-4-ylmethyl)-3,4,5,6-tetrahydro-2H-[1,2']bipyrazinyl Stir together 3'-chloro-3,4,5,6-tetrahydro-2H-[1,2']bipyrazinyl (2.00 g, 10.07 mmol) and 5-methyl-1-phenyl-1H-pyrazole-4-carbaldehyde (2.25 g, 12.08 mmol) in dry tetrahydrofuran (10 mL) at room temperature for 10 min., under nitrogen. Add sodium triacetoxyborohydride (3.20 g, 15.10 mmol) and stir reaction for 1 hr. Quench reaction mixture with saturated aq. sodium bicarbonate (30 mL), then extract with DCM (3×20 mL) and pass through an IST Phase Separator Frit®. Concentrate and purify (silica gel chromatography, eluting with 0:100 to 5:95 methanol:DCM). Concentrate and dry in vacuum oven to give the free base as a brown oil (3.585 g, 96.5%). MS (ES): m/z=369 [M+H]$^+$.

PREPARATION 16M

3'-Chloro-4-(3,5-dimethyl-1-phenyl-1H-pyrazol-4-ylmethyl)-3,4,5,6-tetrahydro-2H-[1,2']bipyrazinyl Prepare 3'-chloro-4-(3,5-dimethyl-1-phenyl-1H-pyrazol-4-ylmethyl)-3,4,5,6-tetrahydro-2H-[1,2']bipyrazinyl essentially as described for 3'-chloro-4-(3-methyl-1-phenyl-1H-pyrazol-4-ylmethyl)-3,4,5,6-tetrahydro-2H-[1,2'] bipyrazinyl (3.313 g, 86%). MS (ES): m/z=383 [M+H]$^+$.

PREPARATION 17M

[2-Fluoro-4-(4,4,5,5-tetramethyl-[1,3,2]dioxaborolan-2-yl)-phenyl]-methanol

Stir together bis(dibenzylideneacetone)palladium(0) (336 mg, 0.585 mmol) and tricyclohexylphosphine (383 mg, 1.37 mmol) in N,N-dimethylacetamide (30 mL) at room temperature under nitrogen for 20 min. Add (4-bromo-2-fluoro-phenyl)-methanol (4.00 g, 19.5 mmol), 4,4,5,5,4',4',5',5'-octamethyl-[2,2']bi[[1,3,2]dioxaborolanyl] (5.20 g, 20.5 mmol) and potassium acetate (2.87 g, 29.3 mmol) and stir at 80° C. for 18 hr. Cool reaction to room temperature, dilute with water (100 mL), then extract with ethyl acetate (2×50 mL) dry over magnesium sulfate, filter and concentrate. Purify (silica gel chromatography, eluting with 0:100 to 20:80 ethyl acetate:isohexane), to give [2-fluoro-4-(4,4,5,5-tetramethyl-[1,3,2]dioxaborolan-2-yl)-phenyl]-methanol as a yellow solid (4.079 g, 83%). MS (ES): m/z=275 [M+Na]$^+$.

PREPARATION 18M

2-Methyl-2-[4-(4,4,5,5-tetramethyl-[1,3,2]dioxaborolan-2-yl)-phenyl]-propionitrile Dissolve [4-(4,4,5,5-tetramethyl-[1,3,2]dioxaborolan-2-yl)-phenyl]-acetonitrile (2.43 g, 10.0 mmol) in dry tetrahydrofuran (50 mL) at room temperature. Add sodium hydride (60% weight dispersion in oil, 1.6 g, 40.0 mmol), stir the reaction for 90 min, then add methyl iodide (2.01 mL, 40.0 mmol). Stir the reaction for 1 hr. under nitrogen. Quench with water and reduce the solvent in vacuo. Add water (20 mL), extract with DCM (5×20 mL) and pass through an IST Phase Separator Frit® and concentrate. Add water (20 mL), filter and dry in vacuum oven overnight to give 2-methyl-2-[4-(4,4,5,5-tetramethyl-[1,3,2]dioxaborolan-2-yl)-phenyl]-propionitrile as crystals (340 mg, 12%). GC-MS: m/z=271 [M+].

PREPARATION 19M

5-[4-(4,4,5,5-Tetramethyl-[1,3,2]dioxaborolan-2-yl)-phenyl]-oxazole

Add 5-(4-bromophenyl)-1,3-oxazole (21.78 mmol, 4.88 g) to 1,4-dioxane (80 mL), then add 4,4,5,5,4',4',5',5'-octamethyl-[2,2']bi[[1,3,2]dioxaborolanyl] (26.14 mmol, 6.64 g), potassium acetate (65.34 mmol, 6.41 g), 1,1'-bis(diphenylphosphino)ferrocene (1.09 mmol, 603.74 mg), and (1,1'-bis(diphenylphosphino)ferrocene)palladium(II) chloride (1.09 mmol, 889.34 mg). Reflux at 80° C. for 24 hr. Pour reaction onto 2 M sodium hydroxide (about 50 mL) and ethyl acetate (about 100 mL), filter through celite, separate organics, dry over magnesium sulfate, filter, and concentrate in vacuo to give a black solid. Purify (silica gel chromatography, eluting with 0:100 to 20:80 ethyl acetate: hexane) to give 5-[4-(4,4,5,5-tetramethyl-[1,3,2]dioxaborolan-2-yl)-phenyl]-oxazole as a white solid (1.90 g; 32% yield). MS (ES): m/z=272 [M+H]$^+$.

PREPARATION 20M

2-[4-(1-Methoxy-ethyl)-phenyl]-4,4,5,5-tetramethyl-[1,3,2]dioxaborolane

1-Bromo-4-(1-methoxy-ethyl)-benzene: Dissolve 1-(4-bromo-phenyl)-ethanol (0.79 mL, 6.62 mmol) in dry N,N-dimethylformamide (7 mL) at ambient temperature under nitrogen atmosphere. Add sodium hydride (60% dispersion in oil, 397 mg, 9.93 mmol), stir the reaction for 30 min., then add methyl iodide (0.50 mL, 7.94 mmol) and stir the reaction for a further 23 hr. under nitrogen. Quench with water (30 mL), extract with DCM (3×30 mL), pass through an IST Phase Separator Frit® and concentrate. Purify using silica gel chromatography, eluting with 0:100 to 20:80 ethyl acetate: isohexane to give 1-bromo-4-(1-methoxy-ethyl)-benzene as a clear oil (1.39 g, 98%). $^1$H-NMR (400 MHz, CDCl$_3$) δ 7.47 (d, 2H), 7.20 (d, 2H), 4.25 (q, 1H), 3.21 (s, 3H), 1.40 (d, 3H).

2-[4-(1-Methoxy-ethyl)-phenyl]-4,4,5,5-tetramethyl-[1,3,2]dioxaborolane: Stir together 1-bromo-4-(1-methoxy-ethyl)-benzene (1.39 g, 6.46 mmol), 4,4,5,5,4',4',5',5'-octamethyl-[2,2']bi[[1,3,2]dioxaborolanyl] (1.80 g, 7.11 mmol), potassium acetate (1.90 g, 19.38 mmol), and palladium acetate (87 mg, 0.39 mmol) in dry N,N-dimethylformamide (25 mL). Degas the reaction for 20 min. then heat to 85° C. for 40 hr. Cool to room temperature, add water (100 mL) and extract with DCM (3×50 mL). Pass the combined DCM extracts through an IST Phase Separator Frit®. Purify (silica gel chromatography, eluting with 0:100 to 20:80 ethyl acetate:isohexane) to give a white powder (400 mg, 24% yield). MS (ES): $^1$H-NMR (400 MHz, CDCl$_3$) δ 7.80 (d, 2H), 7.31 (d, 2H), 4.30 (q, 1H), 3.22 (s, 3H), 1.42 (d, 3H).

PREPARATION 21M

2-[4-(2-Methoxy-ethyl)-phenyl]-4,4,5,5-tetramethyl-[1,3,2]dioxaborolane

2-Bromo-4-(1-methoxy-ethyl)-benzene: Dissolve 2-(4-bromo-phenyl)-ethanol (0.98 mL, 7.0 mmol) in dry N,N-dimethylformamide (7 mL) at ambient temperature under nitrogen atmosphere. Add sodium hydride (60% dispersion in oil, 420 mg, 10.5 mmol), stir the reaction for 1 hr., then add methyl iodide (0.52 mL, 8.4 mmol) and stir the reaction for a further 66 hr. under nitrogen. Quench with water (20 mL), extract with DCM (3×30 mL), pass through an IST Phase Separator Frit® and concentrate. Purify using silica gel chromatography, eluting with 0:100 to 20:80 ethyl acetate: isohexane to give 2-bromo-4-(1-methoxy-ethyl)-benzene as a clear oil (1.211 g, 80%). $^1$H-NMR (400 MHz, CDCl$_3$) δ 7.4 (d, 2H), 7.10 (d, 2H), 3.6 (t, 2H), 3.35 (s, 3H), 2.8 (t, 2H).

2-[4-(2-Methoxy-ethyl)-phenyl]-4,4,5,5-tetramethyl-[1,3,2]dioxaborolane: Stir together 2-bromo-4-(2-methoxy-ethyl)-benzene (1.21 g, 5.63 mmol), 4,4,5,5,4',4',5',5'-octamethyl-[2,2']bi[[1,3,2]dioxaborolanyl] (1.57 g, 6.19 mmol), potassium acetate (1.66 g, 16.89 mmol), and palladium acetate (76 mg, 0.34 mmol) in dry N,N-dimethylformamide (25 mL). Degas the reaction for 20 min. then heat to 85° C. for 40 hr. Cool to room temperature, add water (100 mL) and DCM (20 mL). Extract with DCM (3×50 mL). Pass the combined DCM extracts through an IST Phase Separator Frit®. Purify (silica gel chromatography, eluting with 0:100 to 20:80 ethyl acetate:isohexane) to give a clear oil (274 mg, 19% yield). $^1$H-NMR (400 MHz, CDCl$_3$) 7.74 (d, 2H), 7.23 (d, 2H), 3.59 (t, 2H), 3.34 (s, 3H), 2.89 (t, 2H), 1.33 (s, 12H).

PREPARATION 22M

2-[4-(4,4,5,5-Tetramethyl-[1,3,2]dioxaborolan-2-yl)-phenyl]-acetamide 2-(4-Bromo-phenyl)-acetamide: Add 2-(4-bromo-phenyl)-acetyl chloride (1.00 g, 4.28 mmol) to a solution of ammonia in dioxane (0.5 M, 15 mL) at room temperature. Stir for 30 min., then quench with water. Extract with DCM (10 mL) and pass through an IST Phase Separator Frit® and concentrate until precipitate appears. Collect precipitate by filtration, wash powder with DCM, then dissolve in methanol, filter and concentrate to give a white powder (1.0 g, 109%). $^1$H-NMR (300 MHz, MeOD) δ 7.48 (d, 2H), 7.25 (d, 2H), 3.50 (s, 2H).

2-[4-(4,4,5,5-Tetramethyl-[1,3,2]dioxaborolan-2-yl)-phenyl]-acetamide: Stir together bis(dibenzylideneacetone)palladium(0) (74 mg, 0.13 mmol) and tricyclohexylphosphine (84 mg, 0.30 mmol) in dioxane (20 mL) at room temperature under nitrogen for 20 min. Add 2-(4-bromo-phenyl)-acetamide (4.28 mmol), 4,4,5,5,4',4',5',5'-octamethyl-[2,2']bi[[1,3,2]dioxaborolanyl] (1.96 g, 4.71 mmol) and potassium acetate (630 mg, 6.42 mmol) and stir at 80° C. for 17 hr. Cool reaction to room temperature, pour into brine (50 mL), and extract into DCM (3×20 mL). Pass the combined DCM extracts through an IST Phase Separator Frit®. Concentrate the filtrate and purify (silica gel chromatography, eluting with 0:100 to 20:80 then 50:50 to 100:0 ethyl acetate: isohexane), to give the product as whitish powder (464 mg, 42%). $^1$H-NMR (400 MHz, CDCl$_3$) δ 7.80 (d, 2H), 7.29 (d, 2H), 5.48 (bs, 2H), 3.61 (s, 2H), 1.34 (s, 12H).

PREPARATION 23M

1-(2-Hydroxy-ethyl)-1H-pyrazole-4-carbaldehyde

Combine 1H-pyrazole-4-carbaldehyde (0.110 g, 1.14 mmol), 2-bromoethanol (0.172 g, 1.37 mmol), and potassium carbonate (0.236 g, 1.71 mmol) in acetonitrile (2 mL). Heat in microwave at 150° C. for 20 min. Cool to room temperature and filter, washing with acetonitrile. Concentrate filtrate to give 1-(2-hydroxy-ethyl)-1H-pyrazole-4-carbaldehyde (0.155 g, 97%). GC-MS: m/z=140 [M+].

PREPARATION 24M

3'-(4-Hydroxymethyl-phenyl)-2,3,5,6-tetrahydro-[1,2']bipyrazinyl-4-carboxylic acid tert-butyl ester Dissolve 3'-chloro-2,3,5,6-tetrahydro-[1,2']bipyrazinyl-4-carboxylic acid tert-butyl ester (1.29 g, 4.35 mmol) in tetrahydrofuran (12 mL) and water (6 mL). Add potassium carbonate (1.32 g, 9.56 mmol) then 4-hydroxymethylbenzeneboronic acid (0.924 g, 6.08 mmol) and degas with nitrogen for 15 min. Add tri-n-butylphosphine tetrafluoroborate (50 mg, 0.174 mmol) and tris(dibenzylideneacetone)dipalladium(0) (80 mg, 0.0869 mmol) and reflux for 20 hr. Cool to room temperature then dilute with saturated aq. sodium bicarbonate and extract 3 times with ethyl acetate. Dry (sodium sulfate), filter, concentrate and purify (silica gel chromatography, eluting with 3:97 methanol (with 2 M ammonia): DCM), to give a yellow oil. Dissolve the oil in methanol and add ammonium chloride then sonicate the mixture for 10 min. Evaporate the solution to give 3'-(4-hydroxymethyl-phenyl)-2,3,5,6-tetrahydro-[1,2']bipyrazinyl-4-carboxylic acid tert-butyl ester as a yellow semisolid (0.565 g, 35%). MS (ES): m/z=371 [M+H]$^+$.

PREPARATION 25M

[4-(3,4,5,6-Tetrahydro-2H-[1,2']bipyrazinyl-3'-yl)-phenyl]-methanol

Dissolve 3'-(4-hydroxymethyl-phenyl)-2,3,5,6-tetrahydro-[1,2']bipyrazinyl-4-carboxylic acid tert-butyl ester (0.560 g, 1.51 mmol) in DCM (10 mL) and add trifluoroacetic acid (2 mL) and allow the mixture to stir at room temperature for six hr. Evaporate the solution then dilute with DCM and wash with saturated sodium bicarbonate. Dry the organics over sodium sulfate then filter and evaporate. Chromatograph the residue over silica gel (eluting with 8:92 methanol (with 2 M ammonia):DCM), to give [4-(3,4,5,6-tetrahydro-2H-[1,2'] bipyrazinyl-3'-yl)-phenyl]-methanol as a yellow solid (340 mg, 83%). MS (ES): m/z=271 [M+H]$^+$.

PREPARATION 26M

[4-(3,4,5,6-Tetrahydro-2H-[1,2']bipyrazinyl-3'-yl)-phenyl]-methanol dihydrochloride Dissolve 3'-(4-hydroxymethyl-phenyl)-2,3,5,6-tetrahydro-[1,2']bipyrazinyl-4-carboxylic acid tert-butyl ester (2.76 g, 7.45 mmol) in DCM (25 mL) and add trifluoroacetic acid (5 mL) and allow the mixture to stir at room temperature for six hr. Evaporate the solution then dilute with DCM and wash with saturated sodium bicarbonate. Dry the organics over sodium sulfate then filter and evaporate. Chromatograph the residue over silica gel (eluting with 8:92 methanol (with 2 M ammonia):DCM), then dissolve the solid in methanol and add ammonium chloride then sonicate the mixture for 10 min. Evaporate the solution to give [4-(3,4,5,6-tetrahydro-2H-[1, 2']bipyrazinyl-3'-yl)-phenyl]-methanol dihydrochloride as a white solid (1.303 g, 65%). MS (ES): m/z=271 [M+H]$^+$.

PREPARATION 27M

3'-(4-Methoxymethyl-phenyl)-3,4,5,6-tetrahydro-2H-[1,2']bipyrazinyl dihydrochloride 3'-(4-Methoxymethyl-phenyl)-2,3,5,6-tetrahydro-[1,2']bipyrazinyl-4-carboxylic acid tert-butyl ester Dissolve 3'-chloro-2,3,5,6-tetrahydro-[1,2']bipyrazinyl-4-carboxylic acid tert-butyl ester (1.00 g, 3.26 mmol) in N,N-dimethylacetamide (15 mL). Add potassium carbonate (1.29 g, 9.36 mmol), 4-methoxymethylbenzeneboronic acid (649 mg, 3.90 mmol) and tetrakis(triphenylphosphine)palladium (0) (0.0225 g, 0.034 mmol), then water (5 mL) and degas with nitrogen for 30 min. Heat at 110° C. for 18 hr. under nitrogen. Cool to room temperature, add water (20 mL) and extract with DCM (3×20 mL). Combine the DCM extracts and pass through an IST Phase Separator Frit® and concentrate. Purify (silica gel chromatography, eluting with 20:80 ethyl acetate: isohexane), to give 3'-(4-methoxymethyl-phenyl)-2,3,5,6-tetrahydro-[1,2']bipyrazinyl-4-carboxylic acid tert-butyl ester as a yellow oil (1.32 g, 105%). MS (ES): m/z=385 [M+H]$^+$.

3'-(4-Methoxymethyl-phenyl)-3,4,5,6-tetrahydro-2H-[1,2']bipyrazinyl Dihydrochloride Suspend 3'-(4-methoxymethyl-phenyl)-2,3,5,6-tetrahydro-[1,2']bipyrazinyl-4-carboxylic acid tert-butyl ester (1.3 g, 3.26 mmol) in 1,4-dioxane (10 mL). Add HCl in dioxane (4 M, 10 mL), stir for 2 hr. then filter off the yellow solid. Wash with dioxane then diethyl ether to give 3'-(4-methoxymethyl-phenyl)-3,4,5,6-tetrahydro-2H-[1,2']bipyrazinyl dihydrochloride as yellow solid (935 mg, 80%). MS (ES): m/z=285 [M+H]$^+$.

PREPARATION 28M

1-{4-[4-(1,5-Dimethyl-1H-pyrazol-4-ylmethyl)-3,4,5,6-tetrahydro-2H-[1,2']bipyrazinyl-3'-yl]-phenyl}-ethanone Dissolve 3'-chloro-4-(1,5-dimethyl-1H-pyrazol-4-ylmethyl)-3,4,5,6-tetrahydro-2H-[1,2']bipyrazinyl (921 mg, 3.0 mmol) in N,N-dimethylacetamide (6 mL). Add potassium carbonate (996 mg, 7.2 mmol), 4-acetylbenzene boronic acid (590 mg, 3.6 mmol), tetrakis(triphenylphosphine)palladium (0) (0.0174 g, 0.015 mmol), then water (3 mL). Heat at 120° C. for 17 hr., then cool to room temperature, add water (15 mL) and extract with DCM (3×20 mL). Pass the combined DCM extracts through an IST Phase Separator Frit®. Concentrate the filtrate and purify by SCX-2® chromatography washing with methanol then eluting with 3.5 M ammonia in methanol. Further purify (silica gel chromatography, eluting with 5:95 to 20:80 methanol:DCM), to give 1-{4-[4-(1,5-dimethyl-1H-pyrazol-4-ylmethyl)-3,4,5,6-tetrahydro-2H-[1,2']bipyrazinyl-3'-yl]-phenyl}-ethanone as a yellow powder (1.135 g, 97%). MS (ES): m/z=391 [M+H]$^+$.

PREPARATION 29M

3-{4-[4-(1,5-Dimethyl-1H-pyrazol-4-ylmethyl)-3,4,5,6-tetrahydro-2H-[1,2']bipyrazinyl-3'-yl]-phenyl}-propionic acid Stir together 3'-chloro-4-(1,5-dimethyl-1H-pyrazol-4-ylmethyl)-3,4,5,6-tetrahydro-2H-[1,2']bipyrazinyl (921 mg, 3.00 mmol), [4-(2-ethoxycarbonylethyl)benzene]boronic acid (994 mg, 3.6 mmol), potassium carbonate (996 mg, 7.2 mmol), tetrakis(triphenylphosphine)palladium(0) (0.0174 g, 0.015 mmol) and water (3 mL) in N,N-dimethylacetamide (6 mL) at room temperature under nitrogen. Degas for 10 min. then heat at 120° C. for 20 hr. Load onto SCX-2 column, elute with 2 M ammonia in methanol and purify using silica gel chromatography (eluting with 15:85 to 30:70 methanol: DCM). Concentrate to give 3-{4-[4-(1,5-dimethyl-1H-pyrazol-4-ylmethyl)-3,4,5,6-tetrahydro-2H-[1,2']bipyrazinyl-3'-yl]-phenyl}-propionic acid as a powder (1.01 g, 80%). MS (ES): m/z=421 [M+H]$^+$

PREPARATION 30M

4-[4-(1,5-Dimethyl-1H-pyrazol-4-ylmethyl)-3,4,5,6-tetrahydro-2H-[1,2']bipyrazinyl-3'-yl]-phenol Stir together 3'-chloro-4-(1,5-dimethyl-1H-pyrazol-4-ylmethyl)-3,4,5,6-tetrahydro-2H-[1,2']bipyrazinyl (920 mg, 3.00 mmol), 4-(hydroxy)benzene boronic acid (497 mg, 3.6 mmol), potassium carbonate (996 mg, 7.2 mmol), tetrakis (triphenylphosphine)palladium(0) (0.018 g, 0.015 mmol) and water (6 mL) in N,N-dimethylacetamide (12 mL) at 120° C. for 5 hr. Cool to room temperature, add water (20 mL), extract with DCM (3×30 mL) and pass through an IST Phase Separator Frit®. Purify using SCX chromatography, eluting with 2.5 M ammonia in methanol and further purify using silica gel chromatography (eluting with 5:95 to 15:85 methanol: DCM). Concentrate and dry in a vacuum oven over night to give 4-[4-(1,5-dimethyl-1H-pyrazol-4-ylmethyl)-3,4,5,6-tetrahydro-2H-[1,2']bipyrazinyl-3'-yl]-phenol as a light yellow powder (936 mg, 86%). MS (ES): m/z=365 [M+H].

PREPARATION 31M

3'-(4-Chloromethyl-phenyl)-4-(1,5-dimethyl-1H-pyrazol-4-ylmethyl)-3,4,5,6-tetrahydro-2H-[1,2']bipyrazinyl dihydrochloride Dissolve {4-[4-(1,5-dimethyl-1H-pyrazol-4-ylmethyl)-3,4,5,6-tetrahydro-2H-[1,2']bipyrazinyl-3'-yl]-phenyl}-methanol (1.00 g, 2.64 mmol) in DCM (60 mL). Add thionyl chloride (6 mL) and stir at room temperature for 2 hr. Concentrate in vacuo to give 3'-(4-chloromethyl-phenyl)-4-(1,5-dimethyl-1H-pyrazol-4-ylmethyl)-3,4,5,6-tetrahydro-2H-[1, 2']bipyrazinyl dihydrochloride as a yellow solid (1.20 g, 100%). MS (ES): m/z=397 [M+H]$^+$

PREPARATION 32M

3-Ethyl-1-phenyl-1H-pyrazole-4-carbaldehyde

Add acetic acid (1.00 mL, 17.45 mmol) and phenyl hydrazine (1.98 mL, 20.00 mmol) to a solution of 2-butanone (2.15 mL, 24.00 mmol) in ethanol (90 mL) at room temperature. Stir the reaction for 1 hr., then remove the solvents in vacuo to give N-[1-methyl-prop-(E)-ylidene]-N'-phenyl-hydrazine as a crude orange oil (3.21 g, 99%). MS (ES): m/z=163 [M+H]+.

To an ice cold solution of N,N-dimethylformamide (4.59 mL, 59.36 mmol) and phosphoryl chloride (5.52 mL, 59.36 mmol) add a solution of N-[1-methyl-prop-(E)-ylidene]-N'-phenyl-hydrazine (3.21 g, 19.79 mmol) in N,N-dimethylformamide (2 mL) dropwise. Warm to room temperature, then heat to 75° C. for 5 hr. Cool to room temperature and pour into an ice-cold solution of saturated potassium carbonate. Extract with DCM (3×20 mL), pass through an IST Phase Separator Frit® and concentrate. Purify (silica gel chromatography, eluting with 0:100 to 20:80 ethyl acetate:isohexane), to give the title compound as a brown solid (600 mg, 15%). MS (ES): m/z=201 [M+H]$^+$.

PREPARATION 33M

3'-[4-(Acetylamino-methyl)-phenyl]-2,3,5,6-tetrahydro-[1,2']bipyrazinyl-4-carboxylic acid tert-butyl ester Charge a carousel tube with potassium carbonate (553 mg, 4 mmol), 2333216 (500 mg, 1.67 mmol), (4-acetamidomethylphenyl)boronic acid (393 mg, 2.02 mmol) and tetrakis(triphenylphosphine)palladium (39 mg, 0.033 mmol) in a mixture of DMA (5 mL) and water (2.5 mL). Purge with nitrogen and leave stirring under nitrogen at 120° C. overnight. Cool reaction to room temperature. Dilute with water (10 mL) and extract with DCM (3×20 mL) and discard the aq. layer. Concentrate to dryness. Purify the crude material by flash silica chromatography eluting with (20/80 to 100/00 ethyl acetate: cyclohexane) to give the title compound as a white solid (650 mg, 94%). $^1$H-NMR (400 MHz, CDCl$_3$) δ 8.17 (d, 1H), 8.09 (d, 1H), 7.89 (d, 2H), 7.36 (d, 2H), 5.82 (bs, 1H), 4.50 (d, 2H), 3.41 (m, 4H), 3.14 (m, 4H), 2.02 (s, 3H), 1.45 (t, 9H).

PREPARATION 34M

N-[4-(3,4,5,6-Tetrahydro-2H-[1,2']bipyrazinyl-3'-yl)-benzyl]-acetamide

Add TFA (0.6 mL, 7.94 mmol) to a solution of 3'-[4-(Acetylamino-methyl)-phenyl]-2,3,5,6-tetrahydro-[1,2']bipyrazinyl-4-carboxylic acid tert-butyl ester (650 mg, 1.58 mmol) in DCM (6.5 mL) and maintain stirring for 3 hr. Concentrate material to dryness. Redissolve in DCM (10 mL) and add TFA (1.2 mL). Heat reaction mixture at 40° C. for 3 hr. Purify the mixture by SCX-2® ion exchange chromatography, eluting with 2 M NH$_3$ in MeOH to give the title compound as a yellow oil (454 mg, 92%). $^1$H-NMR (400 MHz, CDCl$_3$) δ 8.14 (d, 1H), 8.08 (d, 1H), 7.90 (d, 2H), 7.36 (d, 2H), 5.81 (bs, 1H), 4.49 (d, 2H), 3.17 (m, 4H), 2.88 (m, 4H), 2.06 (s, 3H).

PREPARATION 35M

{4-[4-(3-Methyl-1-phenyl-1H-pyrazol-4-ylmethyl)-3,4,5,6-tetrahydro-2H-[1,2']bipyrazinyl-3'-y-1]-phenyl}-methanol Charge a carousel tube with potassium carbonate (545 mg, 3.94 mmol), (1-(2-Chloro-pyridin-3-yl)-4-(3-methyl-1-phenyl-1H-pyrazol-4-ylmethyl)-piperazine, (600 mg, 1.63 mmol), (4-hydroxymethyl)phenylboronic acid (304 mg, 1.96 mmol) and tetrakis(triphenylphosphine)palladium (42 mg, 0.036 mmol) in DMA (6 mL) and water (3 mL). Purge with nitrogen and leave stirring under nitrogen at 120° C. overnight. Cool reaction to room temperature. Dilute with water (10 mL) and extract with DCM (3×20 mL) and discard the aq. layer. Concentrate to dryness. Purify the crude material by flash silica chromatography eluting with (2/98 to 12/88 methanol:DCM) to give the title compound (474 mg, 66%). $^1$H-NMR (300 MHz, CDCl$_3$) δ 8.09 (d, 1H), 8.05 (d, 1H), 7.85 (d, 2H), 7.75 (s, 1H), 7.60 (d, 2H), 7.38 (m, 4H), 7.20 (t, 1H), 4.69 (s, 2H), 3.39 (s, 2H), 3.19 (m, 4H), 2.44 (m, 4H), 2.30 (s, 3H).

PREPARATION 36M

3'-(4-Chloromethyl-phenyl)-4-(3-methyl-1-phenyl-1H-pyrazol-4-ylmethyl)-3,4,5,6-tetrahydro-2H-[1,2']bipyrazinyl Add thionyl chloride (0.4 mL, 5.49 mmol) to a solution of {4-[4-(3-Methyl-1-phenyl-1H-pyrazol-4-ylmethyl)-3,4,5,6-tetrahydro-2H-[1,2']bipyrazinyl-3'-yl]-phenyl}-methanol (474 mg, 1.08 mmol) in DCM (20 mL). Maintain stirring for 3 hr. Concentrate to dryness to give the title compound as a yellow material (545 mg) MS (ES): m/z=459/460/461[M+H]$^+$.

EXAMPLE 1M

{4-[4-(1-Ethyl-1H-pyrazol-4-ylmethyl)-3,4,5,6-tetrahydro-2H-[1,2']bipyrazinyl-3'-yl]-phenyl}-methanol hydrochloride

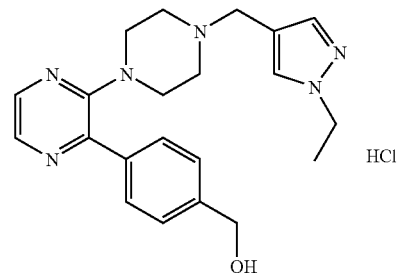

Combine [4-(3,4,5,6-tetrahydro-2H-[1,2']bipyrazinyl-3'-yl)-phenyl]-methanol dihydrochloride (0.177 g, 0.516 mmol), 1-ethyl-1H-pyrazole-4-carbaldehyde (0.064 g, 0.516 mmol) and triethylamine (0.144 mL, 1.03 mmol) in dichloroethane (4 mL). Add glacial acetic acid (42 mL) followed by sodium triacetoxyborohydride (0.153 g, 0.722 mmol). Stir at room temperature for 20 hr. Dilute with saturated aq. sodium bicarbonate then extract three times using DCM. Dry (sodium sulfate), filter, concentrate and purify (silica gel chromatography, eluting with 4.5:95.5 methanol (with 2 M ammonia):DCM), to give a white solid. Dissolve the solid in methanol and add ammonium chloride (1 equivalent) then sonicate the mixture for 10 min. Evaporate the solution to give the title compound as a white solid (0.178 g, 83%). MS (ES): m/z=379

EXAMPLE 2M

{4-[4-(1-Methyl-1H-pyrazol-4-ylmethyl)-3,4,5,6-tetrahydro-2H-[1,2']bipyrazinyl-3'-yl]-phenyl}-methanol hydrochloride

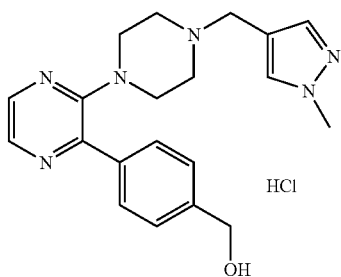

Combine [4-(3,4,5,6-tetrahydro-2H-[1,2']bipyrazinyl-3'-yl)-phenyl]-methanol (0.175 g, 0.647 mmol) and 1-methyl-1H-pyrazole-4-carbaldehyde (0.071 g, 0.647 mmol) in dichloroethane (6 mL). Add glacial acetic acid (60 μL) followed by sodium triacetoxyborohydride (0.206 g, 0.971 mmol). Stir at room temperature for 20 hr. Dilute with saturated aq. sodium bicarbonate then extract three times using DCM. Dry (sodium sulfate), filter, concentrate and purify (silica gel chromatography, eluting with 4.5:95.5 methanol (with 2 M ammonia):DCM), to give the free base as a yellow oil. Dissolve this oil in methanol and add ammonium chloride (1 equivalent) then sonicate the mixture for 10 min. Evaporate the solution to give the title compound as a white solid (0.224 g, 86%). MS (ES): m/z=365 [M+H]

EXAMPLE 3M

{4-[4-(1-Ethyl-3-methyl-1H-pyrazol-4-ylmethyl)-3,4,5,6-tetrahydro-2H-[1,2']bipyrazinyl-3'-yl]-phenyl}-methanol hydrochloride

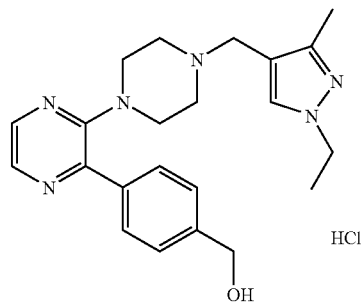

Combine [4-(3,4,5,6-tetrahydro-2H-[1,2']bipyrazinyl-3'-yl)-phenyl]-methanol (0.140 g, 0.518 mmol) and 1-ethyl-3-methyl-1H-pyrazole-4-carbaldehyde (0.072 g, 0.518 mmol) in dichloroethane (5 mL). Add glacial acetic acid (48 μL) followed by sodium triacetoxyborohydride (0.165 g, 0.777 mmol). Stir at room temperature for 20 hr. Dilute with saturated aq. sodium bicarbonate then extract three times using DCM. Dry (sodium sulfate), filter, concentrate and purify (silica gel chromatography, eluting with 4.5:95.5 methanol (with 2 M ammonia):DCM), to give the free base as a yellow solid. Dissolve this solid in methanol and add ammonium chloride (1 equivalent) then sonicate the mixture for 10 min. Evaporate the solution to give the title compound as a white solid (0.193 g, 87%). MS (ES): m/z=393

EXAMPLE 4M

{4-[4-(1-Benzyl-3,5-dimethyl-1H-pyrazol-4-ylmethyl)-3,4,5,6-tetrahydro-2H-[1,2']bipyrazinyl-3'-yl]-phenyl}-methanol hydrochloride

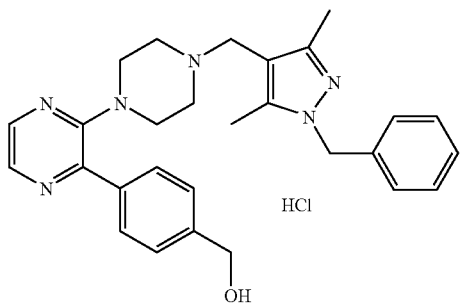

Combine [4-(3,4,5,6-tetrahydro-2H-[1,2']bipyrazinyl-3'-yl)-phenyl]-methanol dihydrochloride (0.210 g, 0.612 mmol), 1-benzyl-3,5-dimethyl-1H-pyrazole-4-carbaldehyde (0.131 g, 0.612 mmol) and triethylamine (0.171 mL, 1.22 mmol) in dichloroethane (5 mL). Add glacial acetic acid (50 μL) followed by sodium triacetoxyborohydride (0.181 g, 0.856 mmol). Stir at room temperature for 3 days. Dilute with saturated aq. sodium bicarbonate then extract three times using DCM. Dry (sodium sulfate), filter, concentrate and purify (silica gel chromatography, eluting with 4.5:95.5 methanol (with 2 M ammonia):DCM), to give a yellow oil. Dissolve the oil in methanol and add ammonium chloride (1 equivalent) then sonicate the mixture for 10 min. Evaporate the solution to give the title compound as a yellow solid (0.241 g, 78%). MS (ES): m/z=469

EXAMPLE 5M

3'-(4-Methoxymethyl-phenyl)-4-(1,3-dimethyl-1H-pyrazol-4-ylmethyl)-3,4,5,6-tetrahydro-2H-[1,2']bipyrazinyl hydrochloride

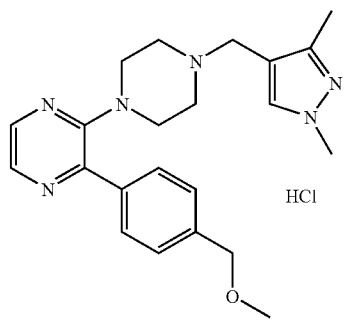

Stir 3'-(4-methoxymethyl-phenyl)-3,4,5,6-tetrahydro-2H-[1,2']bipyrazinyl dihydrochloride (312 mg, 0.87 mmol) in dry tetrahydrofuran (10 mL), and add 1,3-dimethyl-1H-pyrazole-4-carbaldehyde (138 mg, 0.87 mmol). Stir at room temperature for 15 min., and then add sodium triacetoxyborohydride (171 mg, 1.04 mmol). Stir the reaction for 17 hr. at room temperature, then at 50° C. for 20 hr. under nitrogen. Pour the reaction mixture into saturated aq. sodium bicarbonate (20 mL), extract with DCM (3×20 mL) and pass through an IST Phase Separator Frit®. Concentrate and purify using silica gel chromatography (eluting with 2:98 to 5:95 methanol:DCM). Dissolve the oil in acetonitrile and convert to the hydrochloride salt by adding 2 M aq HCl solution. Add water and lyophilize, then free base using an SCX-2® ion exchange cartridge. Further purify by low pH reverse phase HPLC. Form the free base by passing through an SCX-2® ion exchange cartridge washing with methanol then eluting with 3 M ammonia in methanol and concentrate. Dissolve the solid in acetonitrile and convert to the hydrochloride salt by adding 2 M aq HCl solution. Add water and lyophilize to give the title compound as a bright yellow solid (80 mg, 22%). MS (ES): m/z=393 [M+H]+.

EXAMPLE 6M

N-{4-[4-(1,3,5-Trimethyl-1H-pyrazol-4-ylmethyl)-3,4,5,6-tetrahydro-2H-[1,2']bipyrazinyl-3'-yl]-benzyl}-methanesulfonamide hydrochloride

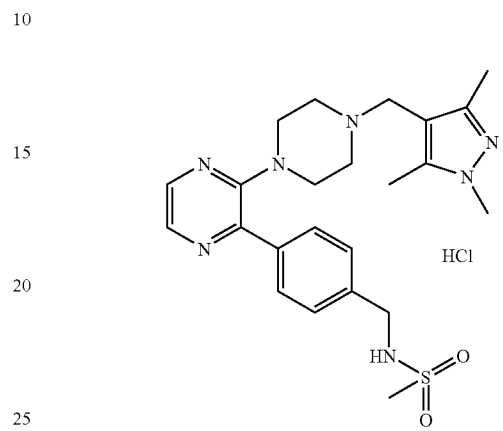

Stir together 4-sulfonamidomethyl benzeneboronic acid (291 mg, 1.27 mmol), 3'-chloro-4-(1,3,5-trimethyl-1H-pyrazol-4-ylmethyl)-3,4,5,6-tetrahydro-2H-[1,2']bipyrazinyl (339 mg, 1.06 mmol), potassium carbonate (354 mg, 2.54 mmol) and tetrakis(triphenylphosphine)palladium(0) (56 mg, 5 µmol) in dry N,N-dimethylacetamide (4 mL) and water (2 mL) at room temperature. Heat to 120° C. for 17 hr. under nitrogen. Cool to room temperature, purify using SCX chromatography and further purify using silica gel chromatography eluting with (5:95 to 20:80 methanol:DCM). Dissolve in acetonitrile, and add 2 M aq. HCl and water then lyophilize to give the title compound as a yellow powder (413 mg, 77%). MS (ES): m/z=470 [M+H].

Compounds of examples 7-9 are prepared essentially as described for Example 6 using the appropriate boronic acid.

| EX | Structure | Compound | Yield (%) | MS (ES) [M + H] |
|---|---|---|---|---|
| 7m | 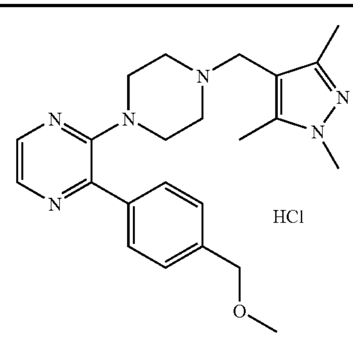 | 3'-(4-methoxymethyl-phenyl)-4-(1,3,5-trimethyl-1H-pyrazol-4-ylmethyl)-3,4,5,6-tetrahydro-2H-[1,2']bipyrazinyl hydrochloride | 83 | 407 |

-continued

| EX | Structure | Compound | Yield (%) | MS (ES) [M + H] |
|---|---|---|---|---|
| 8m | 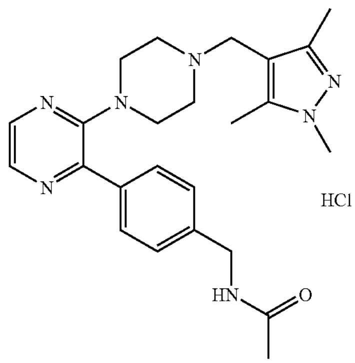 | N-{4-[4-(1,3,5-trimethyl-1H-pyrazol-4-ylmethyl)-3,4,5,6-tetrahydro-2H-[1,2']bipyrazinyl-3'-yl]-benzyl}-acetamide hydrochloride | 99 | 434 |
| 9m | 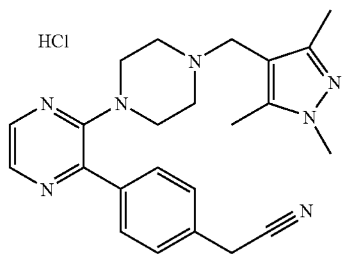 | {4-[4-(1,3,5-trimethyl-1H-pyrazol-4-ylmethyl)-3,4,5,6-tetrahydro-2H-[1,2']bipyrazinyl-3'-yl]-phenyl}-acetonitrile hydrochloride | 64 | 402 |

EXAMPLE 10M

{4-[4-(1,3,5-Trimethyl-1H-pyrazol-4-ylmethyl)-3,4,5,6-tetrahydro-2H-[1,2']bipyrazinyl-3'-yl]-phenyl}-methanol hydrochloride

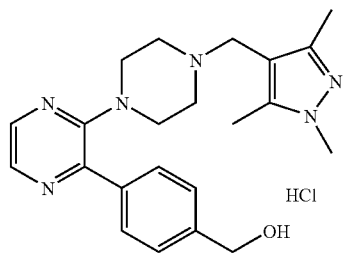

Stir together 4-(hydroxymethyl)benzeneboronic acid (182 mg, 1.2 mmol), 3'-chloro-4-(1,3,5-trimethyl-1H-pyrazol-4-ylmethyl)-3,4,5,6-tetrahydro-2H-[1,2']bipyrazinyl (321 mg, 1.0 mmol), potassium carbonate (332 mg, 2.4 mmol) and tetrakis(triphenylphosphine)palladium(0) (58 mg, 5 µmol) in dry N,N-dimethylacetamide (4 mL) and water (2 mL) at room temperature. Heat to 120° C. for 6 hr. under nitrogen. Cool to room temperature, purify using SCX chromatography and further purify using silica gel chromatography eluting with (5:95 to 20:80 methanol:DCM). Dissolve in acetonitrile, and add 2 M aq. HCl and water then lyophilize to give the title compound as a peach coloured powder (405 mg, 94%). MS (ES): m/z=393 [M+H].

EXAMPLE 11M

{2-Fluoro-4-[4-(5-methyl-1-phenyl-1H-pyrazol-4-ylmethyl)-3,4,5,6-tetrahydro-2H-[1,2']bipyrazinyl-3'-yl]-phenyl}-methanol hydrochloride

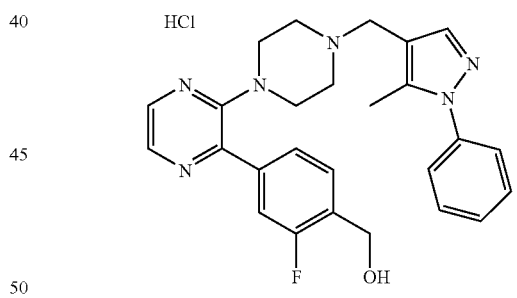

Stir together 3'-chloro-4-(5-methyl-1-phenyl-1H-pyrazol-4-ylmethyl)-3,4,5,6-tetrahydro-2H-[1,2']bipyrazinyl (184 mg, 0.50 mmol), [2-fluoro-4-(4,4,5,5-tetramethyl-[1,3,2]dioxaborolan-2-yl)-phenyl]-methanol (151 mg, 0.60 mmol), potassium carbonate (166 mg, 1.20 mmol) and tetrakis(triphenylphosphine)palladium(0) (0.006 g, 0.003 mmol) and water (1 mL), in N,N-dimethylacetamide (2 mL) at room temperature under nitrogen, then heat at 120° C. for 3 hr. Cool to room temperature, add water (20 mL) and extract with DCM (3×20 mL). Pass the combined DCM extracts through an IST Phase Separator Frit®, concentrate and purify (silica gel chromatography, eluting with 5:95 to 15:85 methanol:DCM). Dry in a vacuum oven over night, then dissolve the yellow powder in acetonitrile. Add 2 M aq. HCl and water then lyophilize to give the title compound as light yellow powder (203 mg, 82%). MS (ES): m/z=459 [M+H].

Compounds of examples 12-15 are prepared essentially as Example 11 using the appropriate chloride and boronic acid or ester.

| EX | Structure | Compound | Yield (%) | MS (ES) [M + H] |
|---|---|---|---|---|
| 12m | 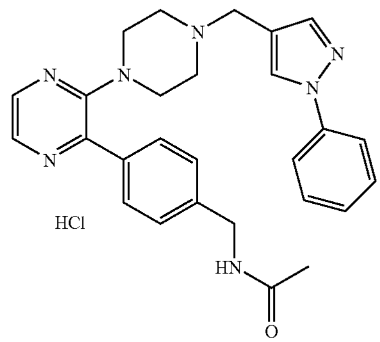 | N-{4-[4-(1-phenyl-1H-pyrazol-4-ylmethyl)-3,4,5,6-tetrahydro-2H-[1,2']bipyrazinyl-3'-yl]-benzyl}-acetamide hydrochloride | 55 | 468 |
| 13m | 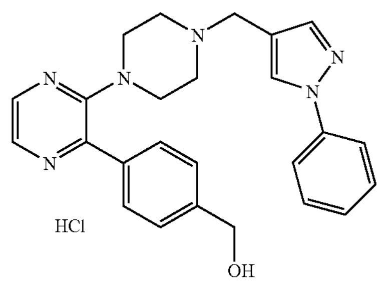 | {4-[4-(1-phenyl-1H-pyrazol-4-ylmethyl)-3,4,5,6-tetrahydro-2H-[1,2']bipyrazinyl-3'-yl]-phenyl}-methanol hydrochloride | 73 | 427 |
| 14m | 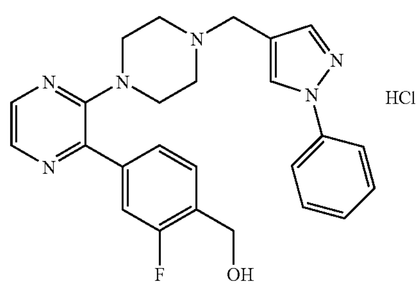 | {2-fluoro-4-[4-(1-phenyl-1H-pyrazol-4-ylmethyl)-3,4,5,6-tetrahydro-2H-[1,2']bipyrazinyl-3'-yl]-phenyl}-methanol hydrochloride | 73 | 445 |
| 15m | 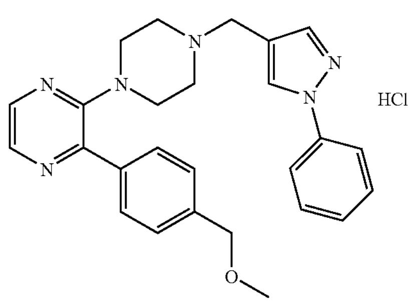 | 3'-(4-methoxymethyl-phenyl)-4-(1-phenyl-1H-pyrazol-4-ylmethyl)-3,4,5,6-tetrahydro-2H-[1,2']bipyrazinyl hydrochloride | 32 | 441 |

EXAMPLE 16M

{4-[4-(1-Phenyl-1H-pyrazol-4-ylmethyl)-3,4,5,6-tetrahydro-2H-[1,2']bipyrazinyl-3'-yl]-phenyl}-acetonitrile hydrochloride

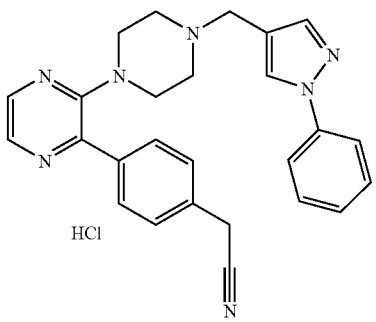

Stir together 3'-chloro-4-(1-phenyl-1H-pyrazol-4-ylmethyl)-3,4,5,6-tetrahydro-2H-[1,2']bipyrazinyl (177 mg, 0.50 mmol), 4-(cyanomethyl)benzene boronic acid (97 mg, 0.60 mmol), potassium carbonate (166 mg, 1.20 mmol) and tetrakis(triphenylphosphine) palladium(0) (0.006 g, 0.003 mmol) and water (1 mL), in N,N-dimethylacetamide (2 mL) at room temperature under nitrogen, then heat at 120° C. for 3 hr. Cool to room temperature, add water (20 mL) and extract with DCM (3×20 mL). Pass the combined DCM extracts through an IST Phase Separator Frit®, concentrate and purify (silica gel chromatography, eluting with 5:95 to 15:85 methanol:DCM). Dry in a vacuum oven over night, then further purify by low pH reverse phase HPLC. Form the free base by passing through an SCX-2® ion exchange cartridge washing with methanol then eluting with 2 M ammonia in methanol and concentrate. Dissolve the solid in acetonitrile and convert to the hydrochloride salt by adding 2 M aq HCl solution. Add water and lyophilize to give the title compound as a bright yellow solid (136 mg, 58%). MS (ES): m/z=436 [M+H]+.

EXAMPLE 17M

2-{4-[3'-(4-Methoxymethyl-phenyl)-2,3,5,6-tetrahydro-[1,2']bipyrazinyl-4-ylmethyl]-pyrazol-1-yl}-ethanol hydrochloride

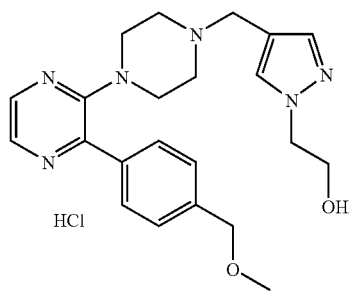

Dissolve 2-[4-(3'-chloro-2,3,5,6-tetrahydro-[1,2']bipyrazinyl-4-ylmethyl)-pyrazol-1-yl]-ethanol (0.201 g, 0.623 mmol) in tetrahydrofuran (1.7 mL) and water (0.9 mL). Add potassium carbonate (189 mg, 1.37 mmol) then 4-methoxymethylbenzeneboronic acid (145 mg, 0.872 mmol) and degas with nitrogen for 15 min. Add tri-n-butylphosphine tetrafluoroborate (7.2 mg, 0.0249 mmol) and tris(dibenzylideneacetone)dipalladium(0) (11.4 mg, 0.0124 mmol) and microwave at 150° C. for 15 min. Cool to room temperature then dilute with saturated aq. sodium bicarbonate and extract 6 times with ethyl acetate. Dry (sodium sulfate), filter, concentrate and purify (silica gel chromatography, eluting with 6:94 methanol (with 2 M ammonia):DCM), to give a yellow oil. Dissolve the oil in methanol and add ammonium chloride (1 equivalent) then sonicate the mixture for 10 min. Evaporate the solution to give the title compound as a yellow solid (0.191 g, 75%). MS (ES): m/z=409 [M+H]+.

EXAMPLE 18M

N-{4-[4-(1-Ethyl-3-methyl-1H-pyrazol-4-ylmethyl)-3,4,5,6-tetrahydro-2H-[1,2']bipyrazinyl-3'-yl]-benzyl}-acetamide hydrochloride

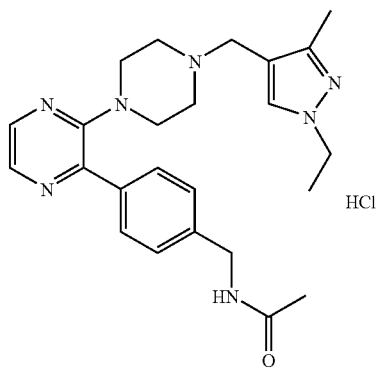

Dissolve 3'-chloro-4-(1-ethyl-3-methyl-1H-pyrazol-4-ylmethyl)-3,4,5,6-tetrahydro-2H-[1,2']bipyrazinyl (0.204 g, 0.636 mmol) in tetrahydrofuran (1.75 mL) and water (0.9 mL). Add potassium carbonate (0.193 g, 1.40 mmol) then 4-acetamidomethylbenzeneboronic acid (0.172 g, 0.890 mmol) and degas with nitrogen for 15 min. Add tri-n-butylphosphine tetrafluoroborate (7.4 mg, 0.0254 mmol) and tris(dibenzylideneacetone)dipalladium(0) (12 mg, 0.0127 mmol) and reflux for 20 hr. Cool to room temperature then dilute with saturated aq. sodium bicarbonate and extract 3 times with ethyl acetate. Dry (sodium sulfate), filter, concentrate and purify (silica gel chromatography, eluting with 4.5:95.5 methanol (with 2 M ammonia):DCM), to give a yellow solid. Dissolve the solid in methanol and add ammonium chloride (1 equivalent) then sonicate the mixture for 10 min. Evaporate the solution to give the title compound as a yellow solid (0.172 g, 51%). MS (ES): m/z [M+H]=434

Examples 19-21 are prepared essentially as described for Example 18 using the corresponding boronic acid and 3'-chloro-4-(1-ethyl-3-methyl-1H-pyrazol-4-ylmethyl)-3,4,5,6-tetrahydro-2H-[1,2']bipyrazinyl.

| Ex | Structure | Compound | Yield (%) | MS (ES) [M + H] |
|---|---|---|---|---|
| 19m | 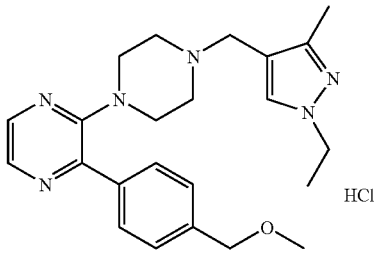 | 4-(1-ethyl-3-methyl-1H-pyrazol-4-ylmethyl)-3'-(4-methoxymethyl-phenyl)-3,4,5,6-tetrahydro-2H-[1,2']bipyrazinyl hydrochloride | 23 | 407 |
| 20m | 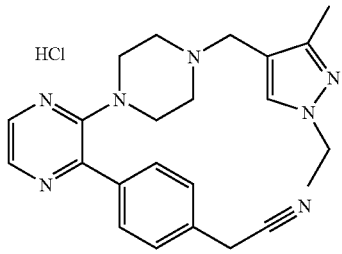 | {4-[4-(1-ethyl-3-methyl-1H-pyrazol-4-ylmethyl)-3,4,5,6-tetrahydro-2H-[1,2']bipyrazinyl-3'-yl]-phenyl}-acetonitrile hydrochloride | 40 | 402 |
| 21m | 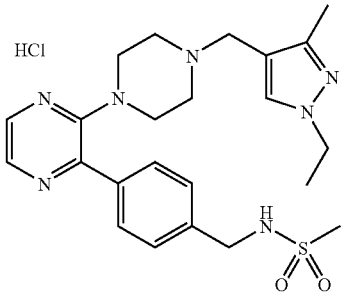 | N-{4-[4-(1-ethyl-3-methyl-1H-pyrazol-4-ylmethyl)-3,4,5,6-tetrahydro-2H-[1,2']bipyrazinyl-3'-yl]-benzyl}-methanesulfonamide hydrochloride | 78 | 470 |

EXAMPLE 22M

{4-[4-(1-Ethyl-5-methyl-1H-pyrazol-4-ylmethyl)-3,4,5,6-tetrahydro-2H-[1,2']bipyrazinyl-3'-yl]-phenyl}-methanol hydrochloride

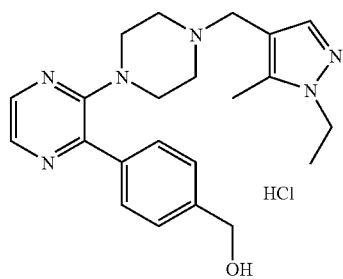

Combine 3'-chloro-4-(1-ethyl-5-methyl-1H-pyrazol-4-ylmethyl)-3,4,5,6-tetrahydro-2H-[1,2']bipyrazinyl (0.300 g, 0.935 mmol), potassium carbonate (0.310 g, 2.24 mmol), 4-(hydroxymethyl)phenylboronic acid (0.170 g, 1.12 mmol), and tetrakis(triphenylphosphine)palladium(0) (0.011 g, 0.009 mmol) in N,N-dimethylacetamide (1.9 mL). Add water (940 μL), and reflux reaction for 6 hr.

Continue to heat at 70° C. for 18 hr. Add 4-(hydroxymethyl)phenylboronic acid (0.085 g, 0.56 mmol) and tetrakis(triphenylphosphine)palladium(0) (0.011 g, 0.009 mmol) and heat to 115° C. for 6 hr. Continue to stir at ambient temperature over 72 hr. Add DCM and wash with water. Extract water layer three times with DCM. Dry combined organics (magnesium sulfate) and purify (silica gel chromatography, eluting with 50:50 to 100:0 ethyl acetate:hexanes then 10:90 to 20:80 methanol:ethyl acetate), to give the free base of the title compound (306 mg, 83%). Dissolve the free base (0.262 g, 0.667 mmol) in acetonitrile (801 μL) and add aq. 1 N HCl solution (801 μL, 0.801 mmol). Shake for 15 min. at ambient

EXAMPLE 23M

N-{4-[4-(1-Ethyl-5-methyl-1H-pyrazol-4-ylmethyl)-3,4,5,6-tetrahydro-2H-[1,2']bipyrazinyl-3'-yl]-benzyl}-acetamide hydrochloride

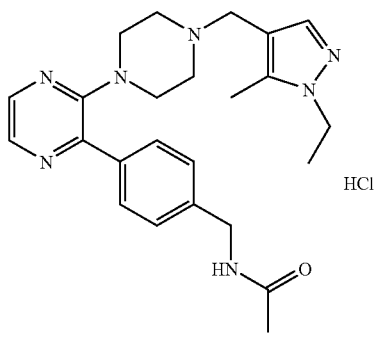

Combine 3'-chloro-4-(1-ethyl-5-methyl-1H-pyrazol-4-ylmethyl)-3,4,5,6-tetrahydro-2H-[1,2']bipyrazinyl (0.300 g, 0.935 mmol), potassium carbonate (0.310 g, 2.24 mmol), (4-acetamidomethylphenyl)boronic acid (0.216 g, 1.12 mmol), and tetrakis(triphenylphosphine)palladium(0) (0.011 g, 0.009 mmol) in N,N-dimethylacetamide (1.9 mL). Add water (940 µL), and reflux reaction for 6 hr. Add DCM and wash with water. Extract water layer three times with DCM. Dry combined organics (magnesium sulfate) and purify (silica gel chromatography, eluting with 50:50 to 100:0 ethyl acetate:hexanes then 10:90 to 20:80 methanol:ethyl acetate), to give the free base of the title compound (384 mg, 95%). Dissolve the free base (0.381 g, 0.880 mmol) in acetonitrile (1.06 mL) and add aq. 1 N HCl solution (1.06 mL, 1.06 mmol). Shake for 15 min. at ambient temperature. Freeze dry to give the title compound (416 mg, 100%). MS (ES): m/z=434 [M+H]+.

EXAMPLE 24M 4-(1-Ethyl-5-methyl-1H-pyrazol-4-ylmethyl)-3'-(4-methoxymethyl-phenyl)-3,4,5,6-tetrahydro-2H-[1,2']bipyrazinyl hydrochloride

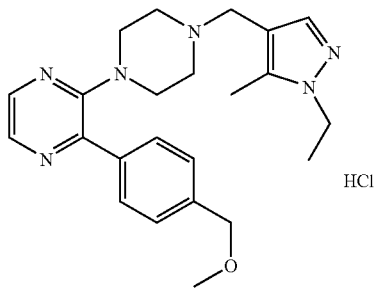

Combine 3'-chloro-4-(1-ethyl-5-methyl-1H-pyrazol-4-ylmethyl)-3,4,5,6-tetrahydro-2H-[1,2']bipyrazinyl (0.300 g, 0.935 mmol), potassium carbonate (0.310 g, 2.24 mmol), 4-methoxymethylphenylboronic acid (0.186 g, 1.12 mmol), and tetrakis(triphenylphosphine)palladium(0) (0.011 g, 0.009 mmol) in N,N-dimethylacetamide (1.9 mL). Add water (940 µL), and reflux reaction for 6 hr. Add DCM and wash with water. Extract water layer three times with DCM. Dry combined organics (magnesium sulfate) and purify (silica gel chromatography, eluting with 50:50 to 100:0 ethyl acetate:hexanes then 10:90 to 20:80 methanol:ethyl acetate), to give the free base of the title compound (256 mg, 67%). Dissolve the free base (0.254 g, 0.624 mmol) in acetonitrile (748 µL) and add aq. 1 N HCl solution (748 µL, 0.748 mmol). Shake for 15 min. at ambient temperature. Freeze dry to give the title compound (273 mg, 99%). MS (ES): m/z=407 [M+H]+.

EXAMPLE 25M

{4-[4-(1-Ethyl-5-methyl-1H-pyrazol-4-ylmethyl)-3,4,5,6-tetrahydro-2H-[1,2']bipyrazinyl-3'-yl]-phenyl}-acetonitrile hydrochloride

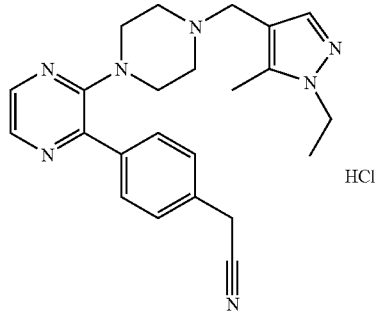

Combine 3'-chloro-4-(1-ethyl-5-methyl-1H-pyrazol-4-ylmethyl)-3,4,5,6-tetrahydro-2H-[1,2']bipyrazinyl (0.300 g, 0.935 mmol), potassium carbonate (0.310 g, 2.24 mmol), (4-Cyanomethylphenyl)boronic acid (0.180 g, 1.12 mmol), and tetrakis(triphenylphosphine)palladium(0) (0.011 g, 0.009 mmol) in N,N-dimethylacetamide (1.9 mL). Add water (940 µL), and reflux reaction for 6 hr. Continue to heat at 70° C. for 18 hr. Add DCM and wash with water. Extract water layer three times with DCM. Dry combined organics (magnesium sulfate) and purify (silica gel chromatography, eluting with 50:50 to 100:0 ethyl acetate:hexanes then 10:90 to 20:80 methanol:ethyl acetate), to give the free base of the title compound (196 mg, 52%). Dissolve the free base (0.194 g, 0.482 mmol) in acetonitrile (579 µL) and add aq. 1 N HCl solution (579 µL, 0.579 mmol). Shake for 15 min. at ambient

EXAMPLE 26M

N-{4-[4-(1-Ethyl-5-methyl-1H-pyrazol-4-ylmethyl)-3,4,5,6-tetrahydro-2H-[1,2']bipyrazinyl-3'-yl]-benzyl}-methanesulfonamide hydrochloride

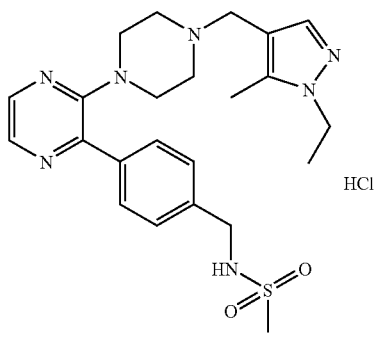

Combine 3'-chloro-4-(1-ethyl-5-methyl-1H-pyrazol-4-ylmethyl)-3,4,5,6-tetrahydro-2H-[1,2']bipyrazinyl (0.300 g, 0.935 mmol), potassium carbonate (0.310 g, 2.24 mmol), (4-methanesulfonylaminomethylphenyl)boronic acid (0.257 g, 1.12 mmol), and tetrakis(triphenylphosphine)palladium(0) (0.011 g, 0.009 mmol) in N,N-dimethylacetamide (1.9 mL). Add water (940 µL), and reflux reaction for 6 hr. Continue to heat at 70° C. for 18 hr. Add (4-methanesulfonylaminomethylphenyl) boronic acid (0.129 g, 0.56 mmol) and tetrakis (triphenylphosphine)palladium(0) (0.011 g, 0.009 mmol) and heat to 115° C. for 6 hr. Continue to stir at ambient temperature over 72 hr. Add DCM and wash with water. Extract water layer three times with DCM. Dry combined organics (magnesium sulfate) and purify (silica gel chromatography, eluting with 50:50 to 100:0 ethyl acetate:hexanes then 10:90 to 20:80 methanol:ethyl acetate), to give the free base of the title compound (371 mg, 85%). Dissolve the free base (0.367 g, 0.781 mmol) in acetonitrile (938 µL) and add aq. 1 N HCl solution (938 µL, 0.938 mmol). Shake for 15 min. at ambient temperature. Freeze dry to give the title compound (397 mg, 100%). MS (ES): m/z=470 [M+H]+.

EXAMPLE 27M

{4-[4-(5-Methyl-1-phenyl-1H-pyrazol-4-ylmethyl)-3,4,5,6-tetrahydro-2H-[1,2']bipyrazinyl-3'-yl]-phenyl}-methanol hydrochloride

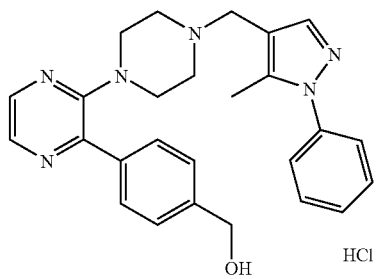

Combine 3'-chloro-4-(5-methyl-1-phenyl-1H-pyrazol-4-ylmethyl)-3,4,5,6-tetrahydro-2H-[1,2']bipyrazinyl (0.290 g, 0.786 mmol), potassium carbonate (0.261 g, 1.89 mmol), 4-(hydroxymethyl)phenylboronic acid (0.143 g, 0.943 mmol), and tetrakis(triphenylphosphine)palladium(0) (0.009 g, 0.008 mmol) in N,N-dimethylacetamide (1.6 mL). Add water (790 µL), and reflux reaction for 18 hr. Add 4-(hydroxymethyl)phenylboronic acid (0.072 g, 0.471 mmol) and tetrakis(triphenyl-phosphine)palladium(0) (0.009 g, 0.008 mmol) and heat to 110° C. for 3.5 hr. Add DCM and wash with water. Extract water layer three times with DCM. Dry combined organics (magnesium sulfate) and purify (silica gel chromatography, eluting with 50:50 to 100:0 ethyl acetate:hexanes then 10:90 methanol:ethyl acetate), to give the free base of the title compound (198 mg, 57%). Dissolve the free base (0.195 g, 0.443 mmol) in acetonitrile (531 µL) and add aq. 1 N HCl solution (531 µL, 0.531 mmol). Shake for 15 min. at ambient temperature. Freeze dry to give the title compound (208 mg, 98%). MS (ES): m/z=441 [M+H]+.

EXAMPLE 28M

N-{4-[4-(5-Methyl-1-phenyl-1H-pyrazol-4-ylmethyl)-3,4,5,6-tetrahydro-2H-[1,2']bipyrazinyl-3'-yl]-benzyl}-acetamide hydrochloride

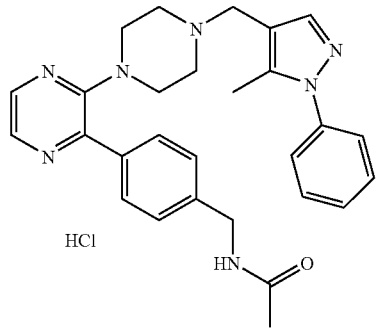

Combine 3'-chloro-4-(5-methyl-1-phenyl-1H-pyrazol-4-ylmethyl)-3,4,5,6-tetrahydro-2H-[1,2']bipyrazinyl (0.290 g, 0.786 mmol), potassium carbonate (0.261 g, 1.89 mmol), (4-acetamidomethylphenyl)boronic acid (0.182 g, 0.943 mmol), and tetrakis(triphenylphosphine)palladium(0) (0.009 g, 0.008 mmol) in N,N-dimethylacetamide (1.6 mL). Add water (790 µL), and reflux reaction for 18 hr. Add DCM and wash with water. Extract water layer three times with DCM. Dry combined organics (magnesium sulfate) and purify (silica gel chromatography, eluting with 50:50 to 100:0 ethyl acetate:hexanes then 10:90 to 20:80 methanol:ethyl acetate), to give the free base of the title compound (365 mg, 96%). Dissolve the free base (0.363 g, 0.754 mmol) in acetonitrile (904 µL) and add aq. 1 N HCl solution (904 µL, 0.904 mmol).

Shake for 15 min. at ambient temperature. Freeze dry to give the title compound (392 mg, 100%). MS (ES): m/z=482 [M+H]+.

EXAMPLE 29M 4-(1-Methyl-1H-pyrazol-4-ylmethyl)-3'-(4-methoxymethyl-phenyl)-3,4,5,6-tetrahydro-2H-[1,2']bipyrazinyl (E)-but-2-enedioic acid

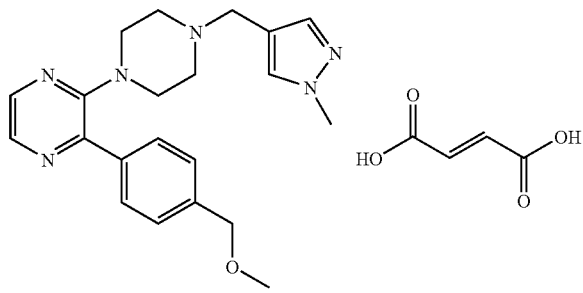

Dissolve 3'-chloro-4-(1-methyl-1H-pyrazol-4-ylmethyl)-3,4,5,6-tetrahydro-2H-[1,2']bipyrazinyl (146 mg, 0.50 mmol) in N,N-dimethylacetamide (degassed with nitrogen for 0.5 hr.) (2 mL). Add potassium carbonate (166 mg, 1.20 mmol) then 4-methoxymethylbenzeneboronic acid (100 mg, 0.60 mmol) and degas with nitrogen for 15 min. Add deoxygenated water (1 mL) and tetrakis(triphenylphosphine)palladium(0) (0.003 g, 0.003 mmol) and degas with nitrogen for 10 min. Heat at 115° C. for 20 hr. Cool to room temperature, add water (5 mL) and extract with DCM (4×5 mL). Pass the combined DCM extracts through an IST Phase Separator Frit®. Concentrate the filtrate and purify by SCX-2® chromatography washing with methanol then eluting with 2 M ammonia in methanol. Purify (silica gel chromatography, eluting with 0:100 to 10:90 methanol:DCM), to give the free base as a yellow oil (183 mg, 94% yield). Dissolve the oil in methanol, add fumaric acid (1 eq), concentrate and wash the solid with diethyl ether, and then lyophilize, to give the title compound as beige powder (50 mg, 20%). MS (ES): m/z=379 [M+H]+.

EXAMPLE 30M 4-(1,5-Dimethyl-1H-pyrazol-4-ylmethyl)-3'-[4-(thiophen-2-ylmethoxymethyl)-phenyl]-3,4,5,6-tetrahydro-2H-[1,2']bipyrazinyl hydrochloride

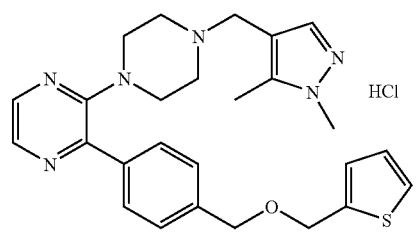

Dissolve 3'-chloro-4-(1,5-dimethyl-1H-pyrazol-4-ylmethyl)-3,4,5,6-tetrahydro-2H-[1,2']bipyrazinyl (307 mg, 1.0 mmol) in N,N-dimethylacetamide (5 mL). Add potassium carbonate (332 mg, 2.40 mmol) then 4-[(-2-thienylmethoxy) methyl]benzene boronic acid (298 mg, 1.20 mmol), tetrakis (triphenylphosphine)palladium(0) (0.012 g, 0.01 mmol). Add water (1 mL) and degas with nitrogen for 30 min., then heat at 110° C. for 18 hr. Cool to room temperature, add water (5 mL) and extract with DCM (3×5 mL). Pass the combined DCM extracts through an IST Phase Separator Frit®. Concentrate the filtrate and purify (silica gel chromatography, eluting with 0:100 to 10:90 methanol: DCM), to give the free base as a yellow oil. Dissolve the oil in acetonitrile and convert to the hydrochloride salt by adding 2 M aq. HCl solution. Add water and lyophilize to give the title compound (258 mg, 50%). MS (ES): m/z=475 [M+H]+.

EXAMPLE 31M

N-{4-[4-(1,3-Dimethyl-1H-pyrazol-4-ylmethyl)-3,4,5,6-tetrahydro-2H-[1,2']bipyrazinyl-3'-yl]-benzyl}-methanesulfonamide hydrochloride

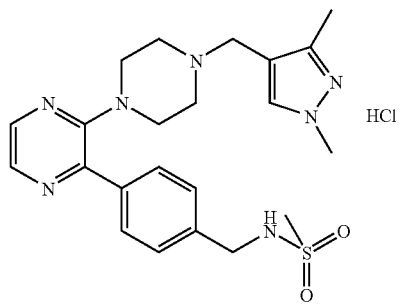

Stir 3'-chloro-4-(1,3-dimethyl-1H-pyrazol-4-ylmethyl)-3,4,5,6-tetrahydro-2H-[1,2']bipyrazinyl (307 mg, 1.00 mmol), potassium carbonate (332 mg, 2.40 mmol), (4-methanesulfonylaminophenyl) boronic acid (275 mg, 1.20 mmol) and tetrakis(triphenylphosphine)palladium(0) (0.058 g, 0.05 mmol) in N,N-dimethylacetamide (2 mL). Add water (1 mL) and heat at 120° C. for 17 hr. Cool to room temperature, add water (10 mL) and extract with DCM (3×10 mL). Pass the combined DCM extracts through an IST Phase Separator Frit®. Concentrate the filtrate and purify by SCX-2® chromatography washing with methanol then eluting with 3 M ammonia in methanol.

Further purify (silica gel chromatography, eluting with 1:99 to 10:90 methanol: DCM), to give the free base as a clear oil. Dissolve the oil in acetonitrile and convert to the hydrochloride salt by adding 2 M aq HCl solution. Add water and lyophilize to give the title compound as a brown/yellow powder (378 mg, 77%). MS (ES): m/z=456 [M+H]⁺.

EXAMPLE 32M

N-{4-[4-(1,5-Dimethyl-1H-pyrazol-4-ylmethyl)-3,4,5,6-tetrahydro-2H-[1,2']bipyrazinyl-3'-yl]-benzyl}-acetamide hydrochloride

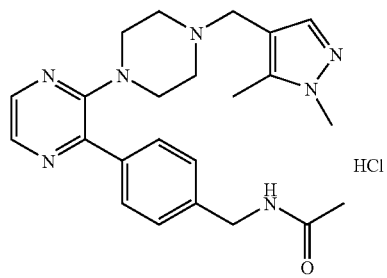

Stir 3'-chloro-4-(1,5-dimethyl-1H-pyrazol-4-ylmethyl)-3,4,5,6-tetrahydro-2H-[1,2']bipyrazinyl (153 mg, 0.50 mmol), potassium carbonate (166 mg, 1.20 mmol), (4-acetamidomethylbenzene) boronic acid (116 mg, 0.60 mmol) and tetrakis(triphenylphosphine)palladium(0) (0.006 g, 0.005 mmol) in N,N-dimethylacetamide (2 mL). Add water (1 mL) and heat at 120° C. for 17 hr. Cool to room temperature, add water (5 mL) and extract with DCM (3×5 mL). Pass the combined DCM extracts through an IST Phase Separator Frit®. Concentrate the filtrate and purify by SCX-2® chromatography washing with methanol then eluting with 2.5 M ammonia in methanol. Further purify (silica gel chromatography, eluting with 5:95 to 20:80 methanol:DCM), to give the free base as a clear oil. Dissolve the oil in acetonitrile and convert to the hydrochloride salt by adding 2 M aq. HCl solution. Add water and lyophilize to give N-{4-[4-(1,5-dimethyl-1H-pyrazol-4-ylmethyl)-3,4,5,6-tetrahydro-2H-[1,2']bipyrazinyl-3'-yl]-benzyl}-acetamide hydrochloride as a light brown powder (73 mg, 16%). MS (ES): m/z=420 [M+H]⁺.

EXAMPLE 33M

3-{4-[4-(1,5-Dimethyl-1H-pyrazol-4-ylmethyl)-3,4,5,6-tetrahydro-2H-[1,2']bipyrazinyl-3'-yl]-phenyl}-propan-1-ol hydrochloride

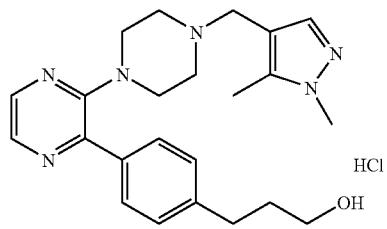

Stir 3'-chloro-4-(1,5-dimethyl-1H-pyrazol-4-ylmethyl)-3,4,5,6-tetrahydro-2H-[1,2']bipyrazinyl (153 mg, 0.50 mmol), potassium carbonate (166 mg, 1.20 mmol), [4-(3-hydroxypropyl)phenyl]boronic acid (108 mg, 0.60 mmol) and tetrakis(triphenyl-phosphine)palladium(0) (0.006 g, 0.005 mmol) in N,N-dimethylacetamide (2 mL). Add water (1 mL) and heat at 120° C. for 20 hr. Cool to room temperature, add water (10 mL) and extract with DCM (3×10 mL). Pass the combined DCM extracts through an IST Phase Separator Frit®. Concentrate the filtrate and purify by SCX-2® chromatography washing with methanol then eluting with 2 M ammonia in methanol. Further purify by high pH reverse phase HPLC, and concentrate to give the free base as a solid. Dissolve the oil in acetonitrile and convert to the hydrochloride salt by adding 2 M aq HCl solution. Add water and lyophilize to give the title compound as a yellow powder (147 mg, 66%). MS (ES): m/z=407 [M+H]⁺.

EXAMPLE 34M 4-(1,5-Dimethyl-1H-pyrazol-4-ylmethyl)-3'-(4-oxazol-2-yl-phenyl)-3,4,5,6-tetrahydro-2H-[1,2']bipyrazinyl hydrochloride

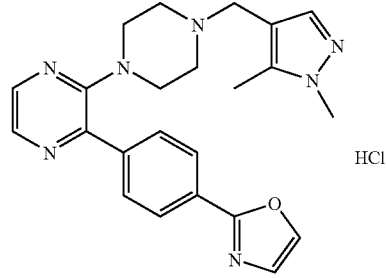

Stir 3'-chloro-4-(1,5-dimethyl-1H-pyrazol-4-ylmethyl)-3,4,5,6-tetrahydro-2H-[1,2']bipyrazinyl (153 mg, 0.50 mmol), potassium carbonate (166 mg, 1.20 mmol), 2-(4-boronic acid-phenyl)-oxazole (113 mg, 0.60 mmol) and tetrakis(triphenylphosphine)palladium(0) (0.006 g, 0.005 mmol) in N,N-dimethylacetamide (1 mL). Add water (0.5 mL), degas for 5 min., and then heat at 120° C. for 17 hr. Cool to room temperature, add water (5 mL) and extract with DCM (3×5 mL). Pass the combined DCM extracts through an IST Phase Separator Frit®.

Concentrate the filtrate and purify by SCX-2® chromatography washing with methanol then eluting with 2 M ammonia in methanol. Further purify by low pH reverse phase HPLC. Form the free base by passing through an SCX-2® ion exchange cartridge washing with methanol then eluting with 2 M ammonia in methanol and concentrate. Dissolve the white solid in acetonitrile and convert to the hydrochloride

EXAMPLE 35M 4-(1,5-Dimethyl-1H-pyrazol-4-ylmethyl)-3'-[4-(2-methoxy-ethyl)-phenyl]-3,4,5,6-tetrahydro-2H-[1,2']bipyrazinyl hydrochloride

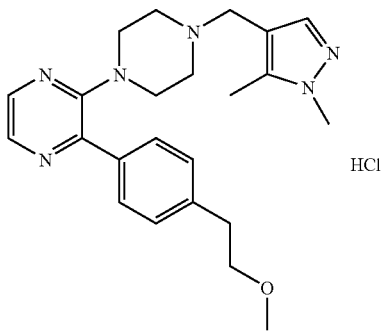

Dissolve 3'-chloro-4-(1,5-dimethyl-1H-pyrazol-4-ylmethyl)-3,4,5,6-tetrahydro-2H-[1,2']bipyrazinyl (267 mg, 0.87 mmol) in N,N-dimethylacetamide (4 mL). Add potassium carbonate (289 mg, 2.09 mmol), 2-[4-(2-methoxy-ethyl)-phenyl]-4,4,5,5-tetramethyl-[1,3,2]dioxaborolane (274 mg, 1.05 mmol), tetrakis(triphenylphosphine)palladium(0) (0.0050 g, 0.0044 mmol), then water (2 mL) and degas with nitrogen for 10 min. Heat at 120° C. for 20 hr., then purify by SCX-2® chromatography washing with methanol. Elute with 2 M ammonia in methanol and concentrate. Further purify high pH reverse phase HPLC, to give the free base as an oil. Dissolve the oil in acetonitrile and convert to the hydrochloride salt by adding 2 M aq HCl solution. Add water and lyophilize to give the title compound as a yellow powder (285 mg, 74%). MS (ES): m/z=407 [M+H]$^+$.

EXAMPLE 36M

N-(2-{4-[4-(1,5-Dimethyl-1H-pyrazol-4-ylmethyl)-3,4,5,6-tetrahydro-2H-[1,2']bipyrazinyl-3'-yl]-phenyl}-ethyl)-methanesulfonamide hydrochloride

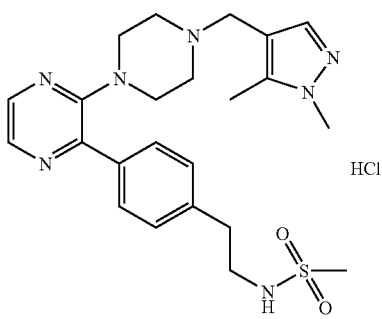

Dissolve 3'-chloro-4-(1,5-dimethyl-1H-pyrazol-4-ylmethyl)-3,4,5,6-tetrahydro-2H-[1,2']bipyrazinyl (307 mg, 1.0 mmol) in N,N-dimethylacetamide (4 mL). Add potassium carbonate (331 mg, 2.4 mmol), 4-sulfonylaminoethyl benzene boronic acid (292 mg, 1.2 mmol), tetrakis(triphenylphosphine)palladium(0) (0.0050 g, 0.0058 mmol), then water (2 mL) and degas with nitrogen for 10 min. Heat at 120° C. for 20 hr., then purify by SCX-2® chromatography washing with methanol. Elute with 2 M ammonia in methanol and concentrate. Recrystallize from DMSO:methanol (1:1), filter and wash with diethyl ether, to give a whitish powder. Dissolve the powder in acetonitrile and convert to the hydrochloride salt by adding 2 M aq HCl solution. Add water and lyophilize to give the title compound as a yellow powder (365 mg, 71%). MS (ES): m/z=470 [M+H]$^+$.

EXAMPLE 37M

2-{4-[4-(1,5-Dimethyl-1H-pyrazol-4-ylmethyl)-3,4,5,6-tetrahydro-2H-[1,2']bipyrazinyl-3'-yl]-phenyl}-2-methyl-propionitrile hydrochloride

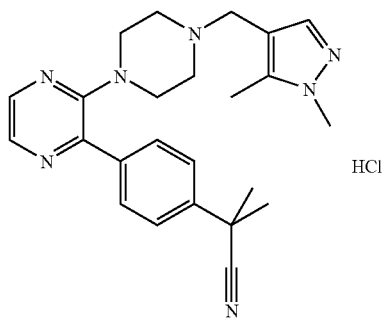

Dissolve 3'-chloro-4-(1,5-dimethyl-1H-pyrazol-4-ylmethyl)-3,4,5,6-tetrahydro-2H-[1,2']bipyrazinyl (307 mg, 1.0 mmol) in N,N-dimethylacetamide (4 mL). Add potassium carbonate (332 mg, 2.4 mmol), 2-methyl-2-[4-(4,4,5,5-tetramethyl-[1,3,2]dioxaborolan-2-yl)-phenyl]-propionitrile (300 mg, 1.2 mmol), tetrakis(triphenylphosphine)palladium (0) (0.0050 g, 0.0058 mmol), then water (2 mL) and degas with nitrogen for 10 min. Heat at 120° C. for 20 hr., then purify by SCX-2® chromatography washing with methanol. Elute with 2 M ammonia in methanol and concentrate. Purify by low pH reverse phase HPLC, then form the free base by passing through an SCX-2® ion exchange cartridge washing with methanol then eluting with 2 M ammonia in methanol and concentrate. Dissolve the free base in acetonitrile and convert to the hydrochloride salt by adding 2 M aq HCl

EXAMPLE 38M

2-{4-[4-(1,5-Dimethyl-1H-pyrazol-4-ylmethyl)-3,4,5,6-tetrahydro-2H-[1,2']bipyrazinyl-3'-yl]-phenyl}-acetamide hydrochloride

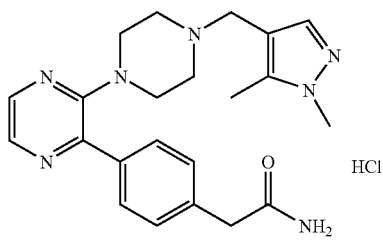

Dissolve 3'-chloro-4-(1,5-dimethyl-1H-pyrazol-4-ylmethyl)-3,4,5,6-tetrahydro-2H-[1,2']bipyrazinyl (307 mg, 1.0 mmol) in N,N-dimethylacetamide (4 mL). Add potassium carbonate (332 mg, 2.4 mmol), 2-[4-(4,4,5,5-tetramethyl-[1,3,2]dioxaborolan-2-yl)-phenyl]-acetamide (313 mg, 1.2 mmol), tetrakis(triphenylphosphine)palladium(0) (0.0050 g, 0.0058 mmol), then water (2 mL) and degas with nitrogen for 5 min. Heat at 120° C. for 20 hr. then purify by SCX-2® chromatography washing with methanol. Elute with 2 M ammonia in methanol and concentrate. Purify using silica gel chromatography (eluting with 5:95 to 20:80 methanol:DCM) to give an oil. Dissolve the free base in acetonitrile and convert to the hydrochloride salt by adding 2 M aq HCl solution. Add water and lyophilize to give the title compound as a light yellow powder (0.165 g, 37%). MS (ES): m/z=406 [M+H]$^+$.

EXAMPLE 39M

3'-(4-tert-Butoxymethyl-phenyl)-4-(1,5-dimethyl-1H-pyrazol-4-ylmethyl)-3,4,5,6-tetrahydro-2H-[1,2']bipyrazinyl hydrochloride

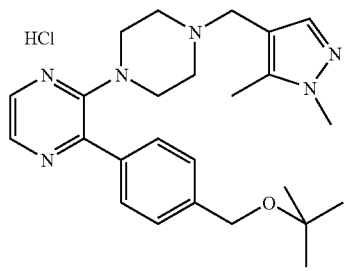

Dissolve 3'-chloro-4-(1,5-dimethyl-1H-pyrazol-4-ylmethyl)-3,4,5,6-tetrahydro-2H-[1,2']bipyrazinyl (307 mg, 1.0 mmol) in N,N-dimethylacetamide (5 mL). Add potassium carbonate (332 mg, 2.40 mmol) then 4-tert-butoxymethyl benzene boronic acid (250 mg, 1.20 mmol), tetrakis(triphenylphosphine)palladium(0) (0.012 g, 0.01 mmol), then water (1 mL) and degas with nitrogen for 30 min. Heat at 110° C. for 18 hr. Cool to room temperature, add water (5 mL) and extract with DCM (3×5 mL). Pass the combined DCM extracts through an IST Phase Separator Frit®. Concentrate the filtrate and purify (silica gel chromatography, eluting with 0:100 to 10:90 methanol:DCM), to give the free base as an oil. Dissolve the oil in acetonitrile and convert to the hydrochloride salt by adding 2 M aq HCl solution. Add water and lyophilize, then purify by SCX-2® chromatography washing with methanol then eluting with 2 M ammonia in methanol and concentrate. Further purify by low pH reverse phase HPLC. Form the free base by passing through an SCX-2® ion exchange cartridge washing with methanol then eluting with 2 M ammonia in methanol and concentrate. Dissolve the solid in acetonitrile and convert to the hydrochloride salt by adding 2 M aq HCl solution. Add water and lyophilize to give the title compound as yellow solid (274 mg, 58%). MS (ES): m/z=435 [M+H]$^+$

EXAMPLE 40M 4-(1,5-Dimethyl-1H-pyrazol-4-ylmethyl)-3'-(4-oxazol-5-yl-phenyl)-3,4,5,6-tetrahydro-2H-[1,2']bipyrazinyl hydrochloride

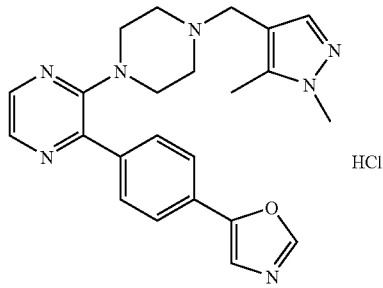

Stir 3'-chloro-4-(1,5-dimethyl-1H-pyrazol-4-ylmethyl)-3,4,5,6-tetrahydro-2H-[1,2']bipyrazinyl (153 mg, 0.50 mmol), potassium carbonate (166 mg, 1.20 mmol), 5-[4-(4,4,5,5-tetramethyl-[1,3,2]dioxaborolan-2-yl)-phenyl]-oxazole (163 mg, 0.60 mmol) and tetrakis(triphenylphosphine)palladium (0) (0.006 g, 0.005 mmol) in N,N-dimethylacetamide (2 mL). Add water (1 mL), degas for 5 min., and then heat at 120° C. for 17 hr. Cool to room temperature, add water (5 mL) and extract with DCM (3×5 mL). Pass the combined DCM extracts through an IST Phase Separator Frit®. Concentrate the filtrate and purify by SCX-2® chromatography washing with methanol then eluting with 2.5 M ammonia in methanol. Recrystallize from DMSO:methanol (50:50, 2.4 mL), filter and wash with diethyl ether. Collect precipitate from filtrate, then combine solids to give the free base 4-(1,5-dimethyl-1H-pyrazol-4-ylmethyl)-3'-(4-oxazol-5-yl-phenyl)-3,4,5,6-tetrahydro-2H-[1,2']bipyrazinyl as a yellow solid (147 mg, 71%). Dissolve the free base (82 mg, 0.20 mmol) in acetonitrile, add 2 M aq. HCl then water. Lyophilize to give the title compound as yellow powder (65 mg, 72%). MS (ES): m/z=416 [M+H].

Prepare compounds of Examples 41 and 42 essentially as described for Example 40, heating the reactions for between 1 and 3 days.

| EX | Structure | Compound | Yield (%) | MS (ES) [M + H] |
|---|---|---|---|---|
| 41m | 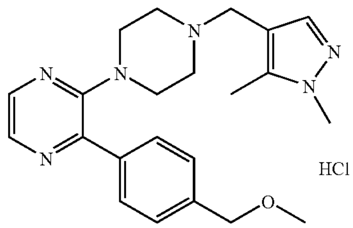 | 4-(1,5-dimethyl-1H-pyrazol-4-ylmethyl)-3'-(4-methoxymethyl-phenyl)-3,4,5,6-tetrahydro-2H-[1,2']bipyrazinyl hydrochloride | 98 | 393 |
| 42m | 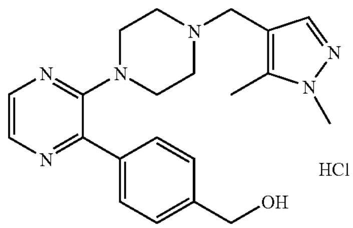 | 4-(1,5-dimethyl-1H-pyrazol-4-ylmethyl)-3'-(4-hydroxymethyl-phenyl)-3,4,5,6-tetrahydro-2H-[1,2']bipyrazinyl hydrochloride | 90 | 379 |

EXAMPLE 43M

{4-[4-(1,5-Dimethyl-1H-pyrazol-4-ylmethyl)-3,4,5,6-tetrahydro-2H-[1,2']bipyrazinyl-3'-yl]-phenyl}-acetonitrile hydrochloride

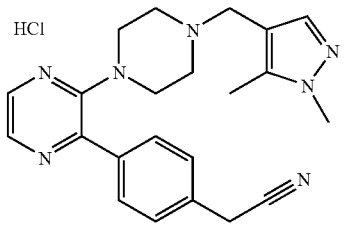

Stir 3'-chloro-4-(1,5-dimethyl-1H-pyrazol-4-ylmethyl)-3,4,5,6-tetrahydro-2H-[1,2']bipyrazinyl (921 mg, 3.00 mmol), potassium carbonate (996 mg, 7.20 mmol), (4-cyanomethyl benzene) boronic acid (579 mg, 3.60 mmol) and tetrakis(triphenylphosphine)palladium(0) (0.017 g, 0.015 mmol) in N,N-dimethylacetamide (6 mL). Add water (3 mL), degas for 5 min., and then heat at 120° C. for 24 hr. Purify by SCX-2® chromatography washing with methanol then eluting with 2 M ammonia in methanol. Further purify (silica gel chromatography, eluting with 0:100 to 20:80 methanol:DCM), to give the free base as a yellow solid (1.24 g, 100%). MS (ES): m/z=388 [M+H]$^+$. Prepare the HCl salt as in Example 41 to give the title compound (93%). MS (ES): m/z=388 [M+H].

EXAMPLE 44M

N-{4-[4-(1,5-Dimethyl-1H-pyrazol-4-ylmethyl)-3,4,5,6-tetrahydro-2H-[1,2']bipyrazinyl-3'-yl]-benzyl}-methanesulfonamide hydrochloride

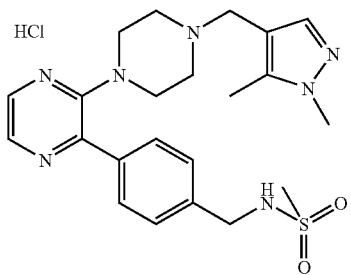

Stir 3'-chloro-4-(1,5-dimethyl-1H-pyrazol-4-ylmethyl)-3,4,5,6-tetrahydro-2H-[1,2']bipyrazinyl (921 mg, 3.00 mmol), potassium carbonate (996 mg, 7.20 mmol), (4-methanesulfonylamino methyl benzene) boronic acid (825 mg, 3.60 mmol) and tetrakis(triphenylphosphine)palladium(0) (0.017 g, 0.015 mmol) in N,N-dimethylacetamide (6 mL). Add water (3 mL) and heat at 120° C. for 17 hr. Cool to room temperature, add water (15 mL) and extract with DCM (3×20 mL). Pass the combined DCM extracts through an IST Phase Separator Frit®. Concentrate the filtrate and purify by SCX-2® chromatography washing with methanol then eluting with 3.5 M ammonia in methanol. Further purify (silica gel chromatography, eluting with 5:95 to 20:80 methanol: DCM), to give the free base as a yellow powder (1.349 g, 99%). MS (ES):

m/z=456 [M+H]⁺. Prepare the HCl salt as in Example 41 to give the title compound (98%). MS (ES): m/z=456 [M+H].

EXAMPLE 45M 4-(1,5-Dimethyl-1H-pyrazol-4-ylmethyl)-3'-[4-(1-methoxy-ethyl)-phenyl]-3,4,5,6-tetrahydro-2H-[1,2']bipyrazinyl hydrochloride isomer 1

EXAMPLE 46M 4-(1,5-Dimethyl-1H-pyrazol-4-ylmethyl)-3'-[4-(1-methoxy-ethyl)-phenyl]-3,4,5,6-tetrahydro-2H-[1,2']bipyrazinyl hydrochloride isomer 2

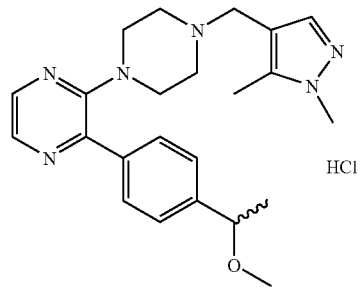

Stir 3'-chloro-4-(1,5-dimethyl-1H-pyrazol-4-ylmethyl)-3,4,5,6-tetrahydro-2H-[1,2']bipyrazinyl (390 mg, 1.27 mmol), racemic 2-[4-(1-methoxy-ethyl)-phenyl]-4,4,5,5-tetramethyl-[1,3,2]dioxaborolane (400 mg, 1.53 mmol), potassium carbonate (421 mg, 3.05 mmol) and tetrakis(triphenylphosphine)palladium(0) (7 mg, 6 µmol) and water (2 mL), in N,N-dimethylacetamide (4 mL) at room temperature under nitrogen. Degas for 10 min. then stir at 120° C. for 20 hr. Cool to room temperature, purify by SCX-2® chromatography washing with methanol then eluting with 2 M ammonia in methanol. Purify again by low pH reverse phase HPLC, and form the free base racemate by passing through an SCX-2® ion exchange cartridge washing with methanol then eluting with 2 M ammonia in methanol. Separate isomers by SFC, using AD-H column, eluting with a gradient of 10% ethanol (with 0.2% isopropylamine) at 3 mL/min, to give the free base of isomer 1 as an oil (176 mg, 34%), and the free base of isomer 2 as an oil (178 mg, 34%). Isomer 1-$[\alpha]_{20}^D$−31.8° (c=0.5 g/100 mL) in methanol. Retention time Isomer 1=10.44 min. Isomer 2-$[\alpha]_{20}^D$+37.3° (c=0.5 g/100 mL) in methanol. Retention time isomer 2=11.47 min. Dissolve each of the free bases in acetonitrile and convert to the hydrochloride salts by adding 2 M aq HCl solution. Add water and lyophilize each separately to give 4-(1,5-dimethyl-1H-pyrazol-4-ylmethyl)-3'-[4-(1-methoxy-ethyl)-phenyl]-3,4,5,6-tetrahydro-2H-[1,2']bipyrazinyl hydrochloride isomer 1 as an off white powder (219 mg, 102%). MS (ES): m/z=407 [M+H]⁺ and 4-(1,5-dimethyl-1H-pyrazol-4-ylmethyl)-3'-[4-(1-methoxy-ethyl)-phenyl]-3,4,5,6-tetrahydro-2H-[1,2']bipyrazinyl hydrochloride isomer 2 as an off white powder (194 mg, 114%). MS (ES): m/z=407 [M+H]⁺.

EXAMPLE 47M

N-{4-[4-(1,5-dimethyl-1H-pyrazol-4-ylmethyl)-3,4,5,6-tetrahydro-2H-[1,2']bipyrazinyl-3'-yl]-phenyl}-acetamide hydrochloride salt

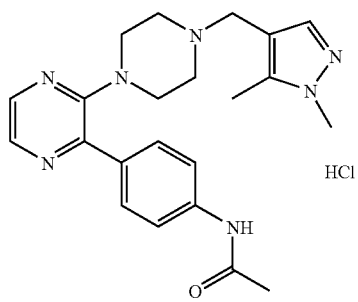

Dissolve 3'-chloro-4-(1,5-dimethyl-1H-pyrazol-4-ylmethyl)-3,4,5,6-tetrahydro-2H-[1,2']bipyrazinyl hydrochloride salt (0.5 g, 1.63 mmol) in N,N-dimethylacetamide (5 mL) and water (2 mL). Add 4-acetamidophenylboronic acid (1.2 eq., 0.35 g, 1.96 mmol). Add tetrakis(triphenylphosphine)palladium(0) (0.01 eq., 0.019 g, 0.016 mmol). Add potassium carbonate (3.6 eq., 0.54 g, 3.9 mmol). Heat at 90° C. for 10 hr. Purify by normal phase chromatography with 6% 7N ammonia-methanol/ethyl acetate to give N-{4-[4-(1,5-dimethyl-1H-pyrazol-4-ylmethyl)-3,4,5,6-tetrahydro-2H-[1,2']bipyrazinyl-3'-yl]-phenyl}-acetamide (0.25 g, 38%). MS (ES): m/z=406.2[M+H]. Dissolve this free base (0.25 g, 0.6 mmol) in acetonitrile (1 mL) and water (4 mL). Add aq. 1 N HCl (1 eq., 0.60 mmol, 0.60 mL). Freeze the solution to −78° C. in a dry-ice/acetone bath. Place the solution in the lyophilize for 48 hr. to give the title compound salt (0.26 g, 99%). MS (ES): m/z=406.2[M+H].

EXAMPLE 48M

{4-[4-(1,5-Dimethyl-1H-pyrazol-4-ylmethyl)-3,4,5,6-tetrahydro-2H-[1,2']bipyrazinyl-3'-yl]-phenyl}-carbamic acid methyl ester hydrochloride

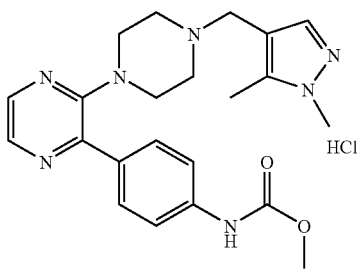

Stir together 3'-chloro-4-(1,5-dimethyl-1H-pyrazol-4-ylmethyl)-3,4,5,6-tetrahydro-2H-[1,2']bipyrazinyl (307 mg, 1.00 mmol), 4-(methoxycarbonylamino)benzene boronic acid (234 mg, 1.2 mmol), potassium carbonate (332 mg, 2.4 mmol) and tetrakis(triphenylphosphine)palladium(0) (0.006 g, 0.005 mmol) and water (2 mL), in N,N-dimethylacetamide (4 mL) at room temperature under nitrogen, then heat at 120° C. for 5 hr. Cool to room temperature, purify using SCX chromatography and further purify using silica gel chromatography eluting with (5:95 to 15:85 methanol:DCM). Dissolve in acetonitrile, and add 2 M aq. HCl and water then lyophilize to give the title compound as light yellow powder (253 mg, 55%). MS (ES): m/z=422 [M+H].

EXAMPLE 49M

Methyl 4-(3-(4-((1,3-dimethyl-1H-pyrazol-4-yl)methyl)piperazin-1-yl)pyrazin-2-yl)benzoate hydrochloride

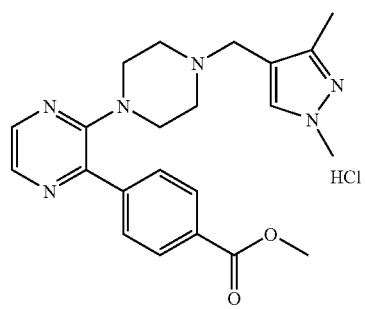

Charge a microwave tube with 3'-chloro-4-(1,3-dimethyl-1H-pyrazol-4-ylmethyl)-3,4,5,6-tetrahydro-2H-[1,2']bipyrazinyl (0.150 g, 0.490 mmoles), bis[(diphenylphosphanyl)methyl]-amine palladium (II) dichloride polymer bound (0.061 g, 0.049 mmoles, 0.1 eq), 4-(methoxycarbonyl)phenylboronic acid (0.176 g, 0.98 mmoles, 2 eq), sodium carbonate (0.192 g, 1.8 mmoles, 3.7 eq) and 3 ml of ethanol. Seal the reaction and heat under microwave conditions at 140° C. for 30 min. Cool down reaction and apply crude material to an SCX column prewashed with 10 ml methanol. Wash material with 10 ml of methanol, and release the product with 20 ml of a 2 N-ammonia/methanol solution. Purify the crude brown oil by reverse phase chromatography (28% isocratic acetonitrile/0.01 M ammonium bicarbonate in water, 80 ml/min., for 8 min., on a 30×75 mm, C18 Xterra column) to provide methyl 4-(3-(4-((1,3-dimethyl-1H-pyrazol-4-yl)methyl)piperazin-1-yl)pyrazin-2-yl)benzoate as a white solid (0.051 g, 26% yield, ES+(m/z) 407 [M+H]). Convert the purified material to the hydrochloride salt by stirring a solution of the free base (0.045 g, 0.294 mmoles) in acetonitrile (5 ml) at room temperature and add 1 N HCl in water (0.294 ml, 0.294 mmoles) to give a yellow solution. After 5 min., freeze the solution and lyophilize to give the title compound as a white solid (0.056 g, 100% yield, ES+(m/z) 407 [M+H]).

EXAMPLE 50M

4-[4-(1,5-Dimethyl-1H-pyrazol-4-ylmethyl)-3,4,5,6-tetrahydro-2H-[1,2']bipyrazinyl-3'-yl]-benzylamine dihydrochloride

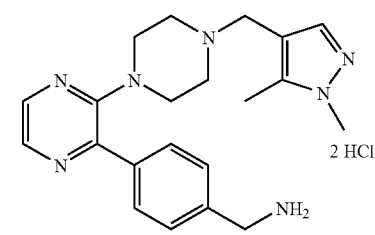

Stir 3'-chloro-4-(1,5-dimethyl-1H-pyrazol-4-ylmethyl)-3,4,5,6-tetrahydro-2H-[1,2']bipyrazinyl (921 mg, 3.00 mmol), potassium carbonate (996 mg, 7.20 mmol), 4-benzyl (carbamic acid tert-butyl ester) boronic acid (940 mg, 3.60 mmol) and tetrakis(triphenylphosphine)palladium(0) (0.017 g, 0.015 mmol) in N,N-dimethylacetamide (6 mL). Add water (3 mL), degas for 5 min., and then heat at 120° C. for 20 hr. Cool to room temperature, add water (10 mL) and extract with DCM (3×10 mL). Pass the combined DCM extracts through an IST Phase Separator Frit®. Concentrate the filtrate and purify by SCX-2® chromatography washing with methanol then eluting with 2 M ammonia in methanol. Further purify (silica gel chromatography, eluting with 5:95 to 15:85 methanol:DCM), to give N-{4-[4-(1,5-dimethyl-1H-pyrazol-4-ylmethyl)-3,4,5,6-tetrahydro-2H-[1,2']bipyrazinyl-3'-yl]-benzyl}-carbamic acid tert-butyl ester as an oil (1.3 g, 91%). MS (ES): m/z=478 [M+H]⁺.

Dissolve the above oil (316 mg, 0.66 mmol) in DCM (10 mL), then add trifluoroacetic acid (1 mL). Stir reaction for 3 hr. at room temperature and then remove solvents in vacuo. Form the free base by passing through an SCX-2® ion exchange cartridge washing with methanol then eluting with 3.5 M ammonia in methanol and concentrate to give 4-[4-(1,5-dimethyl-1H-pyrazol-4-ylmethyl)-3,4,5,6-tetrahydro-2H-[1,2']bipyrazinyl-3'-yl]-benzylamine as an off white solid (230 mg, 92%). MS (ES): m/z=378 [M+H]⁺. Generate the di-HCl salt as in Example 40 to give the title compound. (100%). MS (ES): m/z=378 [M+H]+.

EXAMPLE 51M

2-{4-[4-(1,5-Dimethyl-1H-pyrazol-4-ylmethyl)-3,4,5,6-tetrahydro-2H-[1,2']bipyrazinyl-3'-yl]-phenyl}-ethanol hydrochloride

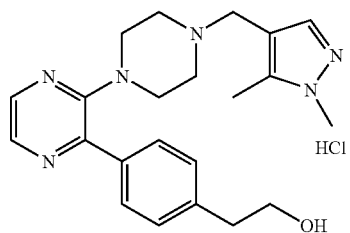

Stir together bis(dibenzylideneacetone)palladium(0) (69 mg, 0.12 mmol) and tricyclohexylphosphine (79 mg, 0.28 mmol) in N,N-dimethylacetamide (8 mL) at room temperature under nitrogen for 20 min. Add 2-(4-bromo-phenyl)-ethanol (0.56 mL, 4.00 mmol), 4,4,5,5,4',4',5',5'-octamethyl-[2,2']bi[[1,3,2]dioxaborolanyl] (1.04 g, 4.10 mmol) and potassium acetate (589 mg, 6.00 mmol) and stir at 80° C. for 16 hr. Cool reaction to room temperature, add 3'-chloro-4-(1,5-dimethyl-1H-pyrazol-4-ylmethyl)-3,4,5,6-tetrahydro-2H-[1,2']bipyrazinyl (614 mg, 2.00 mmol) and potassium carbonate (663 mg, 4.80 mmol), then water (4 mL) and stir at 120° C. for 20 hr. Cool to room temperature, add water (20 mL), then extract with DCM (3×10 mL) and pass through an IST Phase Separator Frit®. Concentrate and purify by SCX-2® chromatography washing with methanol then eluting with 2.5 M ammonia in methanol. Further purify (silica gel chromatography, eluting with 5:95 to 15:85 methanol:DCM), to give the free base as a brown solid. Dissolve the solid in acetonitrile and convert to the hydrochloride salt by adding 2 M aq HCl solution. Add water and lyophilize to give the title compound as a light yellow powder (601 mg, 70%). MS (ES): m/z=393 [M+H]+.

EXAMPLE 52M

N-(2-{4-[4-(1,5-dimethyl-1H-pyrazol-4-ylmethyl)-3,4,5,6-tetrahydro-2H-[1,2']bipyrazinyl-3'-yl]-phenyl}-2-oxo-ethyl)-acetamide hydrochloride

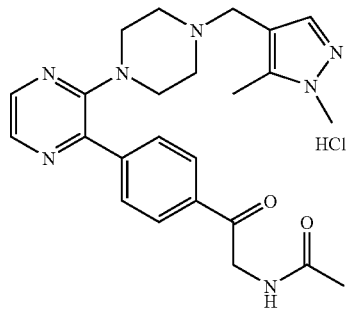

Prepare the title compound using methods similar to Example 51 using N-[2-(4-bromo-phenyl)-2-oxo-ethyl]-acetamide (0.286 g, 59% yield). MS (ES): m/z=448 [M+H]+.

EXAMPLE 53M

2-{4-[4-(1,5-dimethyl-1H-pyrazol-4-ylmethyl)-3,4,5,6-tetrahydro-2H-[1,2']bipyrazinyl-3'-yl]-phenyl}-N-methyl-acetamide hydrochloride

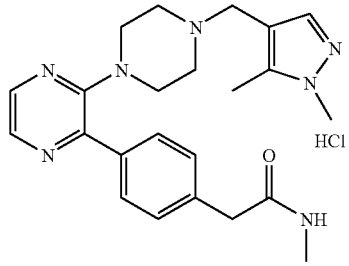

Stir together bis(dibenzylideneacetone)palladium(0) (29 mg, 0.105 mmol) and tricyclohexylphosphine (29 mg, 0.045 mmol) in N,N-dimethylacetamide (3 mL) at room temperature under nitrogen for 20 min. Add 2-(4-bromo-phenyl)-N-methyl-acetamide (342 mg, 1.50 mmol), 4,4,5,5,4',4',5',5'-octamethyl-[2,2']bi[[1,3,2]dioxaborolanyl] (394 mg, 1.55 mmol) and potassium acetate (221 mg, 2.25 mmol) and stir at 80° C. for 4 hr. Cool the reaction to room temperature, add 3'-chloro-4-(1,5-dimethyl-1H-pyrazol-4-ylmethyl)-3,4,5,6-tetrahydro-2H-[1,2']bipyrazinyl (307 mg, 1.00 mmol) and potassium carbonate (332 mg, 2.40 mmol), then water (1.5 mL) and stir at 120° C. for 18 hr. Cool to room temperature and purify by SCX-2® chromatography washing with methanol then eluting with 2 M ammonia in methanol. Further purify (silica gel chromatography, eluting with 5:95 to 20:80 methanol:DCM), to give the free base as an oil. Dissolve the oil in acetonitrile and convert to the hydrochloride salt by adding 2 M aq. HCl solution. Add water and lyophilize to give the title compound as a yellow powder (370 mg, 81%). MS (ES): m/z=420 [M+H]+.

EXAMPLE 54M

{4-[4-(1,5-Dimethyl-1H-pyrazol-4-ylmethyl)-3,4,5,6-tetrahydro-2H-[1,2']bipyrazinyl-3'-yl]-2-fluoro-phenyl}-methanol hydrochloride

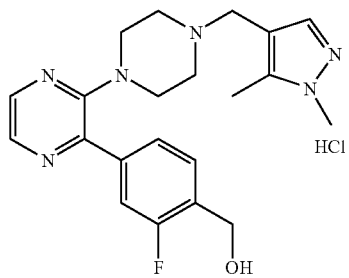

Stir together bis(dibenzylideneacetone)palladium(0) (35 mg, 0.06 mmol) and tricyclohexylphosphine (39 mg, 0.06 mmol) in N,N-dimethylacetamide (4 mL) at room temperature under nitrogen for 20 min. Add (4-bromo-2-fluoro-phenyl)-methanol (410 mg, 2.00 mmol), then 4,4,5,5,4',4',5',5'-octamethyl-[2,2']bi[[1,3,2]dioxaborolanyl] (521 mg, 2.05 mmol) and potassium acetate (294 mg, 3.00 mmol) and stir at 80° C. for 16 hr. Cool reaction to room temperature, add 3'-chloro-4-(1,5-dimethyl-1H-pyrazol-4-ylmethyl)-3,4,5,6-tetrahydro-2H-[1,2']bipyrazinyl (307 mg, 1.00 mmol), potassium carbonate (332 mg, 2.40 mmol) and water (2 mL), then stir at 120° C. for 4 hr. Cool to room temperature, add water (10 mL), then extract with DCM (3×20 mL) and pass through an IST Phase Separator Frit®. Concentrate and purify (silica gel chromatography, eluting with 5:95 methanol:DCM), to give the free base as a light brown powder. Dissolve the powder in acetonitrile and convert to the hydrochloride salt by adding 2 M aq HCl solution. Add water and lyophilize to give the title compound as a light yellow powder (367 mg, 84%). MS (ES): m/z=397 [M+H]+.

EXAMPLE 55M

2-{4-[4-(1,5-dimethyl-1H-pyrazol-4-ylmethyl)-3,4,5,6-tetrahydro-2H-[1,2']bipyrazinyl-3'-yl]-phenyl}-N,N-dimethyl-acetamide hydrochloride

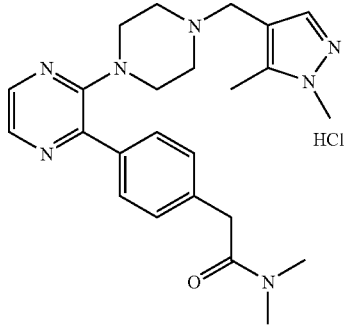

The title compound is prepared using methods similar to Example 54, using 2-(4-bromo-phenyl)-N,N-dimethyl-acetamide (0.404 g, 86% yield). MS (ES): m/z=434 [M+H]+.

EXAMPLE 56M

3-{4-[4-(1,5-Dimethyl-1H-pyrazol-4-ylmethyl)-3,4,5,6-tetrahydro-2H-[1,2']bipyrazinyl-3'-yl]-phenyl}-propionitrile hydrochloride

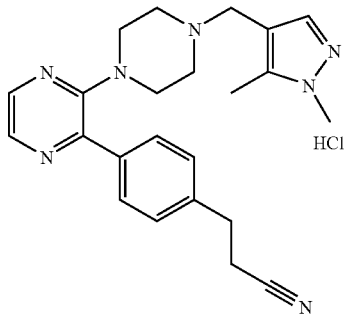

Stir together bis(dibenzylideneacetone)palladium(0) (69 mg, 0.12 mmol) and tricyclohexylphosphine (79 mg, 0.28 mmol) in N,N-dimethylacetamide (8 mL) at room temperature under nitrogen for 20 min. Add 3-(4-bromo-phenyl)-propionitrile (840 mg, 4.00 mmol), 4,4,5,5,4',4',5',5'-octamethyl-[2,2']bi[[1,3,2]dioxaborolanyl] (1.04 g, 4.10 mmol) and potassium acetate (589 mg, 6.00 mmol) and stir at 80° C. for 16 hr. Cool reaction to room temperature, add 3'-chloro-4-(1,5-dimethyl-1H-pyrazol-4-ylmethyl)-3,4,5,6-tetrahydro-2H-[1,2']bipyrazinyl (614 mg, 2.00 mmol) and potassium carbonate (663 mg, 4.80 mmol), then water (4 mL) and stir at 120° C. for 20 hr. Cool to room temperature, add water (20 mL), then extract with DCM (3×10 mL) and pass through an IST Phase Separator Frit®. Concentrate and purify by SCX-2® chromatography washing with methanol then eluting with 2.5 M ammonia in methanol. Further purify (silica gel chromatography, eluting with 5:95 to 15:85 methanol:DCM), concentrate and dry in the vacuum oven to give the free base as a yellow oil. Dissolve the oil in acetonitrile and convert to the hydrochloride salt by adding 2 M aq HCl solution. Add water and lyophilize. Form the free base by passing through an SCX-2® ion exchange cartridge washing with methanol then eluting with 3 M ammonia in methanol and concentrate. Further purify by high pH reverse phase HPLC, and concentrate and dry in vacuum oven to give the free base as a yellow oil. Dissolve the oil in acetonitrile and convert to the hydrochloride salt by adding 2 M aq HCl solution. Add water and lyophilize to give the title compound as a beige powder (425 mg, 50%). MS (ES): m/z=402 [M+H]+.

EXAMPLE 57M

Isomer 1-{4-[4-(1,5-Dimethyl-1H-pyrazol-4-ylmethyl)-3,4,5,6-tetrahydro-2H-[1,2']bipyrazinyl-3'-yl]-phenyl}-propionitrile hydrochloride

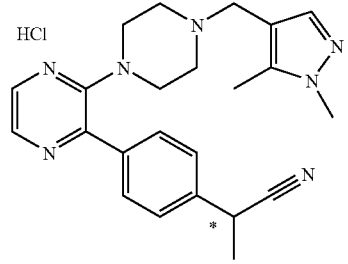

Stir together bis(dibenzylideneacetone)palladium(0) (35 mg, 0.06 mmol) and tricyclohexylphosphine (39 mg, 0.06 mmol) in N,N-dimethylacetamide (4 mL) at room temperature under nitrogen for 20 min. Add racemic 2-(4-bromo-phenyl)-propionitrile (420 mg, 2.00 mmol), then 4,4,5,5,4',4',5',5'-octamethyl-[2,2']bi[[1,3,2]dioxaborolanyl] (521 mg, 2.05 mmol) and potassium acetate (294 mg, 3.00 mmol) and stir at 80° C. for 16 hr. Cool reaction to room temperature, add 3'-chloro-4-(1,5-dimethyl-1H-pyrazol-4-ylmethyl)-3,4,5,6-tetrahydro-2H-[1,2']bipyrazinyl (307 mg, 1.00 mmol), potassium carbonate (332 mg, 2.40 mmol), tetrakis(triphenylphosphine)palladium(0) (0.0050 g, 0.0056 mmol) and water (2 mL), then stir at 120° C. for 8 hr. Cool to room temperature, purify by SCX-2® chromatography washing with methanol then eluting with 2 M ammonia in methanol. Further purify (silica gel chromatography, eluting with 0:100 to 20:80 methanol:DCM), to give the free base racemate 2-{4-[4-(1,5-dimethyl-1H-pyrazol-4-ylmethyl)-3,4,5,6-tetrahydro-2H-

[1,2']bipyrazinyl-3'-yl]-phenyl}-propionitrile as a powder (433 mg, 107%). MS (ES): m/z=402 [M+H]⁺.

Chiral chromatography: Separate isomers by SFC, using AD-H column, eluting with a gradient of 30% ethanol (with 0.2% isopropylamine) at 5 mL/min, to give Isomer 1 2-{4-[4-(1,5-dimethyl-1H-pyrazol-4-ylmethyl)-3,4,5,6-tetrahydro-2H-[1,2']bipyrazinyl-3'-yl]-phenyl}-propionitrile as a solid (171 mg, 39%). MS (ES): m/z=402 [M+H]⁺. Optical Rotation $[\alpha]_{20}^{D}$+6° (c=0.22 g/100 mL) in DCM. Retention time on chiral column=1.47 min. Prepare the HCl salt as in Example 40 to give Isomer 1 2-{4-[4-(1,5-dimethyl-1H-pyrazol-4-ylmethyl)-3,4,5,6-tetrahydro-2H-[1,2']bipyrazinyl-3'-yl]-phenyl}-propionitrile hydrochloride (97%). MS (ES): m/z=402 [M+H].

EXAMPLE 58M

Isomer 2 2-{4-[4-(1,5-Dimethyl-1H-pyrazol-4-ylmethyl)-3,4,5,6-tetrahydro-2H-[1,2']bipyrazinyl-3'-yl]-phenyl}-propionitrile hydrochloride

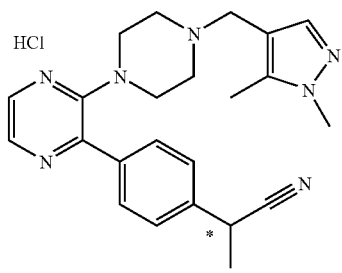

Prepare the free base racemate and conduct chiral chromatography as in Example 41 to get Isomer 2 2-{4-[4-(1,5-dimethyl-1H-pyrazol-4-ylmethyl)-3,4,5,6-tetrahydro-2H-[1,2']bipyrazinyl-3'-yl]-phenyl}-propionitrile as a solid (177 mg, 40%). MS (ES): m/z=393 [M+H]⁺. Optical Rotation $[\alpha]_{20}^{D}$-6° (c=0.22 g/100 mL) in DCM. Retention time on chiral column=1.79 min.

Prepare the HCl salt as in Example 41 to give 2-{4-[4-(1,5-dimethyl-1H-pyrazol-4-ylmethyl)-3,4,5,6-tetrahydro-2H-[1,2']bipyrazinyl-3'-yl]-phenyl}-propionitrile hydrochloride Isomer 2 (90%). MS (ES): m/z=402 [M+H].

EXAMPLE 59M

Racemic 1-{4-[4-(1,5-Dimethyl-1H-pyrazol-4-ylmethyl)-3,4,5,6-tetrahydro-2H-[1,2']bipyrazinyl-3'-yl]-phenyl}-ethanol hydrochloride

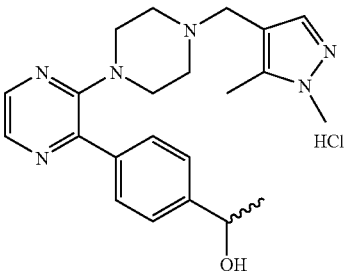

Dissolve 1-{4-[4-(1,5-dimethyl-1H-pyrazol-4-ylmethyl)-3,4,5,6-tetrahydro-2H-[1,2']bipyrazinyl-3'-yl]-phenyl}-ethanone (825 mg, 2.11 mmol) in methanol (30 mL), then add sodium borohydride (120 mg, 3.17 mmol). Stir the reaction at room temperature for 60 min. and then remove some solvent in vacuo. Quench reaction with saturated aq. sodium bicarbonate (10 mL), add water (50 mL) and extract with DCM (3×50 mL). Pass the combined DCM extracts through an IST Phase Separator Frit® and concentrate. Purify by silica gel chromatography, (eluting with 0:100 to 30:70 methanol:DCM), to give the racemate free base as an oil (393 mg, 47%). MS (ES): m/z=393 [M+H]⁺.

Prepare the HCl salt as in Example 40 to give racemic 1-{4-[4-(1,5-dimethyl-1H-pyrazol-4-ylmethyl)-3,4,5,6-tetrahydro-2H-[1,2']bipyrazinyl-3'-yl]-phenyl}-ethanol hydrochloride (100%). MS (ES): m/z=393 [M+H].

EXAMPLE 60M

Isomer 1 1-{4-[4-(1,5-dimethyl-1H-pyrazol-4-ylmethyl)-3,4,5,6-tetrahydro-2H-[1,2']bipyrazinyl-3'-yl]-phenyl}-ethanol hydrochloride

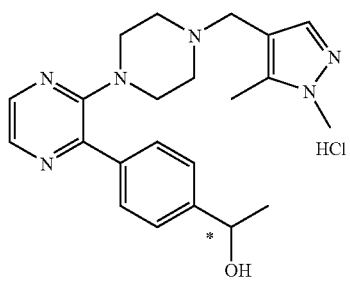

Separate isomers of racemic 1-{4-[4-(1,5-Dimethyl-1H-pyrazol-4-ylmethyl)-3,4,5,6-tetrahydro-2H-[1,2']bipyrazinyl-3'-yl]-phenyl}-ethanol by SFC, using OJ-H column, eluting with a gradient of 10% methanol (with 0.2% isopropylamine) at 5 mL/min., to give isomer 1 as a solid (181 mg, 22%). MS (ES): m/z=393 [M+H]⁺. Optical Rotation $[\alpha]_{20}^{D}$-0.214° (c=1.0 g/100 mL) in DCM. Retention time on chiral column=2.01 min. Prepare the HCl salt as in Example 40 to give Isomer 1 1-{4-[4-(1,5-dimethyl-1H-pyrazol-4-ylmethyl)-3,4,5,6-tetrahydro-2H-[1,2']bipyrazinyl-3'-yl]-phenyl}-ethanol hydrochloride (100%). MS (ES): m/z=393 [M+H].

EXAMPLE 61M

Isomer 2 1-{4-[4-(1,5-Dimethyl-1H-pyrazol-4-ylmethyl)-3,4,5,6-tetrahydro-2H-[1,2']bipyrazinyl-3'-yl]-phenyl}-ethanol hydrochloride

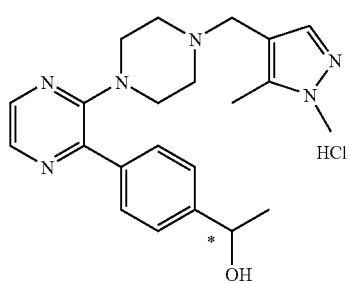

Separate isomers of racemic 1-{4-[4-(1,5-dimethyl-1H-pyrazol-4-ylmethyl)-3,4,5,6-tetrahydro-2H-[1,2']bipyrazinyl-3'-yl]-phenyl}-ethanol by SFC, using OJ-H column, eluting with a gradient of 10% methanol (with 0.2% isopropylamine) at 5 mL/min, to give Isomer 2 as a solid (197 mg, 24%). MS (ES): m/z=393 [M+H]$^+$. Optical Rotation $[\alpha]_{20}^D$ +0.210° (c=1.0 g/100 mL) in DCM. Retention time on chiral column=2.87 min. Prepare the HCl salt as in Example 40 to give the Isomer 2 1-{4-[4-(1,5-dimethyl-1H-pyrazol-4-ylmethyl)-3,4,5,6-tetrahydro-2H-[1,2']bipyrazinyl-3'-yl]-phenyl}-ethanol hydrochloride (100%). MS (ES): m/z=393 [M+H].

EXAMPLE 62M

N-{4-[4-(1,5-dimethyl-1H-pyrazol-4-ylmethyl)-3,4,5,6-tetrahydro-2H-[1,2']bipyrazinyl-3'-yl]-benzyl}-2-methoxy-acetamide hydrochloride

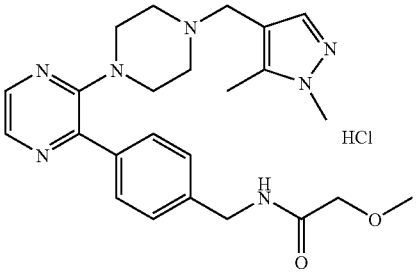

Dissolve 4-[4-(1,5-dimethyl-1H-pyrazol-4-ylmethyl)-3,4,5,6-tetrahydro-2H-[1,2']bipyrazinyl-3'-yl]-benzylamine (0.2 g, 0.53 mmol) in methylene chloride (5 mL). Add methoxy-acetyl chloride (1 eq., 0.058 g, 0.53 mmol). Add polymer bounded morpholine (1.1 eq., 0.234 g, 0.58 mmol). Stir at room temperature for 3 hr. Purify by SCX followed by reverse phase chromatography to give free base N-{4-[4-(1,5-dimethyl-1H-pyrazol-4-ylmethyl)-3,4,5,6-tetrahydro-2H-[1,2']bipyrazinyl-3'-yl]-benzyl}-2-methoxy-acetamide, (0.051 g, 21%). MS (ES): m/z=450.3 [M+H].

Dissolve this free base (0.051 mg, 0.114 mmol) in acetonitrile (1 mL) and water (4 mL). Add aq. 1 N HCl (1 eq., 0.114 mmol, 0.114 mL). Freeze the solution to −78° C. in a dry-ice/acetone bath. Place the solution in the lyophilizer for 48 hr. to give the title compound (0.058 g, 100%). MS (ES): m/z=450.3[M+H].

Prepare Examples 63-72 using the same method as for Example 62. Yields reported are for the two step acylation/HCl salt formation.

| Ex | Structure | Compound | Yield (%) | MS (ES) [M + H] |
|---|---|---|---|---|
| 63m | 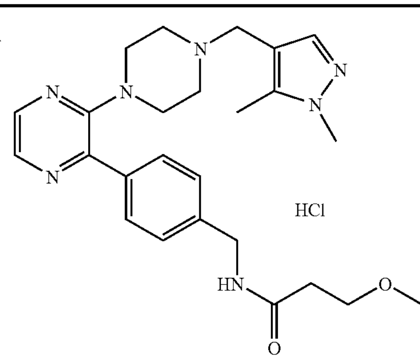 | N-{4-[4-(1,5-dimethyl-1H-pyrazol-4-ylmethyl)-3,4,5,6-tetrahydro-2H-[1,2']bipyrazinyl-3'-yl]-benzyl}-3-methoxy-propionamide hydrochloride | 31 | 464.3 |

-continued

| Ex | Structure | Compound | (%) Yield | MS (ES) [M + H] |
|---|---|---|---|---|
| 64m | 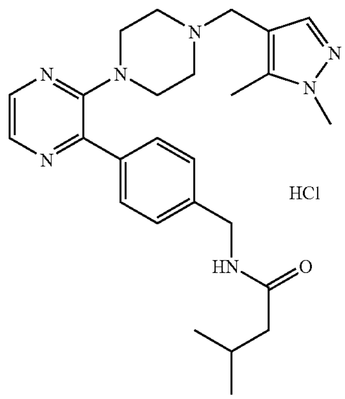 | N-{4-[4-(1,5-dimethyl-1H-pyrazol-4-ylmethyl)-3,4,5,6-tetrahydro-2H-[1,2']bipyrazinyl-3'-yl]-benzyl}-3-methyl-butyramide hydrochloride | 49 | 462.3 |
| 65m | 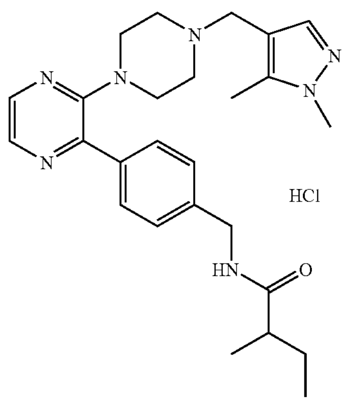 | N-{4-[4-(1,5-dimethyl-1H-pyrazol-4-ylmethyl)-3,4,5,6-tetrahydro-2H-[1,2']bipyrazinyl-3'-yl]-benzyl}-2-methyl-butyramide hydrochloride | 67 | 462.3 |
| 66m | 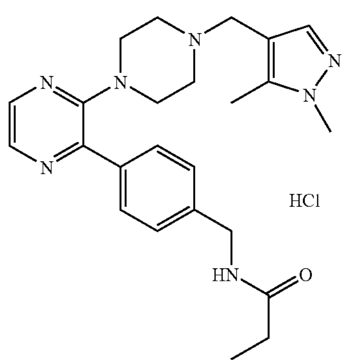 | N-{4-[4-(1,5-dimethyl-1H-pyrazol-4-ylmethyl)-3,4,5,6-tetrahydro-2H-[1,2']bipyrazinyl-3'-yl]-benzyl}-propionamide hydrochloride | 31 | 434.2 |
| 67m | 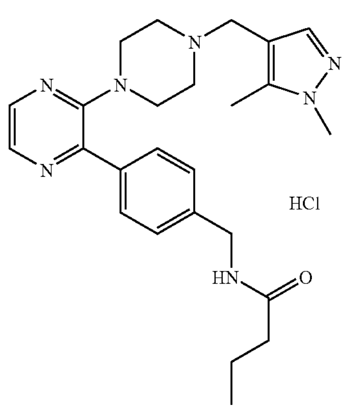 | N-{4-[4-(1,5-dimethyl-1H-pyrazol-4-ylmethyl)-3,4,5,6-tetrahydro-2H-[1,2']bipyrazinyl-3'-yl]-benzyl}-butyramide hydrochloride | 56 | 448.3 |

-continued

| Ex | Structure | Compound | (%) Yield | MS (ES) [M + H] |
|---|---|---|---|---|
| 68m | 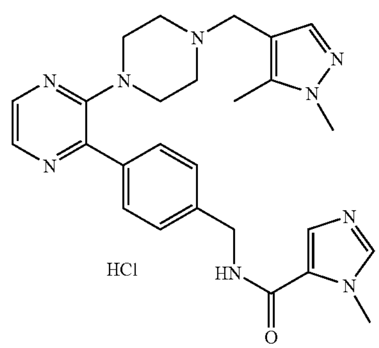 | 3-methyl-3H-imidazole-4-carboxylic acid 4-[4-(1,5-dimethyl-1H-pyrazol-4-ylmethyl)-3,4,5,6-tetrahydro-2H-[1,2']bipyrazinyl-3'-yl]-benzylamide hydrochloride | 3 | 486.3 |
| 69m | 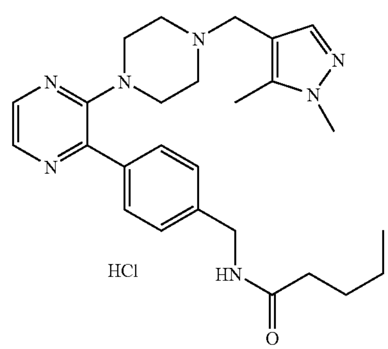 | pentanoic acid 4-[4-(1,5-dimethyl-1H-pyrazol-4-ylmethyl)-3,4,5,6-tetrahydro-2H-[1,2']bipyrazinyl-3'-yl]-benzylamide hydrochloride | 44 | 462.3 |
| 70m | 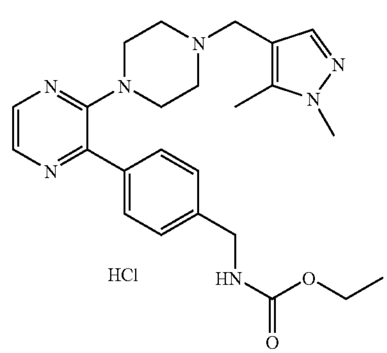 | {4-[4-(1,5-dimethyl-1H-pyrazol-4-ylmethyl)-3,4,5,6-tetrahydro-2H-[1,2']bipyrazinyl-3'-yl]-benzyl}-carbamic acid ethyl ester hydrochloride | 43 | 450.3 |
| 71m | 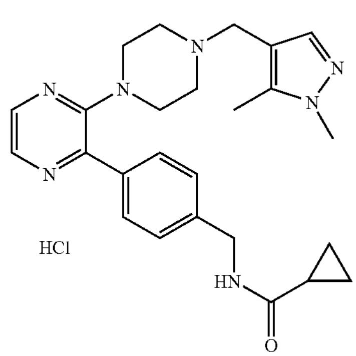 | cyclopropanecarboxylic acid 4-[4-(1,5-dimethyl-1H-pyrazol-4-ylmethyl)-3,4,5,6-tetrahydro-2H-[1,2']bipyrazinyl-3'-yl]-benzylamide hydrochloride | 11 | 446.3 |

| Ex | Structure | Compound | (%) Yield | MS (ES) [M + H] |
|---|---|---|---|---|
| 72m | 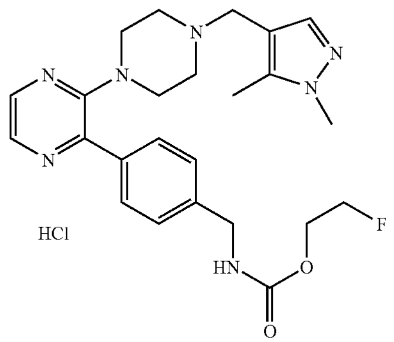 | {4-[4-(1,5-dimethyl-1H-pyrazol-4-ylmethyl)-3,4,5,6-tetrahydro-2H-[1,2']bipyrazinyl-3'-yl]-benzyl}-carbamic acid 2-fluoro-ethyl ester hydrochloride | 42 | 468.3 |

EXAMPLE 73M

Racemic tetrahydro-furan-3-carboxylic acid 4-[4-(1,5-dimethyl-1H-pyrazol-4-ylmethyl)-3,4,5,6-tetrahydro-2H-[1,2']bipyrazinyl-3'-yl]-benzylamide hydrochloride

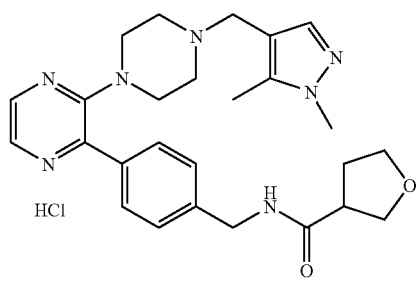

Dissolve racemic tetrahydro-furan-3-carboxylic acid (0.067 g, 0.58 mmol) in methylene chloride (5 mL). Add benzotriazol-1-yloxy-tripyrrolidinophosphonium hexafluorophosphate (PyBOP) (0.453 g, 0.87 mmol). Add 1-hydroxybenzotriazole (0.118 g, 0.87 mmol). Add 4-[4-(1,5-dimethyl-1H-pyrazol-4-ylmethyl)-3,4,5,6-tetrahydro-2H-[1,2']bipyrazinyl-3'-yl]-benzylamine (0.24 g, 0.63 mmol) dissolved in methylene chloride (5 mL). Stir at rt for 5 min. Add diisopropylethylamine (0.113 g, 0.87 mmol). Stir at rt for 4 hr. Purify by normal phase chromatography (4% 7N ammonia-methonal/ethyl acetate) to give racemic tetrahydro-furan-3-carboxylic acid 4-[4-(1,5-dimethyl-1H-pyrazol-4-ylmethyl)-3,4,5,6-tetrahydro-2H-[1,2']bipyrazinyl-3'-yl]-benzylamide (0.107 g, 39%). MS (ES): m/z=476.3[M+H]. Dissolve this racemate (0.107 g, 0.23 mmol) in acetonitrile (1 mL) and water (4 mL). Add aq. 1 N HCl (1 eq., 0.23 mmol, 0.23 mL). Freeze the solution to −78° C. in a dry-ice/acetone bath. Place the solution in the lyophilizer for 48 hr. to give the title compound (0.110 g, 94%). MS (ES): m/z=476.3 [M+H].

EXAMPLE 74M

3-{4-[4-(1,5-Dimethyl-1H-pyrazol-4-ylmethyl)-3,4,5,6-tetrahydro-2H-[1,2']bipyrazinyl-3'-yl]-benzyl}-1,1-dimethyl-urea hydrochloride

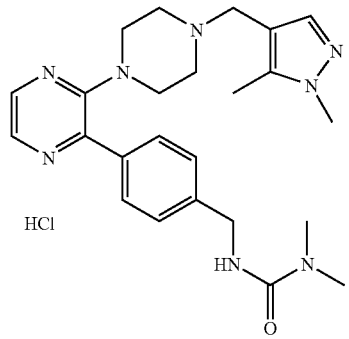

Dissolve 4-[4-(1,5-dimethyl-1H-pyrazol-4-ylmethyl)-3,4,5,6-tetrahydro-2H-[1,2']bipyrazinyl-3'-yl]-benzylamine (200 mg, 0.53 mmol) in DCM (5 mL). Add triethylamine (0.15 mL, 1.06 mmol) then dimethyl carbamoyl chloride (0.04 mL, 0.53 mmol) and stir the reaction at room temperature for 3 hr. Quench the reaction with water (10 mL), and remove the organic layer using an IST Phase Separator Frit®. Concentrate and purify (silica gel chromatography, eluting with 5:95 to 20:80 methanol:DCM). Combine fractions to give the free base as an oil. Dissolve the oil in acetonitrile and convert to the hydrochloride salt by adding 2 M aq HCl solution, add water and lyophilize. Form the free base by passing through an SCX-2® ion exchange cartridge washing with methanol then eluting with 2 M ammonia in methanol. Concentrate then dissolve the oil in acetonitrile and convert to the hydrochloride salt by adding 2 M aq HCl solution. Add

EXAMPLE 75M

1-{4-[4-(1,5-Dimethyl-1H-pyrazol-4-ylmethyl)-3,4,5,6-tetrahydro-2H-[1,2']bipyrazinyl-3'-yl]-benzyl}-3-methyl-urea hydrochloride

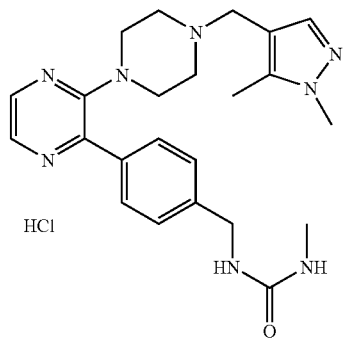

Dissolve 4-[4-(1,5-dimethyl-1H-pyrazol-4-ylmethyl)-3,4,5,6-tetrahydro-2H-[1,2']bipyrazinyl-3'-yl]-benzylamine (200 mg, 0.53 mmol) in DCM (5 mL) at room temperature under nitrogen. Add carbonyl diimidazole (94 mg, 0.58 mmol) and stir for 20 hr. Add a solution of methylamine in tetrahydrofuran (2 M, 2 mL, 4.0 mmol) and stir reaction for 2 hr. at room temperature. Quench reaction with water (10 mL) then extract with DCM (2×10 mL) and pass through an IST Phase Separator Frit®. Purify (silica gel chromatography, eluting with 5:95 to 20:80 methanol:DCM), concentrate and dry in vacuum oven over the weekend to give the free base as an oil. Dissolve the oil in acetonitrile and convert to the hydrochloride salt by adding 2 M aq HCl solution. Add water and lyophilize to give the title compound as a light yellow powder (66 mg, 28%). MS (ES): m/z=435 [M+H].

EXAMPLE 76M

1-{4-[4-(1,5-Dimethyl-1H-pyrazol-4-ylmethyl)-3,4,5,6-tetrahydro-2H-[1,2']bipyrazinyl-3'-yl]-benzyl}-3-ethyl-urea hydrochloride

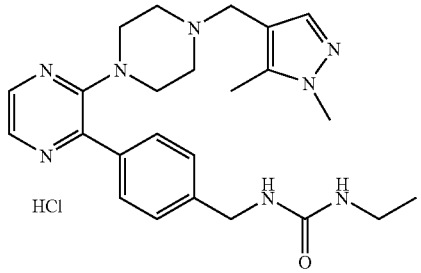

Dissolve 4-[4-(1,5-dimethyl-1H-pyrazol-4-ylmethyl)-3,4,5,6-tetrahydro-2H-[1,2']bipyrazinyl-3'-yl]-benzylamine (0.35 g, 0.93 mmol) in tetrahydrofuran (6 mL). Add isocyanato-ethane (1 eq., 0.06 g, 0.84 mmol). Add 4-(dimethylamino)pyridine (0.05 eq., 0.005 g, 0.043 mmol). Heat at 50° C. for 17 hr. Purify by normal phase chromatography with eluent 4% 7N ammonia-methanol/ethyl acetate to give 1-{4-[4-(1,5-dimethyl-1H-pyrazol-4-ylmethyl)-3,4,5,6-tetrahydro-2H-[1,2']bipyrazinyl-3'-yl]-benzyl}-3-ethyl-urea (0.252 g, 62%). MS (ES): m/z=449.3[M+H]. Dissolve (0.252 g, 0.56 mmol) in acetonitrile (1 mL) and water (4 mL). Add aq. 1 N HCl (1 eq., 0.56 mmol, 0.56 mL). Freeze the solution to −78° C. in a dry-ice/acetone bath. Place the solution in the lyophilizer for 48 hr. to give the title compound (0.250 g, 97% yield). MS (ES): m/z=449.3 [M+H].

EXAMPLE 77M

1-{4-[4-(1,5-Dimethyl-1H-pyrazol-4-ylmethyl)-3,4,5,6-tetrahydro-2H-[1,2']bipyrazinyl-3'-yl]-benzyl}-3-propyl-urea hydrochloride

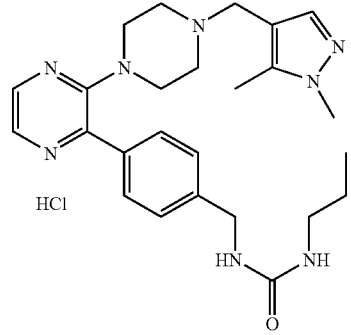

The title compound is obtained using essentially the same methods as for Example 76 using isocyanato-propane (19% yield). MS (ES): m/z=463.3[M+H].

EXAMPLE 78M

1-{4-[4-(1,5-Dimethyl-1H-pyrazol-4-ylmethyl)-3,4,5,6-tetrahydro-2H-[1,2']bipyrazinyl-3'-yl]-benzyl}-3-methyl-thiourea hydrochloride

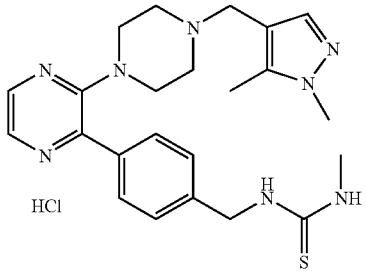

Dissolve 4-[4-(1,5-dimethyl-1H-pyrazol-4-ylmethyl)-3,4,5,6-tetrahydro-2H-[1,2']bipyrazinyl-3'-yl]-benzylamine (115 mg, 0.30 mmol) in DCM (5 mL), under nitrogen, then add methyl isothiocycanate (22 mg, 0.30 mmol). Stir the reaction for 22.5 hr. at room temperature. Add another portion of methyl isothiocyanate (10 mg, 0.13 mmol) and stir for 3 hr. Quench reaction with water (10 mL), extract with DCM (2×5 mL). Pass the combined DCM extracts through an IST Phase Separator Frit®, then concentrate and purify (silica gel chromatography, eluting with 5:95 to 20:80 methanol: DCM), to give the free base as a light yellow oil. Dissolve the oil in water and lyophilize to give the title compound as a yellow powder (178 mg, 63%). MS (ES): m/z=449 [M+H]+ acetonitrile and convert to the hydrochloride salt by adding 2 M aq HCl solution. Add water and lyophilize to give the title compound as a white powder (92 mg, 63%). MS (ES): m/z=451 [M+H]+.

EXAMPLE 79M

{4-[4-(1,5-Dimethyl-1H-pyrazol-4-ylmethyl)-3,4,5,6-tetrahydro-2H-[1,2']bipyrazinyl-3'-yl]-benzyl}-carbamic acid methyl ester hydrochloride

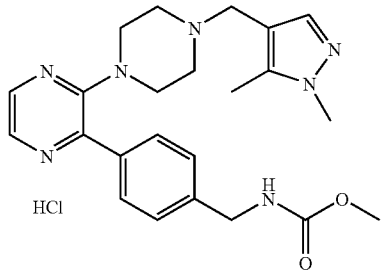

Dissolve 4-[4-(1,5-dimethyl-1H-pyrazol-4-ylmethyl)-3,4,5,6-tetrahydro-2H-[1,2']bipyrazinyl-3'-yl]-benzylamine (200 mg, 0.53 mmol) in DCM (5 mL). Add triethylamine (0.15 mL, 1.06 mmol) then methyl chloroformate (0.04 mL, 0.53 mmol) and stir at room temperature for 1 hr. Quench the reaction with water (10 mL), and remove the organic layer using an IST Phase Separator Frit®. Concentrate and purify (silica gel chromatography, eluting with 5:95 to 20:80 methanol:DCM), to give the free base as an oil. Dissolve the oil in acetonitrile and convert to the hydrochloride salt by adding 2 M aq HCl solution. Add water and lyophilize to give the title compound as an off white powder (213 mg, 84%). MS (ES): m/z=436 [M+H]+.

EXAMPLE 80M

Dimethyl-carbamic acid 4-[4-(1,5-dimethyl-1H-pyrazol-4-ylmethyl)-3,4,5,6-tetrahydro-2H-[1,2']bipyrazinyl-3'-yl]-benzyl ester hydrochloride

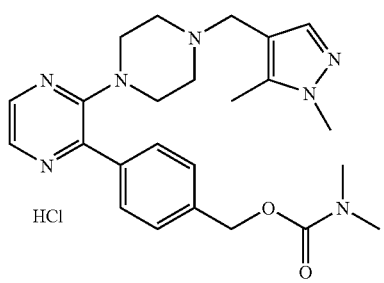

Stir {4-[4-(1,5-dimethyl-1H-pyrazol-4-ylmethyl)-3,4,5,6-tetrahydro-2H-[1,2']bipyrazinyl-3'-yl]-phenyl}-methanol (200 mg, 0.53 mmol) in dry N,N-dimethylformamide (5 mL) under nitrogen. Add sodium hydride (60% dispersion in oil, 32 mg, 0.79 mmol), stir for 30 min., and then add dimethyl carbamoyl chloride (0.04 mL, 0.58 mmol). Stir reaction for 3 hr. at room temperature. Add water (20 mL), then saturated aq. sodium hydrogen carbonate (5 mL), extract with DCM (3×20 mL). Pass the combined DCM extracts through an IST Phase Separator Frit®, concentrate and purify (silica gel chromatography, eluting with 5:95 to 15:85 methanol:DCM), to give the free base as a clear oil. Dissolve the oil in acetonitrile and convert to the hydrochloride salt by adding 2 M aq HCl solution. Add water and lyophilize to give the title compound as a yellow powder (79 mg, 30%). MS (ES): m/z=450 [M+H]+.

EXAMPLE 81M

Methyl-carbamic acid 4-[4-(1,5-dimethyl-1H-pyrazol-4-ylmethyl)-3,4,5,6-tetrahydro-2H-[1,2']bipyrazinyl-3'-yl]-benzyl ester hydrochloride

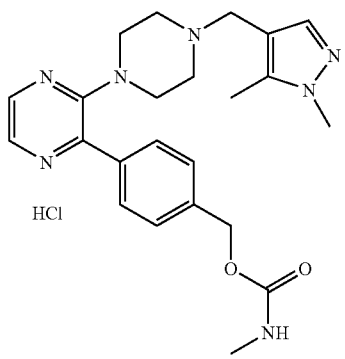

Dissolve {4-[4-(1,5-dimethyl-1H-pyrazol-4-ylmethyl)-3,4,5,6-tetrahydro-2H-[1,2']bipyrazinyl-3'-yl]-phenyl}-methanol (200 mg, 0.53 mmol) in DCM (5 mL) at room temperature under nitrogen. Add carbonyl diimidazole (94 mg, 0.58 mmol) and stir for 20 hr. Add a solution of methylamine in tetrahydrofuran (2 M, 2 mL, 4.0 mmol) and stir reaction for 2 hr. at room temperature. Quench reaction with water (10 mL) then extract with DCM (2×10 mL), pass through an IST Phase Separator Frit® and concentrate. Purify by low pH reverse phase HPLC, and form the free base by passing through an SCX-2® ion exchange cartridge washing with methanol then eluting with 3 M ammonia in methanol. Dissolve the oil in acetonitrile and convert to the hydrochloride salt by adding 2 M aq HCl solution. Add water and

EXAMPLE 82M

3-{4-[4-(1,5-Dimethyl-1H-pyrazol-4-ylmethyl)-3,4,
5,6-tetrahydro-2H-[1,2']bipyrazinyl-3'-yl]-phenyl}-
N-methyl-propionamide hydrochloride

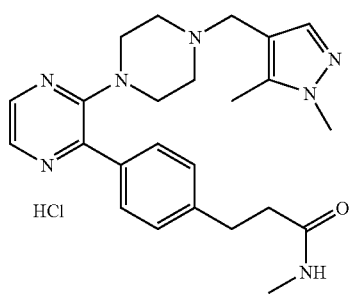

Stir 3-{4-[4-(1,5-dimethyl-1H-pyrazol-4-ylmethyl)-3,4,5,
6-tetrahydro-2H-[1,2']bipyrazinyl-3'-yl]-phenyl}-propionic
acid (420 mg, 1.0 mmol) in thionyl chloride (3 mL) at room
temperature for 2 hr. Concentrate in vacuo then stir in tetrahydrofuran (5 mL) at room temperature. Add a solution of
methylamine in tetrahydrofuran (2 M, 10 mL) and stir for 1 hr.
Quench the reaction with methanol, then reduce solvents in
vacuo. Add water (10 mL), extract into DCM (3×20 mL) and
pass the combined DCM extracts through an IST Phase Separator Frit®. Concentrate the filtrate and purify (silica gel
chromatography, eluting with 0:100 to 15:85 methanol:
DCM), to give the product as a yellow oil. Dissolve the oil in
acetonitrile and convert to the hydrochloride salt by adding 2
M aq HCl solution. Add water and lyophilize to give the title
compound as a dark yellow powder (210 mg, 45%). MS (ES):
m/z=434 [M+H].

EXAMPLE 83M 4-(1,5-Dimethyl-1H-pyrazol-4-ylmethyl)-3'-(4-pyrazol-1-ylmethyl-phenyl)-3,4,5,6-tetrahydro-2H-[1,2']
bipyrazinyl hydrochloride

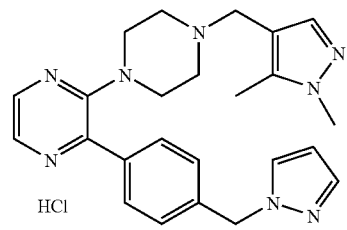

Add sodium hydride (0.172 g of 60% weight suspension in
mineral oil; 2.59 mmol) to a solution of pyrazole (0.183 g;
2.69 mmol) in DMF (5 mL). Cool the mixture to 5° C., stir for
30 min., remove the cooling bath, warm to room temperature
and stir for 30 min. Add 3'-(4-chloromethyl-phenyl)-4-(1,5-
dimethyl-1H-pyrazol-4-ylmethyl)-3,4,5,6-tetrahydro-2H-[1,
2']bipyrazinyl dihydrochloride (0.253 g; 0.540 mmol) in 6
mL of DMF and stir for 20 hr. at room temperature. Quench
with a solution of 10% aq. acetic acid (9 mL), add methanol
(minimal volume to achieve a homogeneous solution) and
add to a 5 gm SCX column (Varian; pre-rinsed with MeOH).
Elute the crude product with 2 M ammonia in methanol (18
mL) and concentrate. Purify via chromatography on silica gel
eluting 0-10% methanol/dichlormethane to give 4-(1,5-dimethyl-1H-pyrazol-4-ylmethyl)-3'-(4-pyrazol-1-ylmethyl-
phenyl)-3,4,5,6-tetrahydro-2H-[1,2']bipyrazinyl (0.140 g;
61%). MS (ES+) m/z: 429 (M+H)+. Purify by high pH reverse
phase HPLC, and concentrate to give the pure free base.
Dissolve the free base in acetonitrile and convert to the hydrochloride salt by adding 1 eq 2 M aq HCl solution. Add water
and lyophilize to give the title compound as an off white
powder (126 mg). MS (ES): m/z=429 [M+H]+.

EXAMPLE 84M 4-(1,5-Dimethyl-1H-pyrazol-4-ylmethyl)-3'-(4-imidazol-1-ylmethyl-phenyl)-3,4,5,6-tetrahydro-2H-[1,
2']bipyrazinyl hydrochloride

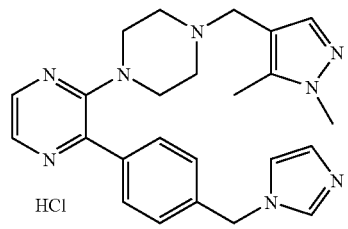

Stir imidazole (116 mg, 1.84 mmol) in dry N,N-dimethylformamide (7 mL) under nitrogen. Add sodium hydride (60%
weight dispersion in oil, 74 mg, 1.85 mmol) and stir for 30
min. at room temperature. Add 3'-(4-chloromethyl-phenyl)-
4-(1,5-dimethyl-1H-pyrazol-4-ylmethyl)-3,4,5,6-tetrahydro-2H-[1,2']bipyrazinyl dihydrochloride (200 mg, 0.43
mmol) at room temperature and stir at room temperature for
18 hr. Quench reaction with water (20 mL), extract with DCM
(3×20 mL). Pass the combined DCM extracts through an IST
Phase Separator Frit®, concentrate and purify (silica gel
chromatography, eluting with 0:100 to 15:85 methanol:
DCM), to give the free base as a clear oil. Dissolve the oil in
acetonitrile and convert to the hydrochloride salt by adding 2
M aq HCl solution. Add water and lyophilize to give the title
compound as a cream coloured powder (119 mg, 65%). MS
(ES): m/z=429 [M+H]+.

EXAMPLE 85M 4-(1,5-Dimethyl-1H-pyrazol-4-ylmethyl)-3'-[4-(2-
methyl-imidazol-1-ylmethyl)-phenyl]-3,4,5,6-tetrahydro-2H-[1,2']bipyrazinyl hydrochloride

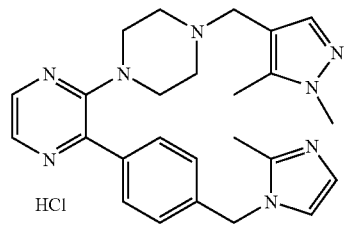

Stir 2-methyl imidazole (164 mg, 2.00 mmol) in dry N,N-dimethylformamide (5 mL) under nitrogen. Add sodium hydride (60% weight dispersion in oil, 77 mg, 2.00 mmol), then stir for 1 hr. at room temperature. Add 3'-(4-chloromethyl-phenyl)-4-(1,5-dimethyl-1H-pyrazol-4-ylmethyl)-3,4,5,6-tetrahydro-2H-[1,2']bipyrazinyl dihydrochloride (233 mg, 0.50 mmol) at room temperature, followed by sodium iodide (75 mg, 0.50 mmol). Stir at room temperature for 20 hr. Quench reaction with water (20 mL), extract with DCM (3×10 mL). Pass the combined DCM extracts through an IST Phase Separator Frit®, concentrate and purify by high pH reverse phase HPLC, and concentrate to give the free base. Dissolve the free base in acetonitrile and convert to the hydrochloride salt by adding 1 eq 2 M aq HCl solution. Add water and lyophilize to give the title compound as a light brown powder (124 mg, 52%). MS (ES): m/z=443 [M+H]$^+$.

EXAMPLE 86M 4-(1,5-Dimethyl-1H-pyrazol-4-ylmethyl)-3'-(4-[1,2,4]triazol-1-ylmethyl-phenyl)-3,4,5,6-tetrahydro-2H-[1,2']bipyrazinyl hydrochloride

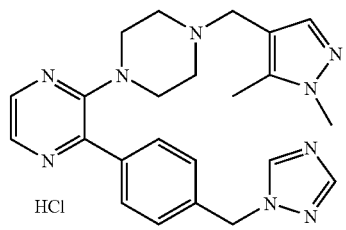

Stir 1,2,4-triazole (138 mg, 2.00 mmol) in dry N,N-dimethylformamide (5 mL) under nitrogen. Add sodium hydride (60% weight dispersion in oil, 77 mg, 2.00 mmol), then stir for 1 hr. at room temperature. Add 3'-(4-chloromethyl-phenyl)-4-(1,5-dimethyl-1H-pyrazol-4-ylmethyl)-3,4,5,6-tetrahydro-2H-[1,2']bipyrazinyl dihydrochloride (233 mg, 0.50 mmol) at room temperature, followed by sodium iodide (75 mg, 0.50 mmol). Stir at room temperature for 20 hr. Quench reaction with water (20 mL), extract with DCM (3×10 mL). Pass the combined DCM extracts through an IST Phase Separator Frit®, concentrate and purify (silica gel chromatography, eluting with 5:95 to 15:85 methanol:DCM), to give the free base as an oil. Dissolve the oil in acetonitrile and convert to the hydrochloride salt by adding 2 M aq HCl solution. Add water and lyophilize to give the title compound as a white powder (118 mg, 53%). MS (ES): m/z=430 [M+H]$^+$.

Prepare Examples 87-88 essentially as described for Example 86 using the appropriate heterocycle and 3'-(4-chloromethyl-phenyl)-4-(1,5-dimethyl-1H-pyrazol-4-ylmethyl)-3,4,5,6-tetrahydro-2H-[1,2']bipyrazinyl dihydrochloride. Yields given are for the two step transformation from the benzyl chloride to the final HCl salt.

| EX | Structure | Compound | Yield (%) | MS (ES) [M + H] |
|---|---|---|---|---|
| 87m | 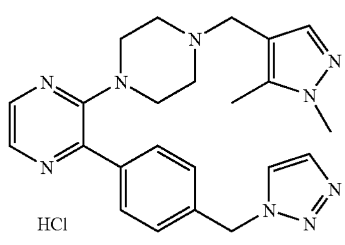 | 4-(1,5-dimethyl-1H-pyrazol-4-ylmethyl)-3'-(4-[1,2,3]triazol-1-ylmethyl-phenyl)-3,4,5,6-tetrahydro-2H-[1,2']bipyrazinyl-hydrochloride | 23 | 430 |
| 88m | 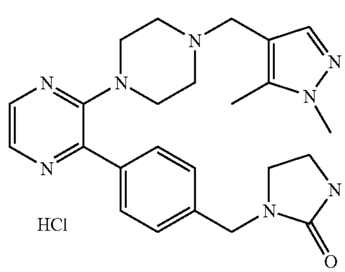 | 1-{4-[4-(1,5-dimethyl-1H-pyrazol-4-ylmethyl)-3,4,5,6-tetrahydro-2H-[1,2']bipyrazinyl-3'-yl]-benzyl}-imidazolidin-2-one hydrochloride | 21 | 447 |

EXAMPLE 89M

1-{4-[4-(1,5-Dimethyl-1H-pyrazol-4-ylmethyl)-3,4,5,6-tetrahydro-2H-[1,2']bipyrazinyl-3'-yl]-benzyl}-piperidin-2-one hydrochloride

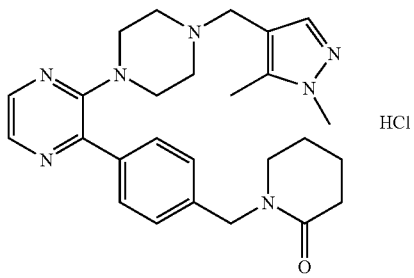

Add sodium hydride (0.175 g of 60% weight suspension in mineral oil; 2.62 mmol) to a solution of piperidin-2-one (0.270 g; 2.73 mmol) in DMF (5 mL). Cool the mixture to 5° C., stir for 30 min., remove the cooling bath, warm to room temperature and stir for 30 min. Add 3'-(4-chloromethyl-phenyl)-4-(1,5-dimethyl-1H-pyrazol-4-ylmethyl)-3,4,5,6-tetrahydro-2H-[1,2']bipyrazinyl dihydrochloride (0.253 g; 0.540 mmol) in 6 mL of DMF and stir for 20 hr. at room temperature. Quench with a solution of 10% aq. acetic acid (9 mL), add methanol (minimal volume to achieve a homogeneous solution) and add to a 5 gm SCX column (Varian; pre-rinsed with MeOH). Elute the crude product with 2 M ammonia in methanol (18 mL) and concentrate. Purify via chromatography on silica gel eluting 0-10% methanol/DCM to give 1-{4-[4-(1,5-dimethyl-1H-pyrazol-4-ylmethyl)-3,4,5,6-tetrahydro-2H-[1,2']bipyrazinyl-3'-yl]-benzyl}-piperidin-2-one (0.180 g; 73%). MS (ES+) m/z: 460 (M+H)$^+$. Purify by high pH reverse phase HPLC, and concentrate to give the free base. Dissolve the free base in acetonitrile and convert to the hydrochloride salt by adding 1 eq. 2 M aq. HCl solution. Add water and lyophilize to give the title compound as a brown powder (164 mg, 66%). MS (ES): m/z=460 [M+H]$^+$.

EXAMPLE 90M

1-{4-[4-(1,5-Dimethyl-1H-pyrazol-4-ylmethyl)-3,4,5,6-tetrahydro-2H-[1,2']bipyrazinyl-3'-yl]-benzyl}-pyrrolidin-2-one hydrochloride

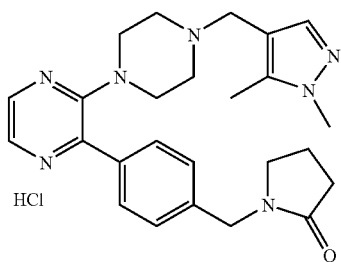

Stir pyrrolidinone (0.14 mL, 1.85 mmol) in dry N,N-dimethylformamide (5 mL) under nitrogen. Add sodium hydride (60% weight dispersion in oil, 74 mg, 1.85 mmol), then more dry N,N-dimethylformamide (5 mL), stir for 30 min. at room temperature, then at 40° C. for 30 min. Add 3'-(4-chloromethyl-phenyl)-4-(1,5-dimethyl-1H-pyrazol-4-ylmethyl)-3,4,5,6-tetrahydro-2H-[1,2']bipyrazinyl dihydrochloride (200 mg, 0.46 mmol) at room temperature, followed by sodium iodide (69 mg, 0.46 mmol). Stir at room temperature for 90 min. Quench reaction with water (15 mL), extract with DCM (3×10 mL). Pass the combined DCM extracts through an IST Phase Separator Frit®, concentrate and purify by SCX-2® chromatography washing with methanol then eluting with 3.5 M ammonia in methanol. Further purify (silica gel chromatography, eluting with 5:95 to 20:80 methanol:DCM), to give the free base as a light yellow oil. Dissolve the oil in acetonitrile and convert to the hydrochloride salt by adding 2 M aq HCl solution. Add water and lyophilize to give the title compound as a pink powder (142 mg, 64%). MS (ES): m/z=446 [M+H]$^+$.

EXAMPLE 91M

3-{4-[4-(1,5-Dimethyl-1H-pyrazol-4-ylmethyl)-3,4,5,6-tetrahydro-2H-[1,2']bipyrazinyl-3'-yl]-benzyl}-oxazolidin-2-one hydrochloride

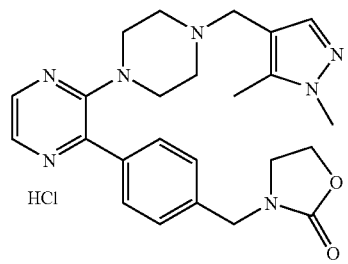

Stir oxazolidin-2-one (160 mg, 1.85 mmol) in dry N,N-dimethylformamide (7 mL) under nitrogen. Add sodium hydride (60% weight dispersion in oil, 74 mg, 1.85 mmol) and stir for 30 min. at room temperature. Add 3'-(4-chloromethyl-phenyl)-4-(1,5-dimethyl-1H-pyrazol-4-ylmethyl)-3,4,5,6-tetrahydro-2H-[1,2']bipyrazinyl dihydrochloride (200 mg, 0.46 mmol) at room temperature, followed by sodium iodide (69 mg, 0.46 mmol). Stir at room temperature for 17 hr. Quench reaction with water (20 mL), extract with DCM (3×15 mL). Pass the combined DCM extracts through an IST Phase Separator Frit®, concentrate and purify by SCX-2® chromatography washing with methanol then eluting with 3.5 M ammonia in methanol. Further purify (silica gel chromatography, eluting with 0:100 to 15:85 methanol:DCM), to give the free base as a light yellow solid. Dissolve the oil in acetonitrile and convert to the hydrochloride salt by adding 2 M aq HCl solution. Add water and lyophilize to give the title compound as a pink powder (142 mg, 64%). MS (ES): m/z=448 [M+H]$^+$.

Prepare Examples 92-93 essentially as described for Example 91 using the appropriate heterocycle and 3'-(4-chloromethyl-phenyl)-4-(1,5-dimethyl-1H-pyrazol-4-ylmethyl)-3,4,5,6-tetrahydro-2H-[1,2']bipyrazinyl dihydrochloride. Yields shown are for the two step transformation from the benzyl chloride to the HCl salt

| EX | Structure | Compound | Yield (%) | MS (ES) [M + H] |
|---|---|---|---|---|
| 92m | 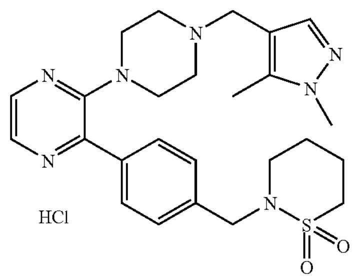 | 4-(1,5-dimethyl-1H-pyrazol-4-ylmethyl)-3'-[4-(1,1-dioxo-1λ⁶-[1,2]thiazinan-2-ylmethyl)-phenyl]-3,4,5,6-tetrahydro-2H-[1,2']bipyrazinyl hydrochloride | 60 | 496 |
| 93m | 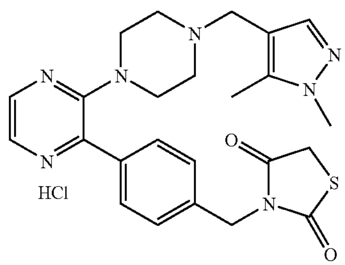 | 3-{4-[4-(1,5-dimethyl-1H-pyrazol-4-ylmethyl)-3,4,5,6-tetrahydro-2H-[1,2']bipyrazinyl-3'-yl]-benzyl}-thiazolidine-2,4-dione hydrochloride | 25 | 478 |

EXAMPLE 94M

N-{4-[4-(1,5-Dimethyl-1H-pyrazol-4-ylmethyl)-3,4,5,6-tetrahydro-2H-[1,2']bipyrazinyl-3'-yl]-benzyl}-N-methyl-acetamide hydrochloride

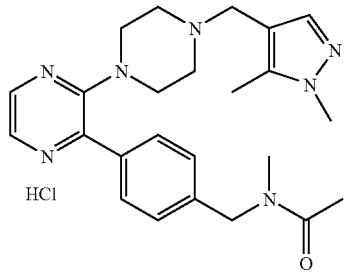

Dissolve N-methyl acetamide (187 mg, 2.55 mmol) in dry N,N-dimethylformamide (5 mL) at room temperature under nitrogen. Add sodium hydride (60% dispersion in oil, 102 mg, 2.55 mmol), stir for 1 hr., then add 3'-(4-chloromethyl-phenyl)-4-(1,5-dimethyl-1H-pyrazol-4-ylmethyl)-3,4,5,6-tetrahydro-2H-[1,2']bipyrazinyl dihydrochloride (300 mg, 0.64 mmol) and sodium iodide (96 mg, 0.64 mmol). Stir the reaction at 50° C. for 20 hr., the quench with water (10 mL). Extract with DCM (4×10 mL) and pass through an IST Phase Separator Frit®. Purify using SCX-2 chromatography, eluting with 3 M ammonia in methanol and further purify using silica gel chromatography (eluting with 5:95 methanol: DCM). Dissolve the clear oil in acetonitrile, and add 2 M aq. HCl and water then lyophilize to give the title compound as light yellow powder (87 mg, 29%). MS (ES): m/z=434 [M+H].

EXAMPLE 95M

2-{4-[4-(1,5-Dimethyl-1H-pyrazol-4-ylmethyl)-3,4,5,6-tetrahydro-2H-[1,2']bipyrazinyl-3'-yl]-benzyloxy}-N-methyl-acetamide hydrochloride

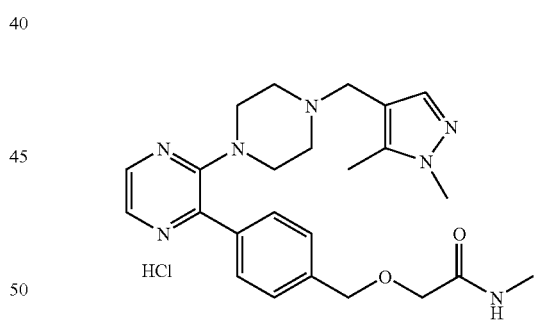

Dissolve {4-[4-(1,5-dimethyl-1H-pyrazol-4-ylmethyl)-3,4,5,6-tetrahydro-2H-[1,2']bipyrazinyl-3'-yl]-phenyl}-methanol (189 mg, 0.50 mmol) in dry N,N-dimethylformamide (3 mL) at room temperature under nitrogen. Add sodium hydride (60% weight dispersion in oil, 24 mg, 0.60 mmol), stir reaction for 1 hr., then add 2-chloro-N-methyl-acetamide (56 mg, 0.53 mmol) and stir reaction for 20 hr. Quench reaction with water (50 mL), then extract with DCM (3×20 mL) and pass through an IST Phase Separator Frit®. Purify (silica gel chromatography, eluting with 5:95 to 20:80 methanol:DCM), concentrate to give the free base as an oil. Dissolve the oil in acetonitrile and convert to the hydrochloride

EXAMPLE 96M

2-{4-[4-(1,5-Dimethyl-1H-pyrazol-4-ylmethyl)-3,4,5,6-tetrahydro-2H-[1,2']bipyrazinyl-3'-yl]-phenoxy}-acetamide hydrochloride

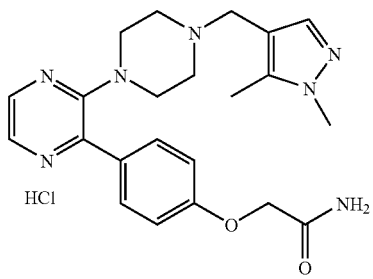

Dissolve 4-[4-(1,5-dimethyl-1H-pyrazol-4-ylmethyl)-3,4,5,6-tetrahydro-2H-[1,2']bipyrazinyl-3'-yl]-phenol (182 mg, 0.50 mmol) in dry N,N-dimethylformamide (3 mL) at room temperature under nitrogen. Add sodium hydride (60% dispersion in oil, 24 mg, 0.60 mmol), stir reaction for 1 hr., then add chloroacetamide (49 mg, 0.53 mmol) and stir reaction for 20 hr. Quench reaction with water (50 mL), extract with DCM (3×10 mL) and pass through an IST Phase Separator Frit®. Purify (silica gel chromatography, eluting with 5:95 to 20:80 methanol:DCM), concentrate to give the free base as an oil. Dissolve the oil in acetonitrile and convert to the hydrochloride salt by adding 2 M aq HCl solution. Add water and lyophilize to give the title compound as a bright yellow powder (164 mg, 72%). MS (ES): m/z=422 [M+H].

EXAMPLE 97M

N-{4-[4-(1,5-Dimethyl-1H-pyrazol-4-ylmethyl)-3,4,5,6-tetrahydro-2H-[1,2']bipyrazinyl-3'-yl]-benzyl}-N-methyl-methanesulfonamide hydrochloride

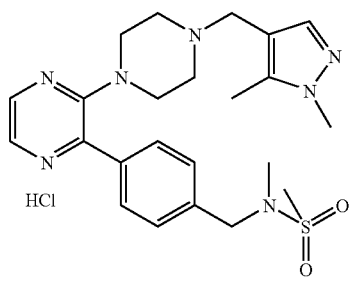

Dissolve N-{4-[4-(1,5-dimethyl-1H-pyrazol-4-ylmethyl)-3,4,5,6-tetrahydro-2H-[1,2']bipyrazinyl-3'-yl]-benzyl}-methanesulfonamide (200 mg, 0.44 mmol) in dry DCM (5 mL) under nitrogen. Add triphenylphosphine (173 mg, 0.66 mmol) and stir for 20 min. at room temperature. Add methanol (0.02 mL, 0.53 mmol) and diethyl azodicarboxylate (0.09 mL, 0.53 mmol) and stir for 2 hr. Add water (10 mL), extract with DCM (3×10 mL), pass the combined DCM extracts through an IST Phase Separator Frit® and concentrate. Purify (silica gel chromatography, eluting with 0:100 to 15:85 methanol: DCM), to give the free base as a clear oil. Dissolve the oil in acetonitrile and convert to the hydrochloride salt by adding 2 M aq HCl solution. Add water and lyophilize to give the title compound as a yellow powder (120 mg, 53%). MS (ES): m/z=470 [M+H]⁺.

EXAMPLE 98M

1-{4-[4-(1,5-Dimethyl-1H-pyrazol-4-ylmethyl)-3,4,5,6-tetrahydro-2H-[1,2']bipyrazinyl-3'-yl]-benzyl}-pyrrolidine-2,5-dione hydrochloride

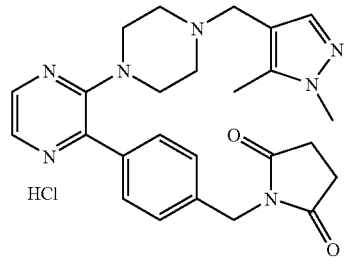

Dissolve succinimide (99 mg, 1.0 mmol) in dry DCM (5 mL) under nitrogen. Add triphenylphosphine (408 mg, 1.5 mmol) and stir for 20 min. at room temperature. Add {4-[4-(1,5-dimethyl-1H-pyrazol-4-ylmethyl)-3,4,5,6-tetrahydro-2H-[1,2']bipyrazinyl-3'-yl]-phenyl}-methanol (378 mg, 1.0 mmol) and diethyl azodicarboxylate (0.19 mL, 1.1 mmol) and stir for 20 hr. Add water (10 mL), extract with DCM (2×5 mL). Pass the combined DCM extracts through an IST Phase Separator Frit®, concentrate and purify by SCX-2® chromatography washing with methanol then eluting with 2 M ammonia in methanol. Further purify (silica gel chromatography, eluting with 0:100 to 5:95 methanol:DCM), to give the free base as a light yellow oil. Purify again by low pH reverse phase HPLC, and form the free base by passing through an SCX-2® ion exchange cartridge washing with methanol then eluting with 3.5 M ammonia in methanol. Dissolve the oil in acetonitrile and convert to the hydrochloride salt by adding 2 M aq HCl solution. Add water and lyophilize to give the title compound as a yellow powder (127 mg, 26%). MS (ES): m/z=460 [M+H]⁺.

EXAMPLE 99M 4-(1,5-Dimethyl-1H-pyrazol-4-ylmethyl)-3'-(4-methanesulfonylmethyl-phenyl)-3,4,5,6-tetrahydro-2H-[1,2']bipyrazinyl hydrochloride

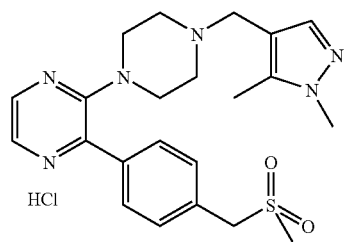

Stir sodium methane sulfinate (188 mg, 1.84 mmol) in dry N,N-dimethylformamide (5 mL) under nitrogen. Add 3'-(4-chloromethyl-phenyl)-4-(1,5-dimethyl-1H-pyrazol-4-ylmethyl)-3,4,5,6-tetrahydro-2H-[1,2']bipyrazinyl dihydrochloride (200 mg, 0.46 mmol) at room temperature, followed by sodium iodide (69 mg, 0.46 mmol). Stir at room temperature for 20 hr. Quench reaction with water (10 mL), extract with DCM (3×10 mL). Pass the combined DCM extracts through an IST Phase Separator Frit®, concentrate and purify by SCX-2® chromatography washing with methanol then eluting with 3.5 M ammonia in methanol. Further purify (silica gel chromatography, eluting with 0:100 to 15:85 methanol:DCM), to give the free base as a clear oil. Dissolve the oil in acetonitrile and convert to the hydrochloride salt by adding 2 M aq HCl solution. Add water and lyophilize to give the title compound as a white powder (36 mg, 17%). MS (ES): m/z=441 [M+H]$^+$.

EXAMPLE 100M

N-{4-[4-(3-Methyl-1-phenyl-1H-pyrazol-4-ylmethyl)-3,4,5,6-tetrahydro-2H-[1,2']bipyrazinyl-3'-yl]-benzyl}-acetamide hydrochloride

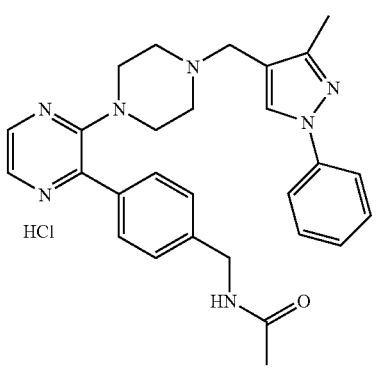

Charge a carousel tube with potassium carbonate (185 mg, 1.34 mmol), 3'-chloro-4-(3-methyl-1-phenyl-1H-pyrazol-4-ylmethyl)-3,4,5,6-tetrahydro-2H-[1,2']bipyrazinyl, (200 mg, 0.54 mmol), (4-acetamidomethylphenyl)boronic acid (127 mg, 0.65 mmol) and tetrakis(triphenylphosphine)palladium (13 mg, 0.011 mmol) in DMA (2 mL). Purge with nitrogen and leave stirring under nitrogen at 120° C. overnight. Cool reaction to room temperature. Dilute with water (10 mL) and extract with DCM (3×10 mL) and discard the aq. layer. Concentrate to dryness. Purify the crude material by flash silica chromatography eluting with (2/98 to 5/95 methanol:DCM) then by preparative HPLC to give the free base (101 mg).

Prepare the hydrochloride salt by adding HCl and lyophilise the solution to give the title compound as a pale yellow solid (86 mg, 30%). MS (ES): m/z=482 [M+H]$^+$.

EXAMPLE 101M

N-{4-[4-(3,5-Dimethyl-1-pyridin-2-yl-1H-pyrazol-4-ylmethyl)-3,4,5,6-tetrahydro-2H-[1,2']bipyrazinyl-3'-yl]-benzyl}-acetamide hydrochloride

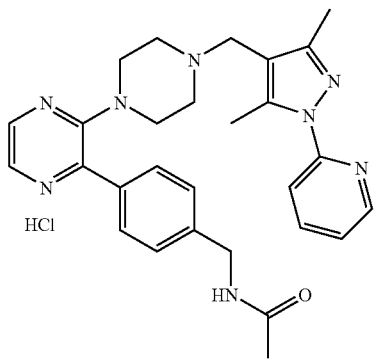

Add sodium triacetoxyborohydride (231 mg, 1.04 mmol) to a solution of N-[4-(3,4,5,6-Tetrahydro-2H-[1,2']bipyrazinyl-3'-yl)-benzyl]-acetamide (215 mg, 0.69 mmol) and 3,5-dimethyl-1-pyridin-2-yl-1H-pyrazole-4-carboxaldehyde (208 mg, 1.03 mmol) in THF (3.5 mL). Maintain stirring for 3 hr. and quench by adding NaHCO$_3$ (5 mL). Extract with DCM (3×10 mL) and discard the aq. phase filtering through an IST phase separator Frit®. Concentrate to dryness and purify by preparative HPLC then purify by SCX-2® ion exchange chromatography, eluting with 2 M NH$_3$ in MeOH to give the free base. Prepare the hydrochloride salt by adding HCl and lyophilise the solution to give the title compound (200 mg, 54%). MS (ES): m/z=497 [M+H]$^+$.

EXAMPLE 102M 4-(3-Methyl-1-phenyl-1H-pyrazol-4-ylmethyl)-3'-(4-[1,2,3]triazol-2-ylmethyl-phenyl)-3,4,5,6-tetrahydro-2H-[1,2']bipyrazinyl hydrochloride

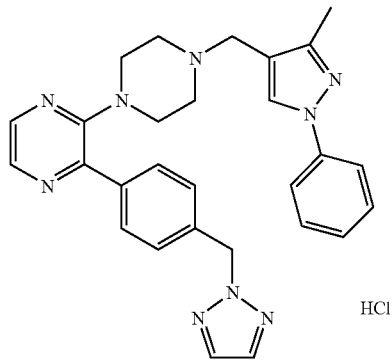

Add sodium hydride (173 mg, 4.33 mmol) to a solution of 1H-1,2,3-triazole (308 mg, 4.33 mmol) in DMF (3 mL). Maintain stirring under nitrogen for 1 hr then add sodium iodide (162 mg, 1.08 mmol) and a solution of 3'-(4-Chloromethyl-phenyl)-4-(3-methyl-1-phenyl-1H-pyrazol-4-ylmethyl)-3,4,5,6-tetrahydro-2H-[1,2']bipyrazinyl (495 mg, 1.08 mmol) in DMF (8 mL). Maintain stirring under nitrogen for 20 hr. Quench by adding water (10 mL), wash with DCM (3×10 mL) and discard the aq. phase. Concentrate to dryness to give a mixture of 4-(3-Methyl-1-phenyl-1H-pyrazol-4-ylmethyl)-3'-(4-[1,2,3]triazol-1-ylmethyl-phenyl)-3,4,5,6-tetrahydro-2H-[1,2']bipyrazinyl and 4-(3-Methyl-1-phenyl-1H-pyrazol-4-ylmethyl)-3'-(4-[1,2,3]triazol-2-ylmethyl-phenyl)-3,4,5,6-tetrahydro-2H-[1,2']bipyrazinyl. Purify first by preparative HPLC then by SCX-2® ion exchange chromatography, eluting with 2 M $NH_3$ in MeOH. to give 4-(3-methyl-1-phenyl-1H-pyrazol-4-ylmethyl)-3'-(4-[1,2,3]triazol-2-ylmethyl-phenyl)-3,4,5,6-tetrahydro-2H-[1,2']bipyrazinyl (98 mg). MS (ES): m/z=492 [M+H]$^+$ 2 min.

Prepare the hydrochloride salt by adding HCl and lyophilising the solution to give the title compound (98 mg, 18%, MS (ES): m/z=492 [M+H]$^+$).

EXAMPLE 103M

{4-[4-(5-Methyl-1-phenyl-1H-pyrazol-4-ylmethyl)-3,4,5,6-tetrahydro-2H-[1,2']bipyrazinyl-3'-yl]-phenyl}-acetonitrile hydrochloride

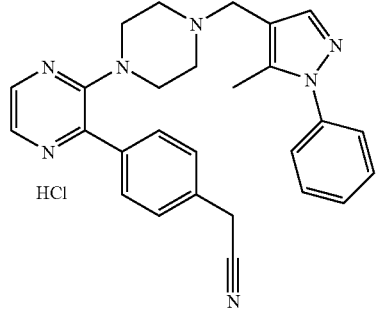

Stir together 3'-chloro-4-(5-methyl-1-phenyl-1H-pyrazol-4-ylmethyl)-3,4,5,6-tetrahydro-2H-[1,2']bipyrazinyl (177 mg, 0.480 mmol), 4-(cyanomethyl)benzene boronic acid (93 mg, 0.576 mmol), potassium carbonate (159 mg, 1.15 mmol) and tetrakis(triphenylphosphine)palladium(0) (0.003 g, 0.003 mmol) and water (1 mL), in N,N-dimethylacetamide (2 mL) at room temperature under nitrogen, then heat at 120° C. for 4 hr. Cool to room temperature, dilute with water (5 mL) and extract with DCM (3×20 mL). Pass the combined DCM extracts through an IST Phase Separator Frit®, concentrate and purify (silica gel chromatography, eluting with 0:100 to 5:95 methanol:DCM). Dry in a vacuum oven over night, then dissolve the yellow oil in acetonitrile. Add 2 M aq. HCl and water then lyophilize to give the title compound as a dark yellow powder (168 mg, 72%). MS (ES): m/z=450.2 [M+H].

Compounds of examples 104-107 are prepared essentially as Example 103 using the appropriate chloride and boronic acid.

| EX | Structure | Compound | Yield (%) | MS (ES) [M + H] |
|---|---|---|---|---|
| 104m | 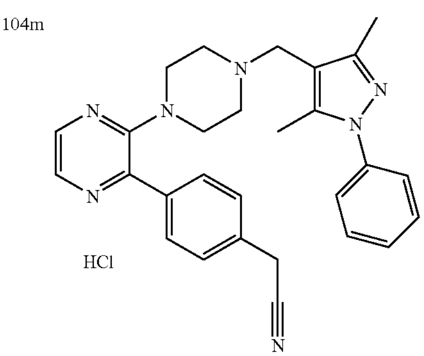 | {4-[4-(3,5-Dimethyl-1-phenyl-1H-pyrazol-4-ylmethyl)-3,4,5,6-tetrahydro-2H-[1,2']bipyrazinyl-3'-yl]-phenyl}-acetonitrile hydrochloride | 62 | 464.2 |

| EX | Structure | Compound | Yield (%) | MS (ES) [M + H] |
|---|---|---|---|---|
| 105m | 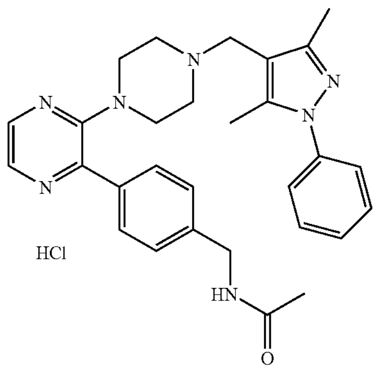 | N-{4-[4-(3,5-Dimethyl-1-phenyl-1H-pyrazol-4-ylmethyl)-3,4,5,6-tetrahydro-2H-[1,2']bipyrazinyl-3'-yl]-benzyl}-acetamide hydrochloride | 69 | 496 |
| 106m | 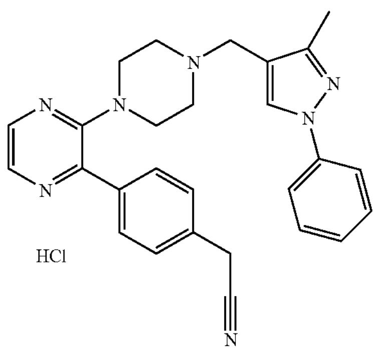 | {4-[4-(3-Methyl-1-phenyl-1H-pyrazol-4-ylmethyl)-3,4,5,6-tetrahydro-2H-[1,2']bipyrazinyl-3'-yl]-phenyl}-acetonitrile hydrochloride | 52 | 450 |
| 107m | 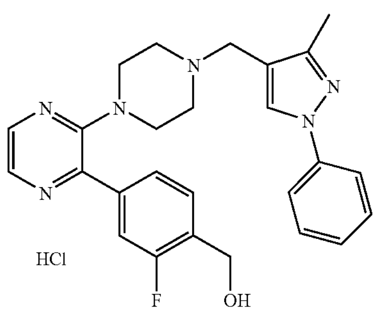 | {2-Fluoro-4-[4-(3-methyl-1-phenyl-1H-pyrazol-4-ylmethyl)-3,4,5,6-tetrahydro-2H-[1,2']bipyrazinyl-3'-yl]-phenyl}-methanol hydrochloride | 59 | 459 |

EXAMPLE 108M

{4-[4-(1,5-Dimethyl-1H-pyrazol-4-ylmethyl)-3,4,5,6-tetrahydro-2H-[1,2']bipyrazinyl-3'-yl]-phenyl}-methanol

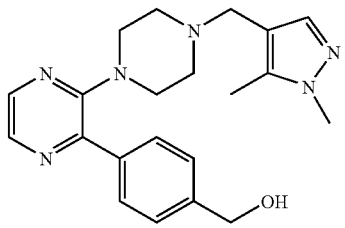

The title compound is prepared using methods essentially as described for N-{4-[4-(1,5-dimethyl-1H-pyrazol-4-ylmethyl)-3,4,5,6-tetrahydro-2H-[1,2']bipyrazinyl-3'-yl]-benzyl}-methanesulfonamide using 4-hydroxymethyl boronic acid. (0.380 g, 100%). MS (ES): m/z=379 [M+H]⁺.

The 5-HT$_7$ receptor antagonists of the present invention are relatively selective for the 5-HT$_7$ receptor. The compounds of the present invention are particularly relatively selective for the 5-HT$_7$ receptor in comparison to other 5-HT receptor subtypes and specifically the 5-HT$_{1A}$, 5-HT$_{1B}$ and 5-HT$_{1D}$ receptors. This selectivity is demonstrated in the following receptor binding assays and receptor antagonist activity assays.

Membrane Preparation:

Membranes for affinity and antagonist activity assays are prepared essentially as follows. AV-12 cells, stably expressing the 5-HT$_7$ receptor, are grown as a monolayer in 5×T-150 flasks in DMEM/F12 (3:1) 5% FBS, 20 mM HEPES, 400 mg/mL geneticin, 50 mg/mL tobramycin. After growing to 90% confluence the media is removed and replaced with Hybritech media containing 2% horse serum, 100 mg/mL dextran sulfate, 1 mg/mL nucellin, 1 mg/mL human transferrin (partially iron saturated), 50 mg/mL tobramycin, 20 mM HEPES, 100 mg/mL geneticin, 0.04% pluronic F68. The cells are grown overnight to condition the media. The next morning the conditioned media (~150 mL total) is removed and set aside in a sterile container. The cells are trypsinized and collected in the conditioned media. Fresh suspension media is added to bring the total volume to 500 mL and a cell density of $5 \times 10^5$ cells/mL. The suspension culture volume is repeatedly increased over the next 3 weeks to the desired volume and density until harvest (approx. $3.5-4.0 \times 10^6$ cells per mL targeted cell density). Cells are harvested by centrifugation at 1,500 g at 4° C. for 30 min. The supernatant is decanted and the cell pellets are resuspended in ice-cold phosphate buffered saline (PBS). The cell suspension is aliquoted into 50 mL centrifuge tubes and centrifuged at 1,500 g at 4° C. for 15 min. The supernatant is removed, the pellets are weighed, and then frozen on dry ice.

To prepare membranes, the above pellets are resuspended in ice-cold Tris buffer (20 mM Tris HCl, pH 7.4 at 23° C., 5 mM EDTA) and homogenized with a Wheaton tissue grinder. The lysate is subsequently centrifuged at 200×g for 5 min. at 4° C. to pellet large fragments which are discarded. The supernatant is collected and centrifuged at 40,000×g for 60 min. at 4° C. The resulting pellet is resuspended in a final buffer containing 50 mM Tris HCl and 0.5 mM EDTA, pH 7.4. Membrane preparations are snap-frozen on dry ice and stored at −80° C. Protein concentrations are determined by the method of Bradford. *Anal. Biochem.*, 72:248-254, 1976.

For cAMP functional assays, the 5-HT$_7$-expressing cells from above are grown in 150 cm$^2$ flasks and processed essentially as follows. The media is aspirated from the flasks and cells are washed with 1 mL PBS. The cells are trypsinized and resuspended in complete media. A sample of the cells is counted and the remainder is centrifuged as above for 3 min. The resulting cell pellet is resuspended in PBS at a concentration of $1 \times 10^6$ cells per mL and used directly in the cAMP assay as described.

5-HT$_7$ Receptor Affinity: Radioligand Binding Assay:

[$^3$H] 5-HT binding is performed using modifications of the assay conditions reported by Kahl et al. (*J. Biomol. Screen*, 2: 33-40 (1997), essentially as follows. Radioligand binding assays are conducted in 96-well microtiter plates, in a total volume of 125 µl containing the following reaction buffer: 50 mM Tris, 10 mM MgCl$_2$, 0.2 mM EDTA, 10 mM pargyline, 0.1% ascorbate, pH 7.4 at room temperature. Competition binding is conducted using eleven test compound concentrations ranging from 0.1 to 10,000 nM, in the presence of 1 nM [$^3$H]5-HT. Unlabeled 5-HT (10 µM) is used to define nonspecific binding. The binding reaction is initiated by addition of 0.15 µg of membrane homogenate (2.5 µg/µl) and 0.5 mg of scintillation proximity assay fluoromicrospheres. The reactions are incubated at room temperature for 3 hr. and then counted in a Trilux Microbeta™ scintillation counter to detect receptor-bound radioligand. Binding data is analyzed by computer-assisted 4 parameter fit analysis (ID Business Solutions Ltd, Guildford, Surrey, UK). IC$_{50}$ values are converted to K$_i$ values using the Cheng-Prusoff equation. *Biochem. Pharmacol.*, 22:3099-3108 (1973).

Binding affinities of compounds of the present invention may be determined essentially as described above and are found to generally have excellent affinity for the 5-HT$_7$ receptor. K$_i$ values are generally $\leq$500 nM. Preferred compounds have K$_i$'s $\leq$50 nM. Most preferred compounds are those with K$_i$'s $\leq$20 nM. Exemplified compounds are tested essentially as described and found to have K$_i$'s $\leq$200 nM. The compound of Example 142 is tested essentially as described and found to have a K$_i$ of about 44 nM.

Affinity for other serotonin receptor subtypes as well as for alpha 1 & 2 adrenergic receptors can readily be determined by modification of the above described radioligand receptor binding assay using membranes derived from cells stably expressing the desired receptor subtype including the 5-HT$_{1A}$, 5-HT$_{1B}$, and 5-HT$_{1D}$ subtypes, as well as the 5-HT$_{2A}$, 5-HT$_{2B}$, 5-HT$_{2C}$, 5-HT$_4$, 5-HT$_5$, and 5-HT$_6$ receptor subtypes. The selectivity ratio of K$_{i-x}$/K$_{i-5HT7}$, where K$_{i-x}$ is the K$_i$ for the receptor being compared, is indicative of the relative affinity of a compound for the 5-HT$_7$ receptor. The binding affinities of compounds of the present invention may be determined at these additional receptor types and are found to generally have selectivity ratios $\geq$2.0 against other serotonergic receptors. Preferred compounds have selectivity ratios of $\geq$10. Generally, selectivity ratios against the andronergic receptors is found to be >20-100. Exemplified compounds are tested and found to have selectivity ratios against other serotonergic receptors of $\geq$2 and against andronergic receptors of $\geq$2. The compound of Example 142 is tested essentially as described and is found to have the following selectivity profile:

| Receptor | Ki (nM) |
|---|---|
| 5-HT$_{1A}$ | 1250 |
| 5-HT$_{1B}$ | >3580 |
| 5-HT$_{1D}$ | >2400 |
| 5-HT$_{2A}$ | >7470 |
| 5-HT$_{2B}$ | >3160 |
| 5-HT$_{2C}$ | >8200 |
| 5-HT$_4$ | >6310 |
| 5-HT$_5$ | >7020 |
| 5-HT$_6$ | >1790 |
| 5-HT$_7$ | 44 |
| alpha 1 adrenergic | >1440 |
| alpha 1 adrenergic | 933 |

Functional Antagonist Assay: Measurement of cAMP Formation:

The 5-HT$_7$ receptor is functionally coupled to a G-protein as measured by the ability of serotonin and serotonergic drugs to stimulate cAMP production in CHO cells transfected with the 5-HT$_7$ receptor. (Ruat, et al., *Proceedings of the National Academy of Sciences* (USA), 90:8547-8551, 1993.) Accordingly, functional receptor activity can be measured by measuring adenylate cyclase activity using a commercially available cell-based, homogeneous, time resolved fluorescence assay kit, as for example the kit produced by Cisbio-US, Inc. (Bedford, Mass.). Essentially, and using the protocol and reagents provided by the manufacturer, approximately 20,000 human 5-HT$_7$ receptor-expressing AV-12 cells (as described above) are used with test compound dose concentrations in the range described for the binding assay. EC-90 dose-response curves for 5-HT are measured in parallel to demonstrate competitive antagonism. A cAMP standard curve is also run in every experiment. After the assay plates are read in an Envision™ instrument (Perkin-Elmer, Wellesley Mass.), the data is normalized to the standard curve and converted to percent inhibition for data analysis as described above for the receptor binding assay results. The K$_b$ (nM) is calculated as a measure of the antagonist potency of the compound.

Compounds of the present invention may be tested essentially as described above and are found to generally be antagonists of the 5-HT$_7$ receptor. Preferred compounds are full antagonists of the 5-HT$_7$ receptor. Other preferred compounds are those having percent inhibition >75%. Still other preferred compounds are those having $K_b$ <50 nM. The compound of Example 74 is tested essentially as described and is found to be a full antagonist showing a Kb of about 44 nM (inhibition=about 96%).

Animal Model of Dural Plasma Protein Extravasation (PPE).

The dural plasma protein extravasation model is an established model for migraine. The ability of a test compound to reduce extravasation of plasma proteins into the dura under assay conditions is considered indicative of the compound's ability to reduce or prevent the dural inflammation thought to be symptomatic of migraine. (see Johnson, K. W., et al., *Neuroreport,* 8 (1997) 2237-2240.)

To assay compounds for their ability to reduce or prevent dural plasma protein extravasation, male Harlan Sprague-Dawley rats (250-350 g) are anesthetized with sodium pentobarbital (65 mg/kg, i.p.) and placed in a stereotaxic frame (David Kopf Instruments) with the incisor bar set at −2.5 mm. Following a midline sagital scalp incision, 2 pairs of bilateral holes are drilled through the skull (3.2 mm posteriorly, 1.8 and 3.8 mm laterally, all coordinates referenced to bregma). Pairs of stainless steel stimulating electrodes, insulated except at the tips (Rhodes Medical Systems, Inc.), are lowered through the holes in both hemispheres to a depth of 9.2 mm.

Test compound is administered intravenously (i.v.) to the femoral vein at a dosing volume of 1 mL/kg. Approximately 8 min. post injection, the animals are dosed with Fluorescein isothiocyanate-bovine serum albumin (FITC-BSA) (20 mg/kg, i.v.). The FITC-BSA functions as a marker for protein extravasation. Ten min. post-injection of the test compound, the left trigeminal ganglion is electrically stimulated for 5 min. at a current intensity of 1.0 mA (5 Hz, 5 msec pulse every 200 msec) with a Model S48 Grass Instrument Stimulator with PSIU6 photoelectric isolation unit (Grass-Telefactor).

Alternatively, rats fasted overnight are dosed orally with test compound via gavage at a volume of 2 mL/kg. Approximately 50 min. post dosing, the animals are anesthetized and placed in the stereotaxic frame as described above. The animals are dosed with FITC-BSA (20 mg/kg, i.v.) at 58 min. post-p.o. dosing. Sixty min. post compound dosing, the animals are electrically stimulated as described above.

Five min. following the termination of stimulation, the animals are killed by exsanguination with 40 mL of saline. The top of the skull is removed and the dural membrane samples are removed from both hemispheres, rinsed with water, and spread flat on microscopic slides. Once dried, the tissues are coverslipped with a 70% glycerol/water solution.

The amount of FITC-BSA for each sample is quantified with a fluorescence microscope (Zeiss) equipped with a grating monochromator, a spectrophotometer, and a computer driven stage. Fluorescence measurements are taken at 25 points in a 5×5 grid in 500 μm steps on each dural sample with an excitation wavelength of approximately 490 nm and emission intensity measured at approximately 535 nm. The mean and standard deviation of the 25 measurements are determined.

The extravasation induced by the electrical stimulation of the trigeminal ganglion is an ipsilateral effect (i.e. occurs only on the side of the dura in which the trigeminal ganglion was stimulated). This allows the use of the other (unstimulated) half of the dura as a control. The ratio of the amount of extravasation in the dura from the stimulated side, over the amount of extravasation in the unstimulated side, is calculated. Control animals dosed only with saline, yield a ratio of approximately 2.0. In contrast, a compound which effectively prevented the extravasation in the dura from the stimulated side would yield a ratio of approximately 1.0.

Compounds of the present invention may be assayed essentially as described above and are typically found to significantly reduce extravasation in the dura. Preferred compounds are those that effectively prevent extravasation. The compound of Example 127 is assayed essentially as described and is found to have a ratio of about 1.16.

Formalin Model of Persistent Pain

The "formalin model" of persistent pain, particularly for inflammatory pain and neuropathic pain, is well known and can be used to test compounds for pain blocking and/or analgesic activity. (see Shibata M. et al., *Pain* (1989) 38: 347-352; and Tjolsen A. et al., *Pain* (1992) 51:5-17.)

Male Sprague Dawley rats (Harlan Labs, Indianapolis, Ind.) weighing between 200-250 g are maintained at constant temperature (21-23° C.) and light (12 hr. light/12 hr. dark), with free access to food and water for 7 days prior to testing. All testing is conducted during the light cycle after fasting over night and with the testing room temperature maintained at constant temperature (21-23° C.).

The measurement of pain-related behavior following injection of formalin into the dorsal or plantar surface of the rat hind paw normally involves manually scoring time spent licking or flinching of the injected paw (Shibata M. et al. supra). The scoring may also be automated based on the method of Jett and Michelson (Jett M. F. and Michelson S. (1996), "The formalin test in rat: validation of an automated system." *Pain* 64:19-25), using commercially available startle chambers (Model SR-Lab, San Diego Instruments, San Diego, Calif.) which detect movements of the rats by means of an accelerometer.

The animals are administered either vehicle or test compound and individually placed in holding cylinders. At specified time points, the rats are removed from the cylinders and administered formalin (50 μL of a 5% solution in saline) subcutaneously into the plantar surface of the right hind paw and immediately placed back into the cylinders. The cylinders are then placed on the load cells of the detection system and the response monitored continuously for 60 min. in 1-second bins (i.e. collections periods). As previously described by Jett and Michelson, the formalin-induced movements, "events," detected by the system include licking and flinching the affected paw. The number of events [the number of 1-second bins with >20-load units (baseline movements)] is totaled in 5-minute intervals. The administration of formalin, results in events that occur in 2 phases, an early phase of events 0-5 min. after formalin administration (corresponding to the early phase of the formalin test by the manual method) and a late phase during the subsequent 10-40-minute period (corresponding to the late phase of the formalin test by the manual method).

Data are evaluated by one-way analysis of variance (ANOVA) and the appropriate contrasts analyzed by the Dunnett 't' test for 2-sided comparisons using JMP statistical analysis program (v5.1.1 SAS Institute Inc., Cary, N.C.). Differences are considered to be significant if the p-value was less than 0.05. Data are presented as means with standard errors of means (±SEM).

Compounds of the present invention may be assayed essentially as described above and are generally found to significantly reduce the number of events compared to vehicle alone. The compound of Example 19 is tested essentially as described and found to be active on both the early and late phases.

L5/L6 Nerve Ligation Model of Persistent Pain Mechanisms:

The L5/L6 Nerve Ligation model (Chung model) is a well established model for persistent pain, specifically neuropathic pain. Surgery is performed on male Sprague Dawley rats (Harlan, Indianapolis, Ind.), weighing 150-200 g at the time of surgery as previously described (Kim and Chung, 1992). Briefly, neuropathic injury is produced by tightly ligating the left L5 and L6 spinal nerves under gas anesthesia with a mixture of isoflurane (3% for induction and 2% for maintenance) and $O_2$. Following surgery, development of neuropathic pain is evaluated daily by measuring mechanical sensitivity of the injured paw to von Frey filaments with incremental bending forces (0.5-15 g) as described by (Chaplan et al., 1994). Animals are considered to be neuropathic when they exhibited mechanical allodynia, i.e. paw flinch behavior response to the application of a bending force of less than 2 g for 2 days. Test drug or vehicle is administered i.p. and the mechanical threshold for paw flinching is measured at 0.5, 1, 2, 3, 4 and 6 hr. after dosing. Measurement of the mechanical threshold for paw flinching is also done prior to surgery (preoperative control). Data are expressed as the threshold force required to elicit a response (g) as means±S.E.M. (standard error of the mean).

Compounds of the present invention may be assayed essentially as described above and are generally found to significantly raise the threshold force required to elicit a response compared to vehicle alone. The compound of Example 186 is tested essentially as described and is found to be active.

Foot Electroshock Stress Induced cGMP Elevation Model for Anxiety

The foot electroshock stress induced cGMP elevation model for anxiety is an established anxiety model, wherein stress from an unavoidable electroshock to the feet induces an elevation in cerebellar cGMP levels, which elevation is reduced or blocked by preadministration of anxiolytic compounds (Sethy and Oien (1991), Pharmacology Biochemistry & Behavior, vol. 39, pg. 379-382). Briefly, adult male CF-1 mice (25-30 g Harlan, Indianapolis, Ind.) are housed under a 12-hr light/dark cycle in a temperature and humidity controlled environment. Mice are habituated to the environment for at least 3 days and all studies are carried out between 9:00 AM and 12:00 noon to reduce the effects of diurnal fluctuations. Test mice are given a single intraperitoneal injection of test compound or control (vehicle is 3% DMSO, 20% emulphor stock, 10% lactic acid stock) and are sacrificed approximately 30 min. after dosing, using a beam of microwave radiation (microwave fixation system model GA5013; Gerling Applied Engineering, Modesto, Calif.) focused on the skull for 0.5 sec. at high power setting. This method preserves tissue cGMP content. After microwaving, a small piece (10-20 mg) of cerebellar cortex is quickly removed from the skull. The tissue is weighed and then homogenized in 2 ml of 1.0% perchloric acid. Tissue homogenate is kept on ice for 30 min followed by 5 min. in a boiling water bath. The homogenate is then centrifuged at 11,700 g for 20 min. 1 mL of supernatant is then acetylated with 40 µl of triethylamine and 20 µl of acetic anhydride, vortexed, and centrifuged at 13,000 g for 20 min at 4° C. Acetylated mouse cerebellum samples are stored at 4° C. pending cGMP analysis by radioimmunoassay with the cGMP $^{125}$I Flash Plate radioimmunoassay test kit (PerkinElmer Life and Analytical Sciences, Boston, Mass.) on duplicate samples from each animal as per manufacturer's instructions.

For stressed mouse groups, 30 min. post injection, mice are subjected to a 1.0 mA foot-shock for 10 sec. in a Habitest Operant cage equipped with a modular shock floor (Habitest Modular Test System, Coulbourn Instruments, Allentown, Pa.). Mice are then sacrificed and cerebellar cortex samples are processed as described.

For each animal, cGMP levels are normalized to wet tissue weight and used to compute group averages and S.E.M. (typically 4-6 mice per group). All data are analyzed on the log scale to correct problems with heterogeneity of variance. Statistical analyses are performed using ANOVA followed by Dunnett's method to compare each treatment group to the vehicle group. The compound of Example 189 is tested essentially as described above, using the known anxiolytics chlordiazepoxide (Librium®), and alprazolam (Xanax®), as well as the known 5-HT$_7$ antagonist SB-269970, as comparator compounds, and found to significantly reduce the stress-induced elevation of cGMP.

| Compound | Vehicle/ stress | 1 mg/kg (ip, 30 min)/ stress | 3 mg/kg (ip, 30 min)/ stress | 10 mg/kg (ip, 30 min)/ stress | 30 mg/kg (ip, 30 min)/ stress | 60 mg/kg (ip, 30 min)/ stress |
|---|---|---|---|---|---|---|
| Ex. 186 | 239# (22.5) | | 278 (33.9) | 264 (25.6) | 234 (34.4) | 117* (25.1) |
| SB-269970 | 240# (22.5) | | 270 (33.0) | 225 (29.0) | 171* (20.4) | |
| Chlordiazepoxide | 187# (14.4) | | | 129 (17.5) | 106* (16.5) | 71* (5.3) |
| Alprazolam | 187# (14.4) | 60* (9.9) | | | | |

All data normalized to vehicle-treated groups of animals that did not receive footshock stress (reported as percent).
Data reported as mean values (s.e.m.).
p < 0.01 vs. vehicle/no stress group;
*p < 0.05 vs. vehicle/stress group While it is possible to administer compounds employed in the methods of this invention directly without any formulation, the compounds are usually administered in the form of pharmaceutical compositions comprising at least one compound of Formula I, or a pharmaceutically acceptable salt thereof, as an active ingredient and at least one pharmaceutically acceptable carrier, diluent and/or excipient. These compositions can be administered by a variety of routes including oral, intranasal, transdermal, subcutaneous, intravenous, intramuscular, and pulmonary. Such pharmaceutical compositions and processes for preparing them are well known in the art. See, e.g., Remington: The Science and Practice of Pharmacy (A. Gennaro, et al., eds., 19$^{th}$ ed., Mack Publishing Co., 1995).

The compositions are preferably formulated in a unit dosage form, each dosage containing from about 0.1 to about 200 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds are generally effective over a wide dosage range. For example, dosages per day will normally fall within the range of about 0.01 to about 30 mg/kg, as for example within the range of about 0.1 to about 15 mg/kg/day, in single or divided dose. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the above lower limit may be adequate, while in other cases still larger doses may be used.

The type of formulation employed for the administration of the compounds employed in the methods of the present invention may be dictated by the particular compound employed, the type of pharmacokinetic profile desired from the selected route of administration, and the state of the patient.

We claim:
1. A compound of the formula:

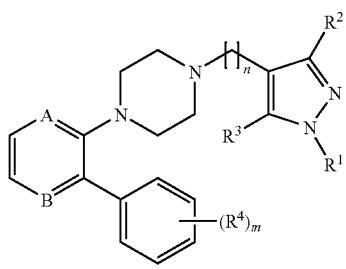

where:
A and B are each —N═;
n is 1, 2, or 3;
m is 0, 1, 2, or 3;
$R^1$ is selected from the group consisting of
  i) hydrogen, ii) $(C_1-C_6)$alkyl-optionally substituted with hydroxy, cyano, or 1 to 5 fluoro substituents, or alternatively, optionally substituted with hydroxy and 1 to 3 fluoro substituents, iii) $(C_3-C_7)$cycloalkyl-$(C_0-C_2)$alkyl-optionally substituted with hydroxy, iv) $(C_1-C_2)$alkyl-O—$(C_1-C_2)$alkyl-, v) $Ph^1$-$(C_0-C_2)$alkyl-, vi) $Ar^1$—$(C_0-C_2)$alkyl-, vii) $(C_1-C_2)$alkyl-S(O)$_2$—$(C_0-C_3)$alkyl-, viii) $Ph^1$-S(O)$_2$—, ix) $Ar^1$—S(O)$_2$—, x) $(C_1-C_2)$alkyl-NH—$(C_1-C_2)$alkyl-, xi) $((C_1-C_2)$alkyl)$_2$-N—$(C_1-C_2)$alkyl-, xii) $(C_1-C_2)$alkyl-NH—C(O)—$(C_0-C_2)$alkyl-, xiii) $((C_1-C_2)$alkyl)$_2$-N—C(O)—$(C_0-C_2)$alkyl-, xiv) pyrrolidin-1-yl-C(O)—$(C_0-C_2)$alkyl-, xv) $(C_1-C_2)$alkyl-C(O)—NH—$(C_1-C_2)$alkyl-, xvi) $(C_1-C_2)$alkyl)-C(O)—N($C_1-C_2$ alkyl)-$(C_1-C_2)$alkyl-, xvii) $(C_1-C_2)$alkyl-S(O)$_2$—NH—$(C_1-C_2)$alkyl-, and xviii) 2-oxo-oxazolidin-5-yl-;
$R^2$ is selected from the group consisting of i) hydrogen, ii) halo, iii) hydroxy, iv) $(C_1-C_4)$alkyl-optionally substituted with hydroxy, cyano, or 1 to 5 fluoro substituents, and v) $(C_1-C_2)$alkyl-O—$(C_0-C_2)$alkyl-;
$R^3$ is selected from the group consisting of hydrogen, halo, and $(C_1-C_4)$alkyl-;
Each $R^4$ is independently selected from the group consisting of i) halogen, ii) $(C_1-C_2)$alkyl optionally further substituted with 1 to 5 fluoro substituents, iii) $(C_1-C_2)$alkoxy optionally further substituted with 1 to 5 fluoro substituents, iv) cyclopropyl-$(C_0-C_1)$alkyl-O—, v) cyano, vi) $(C_1-C_2)$alkyl-S(O)$_2$—, and vii) $(C_1-C_4)$alkyl-C(O)—,
or alternatively, m is 1 or 2, one $R^4$ substituent is selected from the group consisting of viii) $(C_1-C_4)$alkyl further substituted with a substituent selected from the group consisting of (hydroxy, $(C_1-C_4)$alkoxy, cyano, and amino), ix) $(C_1-C_2)$alkyl-O—C(O)—, x) $(C_1-C_2)$alkyl-S(O)$_2$—$(C_1-C_2)$alkyl-, xi) $(C_1-C_4)$alkyl-C(O)—N($R^6$)—, xii) $(C_1-C_4)$alkyl-C(O)—N($R^6$)-methyl-, xiii) cyclopropyl-C(O)—NH-methyl-, xiv) $(C_1-C_2)$alkyl-S(O)$_2$—N($R^6$)—$(C_1-C_2)$alkyl-, xv) $(C_1-C_2)$alkyl-O—$(C_0-C_2)$alkyl-C(O)—N($R^6$)— optionally further substituted with a fluoro group, xvi) $(C_1-C_2)$alkyl-O—$(C_0-C_2)$alkyl-C(O)—N($R^6$)-methyl- optionally further substituted with a fluoro group, xvii) ($R^6$)($R^7$)N—C(O)—$(C_1-C_2)$alkyl-, xviii) $(C_1-C_2)$alkyl-C(O)—NH-methyl-C(O)—, xix) ($R^6$)($R^7$)N—C(O)—N(H)-methyl-, xx) ($R^6$)($R^7$)N—C(S)—N(H)-methyl-, xxi) ($R^6$)($R^7$)N—C(O)—O-methyl-, xxii) ($R^6$)($R^7$)N—C(O)methoxy-, and xxiii) ($R^6$)($R^7$)N—C(O)methoxymethyl-, and if present, the second $R^4$ substituent is fluoro or chloro;
$R^6$ is hydrogen or methyl;
$R^7$ is hydrogen or $(C_1-C_3)$alkyl;
$Ph^1$ is phenyl optionally substituted with a substituent selected from the group consisting of halo, $(C_1-C_2)$alkyl optionally further substituted with 1 to 3 fluoro substituents, and $(C_1-C_2)$alkoxy optionally further substituted with 1 to 3 fluoro substituents;
$Ar^1$ is a heteroaryl moiety selected from pyridyl, pyrimidyl, imidazolyl, pyrrolyl, thienyl, pyrazolyl, oxazolyl, isoxazolyl, thiazolyl, and isothiazolyl, any of which may be optionally further substituted with 1 or 2 substituents independently selected from methyl and ethyl;
or a pharmaceutically acceptable salt thereof.

2. A compound according to claim 1 where each $R^4$ is independently selected from the group consisting of i) halogen, ii) $(C_1-C_2)$alkyl optionally further substituted with 1 to 5 fluoro substituents, iii) $(C_1-C_2)$alkoxy optionally further substituted with 1 to 5 fluoro substituents, iv) cyclopropyl-$(C_0-C_1)$alkyl-O—, v) cyano, vi) $(C_1-C_2)$alkyl-S(O)$_2$—, and vii) $(C_1-C_4)$alkyl-C(O)—;
or a pharmaceutically acceptable salt thereof.

3. A compound according to claim 1 wherein n is 1.
4. A compound according to claim 1 wherein m is 1 or 2.
5. A compound according to claim 1 of the formula

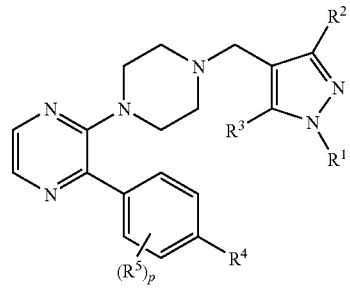

wherein
$R^1$ is selected from i) hydrogen, ii) $(C_1-C_3)$alkyl-optionally mono-substituted with hydroxy, iii) phenyl, iv) benzyl, and v) pyridyl;

$R^2$ is selected from hydrogen and $(C_1-C_3)$alkyl-;
$R^3$ is selected from hydrogen and $(C_1-C_3)$alkyl-;
$R^4$ is selected from the group consisting of i) $(C_1-C_4)$alkyl further substituted with a substituent selected from the group consisting of (hydroxy, $(C_1-C_4)$alkoxy, cyano, and amino), ii) $(C_1-C_2)$alkyl-O—C(O)—, iii) $(C_1-C_2)$alkyl-S(O)$_2$—$(C_1-C_2)$alkyl-, iv) $(C_1-C_4)$alkyl-C(O)—N($R^6$)—, v) $(C_1-C_4)$alkyl-C(O)—N($R^6$)-methyl-, vi) cyclopropyl-C(O)—NH-methyl-, vii) $(C_1-C_2)$alkyl-S(O)$_2$—N($R^6$)—$(C_1-C_2)$alkyl-, viii) $(C_1-C_2)$alkyl-O—$(C_0-C_2)$alkyl-C(O)—N($R^6$)— optionally further substituted with a fluoro group, ix) $(C_1-C_2)$alkyl-O—$(C_0-C_2)$alkyl-C(O)—N($R^6$)-methyl-optionally further substituted with a fluoro group, x) $(R^6)(R^7)$N—C(O)—$(C_1-C_2)$alkyl-, xi) $(C_1-C_2)$alkyl-C(O)—NH-methyl-C(O)—, xii) $(R^6)(R^7)$N—C(O)—N(H)-methyl-, xiii) $(R^6)(R^7)$N—C(S)—N(H)-methyl-, xiv) $(R^6)(R^7)$N—C(O)—O-methyl-, xv) $(R^6)(R^7)$N—C(O)methoxy-, and xvi) $(R^6)(R^7)$N—C(O)methoxymethyl-;
$R^5$ is fluoro or chloro;
$R^6$ is hydrogen or methyl;
$R^7$ is hydrogen or $(C_1-C_3)$alkyl;
p is 0 or 1; and or a pharmaceutically acceptable salt thereof.

6. A compound according to claim 5 wherein $R^1$ is methyl, ethyl, or phenyl; $R^2$ is hydrogen or methyl; $R^3$ is hydrogen or methyl; p is 0; and $R^4$ is selected from the group consisting of hydroxymethyl, hydroxyethyl, methoxymethyl, cyanomethyl, methyl-C(O)—N(H)-methyl-, and methyl-S(O)$_2$—N(H)-methyl-.

7. A compound according to claim 1 which is 2-[4-(3'-Phenyl-2,3,5,6-tetrahydro-[1,2]bipyrazinyl-4-ylmethyl)-pyrazol-1-yl]-ethanol or a pharmaceutically acceptable salt thereof.

8. A compound according to claim 1 which is N-{4-[4-(1,5-Dimethyl-1H-pyrazol-4-ylmethyl)-3,4,5,6-tetrahydro-2H-[1,2']bipyrazinyl-3'-yl]-benzyl}-acetamide or a pharmaceutically acceptable salt thereof.

9. A pharmaceutical composition comprising a compound according to claim 1 as an active ingredient in association with a pharmaceutically acceptable carrier, diluent or excipient.

* * * * *

UNITED STATES PATENT AND TRADEMARK OFFICE
CERTIFICATE OF CORRECTION

PATENT NO. : 8,202,873 B2
APPLICATION NO. : 12/597255
DATED : June 19, 2012
INVENTOR(S) : Valentina O. Badescu et al.

Page 1 of 1

It is certified that error appears in the above-identified patent and that said Letters Patent is hereby corrected as shown below:

In the issued patent, please note the following corrections:

Column 251, Line 57 - In Claim 1, delete "$(C_1-C_2)alkyl)-C(O)-N(C_1-C_2\ alkyl)-$" and insert -- $((C_1-C_2)alkyl)-C(O)-N((C_1-C_2)alkyl-)$ --.

Column 254, Line 10 - In Claim 7, delete "[1,2]" and insert -- [1,2'] --.

Signed and Sealed this
Twenty-first Day of August, 2012

David J. Kappos
*Director of the United States Patent and Trademark Office*